US009441240B2

(12) United States Patent
Burns et al.

(10) Patent No.: US 9,441,240 B2
(45) Date of Patent: Sep. 13, 2016

(54) CORN EVENT MON 87411

(71) Applicant: Monsanto Technology LLC, St. Louis, MO (US)

(72) Inventors: Wen C. Burns, Chesterfield, MO (US); Catherine A. Chay, St. Louis, MO (US); Cheryl L. Cloninger, St. Louis, MO (US); Mingqi Deng, Chesterfield, MO (US); Stanislaw Flasinski, Chesterfield, MO (US); Kunsheng Wu, Ballwin, MO (US)

(73) Assignee: Monsanto Technology LLC, St. Louis, MO (US)

( * ) Notice: Subject to any disclaimer, the term of this patent is extended or adjusted under 35 U.S.C. 154(b) by 515 days.

(21) Appl. No.: 13/890,027

(22) Filed: May 8, 2013

(65) Prior Publication Data

US 2013/0340111 A1 Dec. 19, 2013

Related U.S. Application Data

(60) Provisional application No. 61/644,368, filed on May 8, 2012.

(51) Int. Cl.

| | |
|---|---|
| ***A01H 5/00*** | (2006.01) |
| ***C12N 15/11*** | (2006.01) |
| ***C12N 15/52*** | (2006.01) |
| ***C12N 15/82*** | (2006.01) |
| ***C12Q 1/68*** | (2006.01) |

(52) U.S. Cl.

CPC ....... *C12N 15/8286* (2013.01); *C12N 15/8218* (2013.01); *C12N 15/8275* (2013.01)

(58) Field of Classification Search

None

See application file for complete search history.

(56) References Cited

U.S. PATENT DOCUMENTS

| | | | |
|---|---|---|---|
| 6,252,148 | B1 | 6/2001 | Armstrong |
| 7,288,643 | B2 | 10/2007 | Barbour et al. |
| 7,323,556 | B2 | 1/2008 | Bing et al. |
| 7,361,813 | B2 | 4/2008 | Steiner et al. |
| 7,612,194 | B2 | 11/2009 | Andersen et al. |
| 7,943,819 | B2 | 5/2011 | Baum et al. |
| 8,062,840 | B2 | 11/2011 | Anderson et al. |
| 8,067,671 | B2 | 11/2011 | Boukharov et al. |
| 8,088,976 | B2 | 1/2012 | Boukharov et al. |
| 8,212,113 | B2 | 7/2012 | Beazley et al. |
| 8,232,456 | B2 | 7/2012 | Long et al. |
| 8,404,927 | B2 | 3/2013 | Allen et al. |
| 8,466,346 | B2 | 6/2013 | DeFramond et al. |
| 8,614,370 | B2 | 12/2013 | Andersen et al. |
| 8,686,230 | B2 | 4/2014 | Beazley et al. |
| 8,759,611 | B2 | 6/2014 | Baum et al. |
| 8,946,510 | B2 | 2/2015 | Baum et al. |
| 2006/0127889 | A1 | 6/2006 | Dotson et al. |
| 2006/0272049 | A1 | 11/2006 | Waterhouse et al. |
| 2007/0124836 | A1 | 5/2007 | Baum et al. |
| 2007/0259785 | A1 | 11/2007 | Heck et al. |
| 2008/0028482 | A1 | 1/2008 | Beazley et al. |
| 2010/0179196 | A1 | 7/2010 | Pershing et al. |
| 2010/0192265 | A1 | 7/2010 | Andersen et al. |
| 2011/0126310 | A1 | 5/2011 | Feng et al. |
| 2012/0164205 | A1 | 6/2012 | Baum et al. |
| 2012/0192317 | A1 | 7/2012 | Heck et al. |
| 2013/0232646 | A1 | 9/2013 | Baum et al. |
| 2014/0013471 | A1 | 1/2014 | Baum et al. |
| 2014/0080755 | A1 | 3/2014 | Heck et al. |
| 2014/0194306 | A1 | 7/2014 | Andersen et al. |
| 2014/0287406 | A1 | 9/2014 | Beazley et al. |
| 2014/0325702 | A1 | 10/2014 | Boukharov et al. |
| 2014/0338072 | A1 | 11/2014 | Burns et al. |

FOREIGN PATENT DOCUMENTS

| | | | |
|---|---|---|---|
| CN | 1933723 | A | 3/2007 |
| EP | 2281447 | A3 | 3/2011 |
| WO | WO 2009/075860 | A2 | 6/2009 |
| WO | WO 2005/059103 | | 6/2015 |

OTHER PUBLICATIONS

International Search Report issued in PCT/US2013/040173; dated Dec. 16, 2013.

U.S. Appl. No. 14/262,233, filed Apr. 25, 2014, Burns et al.

U.S. Appl. No. 14/191,117, filed Feb. 26, 2014, Beazley et al.

Nascimento, "Brazil corn seed companies offer almost 500 hybrids to growers," *AgroNews* 2013, available online at <<http://news.agropages.com/News/NewsDetail---9371.htm>>.

Baum et al., "Control of coleopteran insect pests through RNA interference," *Nature Biotechnology* 25(11):1322-1326, 2007.

Extended European Search Report regarding Application No. EP13787568, dated Nov. 27, 2015.

Search Report regarding Chinese Application No. 2013800336548, dated Feb. 19, 2016. (English translation).

Zhao et al., "Research Development of Transgenic Corn," *Corn Science* 8(3):14-17, 2000.

Romer Labs, "AgraStrip GMO TraitChek," found at <<http://www.graintec.com.au/media/25773/PL_AS%20GMO%20SDIX%20leaflet%20TraitChek_ASE_EN_V02.pdf>>, dated 2010.

ArgenBio, "MON 89034 x MON 88017," found at <<http://www.argenbio.org/index.php?action+novedades¬e=571>>, accessed on Aug. 5, 2016.

ArgenBio, "Mon 89034 x Mon 88017," found at <<http://www.argenbio.org/index.php?action+novedades¬e=571>>, accessed on Aug. 5, 2016. (English translation).

Office Action issued in Bolivian Application No. SP-0159-2013, dated May 13, 2016.

*Primary Examiner* — Mykola Kovalenko

(74) *Attorney, Agent, or Firm* — Dentons US LLP; T. K. Ball Esq.; Carine M. Doyle Esq.

(57) ABSTRACT

The invention provides corn event MON 87411, and plants, plant cells, seeds, plant parts, and commodity products comprising event MON 87411. The invention also provides polynucleotides specific for event MON 87411 and plants, plant cells, seeds, plant parts, and commodity products comprising polynucleotides specific for event MON 87411. The invention also provides methods related to event MON 87411.

10 Claims, 4 Drawing Sheets

Figure 2

| Construct | LB | Left PIP trait Cassette | | | | | | Right PIP trait Cassette | | | | | | Herbicide Tolerance Cassette | | | | RB |
|---|---|---|---|---|---|---|---|---|---|---|---|---|---|---|---|---|---|---|
| | [1] | [2] | [3] | [4] | [5] | [6] | | [7] | [8] | [9] | [10] | [11] | | [12] | [13] | [14] | [15] | [16] |
| 417 (SEQ ID NO: 26) | | Ps.RbcS2-E9 3' UTR | **Dv_Snf7o 240-mer INVERTED REPEAT** | Corn DnaK intron | CaMV 35S leader | eCaMV 35S promoter | ← → | Corn PIIG promoter | Wheat Lhcb1 leader | Rice Act1 intron | **cry3Bb ORF** | Wheat Hsp17 3' UTR | → | | | | | |
| 416 (SEQ ID NO: 27) | | Ps.RbcS2-E9 3' UTR | **Dv_Snf7o 240-mer INVERTED REPEAT** | Corn DnaK intron | CaMV 35S leader | eCaMV 35S promoter | ← → | Rice Rcc3 promoter | Wheat Lhcb1 leader | Rice Act1 intron | **cry3Bb ORF** | Wheat Hsp17 3' UTR | → | | | | | |
| 418 (SEQ ID NO: 28) | | Ps.RbcS2-E9 3' UTR | **Dv_Snf7o 240-mer INVERTED REPEAT** | Corn DnaK intron | CaMV 35S leader | eCaMV 35S promoter | ← | Wheat Hsp17 3' UTR | **cry3Bb ORF** | Rice Act1 intron | Wheat Lhcb1 leader<br>ENH FMV 35S promoter | ← | → | | | | | |
| 419 (SEQ ID NO: 29) | | Ps.RbcS2-E9 3' UTR | **Dv_Snf7o 240-mer INVERTED REPEAT** | Corn DnaK intron | CaMV 35S leader | eCaMV 35S promoter | ← | Wheat Hsp17 3' UTR | **cry3Bb ORF** | Rice Act1 intron | Wheat Lhcb1 leader<br>Rice Rcc3 promoter | ← | → | Rice TubA (promoter, leader, intron) | CTP | CP4 EPSPS | Rice TubA 3' UTR | |
| 402 (SEQ ID NO: 30) | | Ps.RbcS2-E9 3' UTR | **Dv_Snf7o 240-mer INVERTED REPEAT** | Corn DnaK intron | Wheat Lhcb1 leader | eFMV 35S promoter | ← → | Rice Rcc3 promoter | Wheat Lhcb1 leader | Rice Act1 intron | **cry3Bb ORF** | Wheat Hsp17 3' UTR | → | | | | | |
| 403 (SEQ ID NO: 31) | | Ps.RbcS2-E9 3' UTR | **Dv_Snf7o 240-mer INVERTED REPEAT** | Corn DnaK intron | Wheat Lhcb1 leader | eFMV 35S promoter | ← → | Corn PIIG promoter | Wheat Lhcb1 leader | Rice Act1 intron | **cry3Bb ORF** | Wheat Hsp17 3' UTR | → | | | | | |
| 404 (SEQ ID NO: 32) | | Ps.RbcS2-E9 3' UTR | **Dv_Snf7o 240-mer INVERTED REPEAT** | Corn DnaK intron | Wheat Lhcb1 leader | eFMV 35S promoter | ← | Wheat Hsp17 3' UTR | **cry3Bb ORF** | Rice Act1 intron | Wheat Lhcb1 leader<br>Rice Rcc3 promoter | ← | → | | | | | |
| 423 (SEQ ID NO: 33) | | Wheat Hsp17 3' UTR | **cry3Bb ORF** | Rice Act1 intron | Lhcb1 + 35S leaders | eCaMV 35S promoter | ← | Ps.RbcS2-E9 3' UTR | **Dv_Snf7o 240-mer INVERTED REPEAT** | Corn DnaK intron | Wheat Lhcb1 leader<br>eFMV 35S promoter | ← | → | | | | | |
| 405 (SEQ ID NO: 34) | | Ps.RbcS2-E9 3' UTR | **Dv_Snf7o 240-mer INVERTED REPEAT** | Corn DnaK intron | FMV 35S promoter | ← | → | eCaMV 35S promoter<br>CaMV 35S leader | Wheat Lhcb1 leader | Rice Act1 intron | **cry3Bb ORF** | Wheat Hsp17 3' UTR | No 3rd cassette | | | | | |
| 406 (SEQ ID NO: 35) | | → | eCaMV 35S promoter<br>CaMV 35S leader | Wheat Lhcb1 leader | Rice Act1 intron | **cry3Bb ORF** | Wheat Hsp17 3' UTR → | Corn ePIIG promoter<br>eCaMV 35S promoter | CaMV 35S leader | Corn DnaK intron | **Dv_Snf7o 240-mer INVERTED REPEAT** | Ps.RbcS2-E9 3' UTR | No 3rd cassette | | | | | |
| 890 (SEQ ID NO: 36) | | Ps.RbcS2-E9 3' UTR | **Dv_Snf7o 240-mer INVERTED REPEAT** | Corn DnaK intron | CaMV 35S leader | eCaMV 35S promoter | ← | // | | | // | | No 2nd or 3rd cassette | | | | | |

← Designates a right-to-left directionality of the cassette.

→ Designates a left-to-right directionality of the cassette.

Figure 4

| Construct | Border | Cassette 1 | Cassette 2 | Cassette 3 | Border |
|---|---|---|---|---|---|
| pMON120417 | LB | e35s/Dv_Snf7o 240mer IR/T-E9:1:1 | Zm.PIIG/Ta.Lhcb1/Os.Act/Cry3Bb/ Ta.Hsp17:1:1 | Os.TubA3//CTP2-EPSPS CP4//TubA3:1:3 | RB |
| pMON120434 | LB | e35s/Dv_Snf7o 240mer IR/T-E9:1:1 | Zm.PIIG/Ta.Lhcb1/Os.Act/Cry3Bb/ Ta.Hsp17:1:1 | Os.TubA3//CTP2-EPSPS CP4//TubA3:1:3 | RB |
| pMON120416 | LB | e35s/Dv_Snf7o 240mer IR/T-E9:1:1 | Os.Rcc3/Ta.Lhcb1/Os.Act/Cry3Bb/ Ta.Hsp17:1:1 | Os.TubA3//CTP2-EPSPS CP4//TubA3:1:3 | RB |
| pMON120419 | LB | e35s/Dv_Snf7o 240mer IR/T-E9:1:1 | Os.Rcc3/Ta.Lhcb1/Os.Act/Cry3Bb/ Ta.Hsp17:1:1 | Os.TubA3//CTP2-EPSPS CP4//TubA3:1:3 | RB |

CORN EVENT MON 87411

REFERENCE TO RELATED APPLICATIONS

This application claims the benefit of U.S. provisional application No. 61/644,368 filed May 8, 2012, which is herein incorporated by reference in its entirety.

INCORPORATION OF SEQUENCE LISTING

The sequence listing contained in the file named "MONS308US_ST25.txt", which is 230 kilobytes (size as measured in Microsoft Windows®) and was created on May 6, 2013, is filed herewith by electronic submission and is incorporated by reference herein.

FIELD OF THE INVENTION

The invention relates to transgenic *Zea mays* event MON 87411. The event provides dual modes of action for resistance to corn rootworm infestations and tolerance to the herbicide glyphosate. The invention also relates to plants, plant parts, plant seeds, plant cells, agricultural products, and methods related to event MON 87411 and provides nucleotide molecules that are unique to the event and were created in connection with the insertion of transgenic DNA into the genome of a *Zea mays* plant.

BACKGROUND OF THE INVENTION

Corn (*Zea mays*) is an important crop in many areas of the world, and the methods of biotechnology have been applied to this crop in order to produce corn with desirable traits. The expression of an insect resistance or herbicide tolerance transgene in a plant can confer the desirable traits of insect resistance and/or herbicide tolerance on the plant, but expression of such transgenes may be influenced by many different factors including the orientation and composition of the cassettes driving expression of the individual genes transferred to the plant chromosome, and the chromosomal location and the genomic result of the transgene insertion. For example, there can be variation in the level and pattern of transgene expression among individual events that are otherwise identical except for the chromosomal insertion site of the transgene. There may also be undesirable phenotypic or agronomic differences between some events. Therefore, it is often necessary to produce and analyze a large number of individual plant transformation events in order to select an event having superior properties relative to the desirable trait and the optimal phenotypic and agricultural characteristics necessary to make it suitable for commercial purposes. Such selection often requires extensive molecular characterization as well as greenhouse and field trials with many events over multiple years, in multiple locations, and under a variety of conditions so that a significant amount of agronomic, phenotypic, and molecular data may be collected. The resulting data and observations must then be analyzed by teams of scientists and agronomists with the goal of selecting a commercially suitable event. Once selected, such an event may then be used for introgressing the desirable trait into other genetic backgrounds using plant breeding methods, and thus producing a number of different crop varieties that contain the desirable trait and are suitably adapted to specific local growing conditions.

To make a transgenic plant containing a single transformation event, a portion of a recombinant DNA construct is transferred into the genome of a corn cell, and the corn cell is subsequently grown into a plant. A corn cell into which the event is initially transferred is regenerated to produce the $R_0$ generation. The $R_0$ plant and progeny plants from the $R_0$ plant can be tested for any desired trait(s), but the effectiveness of the event can be impacted by cis and/or trans factors relative to the integration site in the transformation event. The phenotype conferred by the event can also be impacted by the size and design of the DNA construct, which can vary by the combination of genetic elements in an expression cassette, number of transgenes, number of expression cassettes, and configuration of such elements and such cassettes. Identifying an event with desirable traits can be further complicated by factors such as plant developmental, diurnal, temporal, or spatial patterns of transgene expression; or by extrinsic factors, e.g., environmental plant growth conditions, water availability, nitrogen availability, heat, or stress. Thus, the ability to obtain an event conferring a desirable set of phenotypic traits is not readily predictable.

SUMMARY OF THE INVENTION

The inventors have identified a transgenic corn event MON 87411 exhibiting superior properties and performance compared to existing transgenic corn plants and to new events constructed in parallel. The corn event MON 87411 contains three linked expression cassettes which collectively confer the traits of corn rootworm resistance and glyphosate herbicide tolerance to corn cells, corn tissues, corn seed and corn plants containing the transgenic event MON 87411. The corn event MON 87411 provides two modes of action against corn rootworm pest species (including *Diabrotica* spp., especially when the pest is *Diabrotica virgifera virgifera* (Western Corn Rootworm, WCR), *Diabrotica barberi* (Northern Corn Rootworm, NCR), *Diabrotica virgifera zeae* (Mexican Corn Rootworm, MCR), *Diabrotica balteata* (Brazilian Corn Rootworm (BZR) or Brazilian Corn Rootworm complex (BCR) consisting of *Diabrotica viridula* and *Diabrotica speciosa*), or *Diabrotica undecimpunctata howardii* (Southern Corn Rootworm, SCR)). Dual modes of action provide redundancy and reduces significantly the likelihood of the development of resistance to the pest control traits.

The event MON 87411 is characterized by specific unique DNA segments that are useful in detecting the presence of the event in a sample. A sample is intended to refer to a composition that is either substantially pure corn DNA or a composition that contains corn DNA. In either case, the sample is a biological sample, i.e., it contains biological materials, including but not limited to DNA obtained or derived from, either directly or indirectly, from the genome of corn event MON 87411. "Directly" refers to the ability of the skilled artisan to directly obtain DNA from the corn genome by fracturing corn cells (or by obtaining samples of corn that contain fractured corn cells) and exposing the genome DNA for the purposes of detection. "Indirectly" refers to the ability of the skilled artisan to obtain the target or specific reference DNA, i.e. a novel and unique junction segment described herein as being diagnostic for the presence of the event MON 87411 in a particular sample, by means other than by direct via fracturing of corn cells or obtaining a sample of corn that contains fractured corn cells. Such indirect means include but are not limited to amplification of a DNA segment that contains the DNA sequence targeted by a particular probe designed to bind with specificity to the target sequence, or amplification of a DNA segment that can be measured and characterized, i.e. measured by separation from other segments of DNA through some efficient matrix such as an agarose or acrylamide gel or the like, or characterized by direct sequence analysis of the amplicon or cloning of the amplicon into a vector and direct sequencing of the inserted amplicon present within such vector. Alternatively, a segment of DNA corresponding to the position within the corn chromosome at which the transgenic DNA was inserted into the corn chromosome and which can be used to define the event MON 87411, can be cloned by various means and then identified and characterized for its presence in a particular sample or in a particular corn genome. Such DNA segments are referred to as junction segments or sequences, and can be any length of inserted DNA and adjacent (flanking) corn chromosome DNA so long as the point of joining between the inserted DNA and the corn genome is included in the segment. SEQ ID NO:12 and SEQ ID NO:21 and the reverse complement of each of these are representative of such segments.

The specific sequences identified herein may be present uniquely in event MON 87411, or the construct comprised therein, and the identification of these sequences, whether by direct sequence analysis, by detecting probes bound to such sequences, or by observing the size and perhaps the composition of particular amplicons described herein, when present in a particular corn germplasm or genome and/or present in a particular biological sample containing corn DNA, are diagnostic for the presence of the event MON 87411, or the construct comprised therein, in such sample. It is known that the flanking genomic segments (i.e., the corn genome segments of DNA sequence adjacent to the inserted transgenic DNA) are subject to slight variability and as such, the limitation of at least 99% or greater identity is with reference to such anomalies or polymorphisms from corn genome to corn genome. Nucleotide segments that are completely complementary across their length in comparison to the particular diagnostic sequences referenced herein are intended to be within the scope of the present invention.

The position of the nucleotide segments of the present invention relative to each other and within the corn genome are illustrated in FIG. 3 and the nucleotide sequence of each is illustrated as set forth in SEQ ID NO:1. Nucleotide segments that characterize the event MON 87411 and which are diagnostic for the presence of event MON 87411, or the construct comprised therein, in a sample include SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:12, SEQ ID NO:14, SEQ ID NO:16, SEQ ID NO:18, SEQ ID NO:19, SEQ ID NO:20, SEQ ID NO:21, SEQ ID NO:22, SEQ ID NO:23, SEQ ID NO:24, and SEQ ID NO:25; SEQ ID NO:41, SEQ ID NO:42, SEQ ID NO:43, SEQ ID NO:44, SEQ ID NO:45, SEQ ID NO:49, SEQ ID NO:50, SEQ ID NO:51, or SEQ ID NO:52. These presence of one, or two, or more of these nucleotide sequences in a sample, when such sample contains corn tissue and thus corn DNA, are diagnostic for the presence of the event MON 87411, or the construct comprised therein.

It is intended by use of the word "derived", that a particular DNA molecule is in the corn plant genome, or is capable of being detected in corn plant DNA. "Capable of being detected" refers to the ability of a particular DNA segment to be amplified and its size and or sequence characterized or elucidated by DNA sequence analysis, and can also refer to the ability of a probe to bind specifically to the particular DNA segment, i.e. the target DNA segment, and the subsequent ability to detect the binding of the probe to the target. The particular DNA segment or target DNA segment of the present invention is present within corn that contains the insertion event MON 87411.

By reference to corn it is intended that corn cells, corn seed, corn plant parts and corn plants are within the scope of the present invention so long as each embodiment contains a detectable amount of DNA corresponding to any one, two, or more of the segments that are described herein as being diagnostic for the presence of the corn event MON 87411 DNA. Corn plant parts include cells; pollen; ovules pods; flowers and flower parts such as the cob, silk, and tassel; root tissue; stem tissue; and leaf tissue. Commodity products that are made from corn in which a detectable amount of the segments of DNA described herein as being diagnostic for the presence of the event MON 87411 are within the scope of the invention. Such commodity products may include whole or processed corn seeds, animal feed containing corn or corn by-products, corn oil, corn meal, corn flour, corn starch, corn flakes, corn bran, corn biomass and stover, and fuel products and fuel by-products when made from corn or corn plants and plant parts.

The DNA of corn event MON 87411 is typically present in each cell and in each chromosome of the corn plant, corn seed, and corn tissues containing the event. As the corn genome is transmitted to progeny in Mendelian fashion, if a corn plant were homozygous, each progeny corn plant and cell would contain the event DNA on each of the parental chromosomes generated to the progeny from the parent(s). However, if the corn genome containing the event MON 87411 DNA is a heterozygous or hybrid parent, then only fifty percent of the pollen and fifty percent of the ovules engaged in mating from hybrid parents will contain the corn event MON 87411 DNA, resulting in a mixed population of progeny that contain the event MON 87411 DNA, and the percentage of such progeny arising from such crosses with hybrids can range anywhere from about fifty to about seventy five percent having the event MON 87411 DNA transmitted to such progeny.

The DNA molecules of the present invention may be unique to the corn event MON 87411 inserted DNA or the two junctions between the transgenic inserted DNA and the corn genome DNA that is adjacent to either end of the inserted DNA. These molecules, when present in a particular sample analyzed by the methods described herein using the probes, primers and in some cases using DNA sequence analysis, may be diagnostic for the presence of an amount of event MON 87411 corn in that sample. Such DNA molecules unique to the corn event MON 87411 DNA can be identified and characterized in a number of ways, including by use of probe nucleic acid molecules designed to bind specifically to the unique DNA molecules followed by detection of the binding of such probes to the unique DNA, and by thermal amplification methods that use at least two different DNA molecules that act as probes but the sequence of such molecules may be somewhat less specific than the probes described above. The skilled artisan understands that contacting a particular target DNA with a probe or primer under appropriate hybridization conditions will result in the binding of the probe or primer to the targeted DNA segment.

The DNA molecules of the present invention that are target segments of DNA are capable of amplification and, when detected as one or more amplicons of the represented length obtained by amplification methods of a particular sample, may be diagnostic for the presence of event MON 87411, or the construct comprised therein, in such sample. Such DNA molecules or polynucleotide segments have the nucleotide sequences as set forth in each of, SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:12, SEQ ID NO:14, SEQ ID NO:16, SEQ ID NO:21, SEQ ID NO:25, SEQ ID NO:41, SEQ ID NO:42, SEQ ID NO:43, SEQ ID NO:44, SEQ ID NO:45, SEQ ID NO:49, SEQ ID NO:50, SEQ ID NO:51, and SEQ ID NO:52, and are further defined herein and in the examples below. Primer molecules and/or probes may be provided in kit form along with the necessary reagents, including controls, and packaged together with instructions for use.

Recombinant DNA molecules of the present invention are deemed to be within the scope of the present invention when present within or derived from a microorganism. A microorganism is intended to include any microscopic cell, whether prokaryote or eukaryote or otherwise that contains DNA within a genome or chromosome or an extra-chromosomal DNA structure more commonly referred to as a plasmid or vector. Microscopic organisms include bacteria (prokaryotes) and cells corresponding to higher life forms (eukaryotes) which are beneath the visual range of the average human, typically beneath fifty cubic microns and more generally beneath ten cubic microns. Bacteria are common microscopic microorganisms that more likely than not could contain a vector or plasmid that contains one or more or all of the novel DNA segments of the present invention, including each of the respective expression cassettes present as set forth in SEQ ID NO: 1. Plant cells and particularly corn plant cells are within the scope of the invention when these contain any one, two, or more or all of the novel DNA segments of the present invention.

Probes for use herein are typically characterized as DNA molecules or polynucleotide segments of sufficient length to function under stringent hybridization conditions as defined herein to bind with a particular target DNA segment, i.e., a unique segment of DNA present within and diagnostic for the presence of, event MON 87741 DNA in a sample. Such a probe can be designed to bind only to a single junction or other novel sequence present only in the corn event MON 87411 DNA, or to two or more such single junction segments. In any event, the detection of the binding of such a probe to a DNA molecule in a particular sample suspected of containing corn DNA is diagnostic for the presence of corn event MON 87411 in the sample.

Primers are typically provided as pairs of different oligonucleotides or polynucleotide segments for use in a thermal amplification reaction which amplifies a particular DNA target segment. Each primer in the pair is designed to bind to a rather specific segment of DNA within or near to a segment of DNA of interest for amplification. The primers bind in such way that these then act as localized regions of nucleic acid sequence polymerization resulting in the production of one or more amplicons (amplified target segments of DNA). In the present invention, use of primers designed to bind to unique segments of corn event MON 87411 DNA in a particular biological sample and that amplify particular amplicons containing one or more of the junction segments described herein, and the detection and or characterization of such amplicons upon completion or termination of the polymerase reaction, is diagnostic for the presence of the corn event MON 87411 in the particular sample. The skilled artisan is well familiar with this amplification method and no recitation of the specifics of amplification is necessary here.

Corn plants, corn plant cells, corn plant tissues and corn seed are insensitive to glyphosate herbicide applications due to expression of a glyphosate insensitive CP4 EPSPS enzyme from a rice Rcc3 promoter in an expression cassette at the 3' distal end as set forth in SEQ ID NO: 1. Such seed may be sown into a field. Several days after germination and the appearance of shoots, a weed controlling effective amount of glyphosate herbicide may be applied, which will eliminate substantially all of the weeds in the field but will allow for the continued growth and development of corn plants containing the corn event MON 87411 DNA. The plants are also resistant to infestation by corn rootworms of all known species of rootworm *Diabrotica*, including but not limited to *Diabrotica virgifera virgifera* (Western Corn Rootworm, WCR), *Diabrotica barberi* (Northern Corn Rootworm, NCR), *Diabrotica virgifera zeae* (Mexican Corn Rootworm, MCR), *Diabrotica balteata* (Brazilian Corn Rootworm (BZR) or Brazilian Corn Rootworm complex (BCR) consisting of *Diabrotica viridula* and *Diabrotica speciosa*), and *Diabrotica undecimpunctata howardii* (Southern Corn Rootworm, SCR). The resistance to *Diabrotica* species arises in connection with the expression of two different DNA segments that are operably and covalently linked within the inserted transgenic DNA: a dsRNA is transcribed from the expression cassette at the 5' proximal end of the inserted transgenic DNA as set forth in SEQ ID NO:1 and as illustrated in FIG. 1 by the position of [G] SEQ ID NO:12, and targets for suppression an essential gene in corn rootworms; and a coleopteran toxic Cry3Bb protein is expressed from an expression cassette (approximately centered in SEQ ID NO:1 as shown in FIG. 1 by the position of [H] SEQ ID NO: 14) centered between the cassette expressing dsRNA [G] and the cassette at the 3' distal end of the inserted transgenic DNA as set forth in SEQ ID NO:1 (a glyphosate tolerance expression cassette illustrated in FIG. 1 by [I] SEQ ID NO:16). The dsRNA targets for suppression a yeast orthologous gene referred to as snf7 and is expressed from a CAMV e35S promoter, while the Cry3Bb protein is expressed from a *Zea mays* PIIG promoter. The dsRNA and the Cry3Bb protein are agents toxic to corn rootworm species.

The promoters driving expression of the dsRNA and Cry3Bb toxic agents are divergently positioned so that expression from each promoter of the respective toxic agent is away from a point centered between the two promoters, i.e., transcription of each expression cassette proceeds in opposite directions and does not converge. The glyphosate tolerance CP4 EPSPS expression cassette is downstream of, i.e. proximal to the 3' end as set forth in SEQ ID NO:1 and 3' distal to the cassette driving expression of the Cry3Bb protein. The cassettes driving expression of Cry3Bb and EPSPS produce their respective proteins using a tandem orientation of transcription, Cry3Bb upstream of the EPSPS, and transcribed in the same orientation, but each from their separate respective promoters. Leaving the dsRNA expression cassette and the glyphosate tolerance cassette intact and positioned at the distal ends of the DNA segment intended for insertion into the corn genome, other variant constructs were produced in which the orientation of the Cry3Bb cassette was inverted or reversed relative to the design present in the event MON 87411 DNA. These variant constructs utilized the *Zea mays* PIIG promoter or a rice Rcc3 promoter to drive expression of Cry3Bb.

Transgenic events containing only these variant constructs/orientations of the Cry3Bb expression cassette were compared to the event MON 87411 and to the currently available commercial events MON863 (containing only a Cry3Bb expression cassette), MON88017 (containing a Cry3Bb expression cassette operably linked to a CP4 EPSPS expression cassette), and DAS-59122-7 (containing three operably linked expression cassettes, two expressing in tandem the dual Bt toxin components Cry34 and Cry35 along with a gene conferring glufosinate tolerance). The results as illustrated below in the examples show that the event MON 87411 exhibited superior properties for root directed expression of the Cry3Bb protein and the plurality of transgenic events produced using the construct used for generating the event MON 87411 were each more likely than other events produced with other constructs to exhibit efficacious control of corn rootworms.

Corn plants of the present invention and parts thereof including seed, each containing the DNA corresponding to event MON 87411, are within the scope of the present invention. Such plants are resistant to corn rootworm infestation and are insensitive to applications of the herbicide glyphosate. Such plants include hybrids containing only one MON 87411 allele, i.e., a genome characterized as heterozygous with reference to the locus corresponding to the event MON 87411 DNA. Such hybrids are produced by breeding with desirable germplasm to insure hybrid vigor and other agriculturally desirable properties of corn. Hybrids may be produced by any number of methods but a preferred method takes advantage of a first inbred (homozygous) parent that contains the event MON 87411 specific allele on both chromosomes at the locus at which the event MON 87411 DNA is inserted, and breeding the first inbred together with a second inbred which does not contain the MON 87411 DNA. Both parental inbred varieties will have one or more advantageous properties desirable in the progeny seed, i.e. the hybrid seed.

A transgenic property or allele conferring some additional trait to a plant containing the event MON 87411 DNA is particularly desirable. Such transgenic alleles include other transgenic events conferring corn rootworm resistance, including but not limited to events such as DAS-59122-7; MIR604; and 5307. Each of these events provides a supplemental corn rootworm toxic agent (DAS-59122-7 provides PS149B1 (Cry34/Cry35) exhibiting rootworm toxic properties and herbicide tolerance to glufosinate; MIR604 provides a modified Cry3Aa exhibiting rootworm toxic properties; event 5307 provides FR8a gene exhibiting rootworm toxic properties). Providing additional corn rootworm resistance traits such as these may decrease the likelihood of the development of resistance to any one of the corn rootworm toxic agents provided. Other desirable traits include yield and stress resistance or tolerance traits, nitrogen fixation traits, traits modulating the use of water, resistance to fungal infestation, resistance to herbicides such as dicamba (MON 87427), glufosinate, and the like, as well as resistance to lepidopteran infestations. Lepidopteran infestation resistance traits have been provided in the art and include the transgenic corn events (and respective lepidopteran active proteins) MON810 (Cry1Ab), MON 89034 (Cry1A.105 and Cry2Ab); TC1507 (Cry1Ac and Cry1Fa); DAS-06275-8 also known as TC-6275 (Cry1Fa and bar (providing glufosinate tolerance)); MIR162 (Vip3Aa), BT176 (Cry1Ab); and BT11 (Cry1Ab).

An alternative to providing any combination or all of these traits in a single plant, particularly the insect resistance traits corresponding to the event MON 87411 traits, the other listed corn rootworm resistance traits, or the lepidopteran resistance traits, would be to provide these in various combinations of seed blends, in which certain seed in the blend contain the MON 87411 traits and some combination of only the listed coleopteran resistance traits and act together below the ground to prevent infestations of corn rootworms, while other seed in the blend contain only the lepidopteran resistance traits and confer resistance to lepidopteran infestations of corn above the ground. In this way, the seed in the blend provide refuge for each other, i.e. the coleopteran protected seed and plants act as a refuge for the plants conferring lepidopteran resistance, and vice versa. Typically however, these traits would be provided in some trait combination or package in which the MON 87411 traits would be provided together in a single plant by breeding with one or more of the lepidopteran resistance traits to provide a complete package of pest resistance to the crop in the field, and a small percentage of the seed (perhaps between 1 and 20 percent or any number in between including 2, 3, 4, 5, 6, 7, 8, 9, 10, 11, 12, 13, 14, 15, 16, 17, 18, or 19 percent) would be traited only for herbicide tolerance and would lack any pest protection traits and would be planted into the field in a mix randomly with the pest resistance traited seed or as a structured (separate) stand of crops would act as a refuge both for the pests that attack corn plants above the ground and pests that attack corn plants below the ground.

In one aspect, the invention therefore provides a method of protecting a field of corn plants comprising cultivating a field of corn plants comprised of from about 50 to about 100 percent of corn plants comprising corn event MON 87411.

The construct inserted into the event MON 87411 provides particular advantages relative to the EPSPS expression cassette. First, the presence of this cassette provides for ease of selection of the transgenic events into which the construct has been inserted. Second, the cassette provides for control of weeds in a field into which seed corresponding to event MON 87411 have been planted. The field containing such MON 87411 plants can be sprayed with an effective amount of glyphosate to control the growth of weeks in the field that are susceptible to glyphosate. For weeds that are not susceptible to glyphosate. As noted above, other transgenic events that provide for tolerance to other herbicides such as to dicamba or to glufosinate can be bred into a single hybrid along with the event MON 87411, thus providing an efficient means for controlling weeds in a field by applying two or more of the herbicides glyphosate, dicamba, or glufosinate, as the likelihood that weeds would be present that exhibit tolerance to two or more of these herbicides would be unlikely, and in such case, the corn crop would consist of hybrids that exhibit resistance to such applications of herbicide combinations.

In one aspect, the invention provides a DNA molecule comprising (a) the recombinant polynucleotide as set forth in SEQ ID NO:12; and (b) the recombinant polynucleotide as set forth in SEQ ID NO:14; and (c) the recombinant polynucleotide as set forth in SEQ ID NO:16, wherein said recombinant polynucleotide sequences are linked together by phosphodiester linkage. In one embodiment, the DNA molecule comprises SEQ ID NO:4.

BRIEF DESCRIPTION OF THE DRAWINGS

FIG. 2 illustrates eleven different DNA constructs, (417, 416, 418, 419, 402, 403, 404, 423, 405, 406, and 890) engineered to express up to three distinct cassettes, including two plant-incorporated protectant (PIP) cassettes, targeting Western corn rootworm (WCR), and a single herbicide tolerance cassette. The two PIP cassettes include (a) an expression cassette for a Dv_Snf7o 240-mer inverted repeat, and (b) an expression cassette for a Cry3Bb protein. Each of the constructs depicted comprise these expression cassettes in varying order and orientation. Constructs 405 and 406 contain no herbicide tolerance cassette and construct 890 comprises only a single expression cassette for a Dv_Snf7o 240-mer inverted repeat. The three constructs comprise a total of sixteen genetic elements from the Left Border (LB) through to the Right Border (RB): [1] LB; [2] Ps.RbcS2-E9 3' UTR; [3] 240-mer Dv_Snf7o inverted repeat gene; [4] Corn DnaK intron; [5] CaMV 35S leader; [6] eCaMV 35S promoter; [7] Corn PIIG promoter; [8] Wheat Lhcb1 leader; [9] Rice Act1 intron; [10] cry3Bb ORF; [11] Wheat Hsp17 3' UTR; [12] Rice TubA (promoter, leader, intron); [13] CTP; [14] CP4 EPSPS; [15]Rice TubA 3' UTR; and [16] RB.

Figure 1:
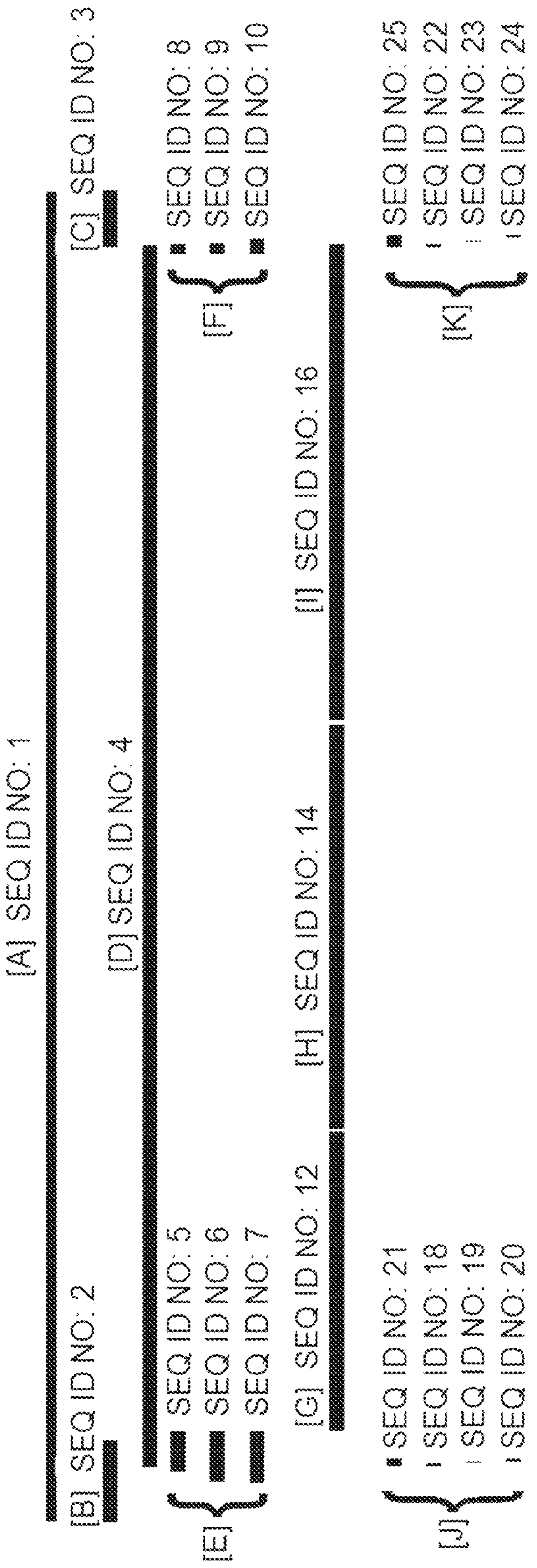
FIG. 1 is a diagrammatical representation of the transgenic insert in the genome of corn event MON 87411: [A] represents SEQ ID NO:1, which is the contiguous sequence of the transgenic DNA insert integrated into the genome of corn LH244 and 5' and 3' genomic DNA flanking the inserted DNA; [B] and [C] correspond to the relative positions of SEQ ID NOs:2 and 3, which form the 5' and 3' transgene/genomic DNA junction sequences of event MON 87411, respectively; [D] represents SEQ ID NO:4, which is the sequence of the transgenic DNA insert integrated into the genome resulting in event MON 87411; [E] corresponds to the relative positions of SEQ ID NO:5, SEQ ID NO:6 and SEQ ID NO:7, each spanning the 5' junction between the terminal ends of the transgenic inserted DNA and the flanking genomic DNA; [F] corresponds to the relative positions of SEQ ID NO:8, SEQ ID NO:9 and SEQ ID NO:10, each spanning the 3' junction between the terminal ends of the transgenic inserted DNA and the flanking genomic DNA; [G], [H] and [I] respectively represent the three different expression cassettes corresponding to the transgenic DNA construct inserted into the corn plant genome resulting in event MON 87411; [J], and [K] represent oligonucleotide primers, oligonucleotide probes, and DNA amplicons corresponding to the junctions of event MON 87411.

[A] nucleotide position 1-500 as set forth in SEQ ID NO:1 corresponds to corn genome DNA adjacent to the transgenic inserted DNA in corn event MON87411, which in this case is arbitrarily assigned as the 5' end of the transgenic inserted DNA.

[B] nucleotide position 807-1439 as set forth in SEQ ID NO:1 corresponds to the reverse complement sequence of a *Pisum sativum* ribulose bis phosphate carboxylase small subunit E9 3' transcription termination and polyadenylation signal.

[C] nucleotide position 1469-2098 as set forth in SEQ ID NO:1 corresponds to the reverse complement sequence designed to be expressed as an RNA molecule that folds into a 240 nucleotide dsRNA and 150 nucleotide hairpin structure that is designed to target for suppression the *Diabrotica* species orthologue of a yeast gene encoding an Snf7 protein when provided in the diet of a *Diabrotica* species. A first 240 nucleotide segment corresponding to a portion of the *Diabrotica* snf7 orthologous gene is provided at nucleotide position 1469-1708 as set forth in SEQ ID NO:1, a second 240 nucleotide segment corresponding to the reverse complement of the first segment is set forth at nucleotide position 1850-2098 as set forth in SEQ ID NO:1, and the first and the second segments are operably linked by a 150 nucleotide spacer at nucleotide position 1709-1858 as set forth in SEQ ID NO:1.

[D] nucleotide position 2135-2938 as set forth in SEQ ID NO:1 corresponds to the reverse complement sequence of an intron derived from a *Zea mays* dnaK gene.

[E] nucleotide position 2839-3298 as set forth in SEQ ID NO:1 corresponds to the reverse complement of a Cauliflower mosaic virus enhanced 35S promoter sequence and an untranslated 5' leader sequence. This promoter, the associated untranslated leader, the intron element [D] and the transcription termination and polyadenylation element [B] regulate the expression of element [C] in corn plant cells.

[F] nucleotide position 3586-4534 as set forth in SEQ ID NO:1 corresponds to a promoter sequence derived from a *Zea mays* physical impedance induced protein gene (Zm.PIIG). This promoter, the associated untranslated leader [G], the intron element [H] and the transcription termination and polyadenylation element [J] regulate the expression of element [I]. This promoter is oriented relative to the promoter [E] such that each promoter ([E] and [F]) will drive divergent expression of their respective elements ([C] and [I]) (see block arrows in FIG. 2 where the arrows are representative of the respective promoters ([E] and [F]) in the indicated direction of expression from the respective promoter).

[G] nucleotide position 4541-4601 as set forth in SEQ ID NO:1 corresponds to an untranslated 5' leader sequence derived from a *Triticum aestivum* light harvesting complex b1 gene (Ta.Lhcb1).

[H] nucleotide position 4618-5097 as set forth in SEQ ID NO:1 corresponds to an intron sequence derived from an *Oryza sativa* Actin-1 gene (Os.Act1).

[I] nucleotide position 5107-7068 as set forth in SEQ ID NO:1 corresponds to the nucleotide sequence encoding a Cry3Bb corn rootworm toxic protein (cry3Bb). The encoded Cry3Bb protein is pesticidal when provided in the diet of a *Diabrotica* (corn rootworm) species.

[J] nucleotide position 7088-7297 as set forth in SEQ ID NO:1 corresponds to the sequence of a *Triticum aestivum* heat shock protein 17 (HSP17) transcription termination and polyadenylation signal.

[K] nucleotide position 7346-9526 as set forth in SEQ ID NO:1 corresponds to a contiguous promoter-leader-intron sequence derived from an *Oryza sativa* alpha tubulin-3 gene (TubA-3). This promoter, with the associated leader and intron, and the transcription termination and polyadenylation element [M] regulate the expression of element [L].

[L] nucleotide position 9531-11126 as set forth in SEQ ID NO:1 corresponds to sequence of an *Arabidopsis thaliana* cytoplasmic targeting peptide (CTP; from nucleotide position 9531-9758), and a sequence of an EPSPS derived from *Agrobacterium* CP4 (from nucleotide position 9759-11126). When this sequence is transcribed and translated into protein in a corn plant cell, the CTP is operably linked to the EPSPS. When expressed in corn plant cells comprising event MON87411, this CTP-EPSPS provides tolerance to the herbicide glyphosate.

[M] nucleotide position 11134-11715 as set forth in SEQ ID NO:1 corresponds to the sequence of an *Oryza sativa* alpha tubulin-3 gene (TubA-3) transcription termination and polyadenylation signal.

[N] nucleotide position 11749-12248 as set forth in SEQ ID NO:1 corresponds to corn genome DNA adjacent to the transgenic inserted DNA in corn event MON87411, which in this case is arbitrarily assigned as the 3' end of the transgenic inserted DNA.

[aa] nucleotide position 501-806 as set forth in SEQ ID NO:1 corresponds to the portion of the *Agrobacterium*

*tumefaciens* octopine left border sequence of the 417 construct adjacent to the genome at the arbitrarily assigned 5' end of the transgenic DNA inserted into the corn genome to form event MON 87411. The 5' end of [aa] as set forth in SEQ ID NO: 1 is linked to the 3' end of element [A] to form the unique 5' transgenic inserted DNA/corn genome junction encompassed by SEQ ID NO:5, SEQ ID NO:6, SEQ ID NO:7, and SEQ ID NO:21. The 3' end of element [aa] is linked to the 5' end of element [B] to form a unique junction within the transgenic inserted DNA that is encompassed by SEQ ID NO:41.

[bb] nucleotide position 1440-1468 as set forth in SEQ ID NO:1 corresponds to the an intervening sequence between elements [B] and [C]. The 5' end of [bb] as set forth in SEQ ID NO:1 is linked to the 3' end of element [B], and the 3' end of element [bb] is linked to the 5' end of element [C] to form a unique junction, encompassed by SEQ ID NO:42, within the transgenic DNA inserted into the corn genome to form event MON 87411.

[cc] nucleotide position 2099-2134 as set forth in SEQ ID NO:1 corresponds to the an intervening sequence between elements [C] and [D]. The 5' end of [cc] as set forth in SEQ ID NO:1 is linked to the 3' end of element [C], and the 3' end of element [cc] is linked to the 5' end of element [D] to form a unique junction, encompassed by SEQ ID NO:43, within the transgenic DNA inserted into the corn genome to form event MON 87411.

[ee] nucleotide position 3299-3585 as set forth in SEQ ID NO:1 corresponds to the an intervening sequence between elements [E] and [F]. The 5' end of [ee] as set forth in SEQ ID NO:1 is linked to the 3' end of element [E], and the 3' end of element [ee] is linked to the 5' end of element [F] to form a unique junction, encompassed by SEQ ID NO:44, within the transgenic DNA inserted into the corn genome to form event MON 87411.

[ff] nucleotide position 4535-4540 as set forth in SEQ ID NO:1 corresponds to the an intervening sequence between elements [F] and [G]. The 5' end of [ff] as set forth in SEQ ID NO:1 is linked to the 3' end of element [F], and the 3' end of element [ff] is linked to the 5' end of element [G] to form a unique junction, encompassed by SEQ ID NO:45, within the transgenic DNA inserted into the corn genome to form event MON 87411.

[gg] nucleotide position 4602-4617 as set forth in SEQ ID NO:1 corresponds to the an intervening sequence between elements [G] and [H]. The 5' end of [gg] as set forth in SEQ ID NO:1 is linked to the 3' end of element [G], and the 3' end of element [gg] is linked to the 5' end of element [H] to form a junction, encompassed by SEQ ID NO:46, within the transgenic DNA inserted into the corn genome to form event MON 87411, but which is not unique to event MON 87411.

[hh] nucleotide position 5098-5106 as set forth in SEQ ID NO:1 corresponds to the an intervening sequence between elements [H] and [I]. The 5' end of [hh] as set forth in SEQ ID NO:1 is linked to the 3' end of element [H], and the 3' end of element [hh] is linked to the 5' end of element [I] to form a junction, encompassed by SEQ ID NO:47, within the transgenic DNA inserted into the corn genome to form event MON 87411, but which is not unique to event MON 87411.

[ii] nucleotide position 7069-7087 as set forth in SEQ ID NO:1 corresponds to the an intervening sequence between elements [I] and [J]. The 5' end of [ii] as set forth in SEQ ID NO:1 is linked to the 3' end of element [I], and the 3' end of element [ii] is linked to the 5' end of element [J] to form a junction, encompassed by SEQ ID NO:48, within the transgenic DNA inserted into the corn genome to form event MON87411, but which is not unique to event MON 87411.

[jj] nucleotide position 7298-7345 as set forth in SEQ ID NO:1 corresponds to the intervening sequence between elements [J] and [K]. The 5' end of [jj] as set forth in SEQ ID NO:1 is linked to the 3' end of element [J], and the 3' end of element [jj] is linked to the 5' end of element [K] to form a unique junction, encompassed by SEQ ID NO:49, within the transgenic DNA inserted into the corn genome to form event MON 87411.

[kk] nucleotide position 9527-9530 as set forth in SEQ ID NO:1 corresponds to the intervening sequence between elements [K] and [L]. The 5' end of [kk] as set forth in SEQ ID NO:1 is linked to the 3' end of element [K], and the 3' end of element [kk] is linked to the 5' end of element [L] to form a unique junction, encompassed by SEQ ID NO:50, within the transgenic DNA inserted into the corn genome to form event MON 87411.

[ll] nucleotide position 11127-11133 as set forth in SEQ ID NO:1 corresponds to the an intervening sequence between elements [L] and [M]. The 5' end of [ll] as set forth in SEQ ID NO:1 is linked to the 3' end of element [L], and the 3' end of element [ll] is linked to the 5' end of element [M] to form a unique junction, encompassed by SEQ ID NO:51, within the transgenic DNA inserted into the corn genome to form event MON 87411.

[mm] nucleotide position 11716-11748 as set forth in SEQ ID NO:1 corresponds to the a portion of the *Agrobacterium tumefaciens* nopaline right border sequence of the 417 construct adjacent to the genome at the arbitrarily assigned 3' end of the transgenic DNA inserted into the corn genome to form event MON 87411. The 5' end of [mm] as set forth in SEQ ID NO:1 is linked to the 3' end of element [M], and the 3' end of element [mm] is linked to the 5' end of element [N] to form a unique transgenic inserted DNA/corn genome junction encompassed by SEQ ID NO:52.

FIG. 4 Illustration of cassette orientation for vectors tested to show higher efficacy of divergent promoters driving expression of corn rootworm toxic agents compared to vectors with a tandem orientation of promoters driving expression of corn rootworm toxic agents.

BRIEF DESCRIPTION OF THE SEQUENCES

SEQ ID NO:1 is a nucleotide sequence of event MON 87411, and represents from 5' to 3', a segment of the 5' genomic DNA flanking (adjacent to) the inserted transgenic DNA (500 nucleotides), the inserted transgenic DNA (11, 248 nucleotides), and a segment of the 3' genomic DNA flanking (adjacent to) the inserted transgenic DNA (500 nucleotides) in event MON 87411.

SEQ ID NO:2 is a nucleotide junction sequence of event MON 87411, and represents from 5' to 3', a segment of the 5' genomic DNA adjacent to the inserted transgenic DNA (500 nucleotides), and the inserted transgenic DNA border remnant (263 nucleotides) of event MON 87411.

SEQ ID NO:3 is a nucleotide junction sequence of event MON 87411, and represents from 5' to 3', the inserted transgenic DNA border remnant (15 nucleotides), and a segment of the 3' genomic DNA adjacent to the inserted genomic DNA (500 nucleotides) of event MON 87411.

SEQ ID NO:4 is a nucleotide sequence of event MON 87411, and represents the inserted genomic DNA (11248 nucleotides) of event MON 87411.

SEQ ID NO:5 is a nucleotide junction sequence of event MON 87411, and represents from 5' to 3', a segment of the 5' genomic DNA adjacent to the inserted transgenic DNA (50 nucleotides), and the inserted transgenic DNA border remnant (263 nucleotides) of event MON 87411.

SEQ ID NO:6 is a nucleotide junction sequence of event MON 87411, and represents from 5' to 3', a segment of the '5 genomic DNA adjacent to the inserted transgenic DNA (110 nucleotides), and the inserted transgenic DNA border remnant (263 nucleotides) of event MON 87411.

SEQ ID NO:7 is a nucleotide junction sequence of event MON 87411, and represents from 5' to 3', a segment of the 5' genomic DNA adjacent to the inserted transgenic DNA (145 nucleotides), and the inserted transgenic DNA border remnant (263 nucleotides) of event MON 87411.

SEQ ID NO:8 is a nucleotide junction sequence of event MON 87411, and represents from 5' to 3', a segment of the inserted transgenic DNA (83 nucleotides), and a segment of the 3' genomic DNA adjacent to the inserted transgenic DNA (34 nucleotides) of event MON 87411.

SEQ ID NO:9 is a nucleotide junction sequence of event MON 87411, and represents from 5' to 3', a segment of the inserted transgenic DNA (83 nucleotides), and a segment of the 3' genomic DNA adjacent to the inserted transgenic DNA (90 nucleotides) of event MON 87411.

SEQ ID NO:10 is a nucleotide junction sequence of event MON 87411, and represents from 5' to 3', a segment of the inserted transgenic DNA (83 nucleotides), and a segment of the 3' genomic DNA adjacent to the inserted transgenic DNA (255 nucleotides) of event MON 87411.

SEQ ID NO:11 is a nucleotide sequence of a cDNA sequence from *Diabrotica virgifera virgifera* (Western Corn Rootworm) encoding an ESCRT-III complex subunit that is orthologous to yeast Snf7.

SEQ ID NO:12 is a nucleotide sequence representing the antisense strand of a DNA expression cassette that includes a recombinant gene engineered to express an inverted repeat RNA molecule. The inverted repeat DNA segments correspond to positions 663 through 902 and to positions 1292 through 1053. The inverted repeat DNA sequences correspond to the nucleotide sequence of SEQ ID NO:11 from nucleotide position 151-390.

SEQ ID NO:13 is a ribonucleotide sequence transcribed from the DNA as set forth in SEQ ID NO:12.

SEQ ID NO:14 is a nucleotide sequence representing the sense strand of a DNA expression cassette that includes a recombinant gene engineered to encode and express a corn rootworm toxic Cry3Bb protein.

SEQ ID NO:15 is an amino acid sequence translation of a polynucleotide corresponding to positions 1522-3480 of SEQ ID NO:14, and representing a corn rootworm toxic Cry3Bb protein.

SEQ ID NO:16 is a nucleotide sequence representing the sense strand of a DNA expression cassette that includes a recombinant gene engineered to encode and express a 5-enolpyruvylshikimate-3-phosphate synthase (EPSPS) protein.

SEQ ID NO:17 is an amino acid sequence translation of a polynucleotide corresponding to positions 2186 through 3781 of SEQ ID NO:16, and representing an EPSPS protein that exhibits insensitivity to the herbicide glyphosate.

SEQ ID NO:18 is a nucleotide sequence of a synthetic oligonucleotide referred to as SQ27011, and is identical to the nucleotide sequence corresponding to positions 462-490 of SEQ ID NO:1.

SEQ ID NO:19 is a nucleotide sequence of a synthetic oligonucleotide referred to as PB3552, and is identical to the reverse complement of the nucleotide sequence corresponding to positions 502-515 of SEQ ID NO:1. PB3552 can be 5' labeled with a 6-carboxyfluorescein moiety (6-FAMT™) and 3' labeled with a quencher moiety for use in combination with a pair of thermal amplification primers, e.g., SQ27011 and SQ9085, and capable of use in TAQMAN® DNA amplification method to detect the presence of event MON 87411 DNA in a biological sample that contains corn event MON 87411 DNA.

SEQ ID NO:20 is a nucleotide sequence of a synthetic oligonucleotide referred to as SQ9085, and is identical to the reverse complement of the nucleotide sequence corresponding to positions 516-541 of SEQ ID NO:1.

SEQ ID NO:21 is a nucleotide sequence of event MON 87411, and corresponds to positions 462-541 of SEQ ID NO:1. An amplicon exhibiting this sequence can be produced with a pair of thermal amplification primers, e.g., SQ27011 and SQ9085.

SEQ ID NO:22 is a nucleotide sequence of a synthetic oligonucleotide referred to as SQ27066, and is identical to the nucleotide sequence corresponding to positions 11710-11728 of SEQ ID NO:1.

SEQ ID NO:23 is a nucleotide sequence of a synthetic oligonucleotide referred to as PB11300, and is identical to the nucleotide sequence corresponding to positions 11731-11755 of SEQ ID NO:1. PB11300 can be 5' labeled with a 6-carboxyfluorescein moiety (6-FAM™) and 3' labeled with a quencher moiety. Labeled this way, PB11300 can be used in combination with a pair of PCR primers, e.g., SQ27066 and SQ26977, to detect event MON 87411 in a TAQMAN® assay.

SEQ ID NO:24 is a nucleotide sequence of a synthetic oligonucleotide referred to as SQ26977, and is identical to the reverse complement of the nucleotide sequence corresponding to positions 11756-11784 of SEQ ID NO:1.

SEQ ID NO:25 is a nucleotide sequence of event MON 87411, and corresponds to positions 11710-11784 of SEQ ID NO:1. An amplicon exhibiting this sequence can be amplified with a pair of primers, e.g. SQ27066 and SQ26977, and is diagnostic of event MON 87411.

SEQ ID NO:26 is a nucleotide sequence representing the DNA construct #417.

SEQ ID NO:27 is a nucleotide sequence representing the DNA construct #416.

SEQ ID NO:28 is a nucleotide sequence representing the DNA construct #418.

SEQ ID NO:29 is a nucleotide sequence representing the DNA construct #419.

SEQ ID NO:30 is a nucleotide sequence representing the DNA construct #402.

SEQ ID NO:31 is a nucleotide sequence representing the DNA construct #403.

SEQ ID NO:32 is a nucleotide sequence representing the DNA construct #404.

SEQ ID NO:33 is a nucleotide sequence representing the DNA construct #423.

SEQ ID NO:34 is a nucleotide sequence representing the DNA construct #405.

SEQ ID NO:35 is a nucleotide sequence representing the DNA construct #406.

SEQ ID NO:36 is a nucleotide sequence representing the DNA construct #890.

SEQ ID NO:37 is a nucleotide sequence of the LH244 corn plant representing the wild-type allele of event MON 87411. An amplicon exhibiting this nucleotide sequence can be produced with a pair of PCR primers, e.g., SQ27011 and SQ26977, and is diagnostic of the wild-type allele of event MON 87411.

SEQ ID NO:38 is a nucleotide sequence of a synthetic oligonucleotide referred to as SQ20221.

SEQ ID NO:39 is a nucleotide sequence of a synthetic oligonucleotide referred to as PB10065. PB10065 can be 5' labeled with VIC™ and 3' labeled with a quencher moiety. Labeled this way, PB10065 can be used in combination with a pair of PCR primers, e.g., SQ10065 and SQ20222, to detect the presence of a segment of an endogenous gene of corn in a TAQMAN® assay.

SEQ ID NO:40 is a nucleotide sequence of a synthetic oligonucleotide referred to as SQ20222.

Figure 3:
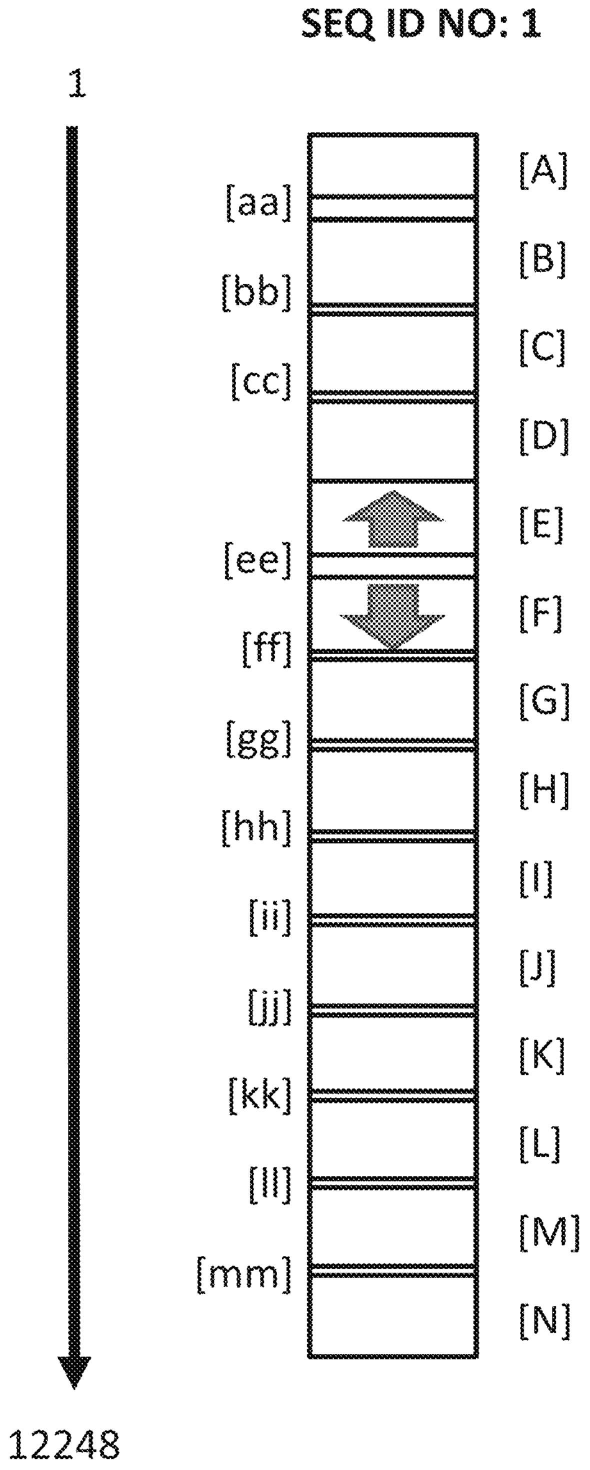
FIG. 3 [A]-[N] and [aa]-[mm] illustrate the operably linked elements and flanking corn genome and their position relative to each other as these are presented within the transgenic DNA insertion position in the corn event MON87411 genome. The following descriptions identify the composition, function and position for each of the elements as set forth in SEQ ID NO:1.

SEQ ID NOs:41-52 are nucleotide sequences of regions of SEQ ID NO:1, where each SEQ ID NO: encompasses a junction formed by intervening sequence and the expression cassette elements as detailed in the brief description for FIG. 3.

DETAILED DESCRIPTION

The inventors have identified a transgenic corn event MON 87411 exhibiting superior properties and performance compared to existing transgenic corn plants. The corn event MON 87411 contains three operably linked expression cassettes which collectively confer the traits of corn rootworm resistance and glyphosate herbicide tolerance to corn cells, corn tissues, corn seed and corn plants containing the transgenic event MON 87411. The corn event MON 87411 provides two modes of action against corn rootworm pest species (including *Diabrotica* spp., especially when the pest is *Diabrotica virgifera virgifera* (Western Corn Rootworm, WCR), *Diabrotica barberi* (Northern Corn Rootworm, NCR), *Diabrotica virgifera zeae* (Mexican Corn Rootworm, MCR), *Diabrotica balteata* (Brazilian Corn Rootworm (BZR) or Brazilian Corn Rootworm complex (BCR) consisting of *Diabrotica viridula* and *Diabrotica speciosa*), or *Diabrotica undecimpunctata howardii* (Southern Corn Rootworm, SCR)). Other transgenic corn events have been referenced in the art that provide various embodiments conferred singly, such as MON863 (conferring the trait of resistance to corn rootworms by expression of a Cry3Bb insecticidal toxin protein), or transgenic corn events providing two or more traits such as in corn event MON88017 (conferring the trait of resistance to corn rootworms by expression of a Cry3Bb insecticidal toxin protein and the trait of resistance to glyphosate herbicide by expression of a glyphosate insensitive EPSPS) and corn event DAS 59122-7 (conferring the trait of resistance to corn rootworms by expression of a binary *Bacillus thuringiensis* toxin PS149B1, also known as Cry34/Cry35, and the trait of tolerance to the herbicide glufosinate). Other art discloses the combination by breeding of the traits conferred by the corn events MON88017 or DAS 59122-7 with a transgenic corn event conferring the trait of corn rootworm resistance resulting from the expression of a dsRNA targeting for suppression a corn rootworm gene essential for the rootworms' survival (U.S. Pat. No. 7,943,819). Inherent in such combinations are the problems associated with the need for breeding these multiple traits located in multiple different loci and on multiple chromosomes within the corn genome together into a single corn plant and maintaining those traits as hybrids in dozens if not hundreds of different corn germplasm varieties. The solution for such problems would be to include combinations of these traits together in a single locus. The inventors herein provide one such solution to the problem in the form of the corn event MON 87411, which combines three covalently linked expression cassettes together in a single locus within the corn genome, these expression cassettes conferring the traits of corn rootworm resistance and glyphosate herbicide tolerance to the corn cells, corn tissues, corn seed and corn plants containing the transgenic event MON87411. Use of corn event MON 87411 provides major benefits to corn growers: a) protection from economic losses due to the corn rootworm larvae by providing two different corn rootworm resistance modes of action, and b) the ability to apply glyphosate containing agricultural herbicides to the corn crop for broad-spectrum weed control. Additionally, the transgenes encoding the corn rootworm and glyphosate tolerant traits are linked on the same DNA segment and occur at a single locus in the genome of MON 87411, providing for enhanced breeding efficiency and enables the use of molecular markers to track the transgene insert in the breeding populations and progeny thereof.

The corn event MON 87411 was produced by an *Agrobacterium* mediated transformation process of an inbred corn line with the plasmid construct pMON120417. This plasmid construct contains the linked plant expression cassettes with the regulatory genetic elements necessary for expression in corn plant cells of a CP4 EPSPS protein, as well as a Cry3Bb protein and a dsRNA targeting for suppression an essential gene in the cells of corn rootworms when corn cells containing corn event MON 87411 are provided in the diet of such corn rootworms. Corn cells were regenerated into intact corn plants and individual plants were selected from the population of plants that showed integrity of the plant expression cassettes and resistance to glyphosate and corn rootworm larvae feeding damage. A corn plant that contains in its genome the linked plant expression cassettes present in corn event MON 87411 is an aspect of the present invention.

The plasmid DNA inserted into the genome of corn event MON 87411 was characterized by detailed molecular analyses. These analyses included: the insert number (number of integration sites within the corn genome), the copy number (the number of copies of the T-DNA within one locus), and the integrity of the transgenic inserted DNA. The plasmid construct containing the three linked expression cassettes inserted into the corn genome giving rise to the event MON 87411 contains multiple segments (junction sequences between elements used to build or construct the several expression cassettes) that are not known to appear naturally in the corn genome nor in other vectors or transgenic events of corn or otherwise (for example, sequences as set forth in SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10; SEQ ID NO:12, SEQ ID NO:14, SEQ ID NO:16, SEQ ID NO:21, SEQ ID NO:25, SEQ ID NO: 41, SEQ ID NO: 42, SEQ ID NO: 43, SEQ ID NO: 44, SEQ ID NO: 45, SEQ ID NO: 49, SEQ ID NO: 50, SEQ ID NO: 51, and SEQ ID NO: 52). In addition, the transformation event that gave rise to the inserted transgenic DNA in the event MON 87411 is characterized herein as an insertion into a single locus in the corn genome, resulting in two new loci or junction sequences between the inserted DNA and the corn genome DNA (additional junction sequences) that are of sufficient length to be unique only to a corn genome comprising event MON 87411. These junction sequences are useful for detecting the presence of the event MON 87411 DNA in corn cells, tissue, seed and plants or plant products (commodity products). DNA molecular probes and primer pairs are described herein that have been developed for use in identifying the presence of these various junction segments in biological samples containing or suspected of containing corn cells, seed, plant parts or plant tissue that contain the event MON 87411 DNA. The data show that event MON 87411 contains a single T-DNA insertion with one copy of the inserted transgenic DNA. No additional elements from the transformation vector pMON120714 other than portions of the *Agrobacterium tumefaciens* left and right border regions used for transgenic DNA transfer from the plant transformation plasmid to the corn genome have been identified in event MON 87411. Finally, thermal amplification producing specific amplicons diagnostic for the presence of such event MON 87411 DNA in a sample, and DNA sequence analyses were performed to determine the arbitrarily assigned 5' and 3' insert-to-plant genome junctions, confirm the organization of the elements within the insert, and determine the complete DNA sequence of the inserted transgene DNA in corn plant event MON 87411 (SEQ ID NO:1).

Dozens of transgenic events were produced using the construct used to produce the transgenic event MON 87411, and different constructs were produced and used to produce many dozens of other transgenic corn events which were compared to the MON 87411 and similar events. These events were all tested for efficacy for controlling corn rootworms in diet bioassays in which the transgenic corn plant event tissues were provided in the diet of corn rootworm larvae. It was determined that the orientation of expression of the two different expression cassettes responsible for conferring the corn rootworm resistance traits to the various events was critical to the efficacy of the events in providing corn rootworm control when the corn event cells expressing these resistance traits were provided in the diet of the corn rootworm larvae. Two different promoters, CAMV e35S and Zm.PIIG, were observed to provide surprising and superior efficacy of corn events containing expression cassettes expressing the dsRNA corn rootworm protectant from the e35S promoter and the Cry3Bb corn rootworm toxic protein from an a Zm.PIIG promoter that was adjacent to and divergent from the e35S promoter. When these promoters were in this particular orientation significantly improved ratios of transgenic events exhibiting efficacy were obtained.

Unless otherwise noted herein, terms are to be understood according to conventional usage by those of ordinary skill in the relevant art. Definitions of common terms in molecular biology may also be found in Rieger et al., *Glossary of Genetics: Classical and Molecular,* 5th edition, Springer-Verlag: New York, 1991; and Lewin, *Genes V*, Oxford University Press: New York, 1994. As used herein, the term “corn” means *Zea mays* and includes all plant varieties that can be bred with corn plants comprising MON 87411. As used herein, the term “comprising” means “including but not limited to”.

The present invention provides for transgenic plants which have been transformed with a DNA construct that contains at least three expression cassettes; a first expression cassette expressing a corn rootworm toxic amount of a dsRNA designed to suppress a corn rootworm essential gene orthologous to a yeast snf7 gene, a second expression cassette expresses corn rootworm toxic amounts of Cry3Bb delta-endotoxin, and a third expression cassette that expresses a glyphosate tolerance enzyme CP4 EPSPS that is insensitive to glyphosate inhibition. Corn plants transformed according to the methods and with the DNA construct disclosed herein are resistant to CRW and tolerant to applications of glyphosate herbicide. The linked agronomic traits provide ease in maintaining these traits together in a breeding population, and exhibit greater corn rootworm efficacy than plants containing only a single corn rootworm inhibition gene or that contain the same corn rootworm inhibition genes (Cry3Bb and dsRNA) that are combined as a breeding stack.

A transgenic “plant” is produced by transformation of a plant cell with heterologous DNA, i.e., a polynucleic acid construct that includes a transgene of interest; regeneration of a population of plants resulting from the insertion of the transgene into the genome of the plant cell, and selection of a particular plant characterized by insertion into a particular genome location. The term “event” refers to the original transformant plant and progeny of the transformant that include the heterologous DNA. The term “event” also includes progeny produced by a sexual outcross between the event and another plant wherein the progeny includes the heterologous DNA. Even after repeated back-crossing to a recurrent parent, the inserted DNA and flanking genomic DNA from the transformed parent event is present in the progeny of the cross at the same chromosomal location. The term “event” also refers to DNA from the original transformant comprising the inserted DNA, and flanking genomic sequence immediately adjacent to the inserted DNA, that would be expected to be transferred to a progeny that receives the inserted DNA including the transgene of interest as the result of a sexual cross of one parental line that includes the inserted DNA (e.g., the original transformant and progeny resulting from selfing) and a parental line that does not contain the inserted DNA. The present invention is related to the transgenic event, corn plant comprising MON 87411, progeny thereof, and DNA compositions contained therein.

A “probe” is an isolated nucleic acid to which is attached a conventional detectable label or reporter molecule, e.g., a radioactive isotope, ligand, chemiluminescent agent, or enzyme. Such a probe is complementary to a strand of a target nucleic acid, in the case of the present invention, to a strand of genomic DNA from MON 87411 whether from a MON 87411 plant or from a sample that includes MON 87411 DNA. Probes according to the present invention include not only deoxyribonucleic or ribonucleic acids, but also polyamides and other probe materials that bind specifically to a target DNA sequence and can be used to detect the presence of that target DNA sequence.

DNA primers are isolated polynucleic acids that are annealed to a complementary target DNA strand by nucleic acid hybridization to form a hybrid between the primer and the target DNA strand, then extended along the target DNA strand by a polymerase, e.g., a DNA polymerase. A DNA primer pair or a DNA primer set of the present invention refer to two DNA primers useful for amplification of a target nucleic acid sequence, e.g., by the polymerase chain reaction (PCR) or other conventional polynucleic acid amplification methods.

DNA probes and DNA primers are generally 11 polynucleotides or more in length, often 18 polynucleotides or more, 24 polynucleotides or more, or 30 polynucleotides or more. Such probes and primers are selected to be of sufficient length to hybridize specifically to a target sequence under high stringency hybridization conditions. Preferably, probes and primers according to the present invention have complete sequence similarity with the target sequence, although probes differing from the target sequence that retain the ability to hybridize to target sequences may be designed by conventional methods.

Primers and probes based on the flanking genomic DNA and insert sequences disclosed herein can be used to confirm (and, if necessary, to correct) the disclosed DNA sequences by conventional methods, e.g., by re-cloning and sequencing such DNA molecules.

The nucleic acid probes and primers of the present invention hybridize under stringent conditions to a target DNA molecule. Any conventional nucleic acid hybridization or amplification method can be used to identify the presence of DNA from a transgenic plant in a sample. Polynucleic acid molecules, also referred to as nucleic acid segments, or fragments thereof are capable of specifically hybridizing to other nucleic acid molecules under certain circumstances. As used herein, two polynucleic acid molecules are said to be capable of specifically hybridizing to one another if the two molecules are capable of forming an anti-parallel, double-stranded nucleic acid structure. A nucleic acid molecule is said to be the "complement" of another nucleic acid molecule if they exhibit complete complementarity. As used herein, molecules are said to exhibit "complete complementarity" when every nucleotide of one of the molecules is complementary to a nucleotide of the other. Two molecules are said to be "minimally complementary" if they can hybridize to one another with sufficient stability to permit them to remain annealed to one another under at least conventional "low-stringency" conditions. Similarly, the molecules are said to be "complementary" if they can hybridize to one another with sufficient stability to permit them to remain annealed to one another under conventional "high-stringency" conditions. Conventional stringency conditions are described by Sambrook et al., 1989, and by Haymes et al., In: *Nucleic Acid Hybridization, A Practical Approach*, IRL Press, Washington, D.C. (1985), Departures from complete complementarity are therefore permissible, as long as such departures do not completely preclude the capacity of the molecules to form a double-stranded structure. In order for a nucleic acid molecule to serve as a primer or probe it need only be sufficiently complementary in sequence to be able to form a stable double-stranded structure under the particular solvent and salt concentrations employed.

As used herein, a substantially homologous sequence is a nucleic acid sequence that will specifically hybridize to the complement of the nucleic acid sequence to which it is being compared under high stringency conditions. Appropriate stringency conditions that promote DNA hybridization, for example, 6.0× sodium chloride/sodium citrate (SSC) at about 45° C., followed by a wash of 2.0×SSC at 50° C., are known to those skilled in the art or can be found in *Current Protocols in Molecular Biology*, John Wiley & Sons, N.Y. (1989), 6.3.1-6.3.6. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C. Both temperature and salt may be varied, or either the temperature or the salt concentration may be held constant while the other variable is changed. In a preferred embodiment, a polynucleic acid of the present invention will specifically hybridize to one or more of the nucleic acid molecules set forth in SEQ ID NOs: 1, 2, 3, 4, 5, 6, 7, 8, 9, 10, 12, 14, 16, 21, 25, 41, 42, 43, 44, 45, 49, 50, 51, or 52 or complements thereof or fragments of either under moderately stringent conditions, for example at about 2.0×SSC and about 65° C. In a particularly preferred embodiment, a nucleic acid of the present invention will specifically hybridize to one or more of the nucleic acid molecules set forth in SEQ ID NOs: 1, 2, 3, 4, 5, 6, 7, 8, 9, 10, 12, 14, 16, 21, 25, 41, 42, 43, 44, 45, 49, 50, 51, or 52 or complements or fragments of either under high stringency conditions. In one aspect of the present invention, a preferred marker nucleic acid molecule of the present invention has the nucleic acid sequence set forth in SEQ ID NO:1, or SEQ ID NO:2, or SEQ ID NO:3, or SEQ ID NO:4, or SEQ ID NO:5, or SEQ ID NO:6, or SEQ ID NO:7, or SEQ ID NO:8, or SEQ ID NO:9, or SEQ ID NO:10; or SEQ ID NO:12, or SEQ ID NO:14, OR SEQ ID NO:16, or SEQ ID NO:21, or SEQ ID NO:25, or SEQ ID NO: 41, or SEQ ID NO: 42, or SEQ ID NO: 43, or SEQ ID NO: 44, or SEQ ID NO: 45, or SEQ ID NO: 49, or SEQ ID NO: 50, or SEQ ID NO: 51, or SEQ ID NO: 52 or complements thereof or fragments of either. The hybridization of the probe to the target DNA molecule can be detected by any number of methods known to those skilled in the art, these can include, but are not limited to, fluorescent tags, radioactive tags, antibody based tags, and chemiluminescent tags.

Regarding the amplification of a target nucleic acid sequence (e.g., by PCR) using a particular amplification primer pair, "stringent conditions" are conditions that permit the primer pair to hybridize only to the target nucleic acid sequence to which a primer having the corresponding wild-type sequence (or its complement) would bind and preferably to produce a unique amplification product, the amplicon, in a DNA thermal amplification reaction.

The term "specific for (a target sequence)" indicates that a probe or primer hybridizes under stringent hybridization conditions only to the target sequence in a sample comprising the target sequence.

As used herein, "amplified DNA" or "amplicon" refers to the product of polynucleic acid amplification method directed to a target polynucleic acid molecule that is part of a polynucleic acid template. For example, to determine whether a corn plant resulting from a sexual cross contains transgenic plant genomic DNA from a corn plant comprising MON 87411 of the present invention, DNA that is extracted from a corn plant tissue sample may be subjected to a polynucleic acid amplification method using a primer pair that includes a primer derived from a DNA sequence in the genome of a MON 87411 comprising plant adjacent to the insertion site of the inserted heterologous DNA (transgene DNA), and a second primer derived from the inserted heterologous DNA to produce an amplicon that is diagnostic for the presence of the MON 87411 plant DNA. The diagnostic amplicon is of a length and has a DNA sequence that is also diagnostic for the plant genomic DNA. The amplicon may range in length from the combined length of the primer pair plus one nucleotide base pair, preferably plus about fifty nucleotide base pairs, more preferably plus about two hundred-fifty nucleotide base pairs, and even more preferably plus about four hundred-fifty nucleotide base pairs or more. Alternatively, a primer pair can be derived from genomic sequence on both sides of the inserted heterologous DNA so as to produce an amplicon that includes the entire insert polynucleotide sequence (e.g., a forward primer isolated from the genomic portion of SEQ ID NO:1 and a reverse primer isolated from the genomic portion of SEQ ID NO:1 that amplifies a DNA molecule comprising the a junction sequence identified herein in the event MON 87411 genome). A member of a primer pair derived from the plant genomic sequence adjacent to the inserted transgenic DNA is located a distance from the inserted DNA sequence, this distance can range from one nucleotide base pair up to about twenty thousand nucleotide base pairs. The use of the term "amplicon" specifically excludes primer dimers that may be formed in the DNA thermal amplification reaction.

Polynucleic acid amplification can be accomplished by any of the various polynucleic acid amplification methods known in the art, including the polymerase chain reaction (PCR). Amplification methods are known in the art and are described, inter alia, in U.S. Pat. Nos. 4,683,195 and 4,683,202 and in *PCR Protocols: A Guide to Methods and Applications*, ed. Innis et al., Academic Press, San Diego, 1990.

PCR amplification methods have been developed to amplify up to 22 kb (kilobase) of genomic DNA and up to 42 kb of bacteriophage DNA (Cheng et al., Proc. Natl. Acad. Sci. USA 91:5695-5699, 1994). These methods as well as other methods known in the art of DNA amplification may be used in the practice of the present invention. The sequence of the heterologous DNA insert or flanking genomic DNA sequence from event MON 87411 can be verified (and corrected if necessary) by amplifying such DNA molecules from event MON 87411 comprising seed or plants grown from the seed deposited with the ATCC having accession no. PTA-12669, using primers derived from the sequences provided herein, followed by standard DNA sequencing of the PCR amplicon or cloned DNA fragments thereof.

DNA detection kits that are based on DNA amplification methods contain DNA primer molecules that hybridize specifically to a target DNA and amplify a diagnostic amplicon under the appropriate reaction conditions. The kit may provide an agarose gel based detection method or any number of methods of detecting the diagnostic amplicon that are known in the art. A kit that contains DNA primers that are homologous or complementary to any portion of the corn genomic region as set forth in SEQ ID NO:1 and to any portion of the inserted transgenic DNA as set forth in SEQ ID NO:1 is an object of the invention. DNA molecules useful as DNA primers can be selected from the disclosed transgene/genomic DNA sequence of MON 87411 (SEQ ID NO:1) by those skilled in the art of DNA amplification.

The diagnostic amplicon produced by these methods may be detected by a plurality of techniques. One such method is Genetic Bit Analysis (Nikiforov, et al. Nucleic Acid Res. 22:4167-4175, 1994) where a DNA oligonucleotide is designed that overlaps both the adjacent flanking genomic DNA sequence and the inserted DNA sequence. The oligonucleotide is immobilized in wells of a microtiter plate. Following PCR of the region of interest (using one primer in the inserted sequence and one in the adjacent flanking genomic sequence), a single-stranded PCR product can be hybridized to the immobilized oligonucleotide and serve as a template for a single base extension reaction using a DNA polymerase and labeled dideoxynucleotide triphosphates (ddNTPs) specific for the expected next base. Readout may be fluorescent or ELISA-based. A signal indicates presence of the transgene/genomic sequence due to successful amplification, hybridization, and single base extension.

Another method is the Pyrosequencing technique as described by Winge (Innov. Pharma. Tech. 00:18-24, 2000). In this method an oligonucleotide is designed that overlaps the adjacent genomic DNA and insert DNA junction. The oligonucleotide is hybridized to single-stranded PCR product from the region of interest (one primer in the inserted sequence and one in the flanking genomic sequence) and incubated in the presence of a DNA polymerase, ATP, sulfurylase, luciferase, apyrase, adenosine 5' phosphosulfate and luciferin. DNTPs are added individually and the incorporation results in a light signal that is measured. A light signal indicates the presence of the transgene/genomic sequence due to successful amplification, hybridization, and single or multi-base extension.

Fluorescence Polarization as described by Chen, et al., (Genome Res. 9:492-498, 1999) is a method that can be used to detect the amplicon of the present invention. Using this method an oligonucleotide is designed that overlaps the genomic flanking and inserted DNA junction. The oligonucleotide is hybridized to single-stranded PCR product from the region of interest (one primer in the inserted DNA and one in the flanking genomic DNA sequence) and incubated in the presence of a DNA polymerase and a fluorescent-labeled ddNTP. Single base extension results in incorporation of the ddNTP. Incorporation can be measured as a change in polarization using a fluorometer. A change in polarization indicates the presence of the transgene/genomic sequence due to successful amplification, hybridization, and single base extension.

Taqman® (PE Applied Biosystems, Foster City, Calif.) is described as a method of detecting and quantifying the presence of a DNA sequence and is fully understood in the instructions provided by the manufacturer. Briefly, a FRET oligonucleotide probe is designed that overlaps the genomic flanking and insert DNA junction. The FRET probe and PCR primers (one primer in the insert DNA sequence and one in the flanking genomic sequence) are cycled in the presence of a thermostable polymerase and dNTPs. Hybridization of the FRET probe results in cleavage and release of the fluorescent moiety away from the quenching moiety on the FRET probe. A fluorescent signal indicates the presence of the transgene/genomic sequence due to successful amplification and hybridization.

Molecular Beacons have been described for use in sequence detection as described in Tyangi, et al. (Nature Biotech. 14:303-308, 1996) Briefly, a FRET oligonucleotide probe is designed that overlaps the flanking genomic and insert DNA junction. The unique structure of the FRET probe results in it containing secondary structure that keeps the fluorescent and quenching moieties in close proximity. The FRET probe and PCR primers (one primer in the insert DNA sequence and one in the flanking genomic sequence) are cycled in the presence of a thermostable polymerase and dNTPs. Following successful PCR amplification, hybridization of the FRET probe to the target sequence results in the removal of the probe secondary structure and spatial separation of the fluorescent and quenching moieties. A fluorescent signal results. A fluorescent signal indicates the presence of the flanking/transgene insert sequence due to successful amplification and hybridization.

DNA detection kits can be developed using the compositions disclosed herein and the methods well known in the art of DNA detection. The kits are useful for identification of corn event MON 87411 DNA in a sample and can be applied to methods for breeding corn plants containing MON 87411 DNA. A kit contains DNA molecules that are useful as primers or probes and that are homologous or complementary to at least the applicable portions of SEQ ID NO:1 as described herein. The DNA molecules can be used in DNA amplification methods (PCR) or as probes in polynucleic acid hybridization methods, i.e., Southern analysis, northern analysis.

Junction sequences may be represented by a sequence from the group consisting of SEQ ID NO:2, SEQ ID NO:3, SEQ ID NO:5, SEQ ID NO:6, SEQ ID NO:7, SEQ ID NO:8, SEQ ID NO:9, SEQ ID NO:10; SEQ ID NO:21, SEQ ID NO:25, SEQ ID NO:41, SEQ ID NO:42, SEQ ID NO:43, SEQ ID NO:44, SEQ ID NO:45, SEQ ID NO:49, SEQ ID NO:50, SEQ ID NO:51, and SEQ ID NO:52. For example, the junction sequences may be arbitrarily represented by the nucleotide sequences provided as SEQ ID NO:5 and SEQ ID NO:8. Alternatively, the junction sequences may be arbitrarily represented by the nucleotide sequences provided as SEQ ID NO:6 and SEQ ID NO:9. Alternatively, the junction sequences may be arbitrarily represented by the nucleotide sequences provided as SEQ ID NO:7 and SEQ ID NO:10. These nucleotides are connected by phosphodiester linkage and in corn event MON 87411 are present as part of the recombinant plant cell genome. The identification of one or more of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:2, SEQ ID NO:25, SEQ ID NO:41, SEQ ID NO:42, SEQ ID NO:43, SEQ ID NO:44, SEQ ID NO:45, SEQ ID NO:49, SEQ ID NO:50, SEQ ID NO:51, or SEQ ID NO:52 in a sample derived from a corn plant, seed, or plant part is determinative that the DNA was obtained from corn event MON 87411 and is diagnostic for the presence in a sample containing DNA from corn event MON 87411. The invention thus provides a DNA molecule that contains at least one of the nucleotide sequences provided as SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:21, SEQ ID NO:25, SEQ ID NO:41, SEQ ID NO:42, SEQ ID NO:43, SEQ ID NO:44, SEQ ID NO:45, SEQ ID NO:49, SEQ ID NO:50, SEQ ID NO:51, or SEQ ID NO:52. Any segment of DNA derived from transgenic corn event MON 87411 that is sufficient to include at least one of the sequences provided as SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:21, SEQ ID NO:25, SEQ ID NO:41, SEQ ID NO:42, SEQ ID NO:43, SEQ ID NO:44, SEQ ID NO:45, SEQ ID NO:49, SEQ ID NO:50, SEQ ID NO:51, or SEQ ID NO:52 is within the scope of the invention. In addition, any polynucleotide comprising a sequence complementary to any of the sequences described within this paragraph is within the scope of the invention.

The invention provides exemplary DNA molecules that can be used either as primers or probes for detecting the presence of DNA derived from a corn plant comprising event MON 87411 DNA in a sample. Such primers or probes are specific for a target nucleic acid sequence and as such are useful for the identification of corn event MON 87411 nucleic acid sequence by the methods of the invention described herein.

A "primer" is typically a highly purified, isolated polynucleotide that is designed for use in specific annealing or hybridization methods that involve thermal amplification. A pair of primers may be used with template DNA, such as a sample of corn genomic DNA, in a thermal amplification, such as polymerase chain reaction (PCR), to produce an amplicon, where the amplicon produced from such reaction would have a DNA sequence corresponding to sequence of the template DNA located between the two sites where the primers hybridized to the template. As used herein, an "amplicon" is a piece or fragment of DNA that has been synthesized using amplification techniques. An amplicon of the invention comprises at least one of the sequences provided as SEQ ID NO:21 or SEQ ID NO:25. A primer is typically designed to hybridize to a complementary target DNA strand to form a hybrid between the primer and the target DNA strand, and the presence of the primer is a point of recognition by a polymerase to begin extension of the primer (i.e., polymerization of additional nucleotides into a lengthening nucleotide molecule) using as a template the target DNA strand. Primer pairs, as used in the invention, are intended to refer to the use of two primers binding opposite strands of a double stranded nucleotide segment for the purpose of amplifying linearly the polynucleotide segment between the positions targeted for binding by the individual members of the primer pair, typically in a thermal amplification reaction or other conventional nucleic-acid amplification methods. A primer pair useful for this application should comprise a first DNA molecule and a second DNA molecule that is different from the first DNA molecule, and wherein both are each of sufficient length of contiguous nucleotides of a DNA sequence to function as DNA primers that, when used together in a thermal amplification reaction with template DNA derived from corn event MON 87411, to produce an amplicon diagnostic for corn event MON 87411 DNA in a sample. Exemplary DNA molecules useful as primers are provided as SEQ ID NO:18, SEQ ID NO:20, SEQ ID NO:22, or SEQ ID NO:24.

A "probe" is an isolated nucleic acid that is complementary to a strand of a target nucleic acid. Probes include not only deoxyribonucleic or ribonucleic acids but also polyamides and other probe materials that bind specifically to a target DNA sequence and the detection of such binding can be useful in diagnosing, discriminating, determining, detecting, or confirming the presence of that target DNA sequence in a particular sample. A probe may be attached to a conventional detectable label or reporter molecule, e.g., a radioactive isotope, ligand, chemiluminescent agent, or enzyme. Exemplary DNA molecules useful as probes are provided as SEQ ID NO:19 and SEQ ID NO:23.

Probes and primers may have complete sequence identity with the target sequence, although primers and probes differing from the target sequence that retain the ability to hybridize preferentially to target sequences may be designed by conventional methods. In order for a nucleic acid molecule to serve as a primer or probe it need only be sufficiently complementary in sequence to be able to form a stable double-stranded structure under the particular solvent and salt concentrations employed. Any conventional nucleic acid hybridization or amplification method can be used to identify the presence of transgenic DNA from corn event MON 87411 in a sample. Probes and primers are generally at least about 11 nucleotides, at least about 18 nucleotides, at least about 24 nucleotides, or at least about 30 nucleotides or more in length. Such probes and primers hybridize specifically to a target DNA sequence under stringent hybridization conditions. Conventional stringency conditions are described by Sambrook et al., 1989, and by Haymes et al., In: *Nucleic Acid Hybridization, A Practical Approach*, IRL Press, Washington, D.C. (1985).

Any number of methods well known to those skilled in the art can be used to isolate and manipulate a DNA molecule, or fragment thereof, disclosed in the invention, including thermal amplification methods. DNA molecules, or fragments thereof, can also be obtained by other techniques such as by directly synthesizing the fragment by chemical means, as is commonly practiced by using an automated oligonucleotide synthesizer.

The DNA molecules and corresponding nucleotide sequences provided herein are therefore useful for, among other things, identifying corn event MON 87411, selecting plant varieties or hybrids comprising corn event MON 87411, detecting the presence of DNA derived from the transgenic corn event MON 87411 in a sample, and monitoring samples for the presence and/or absence of corn event MON 87411 or plant parts derived from corn plants comprising event MON 87411.

The invention provides corn plants, progeny, seeds, plant cells, plant parts (such as pollen, ovule, ear or silk tissue, tassel tissue, root tissue, stem tissue, and leaf tissue), and commodity products. These plants, progeny, seeds, plant cells, plant parts, and commodity products contain a detectable amount of a polynucleotide of the invention, i.e., such as a polynucleotide having at least one of the sequences provided as SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:12, SEQ ID NO:14, SEQ ID NO:16, SEQ ID NO:21, SEQ ID NO:25, SEQ ID NO:41, SEQ ID NO:42, SEQ ID NO:43, SEQ ID NO:44, SEQ ID NO:45, SEQ ID NO:49, SEQ ID NO:50, SEQ ID NO:51, or SEQ ID NO:52. Plants, progeny, seeds, plant cells, and plant parts of the invention may also contain one or more additional transgenes. Such additional transgene may be any nucleotide sequence encoding a protein or RNA molecule conferring a desirable trait including but not limited to increased insect resistance, increased water use efficiency, increased yield performance, increased drought resistance, increased seed quality, improved nutritional quality, and/or increased herbicide tolerance, in which the desirable trait is measured with respect to a corn plant lacking such additional transgene.

The invention provides corn plants, progeny, seeds, plant cells, and plant part such as pollen, ovule, ear or silk tissue, tassel tissue, root or stem tissue, and leaves derived from a transgenic corn plant comprising event MON 87411. A representative sample of corn seed comprising event MON 87411 has been deposited according to the Budapest Treaty with the American Type Culture Collection (ATCC). The ATCC depository has assigned the Patent Deposit Designation PTA-12669 to the event MON 87411 comprising seed.

The invention provides a microorganism comprising a DNA molecule having at least one sequence selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:12, SEQ ID NO:14, SEQ ID NO:16, SEQ ID NO:21, SEQ ID NO:25, SEQ ID NO:41, SEQ ID NO:42, SEQ ID NO:43, SEQ ID NO:44, SEQ ID NO:45, SEQ ID NO:49, SEQ ID NO:50, SEQ ID NO:51, and SEQ ID NO:52 present in its genome. An example of such a microorganism is a transgenic plant cell. Microorganisms, such as a plant cell of the invention, are useful in many industrial applications, including but not limited to: (i) use as research tool for scientific inquiry or industrial research; (ii) use in culture for producing endogenous or recombinant carbohydrate, lipid, nucleic acid, or protein products or small molecules that may be used for subsequent scientific research or as industrial products; and (iii) use with modern plant tissue culture techniques to produce transgenic plants or plant tissue cultures that may then be used for agricultural research or production. The production and use of microorganisms such as transgenic plant cells utilizes modern microbiological techniques and human intervention to produce a man-made, unique microorganism. In this process, recombinant DNA is inserted into a plant cell's genome to create a transgenic plant cell that is separate and unique from naturally occurring plant cells. This transgenic plant cell can then be cultured much like bacteria and yeast cells using modern microbiology techniques and may exist in an undifferentiated, unicellular state. The transgenic plant cell's new or altered genetic composition and phenotype is a technical effect created by the integration of the heterologous DNA into the genome of the cell. Microorganisms of the invention, such as transgenic plant cells, include (i) methods of producing transgenic cells by integrating recombinant DNA into the genome of the cell and then using this cell to derive additional cells possessing the same heterologous DNA; (ii) methods of culturing cells that contain recombinant DNA using modern microbiology techniques; (iii) methods of producing and purifying endogenous or recombinant carbohydrate, lipid, nucleic acid, or protein products from cultured cells; and (iv) methods of using modern plant tissue culture techniques with transgenic plant cells to produce transgenic plants or transgenic plant tissue cultures.

Plants of the invention may pass along the event DNA, including the transgene, to progeny. As used herein, "progeny" includes any plant, seed, plant cell, and/or regenerable plant part comprising the event DNA derived from an ancestor plant and/or comprising a DNA molecule having at least one sequence selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:12, SEQ ID NO:14, SEQ ID NO:16, SEQ ID NO:21, SEQ ID NO:25; SEQ ID NO: 41, SEQ ID NO: 42, SEQ ID NO: 43, SEQ ID NO: 44, SEQ ID NO: 45, SEQ ID NO: 49, SEQ ID NO: 50, SEQ ID NO: 51, and SEQ ID NO:52. Plants, progeny, and seeds may be homozygous or heterozygous for the transgene. Progeny may be grown from seeds produced by a corn event MON 87411 containing plant and/or from seeds produced by a plant fertilized with pollen from a corn event MON 87411 containing plant.

Progeny plants may be self-pollinated (also known as "selfing") to generate a true breeding line of plants, i.e., plants homozygous for the transgene. Selfing of appropriate progeny can produce plants that are homozygous for both added, exogenous genes.

Alternatively, progeny plants may be outcrossed, e.g., bred with another unrelated plant, to produce a varietal or a hybrid seed or plant. The other unrelated plant may be transgenic or nontransgenic. A varietal or hybrid seed or plant of the invention may thus be derived by crossing a first parent that lacks the specific and unique DNA of the corn event MON 87411 with a second parent comprising corn event MON 87411, resulting in a hybrid comprising the specific and unique DNA of the corn event MON 87411. Each parent can be a hybrid or an inbred/varietal, so long as the cross or breeding results in a plant or seed of the invention, i.e., a seed having at least one allele containing the DNA of corn event MON 87411 and/or a DNA molecule having at least one sequence selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:12, SEQ ID NO:14, SEQ ID NO:16, SEQ ID NO:21, SEQ ID NO:25; SEQ ID NO: 41, SEQ ID NO: 42, SEQ ID NO: 43, SEQ ID NO: 44, SEQ ID NO: 45, SEQ ID NO: 49, SEQ ID NO: 50, SEQ ID NO: 51, and SEQ ID NO: 52. Two different transgenic plants may thus be crossed to produce hybrid offspring that contain two independently segregating, added, exogenous genes. For example, the event MON 87411 corn containing resistance to corn rootworm infestations and glyphosate tolerance can be crossed with different transgenic corn plants to produce a hybrid or inbred plant having the characteristics of both transgenic parents. One example of this would be a cross of event MON 87411 containing resistance to corn rootworm infestations and glyphosate tolerance with a corn plant having one or more additional traits such as herbicide tolerance and/or insect control, resulting in a progeny plant or seed that is resistant to corn rootworm infestations and tolerant to glyphosate and has at least one or more additional traits. Back-crossing to a parental plant and out-crossing with a non-transgenic plant are also contemplated, as is vegetative propagation. Descriptions of other breeding methods that are commonly used for different traits and crops can be found in one of several references, e.g., Fehr, in Breeding Methods for Cultivar Development, Wilcox J. ed., American Society of Agronomy, Madison Wis. (1987).

The invention provides a plant part that is derived from corn plants comprising event MON 87411. As used herein, a "plant part" refers to any part of a plant which is comprised of material derived from a corn plant comprising event MON 87411. Plant parts include but are not limited to pollen, ovule, ear or silk, tassel, root or stem tissue, fibers, and leaves. Plant parts may be viable, nonviable, regenerable, and/or nonregenerable.

The invention provides a commodity product that is derived from corn plants comprising event MON 87411 and that contains a detectable amount of a nucleic acid specific for event MON 87411. As used herein, a "commodity product" refers to any composition or product which contains material derived from a corn plant, whole or processed corn seed, one or more plant cells and/or plant parts containing the corn event MON 87411 DNA. Commodity products may be sold to consumers and may be viable or nonviable. Nonviable commodity products include but are not limited to nonviable corn seeds; processed corn seeds, corn seed parts, and corn plant parts; corn seeds and corn plant parts processed for feed or food, oil, meal, flour, flakes, bran, biomasses, and fuel products. Viable commodity products include but are not limited to corn seeds, corn plants, and corn plant cells. The corn plants comprising event MON 87411 can thus be used to manufacture any commodity product typically acquired from corn. Any such commodity product that is derived from corn plants containing corn event MON 87411 DNA that contains at least a detectable amount of one or more specific and unique DNA molecules, the presence of which are determinative of corn event MON 87411, and specifically may contain a detectable amount of a polynucleotide comprising a DNA molecule having at least one sequence selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:12, SEQ ID NO:14, SEQ ID NO:16, SEQ ID NO:21, SEQ ID NO:25; SEQ ID NO: 41, SEQ ID NO: 42, SEQ ID NO: 43, SEQ ID NO: 44, SEQ ID NO: 45, SEQ ID NO: 49, SEQ ID NO: 50, SEQ ID NO: 51, and SEQ ID NO:52. Any standard method of detection for nucleotide molecules may be used, including methods of detection disclosed herein. A commodity product is within the scope of the invention if there is any detectable amount of a DNA molecule having at least one diagnostic sequence selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:12, SEQ ID NO:14, SEQ ID NO:16, SEQ ID NO:21, SEQ ID NO:25; SEQ ID NO: 41, SEQ ID NO: 42, SEQ ID NO: 43, SEQ ID NO: 44, SEQ ID NO: 45, SEQ ID NO: 49, SEQ ID NO: 50, SEQ ID NO: 51, and SEQ ID NO: 52 in the commodity product.

The plants, progeny, seeds, plant cells, plant parts (such as pollen, ovule, ear or silk, tassel, root or stem tissue, and leaves), and commodity products of the invention are therefore useful for, among other things, growing plants for the purpose of producing seed and/or plant parts comprising corn event MON 87411 for agricultural purposes, producing progeny comprising corn event MON 87411 for plant breeding and research purposes, use with microbiological techniques for industrial and research applications, and sale to consumers.

The invention provides methods for controlling weeds and methods for producing plants using glyphosate herbicide and corn event MON 87411. A method for controlling weeds in a field is provided and consists of planting corn event MON 87411 containing varietal or hybrid plants in a field and applying a herbicidally effective dose of glyphosate to the field for the purpose of controlling weeds in the field without injuring the MON 87411 containing plants. Such application of glyphosate herbicide may be pre-emergence, i.e., any time after MON 87411 containing seed is planted and before MON 87411 containing plants emerge, or post-emergence, i.e., any time after MON 87411 containing plants emerge. Another method for controlling weeds in a field is also provided and consists of applying an effective dose of glyphosate herbicide to control weeds in a field and then planting corn plants comprising event MON 87411 in the field. Such application of glyphosate herbicide would be pre-planting, i.e., before MON 87411 containing seed is planted, and could be done any time pre-planting including, but not limited to, about 14 days pre-planting to about 1 day pre-planting. The invention also provides a method for producing corn seed essentially free of weed seeds by planting seeds of a glyphosate tolerant corn plant comprising MON 87411 in a field, applying a post-emergence effective dose of glyphosate herbicide sufficient to kill the weed to the field, and harvesting seed from the field. A herbicidally effective dose of glyphosate for use in the field should consist of a range from about 0.125 pounds per acre to about 6.4 pounds per acre of glyphosate over a growing season. In one embodiment, a total of about 1.5 pounds per acre of glyphosate is applied over a growing season. Multiple applications of glyphosate may be used over a growing season, for example, two applications (such as a pre-planting application and a post-emergence application or a pre-emergence application and a post-emergence application) or three applications (such as a pre-planting application, a pre-emergence application, and a post-emergence application).

Methods for producing an insect and herbicide tolerant corn plant comprising the DNA sequences specific and unique to event MON 87411 of the invention are provided. Transgenic plants used in these methods may be homozygous or heterozygous for the transgene. Progeny plants produced by these methods may be varietal or hybrid plants; may be grown from seeds produced by a corn event MON 87411 containing plant and/or from seeds produced by a plant fertilized with pollen from a corn event MON 87411 containing plant; and may be homozygous or heterozygous for the transgene. Progeny plants may be subsequently self-pollinated to generate a true breeding line of plants, i.e., plants homozygous for the transgene, or alternatively may be outcrossed, e.g., bred with another unrelated plant, to produce a varietal or a hybrid seed or plant.

Methods of detecting the presence of DNA derived from a corn cell, tissue, seed, or plant comprising corn event MON 87411 in a sample are provided. One method consists of (i) extracting a DNA sample from at least one corn cell, tissue, seed, or plant, (ii) contacting the DNA sample with at least one primer that is capable of producing DNA sequence specific to event MON 87411 DNA under conditions appropriate for DNA sequencing, (iii) performing a DNA sequencing reaction, and then (iv) confirming that the nucleotide sequence comprises a nucleotide sequence specific for event MON 87411, or the construct comprised therein, such as one selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:12, SEQ ID NO:14, SEQ ID NO:16, SEQ ID NO:21, SEQ ID NO:25, SEQ ID NO: 41, SEQ ID NO: 42, SEQ ID NO: 43, SEQ ID NO: 44, SEQ ID NO: 45, SEQ ID NO: 49, SEQ ID NO: 50, SEQ ID NO: 51, and SEQ ID NO: 52. Another method consists of (i) extracting a DNA sample from at least one corn cell, tissue, seed, or plant, (ii) contacting the DNA sample with a primer pair that is capable of producing an amplicon from event MON 87411 DNA under conditions appropriate for DNA amplification, (iii) performing a DNA amplification reaction, and then (iv) detecting the amplicon molecule and/or confirming that the nucleotide sequence of the amplicon comprises a nucleotide sequence specific for event MON 87411, such as one selected from the group consisting of SEQ ID NO:21 and SEQ ID NO:25. The amplicon should be one that is specific for event MON 87411, such as an amplicon that comprises SEQ ID NO:21 or SEQ ID NO:25. The detection of a nucleotide sequence specific for event MON 87411 in the amplicon is determinative and/or diagnostic for the presence of the corn event MON 87411 specific DNA in the sample. An example of a primer pair that is capable of producing an amplicon from event MON 87411 DNA under conditions appropriate for DNA amplification is provided as SEQ ID NO:18, SEQ ID NO:24, SEQ ID NO:20, and SEQ ID NO:22. Other primer pairs may be readily designed by one of skill in the art and would produce an amplicon comprising SEQ ID NO:21 or SEQ ID NO:25, wherein such a primer pair comprises at least one primer within the genomic region flanking the insert and a second primer within the insert. Another method of detecting the presence of DNA derived from a corn cell, tissue, seed, or plant comprising corn event MON 87411 in a sample consists of (i) extracting a DNA sample from at least one corn cell, tissue, seed, or plant, (ii) contacting the DNA sample with a DNA probe specific for event MON 87411 DNA, (iii) allowing the probe and the DNA sample to hybridize under stringent hybridization conditions, and then (iv) detecting hybridization between the probe and the target DNA sample. An example of the sequence a DNA probe that is specific for event MON 87411 DNA is provided as SEQ ID NO:19 or SEQ ID NO:23. Other probes may be readily designed by one of skill in the art and would comprise at least one fragment of genomic DNA flanking the insert and at least one fragment of insert DNA, such as sequences provided in, but not limited to, SEQ ID NO:2, SEQ ID NO:3, SEQ ID NO:5, SEQ ID NO:6, SEQ ID NO:7, SEQ ID NO:8, SEQ ID NO:9, SEQ ID NO:10, SEQ ID NO:21, and SEQ ID NO:25. Detection of probe hybridization to the DNA sample is diagnostic for the presence of corn event MON 87411 specific DNA in the sample. Absence of hybridization is alternatively diagnostic of the absence of corn event MON 87411 specific DNA in the sample.

DNA detection kits are provided that are useful for the identification of corn event MON 87411 DNA in a sample and can also be applied to methods for breeding corn plants containing the appropriate event DNA. Such kits contain DNA primers and/or probes comprising fragments of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:12, SEQ ID NO:14, SEQ ID NO:16, SEQ ID NO:21, SEQ ID NO:25, SEQ ID NO: 41, SEQ ID NO: 42, SEQ ID NO: 43, SEQ ID NO: 44, SEQ ID NO: 45, SEQ ID NO: 49, SEQ ID NO: 50, SEQ ID NO: 51, and SEQ ID NO: 52. One example of such a kit comprises at least one DNA molecule of sufficient length of contiguous nucleotides of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:12, SEQ ID NO:14, SEQ ID NO:16, SEQ ID NO:21, SEQ ID NO:25, SEQ ID NO: 41, SEQ ID NO: 42, SEQ ID NO: 43, SEQ ID NO: 44, SEQ ID NO: 45, SEQ ID NO: 49, SEQ ID NO: 50, SEQ ID NO: 51, and SEQ ID NO: 52 to function as a DNA probe useful for detecting the presence and/or absence of DNA derived from transgenic corn plants comprising event MON 87411 in a sample. The DNA derived from transgenic corn plants comprising event MON 87411 would comprise a DNA molecule having at least one sequence selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:12, SEQ ID NO:14, SEQ ID NO:16, SEQ ID NO:21, SEQ ID NO:25, SEQ ID NO: 41, SEQ ID NO: 42, SEQ ID NO: 43, SEQ ID NO: 44, SEQ ID NO: 45, SEQ ID NO: 49, SEQ ID NO: 50, SEQ ID NO: 51, and SEQ ID NO: 52. A DNA molecule sufficient for use as a DNA probe is provided that is useful for determining, detecting, or diagnosing the presence and/or absence of corn event MON 87411 DNA in a sample is provided as SEQ ID NO:19 and SEQ ID NO:23. Other probes may be readily designed by one of skill in the art and should comprise a sufficient number of contiguous nucleic acids, including at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, or at least 40 contiguous nucleotides of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:12, SEQ ID NO:14, SEQ ID NO:16, SEQ ID NO:21, SEQ ID NO:25, SEQ ID NO: 41, SEQ ID NO: 42, SEQ ID NO: 43, SEQ ID NO: 44, SEQ ID NO: 45, SEQ ID NO: 49, SEQ ID NO: 50, SEQ ID NO: 51, and SEQ ID NO: 52 and be sufficiently unique to corn event MON 87411 DNA in order to identify DNA derived from the event. Another type of kit comprises a primer pair useful for producing an amplicon useful for detecting the presence and/or absence of DNA derived from transgenic corn event MON 87411 in a sample. Such a kit would employ a method comprising contacting a target DNA sample with a primer pair as described herein, then performing a nucleic acid amplification reaction sufficient to produce an amplicon comprising a DNA molecule having at least one sequence selected from the group consisting of SEQ ID NO:21 and SEQ ID NO:25, and then detecting the presence and/or absence of the amplicon. Such a method may also include sequencing the amplicon or a fragment thereof, which would be determinative of, i.e. diagnostic for, the presence of the corn event MON 87411 specific DNA in the target DNA sample. Other primer pairs may be readily designed by one of skill in the art and should comprise a sufficient number of contiguous nucleic acids, including at least 15, at least 16, at least 17, at least 18, at least 19, at least 20, at least 21, at least 22, at least 23, at least 24, at least 25, at least 26, at least 27, at least 28, at least 29, or at least 30 contiguous nucleotides of sequences provided in, but not limited to SEQ ID NO:1, SEQ ID NO:2, SEQ ID NO:3, SEQ ID NO:5, SEQ ID NO:6, SEQ ID NO:7, SEQ ID NO:8, SEQ ID NO:9, or SEQ ID NO:10, SEQ ID NO:12, SEQ ID NO:14, SEQ ID NO:16, SEQ ID NO: 41, SEQ ID NO: 42, SEQ ID NO: 43, SEQ ID NO: 44, SEQ ID NO: 45, SEQ ID NO: 49, SEQ ID NO: 50, SEQ ID NO: 51, and SEQ ID NO: 52 and be sufficiently unique to corn event MON 87411 DNA in order to identify DNA derived from the event.

The kits and detection methods of the invention are useful for, among other things, identifying corn event MON 87411, selecting plant varieties or hybrids comprising corn event MON 87411, detecting the presence of DNA derived from the transgenic corn plants comprising event MON 87411 in a sample, and monitoring samples for the presence and/or absence of corn plants comprising event MON 87411 or plant parts derived from corn plants comprising event MON 87411.

The sequence of the heterologous DNA insert, junction sequences, or flanking sequences from corn event MON 87411 can be verified (and corrected if necessary) by amplifying such sequences from the event using primers derived from the sequences provided herein followed by standard DNA sequencing of the amplicon or of the cloned DNA.

The following examples are included to demonstrate examples of certain preferred embodiments of the invention. It should be appreciated by those of skill in the art that the techniques disclosed in the examples that follow represent approaches the inventors have found function well in the practice of the invention, and thus can be considered to constitute examples of preferred modes for its practice. However, those of skill in the art should, in light of the present disclosure, appreciate that many changes can be made in the specific embodiments that are disclosed and still obtain a like or similar result without departing from the spirit and scope of the invention.

DEPOSIT INFORMATION

A deposit of a representative sample of corn seed comprising event MON 87411 has been made on Mar. 14, 2012 according to the Budapest Treaty with the American Type Culture Collection (ATCC) having an address at 10801 University Boulevard, Manassas, Va. USA, Zip Code 20110, and assigned ATCC Accession No. PTA-12669. Access to the deposits will be available during the pendency of the application to the Commissioner of Patents and Trademarks and persons determined by the Commissioner to be entitled thereto upon request. Upon issuance of the patent, all restrictions upon availability to the public will be irrevocably removed. The deposit will be maintained in the depository for a period of 30 years, or 5 years after the last request, or for the effective life of the patent, whichever is longer, and will be replaced as necessary during that period.

EXAMPLES

Example 1

This example describes the design and selection of a construct designated 417 and the engineering and evaluation of different DNA constructs. Table 1 tabulates these DNA constructs by test criteria and results.

DNA constructs were engineered to express an RNA-based plant-incorporated protectant (PIP) in corn, targeting Western corn rootworm (WCR). Variations of the RNA transcript were tested for different target genes of WCR (Group 1), different lengths of RNA (Group 2), with or without neutral RNA carrier (Group 2), different secondary structures (Group 4), and different target segments of Dv_Snf7o (Groups 2 and 3). Variations on multiple transgenes were also tested, e.g., the RNA transcript+a WCR-active protein (Groups 3 and 5), and two RNA transcripts targeting two WCR targets (Groups 1 and 4). Variations on the number and configuration of expression cassettes and elements used were also tested (all groups).

TABLE 1

Forty-five DNA constructs were stably transformed into corn plants. Progeny plants from multiple transformation events per DNA construct were evaluated.

| Construct | Group | Criteria and Results |
|---|---|---|
| 043 | 1 | Tested inhibition of WCR activity on plants |
| 043 | | expressing vector stacked combinations of |
| 059 | | RNA segments targeting transcripts of |
| | | 4 different WCR endogenous genes. |
| | | WCR activity was inhibited on plants |
| | | expressing an RNA segment targeting |
| | | the Dv_Snf7o gene transcript. |
| 503 | 2 | Tested inhibition of WCR activity on plants |
| 475 | | expressing various sizes of RNA segments |
| 970 | | targeting the Dv_Snf7o gene transcript |
| 474 | | (from a 27-mer up to a 429-mer) |
| 477 | | engineered to express as an inverted-repeat |
| 306 | | RNA (IR). |
| 476 | | Also tested a 150-mer neutral IR carrier that was |
| 713 | | embedded with and without a 27-mer targeting |
| | | Dv_Snf7o. |
| | | Optimal WCR activity was observed on plants |
| | | expressing Dv_Snf7o target segments equal or |
| | | longer than 100 base pairs in length. |
| 868 | 3 | Tested inhibition of WCR activity on plants |
| 870 | | expressing: |
| 871 | | (a) a 240-mer Dv_Snf7o IR, and (b) a pair of |
| 875 | | proteins TIC809 and TIC810 having WCR |
| 310 | | inhibitory activity; |
| 311 | | both under one expression cassette in one DNA |
| 330 | | construct. |
| 331 | | Tested inhibition of WCR activity on plants |
| 950 | | expressing: |
| 890 | | (a) the 240-mer Dv_Snf7o IR, and (b) the pair of |
| 867 | | proteins TIC809 and TIC810 having WCR |
| 946 | | inhibitory activity; each |
| 878 | | independently- and operably-linked to separate |
| 823 | | expression |
| 879 | | cassettes in one DNA construct. |
| 880 | | Tested these IR + protein combinations using |
| 401 | | different combinations of different promoters and |
| | | expression cassette configurations. |
| | | In-planta expression of the 240-mer Dv_Snf7o IR |
| | | inhibited WCR activity on such plants, with or |
| | | without expression of the TIC809 and TIC810 |
| | | protein pair. |
| 354 | 4 | Tested progeny plants of a hybrid cross between |
| 253 | | plants containing events harboring DNA construct |
| 254 | | #503 (a 429-mer Dv_Snf7o IR) and plants |
| 255 | | comprising event |
| 256 | | MON 88017 (Cry3Bb). |
| 892 | | Tested inhibition of WCR activity on plants |
| 365 | | expressing a 150- or 240-mer Dv_Snf7o IR. |
| | | Tested inhibition of WCR activity on plants |
| | | expressing: |
| | | (a) Dv_Snf7o IR, and (b) vATPase A IR. |
| | | Tested IR versus non-IR secondary RNA |
| | | structures for suppressing Dv_Snf7o, |
| | | vATPase A, and the combination. |
| | | In-planta Expression of the 240-mer Dv_Snf7o IR |
| | | inhibited WCR activity, with or without |
| | | expression of the vATPase A RNA segment. |
| | | WCR inhibition was better in-planta when |
| | | Dv_Snf7o IR was expressed together with |
| | | Cry3Bb, when compared to expressing |
| | | Dv_Snf7o IR alone or Cry3Bb alone. |
| 416 | 5 | Tested inhibition of WCR activity on plants |
| 417 | | expressing both (a) the 240-mer Dv_Snf7o IR, |
| 418 | | and (b) the Cry3Bb |
| 419 | | protein having *Diabrotica virgifera* pesticidal |
| 423 | | activity; each transgene in separate expression |
| 402 | | cassettes in a DNA construct. |
| 403 | | Tested ten DNA constructs having combinations |
| 404 | | of different promoters, and combinations of |
| 405 | | different expression cassette configurations. |
| 406 | | DNA construct #417 was selected. |

Using the DNA constructs of Group 2 as an example, 7 DNA constructs were engineered to test the targeting of various lengths of Dv_Snf7o (from 27 up to 429 nt in length). Each DNA construct was produced, plant cells transformed, plants obtained, and inbreds evaluated in growth chamber efficacy bioassays. Results showed a correlation between length of inverted repeat RNA (IR) and WCR activity (Table 2, columns (B) and (H)).

TABLE 2

Correlation between length of IR and WCR-activity.

| (A) DNA Construct No. | (B) Dv_Snf7o RNA segment length (nt) | (C) No. of embryos transformed | (D) No. of embryos w/shoots | (E) No. of $R_0$ plants to soil | (F) No. of $R_0$ plants expected to harbor a single event | (G) No. of events advanced for multi-plant testing | (H) WCR-activity on plants? |
|---|---|---|---|---|---|---|---|
| 503 | 429 | 2085 | 433 | 308 | 233 | 78 | +++++ |
| 475 | 150 | 230 | 57 | 45 | 39 | 23 | +++++ |
| 970 | 27† | 220 | 79 | 47 | 44 | 21 | ++ |
| 474 | 27 | 230 | 81 | 51 | 49 | 23 | – |
| 477 | 50 | 220 | 50 | 36 | 31 | 23 | ++ |
| 306 | 75 | 230 | 37 | 27 | 18 | 15 | ++ |
| 476 | 100 | 220 | 53 | 40 | 33 | 22 | +++++ |

Column (B) displays the variable lengths of Dv_Snf7o target RNA engineered to express as an inverted repeat RNA (IR) secondary structure in corn plants. Column (C) displays the number of corn embryos that were transformed. Column (D) displays the number of corn embryos that developed shoots. Column (E) displays the number of regenerated corn plants (designated as generation R0) viable on soil. Column (F) displays the number of R0 plants expected to harbor a single copy of insert DNA in the transformation event. Column (G) displays the number of R0 plants that were expected to harbor a single transformation event, and that produced enough seed for multi-plant growth chamber bioassay. Column (H) displays the results of plant growth chamber studies designed to evaluate WCR-activity. "+++++" indicates average RDR was less than 0.5 RDR. "++" indicates average RDR was between 0.5 RDR and 2.0 RDR. "–" means average RDR was about 2.0 RDR, which was comparable to negative controls in growth chamber efficacy studies.

† the same 27-mer as in DNA construct #474 but embedded in a neutral 150-mer IR. To evaluate WCR activity on plants grown in growth chambers, 6 to 8 plants for each of 10-20 events per construct were grown in peat pots. Plants were tested for the presence of the insert DNA and for expression of the transgene(s) in both leaf and root tissues. Plants confirmed to have expression of the transgene were then transplanted into larger pots infested with WCR eggs. Non-transgenic corn lines LH59 and LH244 were included as negative controls. Plants containing event MON 88017 (expressing Cry3Bb) were included as positive controls. Root damage of the growing corn plants was assessed after 4 weeks. Root damage ratings (RDR) were assessed on a three-point scale, with 0 RDR having no root damage and 3 RDR having maximum root damage.

Study results guided the design of the DNA constructs of Group 5 to contain (a) an expression cassette for a 240-mer Dv_Snf7o IR, and (b) an expression cassette for a Cry3Bb protein (FIG. 2). The 240-mer Dv_Snf7o IR was selected because (a) plants expressing the identical 240-mer Dv_Snf7o IR were repeatedly successful in inhibiting CRW activity (Groups 2-4), (b) segments larger than 100 nt in length decrease the probability of development of WCR resistance, and (c) segments larger than 240 nt would make it more difficult to transfer intact into the corn genome. The DNA constructs were designed to test different regulatory genetic elements in each expression cassette and different configurations of each expression cassette in the DNA construct. DNA constructs of Group 5 also included constructs with and without glyphosate tolerance expression cassettes; and a control construct from group 3 that expressed only the 240-mer Dv_Snf7o IR. Each DNA construct was designed, plant cells transformed, plants obtained, and inbreds evaluated in growth chamber efficacy bioassays (Table 3 (C) through (H)).

TABLE 3

Plant production numbers from transformation of Group 5 DNA constructs.

| | (A) DNA Construct No. | (B) DNA construct composition | (C) Number of embryos transformed | (D) Number of embryos w/shoots | (E) Number of $R_0$ plants to soil | (F) Number of $R_0$ plants expected to harbor a single event | (G) Number of $R_0$ events advanced to growth chamber | (H) Inbred and hybrid progeny plant performance |
|---|---|---|---|---|---|---|---|---|
| (1) | 416 | Dv_Snf7o | 820 | 72 | 72 | 42 | 27 | +++++ |
| (2) | 417 | IR + | 521 | 212 | 94 | 71 | 44 | +++++ |
| (3) | 418 | Cry3Bb + | 588 | 79 | 65 | 44 | 28 | +++++ |
| (4) | 419 | EPSPS | 651 | 106 | 95 | 68 | 43 | ++++ |
| (5) | 423 | | 754 | 93 | 84 | 66 | 41 | ++++ |
| (6) | 402 | | 786 | 84 | 84 | 58 | 43 | ++++ |
| (7) | 403 | | 714 | 199 | 84 | 46 | 40 | ++++ |
| (8) | 404 | | 740 | 50 | 50 | 34 | 29 | ++++ |
| (9) | 405 | Dv_Snf7o | 21663 | 1586 | 1586 | 86 | 58 | +++ |

TABLE 3-continued

Plant production numbers from transformation of Group 5 DNA constructs.

| | (A) DNA Construct No. | (B) DNA construct composition | (C) Number of embryos transformed | (D) Number of embryos w/shoots | (E) Number of $R_0$ plants to soil | (F) Number of $R_0$ plants expected to harbor a single event | (G) Number of $R_0$ events advanced to growth chamber | (H) Inbred and hybrid progeny plant performance |
|---|---|---|---|---|---|---|---|---|
| (10) | 406 | IR + Cry3Bb | 21965 | 1539 | 1539 | 170 | 112 | ++++ |
| (11) | 890 | Dv_Snf7o IR | 3996 | 656 | 394 | 235 | 136 | +++ |

Column (A) lists the DNA constructs tested in stage 5 (also see FIG. 2 for breakdown of the genetic elements). Column (B) displays the combination of transgene. Column (C) displays the number of corn embryos that were transformed. Column (D) displays the number of corn embryos that developed shoots. Column (E) displays the number of regenerated corn plants (designated as generation R0) viable on soil. Column (F) displays the number of R0 plants expected to harbor a single transformation event. Column (G) displays the number of R0 plants expected to harbor a single transformation event, and that produced enough seed for subsequent multi-plant testing. Column (H) summarizes the performance of plants infested with WCR (See following paragraph for details).

As shown in Table 3, column (H), "+++++" describes DNA constructs that on average provided the highest sustained gene expression to transgenic plants throughout their development, most WCR inhibition during development, and most WCR inhibition in self-fertilized and cross-hybridized generations. "++++" describes DNA constructs that on average provided WCR inhibition to transgenic plants but lower gene expression when compared to the "+++++" plants. "+++" describes DNA constructs that on average provided lower WCR inhibition to transgenic plants when compared to the "++++" and "+++++" plants. Therefore, DNA construct #417 was advanced for further analysis. This construct has sixteen genetic elements organized into three expression cassettes from the Left Border (LB) through to the Right Border (RB). The construct is shown in FIG. 2 and the sequence given in SEQ ID NO:26. The vector components are as follows:

[1] LB: Corresponds to the reverse complement of positions 1 through 442 of SEQ ID NO:26. This element represents the octopine Left border sequence from *Agrobacterium tumefaciens.*

[2] Ps.RbcS2-E9 3' UTR: Corresponds to the reverse complement of positions 486 through 1118 of SEQ ID NO:26. Represents 3' untranslated region (UTR) from the ribulose 1,5-bisphosphate carboxylase small subunit E9 (rbcS-E9) gene transcript from *Pisum sativum* (pea).

[3] 240-mer Dv_Snf7o inverted repeat gene: Corresponds to the reverse complement of positions 1148 through 1777 of SEQ ID NO:26. This gene transcribes RNA containing two 240-mer ribonucleotide segments that align identically to each other in reverse complement fashion, separated by a neutral segment of 150 ribonucleotides, and forming an inverted repeat RNA (IR). The sequence of the 240-bp segment aligns to a WCR gene orthologous to yeast Snf7.

[4] Corn DnaK intron: Corresponds to the reverse complement of positions 1814 through 2617 of SEQ ID NO:26. This element consists of 10 nucleotides of exon 1, intron 1, and 11 nucleotides of exon 2 from the heat shock protein 70 gene from *Zea mays* (corn). The 11 nucleotides of exon 2 were modified to remove an initiating methionine residue.

[5] CaMV 35S leader: Corresponds to the reverse complement of positions 2618-2626 of SEQ ID NO:26. Represents the 5' untranslated region (UTR) from the 35S RNA transcript of the Cauliflower mosaic virus (CaMV) beginning at the +1 position of the mRNA transcriptional start of the gene.

[6] eCaMV 35S promoter: Corresponds to the reverse complement of positions 2627-3238 of SEQ ID NO:26. Represents the promoter of 35S RNA from Cauliflower mosaic virus (CaMV) containing a duplication of the −90 to −350 region.

[7] Corn PIIG promoter: Corresponds to positions 3265-4213 of SEQ ID NO:26. This genetic element represents the promoter of the physical impedance induced protein (PIIG) gene from *Zea mays.*

[8] Wheat Lhcb1 leader: Corresponds to positions 4220-4280 of SEQ ID NO:26. This genetic element represents the 5' untranslated region (UTR) of the light harvesting complex b1 (Lhcb1) gene from *Triticum aestivum* (wheat).

[9] Rice Act1 intron: Corresponds to positions 4297-4776 of SEQ ID NO:26. Consists of a contiguous sequence of 12 nucleotides of exon 1, intron 1, and 7 nucleotides of exon 2 from the Actin 1 (Act1) gene of *Oryza sativa* (rice).

[10] Cry3Bb ORF: Corresponds to positions 4786-6747 of SEQ ID NO:26. Represents the coding region of a non-naturally occurring pesticidal Cry3B protein engineered to exhibit modifications H231R, S311L, N313T, E317K, and Q349R as compared to the native Bt Cry3Bb protein encoding gene. The nucleotide sequence aligns to the cry3Bb gene sequence contained in event MON 88017.

[11] Wheat Hsp17 3' UTR: Corresponds to positions 6767-6976 of SEQ ID NO:26. This genetic element represents the 3' UTR of the heat shock protein 17 (HSP17) gene from *Triticum aestivum* (wheat).

[12] Rice TubA (promoter, leader, intron): Corresponds to positions 7025-9205 of SEQ ID NO:26. Represents the contiguous promoter, leader, intron, and 4 nucleotides of exon 2 from the alpha tubulin gene (TubA-3) of *Oryza sativa* (rice).

[13] CTP: Corresponds to positions 9210-9437 of SEQ ID NO:26. Represents engineered coding region encoding the N-terminal CTP from 5-enolpyruvylshikimate-3-phosphate synthase (EPSPS) from *A. thaliana*. This element differs from the native gene (GenBank Accession No. X06613) at the last GAG codon (glutamic acid) by modification to TGC (cysteine).

[14] CP4 EPSPS: Corresponds to positions 9438-10805 of SEQ ID NO:26. Represents engineered coding region of the EPSPS from *Agrobacterium* CP4. Differs from the native *Agrobacterium* gene at the second codon by modification from encoding serine to CTT (leucine) and four silent substitutions.

[15] Rice TubA 3' UTR: Corresponds to positions 10813-11394 of SEQ ID NO:26. Represents the 3' untranslated region (UTR) of an alpha tubulin gene (TubA-3) from *Oryza sativa* (rice).

[16] RB: Corresponds to positions 11413-11743 of SEQ ID NO:26. Represents nopaline right border sequence from *A. tumefaciens.*

Example 2

This example describes the transformation and selection of event MON 87411 from among a plurality of transgenic events.

Embryos were excised from kernels of corn line LH244, and inoculated with recombinant *Agrobacterium* harboring DNA construct #417. Co-cultured embryos were transferred onto selection and growth media to generate transgenic callus tissue with developing shoots. Developing shoots were transferred to rooting medium for development into plantlets. Plantlets were regenerated into whole $R_0$ plants in soil. $R_0$ plants recovered this way were screened for a single copy of introduced construct DNA. As shown in Table 3, putative single-copy events were provided in 71 unique $R_0$ transformants. Each $R_0$ transformant was placed under nursery conditions to produce progeny $R_1$ seed. Forth-four events were advanced. At least 8 $R_1$ seeds produced by each of the 44 $R_0$ plants were planted in soil and $R_1$ plants were grown to produce $R_2$ seed. A single $R_1$ plant per event was selected to continue each line containing each separate event, and seed from the single $R_1$ plant was bulked for subsequent testing by (a) self-fertilization ($R_{3, 4, \ldots, N}$), and (b) cross-fertilization with other corn lines, e.g., corn line 93IDI3. Plants representing events from transformation of DNA construct #890 (row 11 of Table 3) were also regenerated to serve as comparative controls for subsequent field trials described below and in this example.

Of the 44 events, 25 events were chosen to go forward based on a phenotype including Cry3Bb expression. The $R_1$ plants representing these 25 events were further evaluated for WCR inhibition in growth chamber efficacy methods described in Example 1, and for copy-number of multiple genetic elements of the insert DNA. Seventeen events out of the 25 events were taken forward, as four events exhibited more than one copy of the Ps.RbcS2-E9 3' UTR genetic element, and $R_1$ plants representing 4 other events exhibited root damage ratings greater than 0.8 RDR.

Progeny plants comprising the remaining 17 events, i.e., "A", MON 87411, and "C" through "Q", were further analyzed in parallel for molecular and for in-field performance (see Tables 4 and 5).

TABLE 4

Molecular analysis of 17 transgenic corn events harboring insert DNA from DNA transformation vector #417.

| Event | (A) Backbone absent | (B) Single Insert and Single Copy-number | (C) Intact insert | (D) Above threshold Cry3Bb protein expression | (E) Above threshold IR Dv_Snf7o dsRNA expression | (F) Neutral insertion site | (G) Expected transcript size |
|---|---|---|---|---|---|---|---|
| A | + | + | + | + | + | + | + |
| MON 87411 | + | + | + | + | + | + | + |
| C | + | + | + | + | + | + | + |
| D | + | + | − | + | + | + | + |
| E | + | + | + | + | + | − | NA |
| F | + | + | + | + | + | − | NA |
| G | + | + | + | + | + | − | NA |
| H | + | + | NA | NA | NA | NA | NA |
| I | + | + | NA | NA | NA | NA | NA |
| J | + | + | NA | NA | NA | NA | NA |
| K | + | − | NA | NA | NA | NA | NA |
| L | − | − | NA | NA | NA | NA | NA |
| M | − | + | NA | NA | NA | NA | NA |
| N | − | − | NA | NA | NA | NA | NA |
| O | − | + | NA | NA | NA | NA | NA |
| P | − | − | NA | NA | NA | NA | NA |
| Q | − | − | NA | NA | NA | NA | NA |

"−" indicates that the event did not meet the molecular criteria of the corresponding molecular analysis. "+" indicates that the event met the molecular criteria of the corresponding molecular analysis. "NA" indicates that the data was not available.

Events were screened for backbone DNA segments of the *Agrobacterium* transformation vector and for single copy-number of all portions of the intended insert DNA (Table 4, Columns (A) and (B)). Seven events (MON 87411, A, C, D, E, F, and G) were analyzed for sequence of the inserted DNA which identical to the transformation vector #417, with the exception of nick site variations at the *agrobacterium* left and right borders that occur during Agro-mediated insertion, event D failed this sequence analysis (Table 4, Column (C)). These 7 events were also evaluated for sustained plant expression of Cry3Bb protein and Dv_Snf7o IR RNA throughout plant development and several generations, and all 7 events met the passing criteria for sustained plant expression (Table 4, Column (D)). Each of the 7 events were analyzed for genomic insertion site characteristics (i.e., neutral insertion site), such as DNA displacement, duplications and repetitiveness, proximity to an endogenous gene, interruption of an endogenous gene, and proximity to QTLs and biotech traits, events E, F, and G failed this analysis (Table 4, Column (F)). Northern blots were performed on plant tissue containing events MON 87411, A, C, and D to determine if the expected sizes of the two RNA transcript encoding Cry3Bb, or producing the Dv_Snf7o IR RNA were present in RNA from the events, and all events evaluated passed this criteria (Table 4, Column (G)).

These 17 events were evaluated in agronomic, insect efficacy and glyphosate tolerance efficacy field trials, the results are summarized in Table 5. The column headers of Table 5 describe the type of field trial ("Agronomics", "Insect", or "Glyphosate"), the controls to which the events were being compared/contrasted are listed, and the genetic inbred used to generate event hybrid is also listed. The field trials summarized in columns (A) through (C) were planted one calendar year before the field trials summarized in columns (D) through (H), and two years before the field trials summarized in column (I).

TABLE 5

Results from Agronomic, Insect efficacy, and glyphosate efficacy field trials of events generated with transformation vector #417.

| Type of field trial | (A) Agronomics | (B) Agronomics | (C) Insect Efficacy | (D) Agronomics | (F) Glyphosate Efficacy | (G) Glyphosate Efficacy | (H) Insect Efficacy | (I) Agronomics |
|---|---|---|---|---|---|---|---|---|
| Controls used as comparison | LH244, #890 | LH244 × 93IDI3, #890 | LH244, MON 88017 #890 | LH244, MON 88017 | MON 88017, | MON 88017 | MON 88017, #890 | LH244, #890 |
| Inbred or Hybrid → | R3 inbred | R3 inbred | R2 inbred X 93IDI3 | R5 inbred | R5 inbred | R4 inbred X MON 89034 | R4 inbred X MON 89034 | R5 inbred |
| Test Event | | | | | | | | |
| A | = | = | <0.10 RDR | = | = | = | ~0.10 RDR | – |
| MON 87411 | = | = | NA | = | = | = | ~0.10 RDR | = |
| C | = | = | ~0.10 RDR | = | – | NA | NA | NA |
| D | = | = | ~0.10 RDR | + | = | = | ~0.20 RDR | NA |
| E | = | = | NA | + | = | = | ~0.15 RDR | = |
| F | = | = | NA | + | – | NA | NA | NA |
| G | = | = | NA | + | = | = | ~0.15 RDR | = |
| H‡ | – | = | ~0.10 RDR | NA | NA | NA | NA | NA |
| I‡ | – | = | NA | NA | NA | NA | NA | NA |
| J† | = | = | NA | NA | NA | NA | NA | NA |
| K | – | = | ~0.15 RDR | = | NA | NA | NA | NA |
| L | = | = | NA | = | NA | NA | NA | NA |
| M | = | = | ~0.20 RDR | + | NA | NA | NA | NA |
| N | – | = | NA | – | NA | NA | NA | NA |
| O | = | = | NA | NA | NA | NA | NA | NA |
| P | – | = | NA | NA | NA | NA | NA | NA |
| Q | = | = | NA | NA | NA | NA | NA | NA |

Events were compared to control(s) in each field trial. Data for each field trial were averaged by replicate plots over multiple locations. LH244 is the control for the transformation line. The DNA vector "#890" was used to produce events expressing only the 240-mer Dv_Snf7o IR. The commercial event, MON 88017, which provides coleopteran resistance and glyphosate tolerance to corn plants was used as a control. "$R_N$ inbred" specifies the $N^{th}$ generation progeny. Hybrid events evaluated in the field trials were grown from seed harvested from a cross with one parent from the event under evaluation (MON 87411, or A through Q), and one parent as indicated in Table 5 (Column C, G, or H). Specifically, in Table 5, column R2 inbred X 931DI3 specifies that an R2 inbred of the event under evaluation was crossed with inbred corn line 931DI3 to make the hybrid seed. Similarly, in Table 5, columns G and H, R4 inbred X MON 89034 specifies that an R4 inbred progeny of the event under evaluation was crossed with a plant containing event MON 89034 to make the hybrid seed. "NA" indicates that data for this test event was not available. "=" represents trait equivalency compared to controls. "–" represents a trait hit compared to controls. "+" represents an increase in performance compared to controls. "RDR" is root damage rating. "‡" represents that contemporaneous greenhouse studies showed that the applicable event exhibited phenotypic off-types in plants grown in the nursery. "†" represents that contemporaneous greenhouse studies showed that the applicable event did not provide WCR efficacy.

Agronomic field trials were conducted at multiple North American and South American locations, the results were averaged across all locations. as summarized Table 5, columns A, B, D, and I. For these agronomic field trials, corn kernels were planted in a randomized complete block (RCB) design in triplicate plots per event per location. Each replicate plot consisted of 100 kernels. Trial maintenance was designed to optimize grain production and eliminate natural WCR pressure One or more of the following standard agronomic field trial ratings were collected: degree units to 50% shed (GDU), Breeder's score (BR), seedling vigor (SDV), stalk lodging (STLC), root lodging (RTLC), ear height of mature plants (EHT), plant height of mature plants (PHT), grain moisture (MST), and grain test weight (TWT), phenotypic off-types, and grain yield. Both inbred and hybrid events were evaluated and the results are summarized in Table 5, columns A, B, D, and I. Appropriate controls were included in triplicate plots per control per location. The ratings were averaged by plot across all locations. Data were subjected to an analysis of variance and means separated at the least significant difference at the 5% probability level (LSD (0.05)).

Results of insect efficacy field trials that included analyses for WCR damage averaged across multiple North American locations are summarized in Table 5, columns C and H. For these efficacy field trials, corn kernels were planted in a RCB design in triplicate plots per event per location; each replicate plot consisted of 25 kernels. Test events were presented in hybrid plants. Appropriate controls were included in triplicate plots per control per location. When plots of corn reached their V2 growth stage, 5 plants per plot were infested with WCR eggs at a rate of 3,330 eggs per plant. During the V10 growth stage, the roots of the 5 infested plants per plot were dug up, washed, and evaluated for feeding damage based on a root damage rating (RDR) of 0 to 3, with 0 RDR having no root damage and 3 RDR having maximum root damage. RDRs for test events and control plants were averaged by plant across all plots in all locations. Negative control plants of each insect efficacy field trial exhibited respective average RDRs of 1.7 and 1.5 RDR.

Commercial checks of each insect efficacy field trial exhibited respective average RDRs of 0.25 and 0.20 RDR. Plants containing events from DNA construct #890 exhibited a range of RDRs from about 0.35 to 0.50 RDR. Events from DNA Construct #417 consistently provided plants with average RDR scores less than the economic injury threshold of 0.25 RDR.

Results of efficacy field trials evaluating vegetative tolerance to glyphosate herbicide treatments were conducted across multiple North American locations and are summarized in Table 5, columns F and G. For these efficacy field trials, the glyphosate application regimen used for the specific trial is presented in Table 6 (corresponding to Table 5, column F) and Table 7 (corresponding to Table 5, column G).

TABLE 6

Herbicide Field Trial Treatments.

| Treatment | Rate (lbs ae/A) | Schedule (by plant stage) |
|---|---|---|
| Glyphosate | 1.5 | V2 |
| Glyphosate | 1.5, 0.75, 0.75 | V2, V8, V10 |
| Glyphosate | 1.5, 1.125, 1.125 | V2, V8, V10 |

"lbs ae" indicates pound acid equivalent.
"A" indicates acre.

TABLE 7

Herbicide Field Trial Treatments.

| Treatment | Rate (lbs ae/A) | Schedule (by plant stage) |
|---|---|---|
| Untreated | 0.0 | n/a |
| Glyphosate | 1.5, 1.5 | V4, V8 |
| Glyphosate | 3.0, 3.0 | V4, V8 |
| Glyphosate | 4.5, 4.5 | V4, V8 |

"lbs ae" indicates pound acid equivalent.
"A" indicates acre.

Each plot of 100 plants was rated for crop injury 7-10 days after the last spray of each treatment. Crop injury ratings included chlorosis, malformation, and average lower plant height, all of which indicate lower tolerance to the glyphosate herbicide. Each plot was also rated for PHT, EHT, days to 50% pollen shed (D50P), days to 50% silk emergence (D50S), TWT, MST, and yield. Events were provided as inbred plants and hybrid plants and compared to event MON 88017. Events "A", MON 87411, "D", "E", and "G" were equivalent to event MON 88017 relative to crop injury, PHT, EHT, D50P, D50S, TWT, MST, and yield ratings. Based on these results coupled with the significant RDR advantage of event MON87411 compared to other events and to the commercial MON88017 event, event MON 87411 was selected.

Example 3

This example describes the molecular characterization of event MON 87411. A sample of Leaf tissue was sampled from an ($R_0$) MON87411 plant. Sequencing of the genomic DNA corresponding to the transgenic insertion site in event MON 87411 was obtained and no differences were observed compared to the sequence in the transformation vector corresponding to vector #417.

The flanking sequences were mapped to corn genome reference sequences, including the maize B73 reference genome (Ref B73). Event MON 87411 was determined to be physically located on chromosome 9. The flanking sequence ending at the left flank/insert DNA junction corresponds to position ZM_B73_CR09:39261797. The flanking sequence ending at the right flank/insert DNA junction corresponds to position ZM_B73_CR09:39261915. The flanking sequences for event MON 87411 were analyzed for genome duplications, repeats, and endogenous genes. None were detected.

The sequence analysis of the inserted DNA in event MON 87411 confirmed that only 263 nucleotides of the *Agrobacterium* left border (arbitrarily set as the 5' end of the insert), and only 15 nucleotides of the *Agrobacterium* right border (arbitrarily set as the 3' end of the insert) were retained in the inserted DNA at the genomic insertion site of event MON 87411.

A comparative analysis of the genomic sequence flanking the inserted DNA of event MON 87411 and the corresponding genomic region of the site of insertion in the wild-type allele from LH244 was conducted. This analysis determined that a 118 base pair segment of LH244 genomic DNA was displaced by the inserted DNA of the transformation vector #417 in the process of generating event MON 87411.

Example 4

This example describes methods which are useful in identifying the presence of DNA derived from event MON 87411 in a corn sample. A pair of primers and a probe were designed for the purpose of identifying the unique junction formed between the genomic DNA and the arbitrarily assigned 5' end of the inserted DNA of event MON 87411 (i.e., the left junction) and encompassed in SEQ ID NO:1, SEQ ID NO:2, SEQ ID NO:4, SEQ ID NO:5, SEQ ID NO:6, SEQ ID NO:7, or SEQ ID NO:21. The sequence of the oligonucleotide forward primer SQ27011 (SEQ ID NO:18) is identical to the nucleotide sequence corresponding to positions 462 through 490 of SEQ ID NO:1 and SEQ ID NO:2, positions 107 through 135 of SEQ ID NO:7, positions 72 through 100 of SEQ ID NO:6, positions 12 through 40 of SEQ ID NO:5, and positions 1 through 29 of SEQ ID NO:21. The sequence of the oligonucleotide reverse primer SQ9085 (SEQ ID NO:20) is identical to the reverse complement of the nucleotide sequence corresponding to positions 516 through 541 of SEQ ID NO:1 and SEQ ID NO:2, positions 161 through 186 of SEQ ID NO:7, positions 126 through 151 of SEQ ID NO:6, positions 66 through 91 of SEQ ID NO:5, positions 16 through 41 of SEQ ID NO:4, and positions 55 through 80 of SEQ ID NO:21. The sequence of the oligonucleotide probe PB3552 (SEQ ID NO:19) is identical to the reverse complement of the nucleotide sequence corresponding to positions 502 through 515 of SEQ ID NO:1 and SEQ ID NO:2, positions 147 through 160 of SEQ ID NO:7, positions 112 through 125 of SEQ ID NO:6, positions 52 through 65 of SEQ ID NO:5, positions 2 through 15 of SEQ ID NO:4, and positions 41 through 54 of SEQ ID NO:21. The PCR primers SQ27011 (SEQ ID NO:18) and SQ9085 (SEQ ID NO:20) amplify a 79 nucleotide amplicon of the unique the genomic/insert DNA at the left junction of event MON 87411. This same primer pair with probe PB3552 (SEQ ID NO:19), which has been fluorescently labeled (i.e., a 6FAM™ fluorescent label), can be used in an Endpoint TaqMan® PCR assay to identify the presence of DNA derived from event MON 87411 in a sample.

A pair of primers and a probe were designed for the purpose of identifying the unique junction formed between the genomic DNA and the arbitrarily assigned 3' end of the inserted DNA of event MON 87411 (i.e., the right junction)

and encompassed in SEQ ID NO:1, SEQ ID NO:3, SEQ ID NO:4, SEQ ID NO:8, SEQ ID NO:9, SEQ ID NO:10, or SEQ ID NO:25. The sequence of the oligonucleotide forward primer SQ27066 (SEQ ID NO:22) is identical to the nucleotide sequence corresponding to positions 11710 through 11728 of SEQ ID NO:1, positions 11210 through 11228 of SEQ ID NO:4, positions 45 through 63 of SEQ ID NO:8, SEQ ID NO:9, and SEQ ID NO:10, and positions 1 through 19 of SEQ ID NO:25. The sequence of the oligonucleotide reverse primer SQ26977 (SEQ ID NO:24) is identical to the reverse complement of the nucleotide sequence corresponding to positions 11756 through 11784 of SEQ ID NO:1, positions 91 through 117 of SEQ ID NO:8, positions 91 through 119 of SEQ ID NO:9 and SEQ ID NO:10, positions 23 through 51 of SEQ ID NO:3, and positions 47 through 75 of SEQ ID NO:25. The sequence of the oligonucleotide probe PB11300 (SEQ ID NO:23) is identical to the nucleotide sequence corresponding to positions 11731 through 11755 of SEQ ID NO:1, positions 11231 through 11248 of SEQ ID NO:4, positions 66 through 90 of SEQ ID NO:8, SEQ ID NO:9, and SEQ ID NO:10, positions 1 through 22 of SEQ ID NO:3, and positions 22 through 46 of SEQ ID NO:25. The PCR primers SQ27066 (SEQ ID NO:22) and SQ26977 (SEQ ID NO:24) amplify a 75 nucleotide amplicon of the unique the genomic/insert DNA at the right junction of event MON 87411. This same primer pair with probe PB11300 (SEQ ID NO:23), which has been fluorescently labeled (i.e., a 6FAM™ fluorescent label), can be used in an Endpoint TaqMan® PCR assay to identify the presence of DNA derived from event MON 87411 in a sample.

In addition to SQ27011, SQ9085, PB3552, SQ27066, SQ26977, and PB11300, it should be apparent to persons skilled in the art that other primers and/or probes can be designed to either amplify and/or hybridize to sequences within SEQ ID NO:1 which are unique to, and useful for, detecting the presence of DNA derived from event MON 87411 in a sample.

Based on molecular and sequence analysis, PCR assays for event identification assays were developed for event MON 87411. Following standard molecular biology laboratory practices, the parameters of either a standard PCR assay or a TaqMan® PCR assay were optimized with each set of primer pairs and probes (i.e. probes labeled with a fluorescent tag such as 6FAM™) used to detect the presence of DNA derived from event MON 87411 in a sample (SQ27011, SQ9085, and/or PB3552, or SQ27066, SQ26977, and/or PB11300). Generally, the parameters which were optimized included primer and probe concentration, amount of template DNA, and PCR amplification cycling parameters. A control for the PCR reaction included primers (SQ20221 (SEQ ID NO:38) and SQ20222 (SEQ ID NO:40)) and/or probe (PB10065 (SEQ ID NO:39)) (probe labeled with a fluorescent tag such as VIC™), which are specific for an internal control, single copy gene in the corn genome. One of skill in the art will know how to design other PCR primers specific for a single copy gene in the corn genome which can be used to amplify an amplicon to be used as an internal control probe, or as an internal control in a PCR assay (e.g. TaqMan®). DNA was extracted from leaf tissue for each of the following: [1] leaf sample to be analyzed; [2] negative control (non-transgenic corn DNA); [3] negative water control (no template); and [4] positive control MON 87411 DNA. Detection of the amplicons from a standard PCR assay would be visualization by DNA gel electrophoresis, and for a TaqMan® PCR assay by fluorescence detection.

A zygosity assay is useful for determining if a plant comprising an event is homozygous for the event DNA; that is comprising the exogenous DNA in the same location on each chromosome of a chromosomal pair; or heterozygous for an event DNA, that is comprising the exogenous DNA on only one chromosome of a chromosomal pair; or is null for the event DNA, that is wildtype. The zygosity of a corn plant containing event MON 87411 can be determined by thermal amplification (PCR) or by endpoint TaqMan® methods. For example, for PCR amplification, the primer pair SQ27011 (SEQ ID NO:18) and SQ26977 (SEQ ID NO:22) hybridize within the genomic DNA flanking the event MON87411 insert. This primer pair will generate an amplicon which is 11323 nucleotides in length when DNA derived from event MON 87411 is present in the sample. This same primer pair will generate an amplicon which is only about 150 nucleotides long when corn DNA in the sample is not derived from event MON 87411. On DNA gel electrophoresis, a single band of 11323 bp is indicative that the DNA in the sample is from a homozygous MON 87411 event, a single band of about 150 bp is indicative that the DNA in the sample is not from a MON 87411 event, and the presence of both a band of 11323 bp and a band of about 150 bp is indicative that the DNA in the sample is from a corn plant heterozygous for MON 87411 event.

A TaqMan® assay can be developed to determine the zygosity of a corn plant containing event MON 87411. For this assay, three or four primers and two probes would be designed where [1] a first primer pair and a first probe are specific for detecting the presence of event MON 87411 DNA in a sample, and [2] a second primer pair, different from the first primer pair, and a second probe, different from the first probe, are specific for detecting the presence of wildtype corn DNA (i.e., sample not containing event MON 87411). In a TaqMan®, or similar assay, a fluorescent signal only from the first probe is indicative of and diagnostic for a plant homozygous for event MON 87411; a fluorescent signal from both the first probe and second probe is indicative of and diagnostic for a plant heterozygous for event MON 87411; and a fluorescent signal only from the second probe is indicative of and diagnostic for a plant which is homozygous for the wildtype allele (i.e., is null for event MON 87411).

Example 5

This example describes the superior protection of plant comprising event MON 87411 from corn rootworm damage when compared to current commercial products (MON 88017 and DAS-59122-7) and negative control plants. Efficacy field trials were conducted comparing 135 plants each of event MON 87411, MON 88017, DAS-59122-7, and negative controls. Root damage ratings (RDR) were collected, and the percentage plants with an RDR less than the economic injury level (0.25 RDR) is shown in Table 8.

Table 8 shows that only about 4% of plants containing event MON 87411 exhibited RDRs greater than the economic threshold of 0.25 RDR. In contrast, 22% of the commercially available plants containing MON 88017 exhibited RDRs greater than the economic threshold of 0.25 RDR. And, 20% of the commercially available plants containing DAS-59122-7 exhibited RDRs greater than the economic threshold of 0.25 RDR. And, 96% of the negative control plants exhibited RDRs greater than the economic threshold of 0.25 RDR. The conclusion from these data is that event MON 87411 is clearly superior at providing protection from corn rootworm damage as compared to commercial products MON 88071 and DAS-59122-7, and a negative control.

TABLE 8

| Results of efficacy field trial with the approximate percentage of plants exhibiting ≤0.25 RDR. | |
|---|---|
| Event tested | Approximate percentage of plants exhibiting ≤0.25 RDR |
| event MON 87411 | 96 |
| MON 88017 | 78 |
| DAS-59122-7 | 80 |
| negative control plants | 4 |

Trial included 135 plants for each event tested.

Efficacy green house trials were conducted to test the performance of event MON 87411 with extreme infestation pressure of corn root worm. In this trial the following event were evaluated: event MON 87411, an event from transformation with DNA vector #890 expressing only the dsRNA; MON 88017; DAS-59122-7; and negative control. For these high-pressure efficacy trials, the corn plants under evaluation were grown in pots in a green house. Extreme infestation pressure was achieved by sequential infestation of each potted plant with approximately 2,000 WCR eggs per pot at their V2 growth stage, and, at 4 additional times occurring at 1 to 1½ week intervals with approximately 1,000 WCR eggs per pot per infestation for a total of approximately 6,000 WCR eggs added to each pot. Plant roots were removed, washed, and rated for RDR at their VT growth stage. The roots from all thirteen (N=13) negative control plants exhibited maximum root damage, or an absolute RDR of 3 RDR. These results illustrate that event MON 87411 is more superior to other corn events available for controlling corn rootworm (Table 9).

TABLE 9

| Root Damage Rating (RDR) under high corn rootworm infestation pressure. | | |
|---|---|---|
| Event | Average RDR | Lower and Upper 95% confidence limits |
| Negative Control (N = 13) | 3.0 | Absolute |
| only dsRNA (N = 11) | 0.36 | 0.17/0.54 |
| MON 88017(N = 11) | 2.1 | 1.8/2.4 |
| DAS-59122-7 (N = 16) | 0.29 | 0.17/0.42 |
| MON 87411 (N = 13) | 0.06 | 0.03/0.08 |

(N = the number of plants evaluated).

One measure of efficacy of corn rootworm transgenic events is by a determining the emergence of adult beetles from the potted soil of plants cultivated in a green house. To determine adult corn rootworm beetle emergence from the soil of event MON 87411 plants grown in pots, 10 to 15 plants were germinated in pots containing soil infested with WCR eggs, similar to that described above. Throughout the growth period, each corn plant was covered with mesh bag to contain any emerging adult beetles.

Counts of above ground adult beetles were made at 6, 12, and 18 weeks after plant emergence, and at the end of the trial the roots were evaluated for RDR. Plants containing event MON 87411 were compared to negative control plants, and other corn rootworm protective transgenic events. The results were that significantly fewer beetles were observed to emerge from soils in which event MON 87411 plants were potted compared to the other corn rootworm protective transgenic events, illustrating the superior properties of event MON 87411 to protect against corn rootworm damage.

Example 6

This example illustrates that the orientation of expression of two different promoters in a corn cell, each driving expression of a different corn rootworm toxic agent, can result in significantly improved ratios of transgenic events exhibiting efficacy when provided in the diet of corn rootworm larvae.

Corn cells were transformed with one of four different plant transformation vectors, pMON120417, pMON120434, pMON120416, or pMON120419, and transgenic events were obtained that were regenerated into transgenic corn plants.

With reference to FIG. 4, all of the plant transformation vectors contain three expression cassettes 1, 2, and 3, bounded on one end by an *Agrobacterium* left border (LB), and at the opposite end by an *Agrobacterium* right border (RB). A corn rootworm toxic dsRNA is expressed from cassette 1 in all four vectors from an enhanced Cauliflower mosaic virus 35S (e35S) promoter. A corn rootworm toxin protein, Cry3Bb, in vectors pMON120417, pMON120434 is expressed from cassette 2 from a Zm.PIIG promoter. A corn rootworm toxin protein, Cry3Bb, in vectors pMON120416, pMON120419 is expressed from cassette 2 from an Os.Rcc3 promoter. In all four vectors, a protein, conferring glyphosate herbicide tolerance, CTP-EPSPS CP4, is expressed from cassette 3 from an Os.TubA3 promoter. In all four vectors cassette 1 and cassette 3 are in the same relative orientation. With reference to FIG. 4, the block arrows indicate the direction of expression from the promoter in each of the respective cassettes.

The relative orientation of cassette 2 in vectors pMON120417 and pMON120434 is reversed, as illustrated by the block arrows (FIG. 4) indicating the direction of expression from the promoter. Expression of Cry3Bb corn rootworm toxin protein in pMON120417 from cassette 2 is divergent from the direction of expression of the corn rootworm toxic dsRNA expressed from cassette 1. Expression of Cry3Bb corn rootworm toxin protein in pMON120434 from cassette 2 is in the same orientation as expression of the corn rootworm toxic dsRNA from cassette 1.

The relative orientation of cassette 2 in vectors pMON120416 and pMON120419 is reversed, as illustrated by the block arrows (FIG. 4) indicating the direction of expression from the promoter. Expression of Cry3Bb corn rootworm toxin protein in pMON120416 from cassette 2 is divergent from the direction of expression of the corn rootworm toxic dsRNA expressed from cassette 1. Expression of Cry3Bb corn rootworm toxin protein in pMON120419 from cassette 2 is in the same orientation as expression of the corn rootworm toxic dsRNA from cassette 1.

As seen from Table 10, when tissue from transgenic corn plants was provided in the diet of *Diabrotica* species of corn root worm, the plants generated by transformation with either construct pMON120417 or pMON120416 (divergent expression of the corn rootworm toxic components) was more efficacious with respect to pesticidal activity when compared to plants generated by transformation with either construct pMON120434 or pMON120419 (tandem or same orientation of expression) (Table 10). The ratio of efficacious events generated from transformation using the vectors pMON120417 and pMON120416, compared to the ratio of efficacious events from the vectors pMON120416 and pMON120419, was significantly greater as shown by the data in Table 10. For example, for events generated from vector pMON120417 with the divergent promoter driven expression of the corn rootworm toxic components, 11 of 43 events, or almost 25% of the events exhibited rootworm efficacious control. In contrast, there were no efficacious events obtained for events generated from vector pMON120434 with the promoter driven expression in the tandem orientation of the corn rootworm toxic components. For events generated from vector pMON120416 with the divergent promoter driven expression of the corn rootworm toxic components, 17 of 27 events, or about 63% of the events exhibited rootworm efficacious control. In contrast, there only about 18.5% efficacious events obtained for events generated from vector pMON120419 with the promoter driven expression in the tandem orientation of the corn rootworm toxic components. These data demonstrate the significantly improved number of efficacious events, and improved ratios of transgenic events exhibiting efficacy, when transgenic corn plants are generated from a plant transformation vector with two different promoters each driving expression in divergent directions of two different corn rootworm toxic agents, and the transgenic corn plants are provided in the diet of corn rootworm larvae.

TABLE 10

Results showing the number of R0 events and the number efficacious events obtained from four plant transformation vectors.

| Construct | No. of R0 Events | # Efficacious events |
|---|---|---|
| pMON120417 | 43 | 11 |
| pMON120434 | 8 | 0 |
| pMON120416 | 27 | 17 |
| pMON120419 | 43 | 8 |

Example 7

To produce corn plants or plant parts thereof which comprise enhanced agronomic, insecticidal, or herbicidal properties, corn plants containing event MON 87411 can be crossed with corn plants containing potentially any other corn event or combination thereof and phenotypes evaluated to determine the resulting properties of the progeny plants. As a non-limiting example, MON 87411 can be crossed with corn plants including one or more combinations, of the following: DAS-59122-7; MIR604; MON 89034; MON 87411; MON 87427; TC1507; 5307; DAS-06275-8; BT176; BT11; and MIR162.

What is claimed is:

1. A recombinant DNA molecule detectable in a sample containing corn DNA, wherein the nucleotide sequence of said molecule is selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:21, SEQ ID NO:25 and a complete complement thereof, wherein the presence of such DNA molecule is diagnostic for corn event MON 87411 DNA in said sample.

2. The recombinant DNA molecule of claim 1, wherein said DNA molecule is from corn event MON 87411, a representative sample of seed comprising corn event MON 87411 having been deposited under ATCC Accession No. PTA-12669.

3. The recombinant DNA molecule of claim 1, wherein said recombinant DNA molecule comprises SEQ ID NO:21 or SEQ ID NO:25, and wherein said recombinant DNA molecule is in a corn plant, corn plant cell, corn seed, progeny corn plant, corn plant part, or commodity corn product.

4. A DNA molecule comprising a polynucleotide segment of sufficient length to function as a DNA probe that hybridizes under stringent hybridization conditions with corn event MON 87411 DNA in a sample, wherein said probe specifically hybridizes under said conditions to one or more junction segments diagnostic for corn event MON 87411 as set forth in SEQ ID NO:1, and wherein detecting hybridization of said DNA probe under said hybridization conditions is diagnostic for corn event MON 87411 DNA in said sample, and wherein said probe comprises SEQ ID NO:21 or SEQ ID NO:25.

5. A method of detecting the presence of a DNA segment diagnostic for corn event MON 87411 in a sample, the method comprising:

(a) contacting said sample with the DNA molecule of claim 4;

(b) subjecting said sample and said DNA molecule to stringent hybridization conditions; and (c) detecting hybridization of said DNA molecule to said DNA segment diagnostic for corn event MON 87411 DNA, wherein said detecting step is diagnostic for the presence of said corn event MON87411 molecule in said sample.

6. A corn commodity product comprising a detectable amount of a DNA molecule unique for event MON 87411, wherein said molecule comprises the recombinant DNA molecule of claim 1.

7. The corn commodity product of claim 6, further defined as a commodity product selected from the group consisting of whole or processed corn seeds, animal feed comprising corn, corn oil, corn meal, corn flour, corn flakes, corn bran, corn biomass, and fuel products produced using corn and corn parts.

8. A non-living plant material comprising a detectable amount of the recombinant DNA molecule of claim 1.

9. A microorganism comprising a detectable amount of the recombinant DNA molecule of claim 1.

10. The microorganism of claim 9, wherein said microorganism is a plant cell.

* * * * *

SEQUENCE LISTING

```
<160> NUMBER OF SEQ ID NOS: 52

<210> SEQ ID NO 1
<211> LENGTH: 12248
<212> TYPE: DNA
<213> ORGANISM: Artificial Sequence
<220> FEATURE:
<223> OTHER INFORMATION: is a nucleotide sequence of event MON 87411
<220> FEATURE:
<221> NAME/KEY: misc_feature
<222> LOCATION: (1)..(500)
<223> OTHER INFORMATION: represents the genomic DNA flanking the left
      border of the TDNA
<220> FEATURE:
<221> NAME/KEY: misc_feature
<222> LOCATION: (501)..(11748)
<223> OTHER INFORMATION: represents the TDNA
<220> FEATURE:
<221> NAME/KEY: promoter
<222> LOCATION: (2948)..(3559)
<223> OTHER INFORMATION: represents the reverse complement sequence of
      an enhanced CaMV 35S promoter
<220> FEATURE:
<221> NAME/KEY: promoter
<222> LOCATION: (2948)..(4534)
<223> OTHER INFORMATION: represents a divergent promoter region that
      promotes bidirectional transcription
<220> FEATURE:
<221> NAME/KEY: promoter
<222> LOCATION: (3586)..(4534)
<223> OTHER INFORMATION: represents a Corn PIIG promoter
<220> FEATURE:
<221> NAME/KEY: misc_feature
<222> LOCATION: (11749)..(12248)
<223> OTHER INFORMATION: represents the genomic DNA flanking the right
      border of the TDNA

<400> SEQUENCE: 1

ccctagcgtt gggcccaact agtcagtctg ccttccctcc cagtcgctga cctccttggt      60

ccacttgtca gctttcgcgc tcagatctaa tctcaactgt cgatctgtga tcgggtggcc     120

gagatcaccc gatgcccgtt cgtttgcaaa agttgttaaa agaccctctg tttcttagaa     180
```

-continued aataacctac attcatgttt cttgcgatta ggcccctggt ttcttgtaga gaagcccctt 240
gctttatttt aatcacaaaa ataaatctaa tttagtgttt tgaattctaa aacttgtgaa 300
tttcatatct tttgcatatg aactctaaat tgggtggttt aaattgcaaa atgatcataa 360
tattattctc tatctgttta aattataata tttcactgtc tacatgtatg tattttatga 420
ctagacaata ggttcattta aagtgatgga ttatttatta aaaggaaaat aaaaaggcaa 480
aacactaatg aatagttaag tggcttcatg tccgggaaat ctacatggat cagcaatgag 540
tatgatggtc aatatggaga aaaagaaaga gtaattacca atttttttc aattcaaaaa 600
tgtagatgtc cgcagcgtta ttataaaatg aaagtacatt ttgataaaac gacaaattac 660
gatccgtcgt atttataggc gaaagcaata aacaaattat tctaattcgg aaatctttat 720
ttcgacgtgt ctacattcac gtccaaatgg gggcttagat gagaaacttc acgatcgatg 780
cggccaccac tcgaggtcga ggtaccgttg tcaatcaatt ggcaagtcat aaaatgcatt 840
aaaaaatatt ttcatactca actacaaatc catgagtata actataatta taaagcaatg 900
attagaatct gacaaggatt ctggaaaatt acataaagga aagttcataa atgtctaaaa 960
cacaagagga catacttgta ttcagtaaca tttgcagctt ttctaggtct gaaaatatat 1020
ttgttgccta gtgaataagc ataatggtac aactacaagt gttttactcc tcatattaac 1080
ttcggtcatt agaggccacg atttgacaca tttttactca aaacaaaatg tttgcatatc 1140
tcttataatt tcaaattcaa cacacaacaa ataagagaaa aaacaaataa tattaatttg 1200
agaatgaaca aaaggaccat atcattcatt aactcttctc catccatttc catttcacag 1260
ttcgatagcg aaaaccgaat aaaaaacaca gtaaattaca agcacaacaa atggtacaag 1320
aaaaacagtt ttcccaatgc cataatactc aaactcagta ggattctggt gtgtgcgcaa 1380
tgaaactgat gcattgaact tgacgaacgt tgtcgaaacc gatgatacga acgaaagcta 1440
ggcctcagcg agtaccgctg gcgatctaat ccatgatatc gtgaacatca tctacattca 1500
aattcttatg agctttctta agggcatctg cagcattttt catagaatct aatacagcag 1560
tatttgtgct agctccttcg agggcttccc tctgcatttc aatagttgta agggttccat 1620
ctatttgtag ttgggtcttt tccaatcgtt tcttcttttt gagggcttgg agtgcaactc 1680
ttttattttt cgacgcattt ttctttgcgc tcctgcaggc ggccgcgtgg atgaggagtt 1740
aatcggtcgt gtgagagtag tgatcgagtg gatgtcgtcg agagtgatga gtgttgatgt 1800
tgttagtgat atgtggtaga aggtatcgtg ataaagcgtt aacgcgatcg cagtacttgc 1860
aaagaaaaat gcgtcgaaaa ataaaagagt tgcactccaa gccctcaaaa agaagaaacg 1920
attggaaaag acccaactac aaatagatgg aaccccttaca actattgaaa tgcagaggga 1980
agccctcgaa ggagctagca caaatactgc tgtattagat tctatgaaaa atgctgcaga 2040
tgcccttaag aaagctcata agaatttgaa tgtagatgat gttcacgata tcatggatgg 2100
tatcgcacag cgactgctga gggacgtcga gctcccgctt ggtatctgca ttacaatgaa 2160
atgagcaaag actatgtgag taacactggt caacactagg gagaaggcat cgagcaagat 2220
acgtatgtaa agagaagcaa tatagtgtca gttggtagat actagatacc atcaggaggt 2280
aaggagagca acaaaaagga aactctttat ttttaaattt tgttacaaca aacaagcaga 2340
tcaatgcatc aaaatactgt cagtacttat ttcttcagac aacaatattt aaaacaagtg 2400
catctgatct tgacttatgg tcacaataaa ggagcagaga taaacatcaa aatttcgtca 2460
tttatattta ttccttcagg cgttaacaat ttaacagcac acaaacaaaa acagaatagg 2520
aatatctaat tttggcaaat aataagctct gcagacgaac aaattattat agtatcgcct 2580

-continued

```
ataatatgaa tccctatact attgacccat gtagtatgaa gcctgtgcct aaattaacag   2640
caaacttctg aatccaagtg ccctataaca ccaacatgtg cttaaataaa taccgctaag   2700
caccaaatta cacatttctc gtattgctgt gtaggttcta tcttcgtttc gtactaccat   2760
gtccctatat tttgctgcta caaaggacgg caagtaatca gcacaggcag aacacgattt   2820
cagagtgtaa ttctagatcc agctaaacca ctctcagcaa tcaccacaca agagagcatt   2880
cagagaaacg tggcagtaac aaaggcagag ggcggagtga gcgcgtaccg aagacggttc   2940
agcgtgtcct ctccaaatga aatgaacttc cttatataga ggaagggtct tgcgaaggat   3000
agtgggattg tgcgtcatcc cttacgtcag tggagatatc acatcaatcc acttgctttg   3060
aagacgtggt tggaacgtct tctttttcca cgatgctcct cgtgggtggg ggtccatctt   3120
tgggaccact gtcggcagag gcatcttcaa cgatggcctt tcctttatcg caatgatggc   3180
atttgtagga gccaccttcc ttttccacta tcttcacaat aaagtgacag atagctgggc   3240
aatggaatcc gaggaggttt ccggatatta ccctttgttg aaaagtctca atcggaccat   3300
cacatcaatc cacttgcttt gaagacgtgg ttggaacgtc ttctttttcc acgatgctcc   3360
tcgtgggtgg gggtccatct ttgggaccac tgtcggcaga ggcatcttca acgatggcct   3420
ttcctttatc gcaatgatgg catttgtagg agccaccttc cttttccact atcttcacaa   3480
taaagtgaca gatagctggg caatggaatc cgaggaggtt tccggatatt accctttgtt   3540
gaaaagtctc aatcggacct gcagcctgca ggctagcggc gcgccacaaa tcacaggcca   3600
tgaaccctac tcatgcttcg atttgtccaa cacacactta ccaaaactca aatcatgtcc   3660
ttgacagtca ctcgggactc ataacatggg tacgtatcga ctatgtcaac tatatgtgtt   3720
ctcatcagat tatagattgg cctagtacgt agtgatattt ccactagcac tgtggttatg   3780
gctgtacctg atagtgatat cagcaccggg tcatggctct actaccaggt agtgagagtg   3840
acctttatac tgtcagactg taactaagga tttccaatca ctgttcggat cctaggctta   3900
gaattaagta aaactctatc actataggct gcagcacact cggtatatat tgatgggcca   3960
acagaaattg tgcgtactat gcgcgatgta aaatggacat aaaccctacc catatacaat   4020
gcaataactt ttgtccggtc tgggccaccg gttagcagag gtcctgattt cggtggtagt   4080
ggtagcttga tctggtcgtc gtatcgtaga gggatatata aaatcatgtc acttttgaag   4140
ggagcgctca cagaaataat aggtattcgc gggagccgcc cccgcagaac acaaaataag   4200
gcgagcacgc acacgcatca gtttcgataa aataataata gcgccagctg atcggaacaa   4260
ttccagctag cactaatgta tttctgcatt gatctgttta tacaacatgc tacctcgttg   4320
agtgattttg acatgatttg tcaacttgct ccgatcctat atctcgatcg atctccacat   4380
gacgatggtt gttgtcctgt atcccatgac aaccaggcaa cgctcaaagc acacatgcgt   4440
tgccgattac ccgtgcatgc cgccaagcac gaaagcacct ccctccacac cgtccatcag   4500
ctataaaaac catgccaagc accctgtgaa aagccccggg aaccatcttc cacacactca   4560
agccacacta ttggagaaca cacagggaca acacaccata agatccaagg gaggcctccg   4620
ccgccgccgg taaccacccc gcccctctcc tctttctttc tccgtttttt tttccgtctc   4680
ggtctcgatc tttggccttg gtagtttggg tgggcgagag gcggcttcgt gcgcgcccag   4740
atcggtgcgc gggaggggcg ggatctcgcg gctggggctc tcgccggcgt ggatccggcc   4800
cggatctcgc ggggaatggg gctctcggat gtagatctgc gatccgccgt tgttggggga   4860
gatgatgggg ggtttaaaat ttccgccgtg ctaaacaaga tcaggaagag gggaaaaggg   4920
```

-continued

```
cactatggtt tatattttta tatatttctg ctgcttcgtc aggcttagat gtgctagatc   4980
tttctttctt ctttttgtgg gtagaatttg aatccctcag cattgttcat cggtagtttt   5040
tcttttcatg atttgtgaca aatgcagcct cgtgcggagc ttttttgtag gtagaagtga   5100
tcaaccatgg ccaaccccaa caatcgctcc gagcacgaca cgatcaaggt cacccccaac   5160
tccgagctcc agaccaacca caaccagtac ccgctggccg acaaccccaa ctccaccctg   5220
gaagagctga actacaagga gttcctgcgc atgaccgagg actcctccac ggaggtcctg   5280
gacaactcca ccgtcaagga cgccgtcggg accggcatct ccgtcgttgg gcagatcctg   5340
ggcgtcgttg gcgtcccctt cgcaggtgct ctcacctcct tctaccagtc cttcctgaac   5400
accatctggc cctccgacgc cgacccctgg aaggccttca tggcccaagt cgaagtcctg   5460
atcgacaaga agatcgagga gtacgccaag tccaaggccc tggccgagct gcaaggcctg   5520
caaaacaact tcgaggacta cgtcaacgcg ctgaactcct ggaagaagac gcctctgtcc   5580
ctgcgctcca agcgctccca ggaccgcatc cgcgagctgt tctcccaggc cgagtcccac   5640
ttccgcaact ccatgccgtc cttcgccgtc tccaagttcg aggtcctgtt cctgcccacc   5700
tacgcccagg ctgccaacac ccacctcctg ttgctgaagg acgcccaggt cttcggcgag   5760
gaatggggct actcctcgga ggacgtcgcc gagttctacc gtcgccagct gaagctgacc   5820
caacagtaca ccgaccactg cgtcaactgg tacaacgtcg gcctgaacgg cctgaggggc   5880
tccacctacg acgcatgggt caagttcaac cgcttccgca gggagatgac cctgaccgtc   5940
ctggacctga tcgtcctgtt ccccttctac gacatccgcc tgtactccaa gggcgtcaag   6000
accgagctga cccgcgacat cttcacggac cccatcttcc tgctcacgac cctccagaag   6060
tacggtccca ccttcctgtc catcgagaac tccatccgca agccccacct gttcgactac   6120
ctccagggca tcgagttcca cacgcgcctg aggccaggct acttcggcaa ggactccttc   6180
aactactggt ccggcaacta cgtcgagacc aggccctcca tcggctcctc gaagacgatc   6240
acctcccctt tctacggcga caagtccacc gagcccgtcc agaagctgtc cttcgacggc   6300
cagaaggtct accgcaccat cgccaacacc gacgtcgcgg cttggccgaa cggcaaggtc   6360
tacctgggcg tcacgaaggt cgacttctcc cagtacgatg accagaagaa cgagacctcc   6420
acccagacct acgactccaa gcgcaacaat ggccacgtct ccgcccagga ctccatcgac   6480
cagctgccgc ctgagaccac tgacgagccc ctggagaagg cctactccca ccagctgaac   6540
tacgcggagt gcttcctgat gcaagaccgc aggggcacca tccccttctt cacctggacc   6600
caccgctccg tcgacttctt caacaccatc gacgccgaga agatcaccca gctgcccgtg   6660
gtcaaggcct acgccctgtc ctcgggtgcc tccatcattg agggtccagg cttcaccggt   6720
ggcaacctgc tgttcctgaa ggagtcctcg aactccatcg ccaagttcaa ggtcaccctg   6780
aactccgctg ccttgctgca acgctaccgc gtccgcatcc gctacgcctc caccacgaac   6840
ctgcgcctgt tcgtccagaa ctccaacaat gacttcctgg tcatctacat caacaagacc   6900
atgaacaagg acgatgacct gacctaccag accttcgacc tcgccaccac gaactccaac   6960
atgggcttct cgggcgacaa gaatgaactg atcattggtg ctgagtcctt cgtctccaac   7020
gagaagatct acatcgacaa gatcgagttc atccccgtcc agctgtgata ggaactctga   7080
ttgaattctg catgcgtttg gacgtatgct cattcaggtt ggagccaatt tggttgatgt   7140
gtgtgcgagt tcttgcgagt ctgatgagac atctctgtat tgtgtttctt tccccagtgt   7200
tttctgtact tgtgtaatcg gctaatcgcc aacagattcg gcgatgaata aatgagaaat   7260
aaattgttct gattttgagt gcaaaaaaaa aggaattaga tctgtgtgtg ttttttggat   7320
```

-continued

```
cccattttcg acaagcttgc ctcgagacaa caacatgctt ctcatcaaca tggagggaag   7380
agggagggag aaagtgtcgc ctggtcacct ccattgtcac actagccact ggccagctct   7440
cccacaccac caatgccagg ggcgagcttt agcacagcca ccgcttcacc tccaccaccg   7500
cactacccta gcttcgccca acagccaccg tcaacgcctc ctctccgtca acataagaga   7560
gagagagaag aggagagtag ccatgtgggg aggaggaata gtacatgggg cctaccgttt   7620
ggcaagttat tttgggttgc caagttaggc caataagggg agggatttgg ccatccggtt   7680
ggaaaggtta ttggggtagt atctttttac tagaattgtc aaaaaaaaat agtttgagag   7740
ccatttggag aggatgttgc ctgttagagg tgctcttagg acatcaaatt ccataaaaac   7800
atcagaaaaa ttctctcgat gaagatttat aaccactaaa actgccctca attcgaaggg   7860
agttcaaaac aattaaaatc atgttcgaat tgagtttcaa tttcacttta acccctttga   7920
aatctcaatg gtaaaacatc aacccgtcag gtagcatggt tctttttatt cctttcaaaa   7980
agagttaatt acaaacagaa tcaaaactaa cagttaggcc caaggcccat ccgagcaaac   8040
aatagatcat gggccaggcc tgccaccacc ctccccctcc tggctcccgc tcttgaattt   8100
caaaatccaa aaatatcggc acgactggcc gccgacggag cgggcggaaa atgacggaac   8160
aacccctcga attctacccc aactacgccc accaacccac acgccactga caatccggtc   8220
ccacccttgt gggcccacct acaagcgaga cgtcagtcgc tcgcagcaac cagtgggccc   8280
acctcccagt gagcggcggg tagatctgga ctcttaccca cccacactaa acaaaacggc   8340
atgaatattt tgcactaaaa ccctcagaaa aattccgata ttccaaacca gtacagttcc   8400
tgaccgttgg aggagccaaa gtggagcgga gtgtaaaatt gggaaactta atcgaggggg   8460
ttaaacgcaa aaacgccgag gcgcctcccg ctctatagaa aggggaggag tgggaggtgg   8520
aaaccctacc acaccgcaga gaaaggcgtc ttcgtactcg cctctctccg cgccctcctc   8580
cgccgccgct cgccgccgtt cgtctccgcc gccaccggct agccatccag gtaaaacaaa   8640
caaaaacgga tctgatgctt ccattcctcc gtttctcgta gtagcgcgct tcgatctgtg   8700
ggtggatctg ggtgatcctg gggtgtggtt cgttctgttt gatagatctg tcggtggatc   8760
tggccttctg tggttgtcga tgtccggatc tgcgttttga tcagtggtag ttcgtggatc   8820
tggcgaaatg ttttggatct ggcagtgaga cgctaagaat cgggaaatga tgcaatatta   8880
ggggggtttc ggatggggat ccactgaatt agtctgtctc cctgctgata atctgttcct   8940
ttttggtaga tctggttagt gtatgtttgt ttcggataga tctgatcaat gcttgtttgt   9000
tttttcaaat tttctaccta ggttgtatag gaatggcatg cggatctggt tggattgcca   9060
tgatccgtgc tgaaatgccc ctttggttga tggatcttga tattttactg ctgttcacct   9120
agatttgtac tcccgtttat acttaatttg ttgcttatta tgaatagatc tgtaacttag   9180
gcacatgtat ggacggagta tgtggatctg tagtatgtac attgctgcga gctaagaact   9240
atttcagagc aagcacagaa aaaaatattt agacagattg ggcaactatt tgatggtctt   9300
tggtatcatg ctttgtagtg ctcgtttctg cgtagtaatc ttttgatctg atctgaagat   9360
aggtgctatt atattcttaa aggtcattag aacgctatct gaaaggctgt attatgtgga   9420
ttggttcacc tgtgactccc tgttcgtctt gtcttgataa atcctgtgat aaaaaaaatt   9480
cttaaggcgt aatttgttga aatcttgttt tgtcctatgc agcctgatcc atggcgcaag   9540
ttagcagaat ctgcaatggt gtgcagaacc catctcttat ctccaatctc tcgaaatcca   9600
gtcaacgcaa atctccctta tcggtttctc tgaagacgca gcagcatcca cgagcttatc   9660
```

-continued

```
cgatttcgtc gtcgtgggga ttgaagaaga gtgggatgac gttaattggc tctgagcttc   9720
gtcctcttaa ggtcatgtct tctgtttcca cggcgtgcat gcttcacggt gcaagcagcc   9780
ggcccgcaac cgcccgcaaa tcctctggcc tttccggaac cgtccgcatt cccggcgaca   9840
agtcgatctc ccaccggtcc ttcatgttcg gcggtctcgc gagcggtgaa acgcgcatca   9900
ccggccttct ggaaggcgag gacgtcatca atacgggcaa ggccatgcag gcgatgggcg   9960
cccgcatccg taaggaaggc gacacctgga tcatcgatgg cgtcggcaat ggcggcctcc  10020
tggcgcctga ggcgccgctc gatttcggca atgccgccac gggctgccgc ctgacgatgg  10080
gcctcgtcgg ggtctacgat ttcgacagca ccttcatcgg cgacgcctcg ctcacaaagc  10140
gcccgatggg ccgcgtgttg aacccgctgc gcgaaatggg cgtgcaggtg aaatcggaag  10200
acggtgaccg tcttcccgtt accttgcgcg ggccgaagac gccgacgccg atcacctacc  10260
gcgtgccgat ggcctccgca caggtgaagt ccgccgtgct gctcgccggc ctcaacacgc  10320
ccggcatcac gacggtcatc gagccgatca tgacgcgcga tcatacggaa aagatgctgc  10380
agggctttgg cgccaacctt accgtcgaga cggatgcgga cggcgtgcgc accatccgcc  10440
tggaaggccg cggcaagctc accggccaag tcatcgacgt gccgggcgac ccgtcctcga  10500
cggccttccc gctggttgcg gccctgcttg ttccgggctc cgacgtcacc atcctcaacg  10560
tgctgatgaa ccccacccgc accggcctca tcctgacgct gcaggaaatg ggcgccgaca  10620
tcgaagtcat caacccgcgc cttgccggcg gcgaagacgt ggcggacctg cgcgttcgct  10680
cctccacgct gaagggcgtc acggtgccgg aagaccgcgc gccttcgatg atcgacgaat  10740
atccgattct cgctgtcgcc gccgccttcg cggaaggggc gaccgtgatg aacggtctgg  10800
aagaactccg cgtcaaggaa agcgaccgcc tctcggccgt cgccaatggc ctcaagctca  10860
atggcgtgga ttgcgatgag ggcgagacgt cgctcgtcgt gcgtggccgc cctgacggca  10920
aggggctcgg caacgcctcg ggcgccgccg tcgccaccca tctcgatcac cgcatcgcca  10980
tgagcttcct cgtcatgggc ctcgtgtcgg aaaaccctgt cacggtggac gatgccacga  11040
tgatcgccac gagcttcccg gagttcatgg acctgatggc cgggctgggc gcgaagatcg  11100
aactctccga tacgaaggct gcctgatgag ctccagggtt cttgcctggt gccttggcaa  11160
tgcttgatta ctgctgctat cctatgatct gtccgtgtgg gcttctatct atcagtttgt  11220
gtgtctggtt ttgaaaaaca tttgcttttc gattatgtag ggtttgcttg tagctttcgc  11280
tgctgtgacc tgtgttgttt atgtgaacct tctttgtggc atctttaata tccaagttcg  11340
tggtttgtcg taaaacgaag cctctacttc gtaaagttgt gtctatagca ttgaaatcgt  11400
ttttttgctc gagaataatt gtgaccttta gttggcgtga aactagtttt ggatatctga  11460
ttctctggtt cgcaatcttg agatcgtcgc tgcttaggtg agctaagtga tgttcctaag  11520
taaatgctcc tcaccagaat acgtagctgt gtgaaaagag aacgcgtgaa tacgtagctg  11580
tgtaaagatt gtgtcccaag taaacctcag tgatttttgt ttggattttt aatttagaaa  11640
cattcgactg ggagcggcta gagccacacc caagttccta actatgataa agttgctctg  11700
taacagaaaa caccatctag agcggccgcg tttaaactat cagtgtttag agaatcacaa  11760
acctctagat gtattaatct accctagaac tagttcactt ttgtgtgcat acttttctat  11820
tgaactggtg ttcactttgt tgcatatgtt ttgtgtactg tttatttgtc attgcccaaa  11880
tgtgtttaat gagtgattgc tttgcgtaga caacgagcag ttcaaggttt ccgagtgtgt  11940
tgcaaaagac ttccctgagc agcaacctgg tgaaggtaag tgtcctctga cccattatgt  12000
catatttact ttataattat atccttaaca atatgattaa agattaacac caaattatat  12060
```

```
acatacatat gttaaaattt taaatgtcaa ataattcaga tgtttagaat gcatccctaa  12120

gacggccagt gcaggctcgt acgatgcata cgaaaaccta tccctagtgt tcgcttcgaa  12180

ttaatgccga cagtttaaac tactgcatct gcaatctata gagacaaaaa cactatgaaa  12240

atagtaga                                                           12248


<210> SEQ ID NO 2
<211> LENGTH: 763
<212> TYPE: DNA
<213> ORGANISM: Artificial Sequence
<220> FEATURE:
<223> OTHER INFORMATION: is a nucleotide sequence of event MON 87411
<220> FEATURE:
<221> NAME/KEY: misc_feature
<222> LOCATION: (1)..(500)
<223> OTHER INFORMATION: represents the genomic DNA flanking the left
      border of the TDNA
<220> FEATURE:
<221> NAME/KEY: misc_feature
<222> LOCATION: (501)..(763)
<223> OTHER INFORMATION: left border remnant

<400> SEQUENCE: 2

ccctagcgtt gggcccaact agtcagtctg ccttccctcc cagtcgctga cctccttggt     60

ccacttgtca gctttcgcgc tcagatctaa tctcaactgt cgatctgtga tcgggtggcc    120

gagatcaccc gatgcccgtt cgtttgcaaa agttgttaaa agaccctctg tttcttagaa    180

aataacctac attcatgttt cttgcgatta ggcccctggt ttcttgtaga gaagcccctt    240

gctttatttt aatcacaaaa ataaatctaa tttagtgttt tgaattctaa aacttgtgaa    300

tttcatatct tttgcatatg aactctaaat tgggtggttt aaattgcaaa atgatcataa    360

tattattctc tatctgttta aattataata tttcactgtc tacatgtatg tattttatga    420

ctagacaata ggttcattta aagtgatgga ttatttatta aaaggaaaat aaaaaggcaa    480

aacactaatg aatagttaag tggcttcatg tccgggaaat ctacatggat cagcaatgag    540

tatgatggtc aatatggaga aaaagaaaga gtaattacca atttttttc aattcaaaaa    600

tgtagatgtc cgcagcgtta ttataaaatg aaagtacatt ttgataaaac gacaaattac    660

gatccgtcgt atttataggc gaaagcaata aacaaattat tctaattcgg aaatctttat    720

ttcgacgtgt ctacattcac gtccaaatgg gggcttagat gag                      763


<210> SEQ ID NO 3
<211> LENGTH: 515
<212> TYPE: DNA
<213> ORGANISM: Artificial Sequence
<220> FEATURE:
<223> OTHER INFORMATION: is a nucleotide sequence of event MON 87411
<220> FEATURE:
<221> NAME/KEY: misc_feature
<222> LOCATION: (1)..(15)
<223> OTHER INFORMATION: right border remnant
<220> FEATURE:
<221> NAME/KEY: misc_feature
<222> LOCATION: (16)..(515)
<223> OTHER INFORMATION: represents the genomic DNA flanking the right
      border of the TDNA

<400> SEQUENCE: 3

aaactatcag tgtttagaga atcacaaacc tctagatgta ttaatctacc ctagaactag     60

ttcacttttg tgtgcatact tttctattga actggtgttc actttgttgc atatgttttg    120

tgtactgttt atttgtcatt gcccaaatgt gtttaatgag tgattgcttt gcgtagacaa    180
```

-continued

```
cgagcagttc aaggtttccg agtgtgttgc aaaagacttc cctgagcagc aacctggtga    240

aggtaagtgt cctctgaccc attatgtcat atttacttta taattatatc cttaacaata    300

tgattaaaga ttaacaccaa attatataca tacatatgtt aaaattttaa atgtcaaata    360

attcagatgt ttagaatgca tccctaagac ggccagtgca ggctcgtacg atgcatacga    420

aaacctatcc ctagtgttcg cttcgaatta atgccgacag tttaaactac tgcatctgca    480

atctatagag acaaaaacac tatgaaaata gtaga                               515
```

```
<210> SEQ ID NO 4
<211> LENGTH: 11248
<212> TYPE: DNA
<213> ORGANISM: Artificial Sequence
<220> FEATURE:
<223> OTHER INFORMATION: is a nucleotide sequence of Event MON 87411,
      and represents the TDNA of event MON 87411
<220> FEATURE:
<221> NAME/KEY: misc_feature
<222> LOCATION: (1)..(263)
<223> OTHER INFORMATION: left border remnant
<220> FEATURE:
<221> NAME/KEY: promoter
<222> LOCATION: (2086)..(4034)
<223> OTHER INFORMATION: Corn PIIG promoter
<220> FEATURE:
<221> NAME/KEY: promoter
<222> LOCATION: (2448)..(3059)
<223> OTHER INFORMATION: represents the reverse complement sequence of
      an enhanced CaMV 35S promoter
<220> FEATURE:
<221> NAME/KEY: promoter
<222> LOCATION: (2448)..(4034)
<223> OTHER INFORMATION: represents a divergent promoter region that
      promotes bidirectional transcription
<220> FEATURE:
<221> NAME/KEY: misc_feature
<222> LOCATION: (11233)..(11248)
<223> OTHER INFORMATION: right border remnant

<400> SEQUENCE: 4

tggcttcatg tccgggaaat ctacatggat cagcaatgag tatgatggtc aatatggaga     60

aaaagaaaga gtaattacca attttttttc aattcaaaaa tgtagatgtc cgcagcgtta    120

ttataaaatg aaagtacatt ttgataaaac gacaaattac gatccgtcgt atttataggc    180

gaaagcaata aacaaattat tctaattcgg aaatctttat ttcgacgtgt ctacattcac    240

gtccaaatgg gggcttagat gagaaacttc acgatcgatg cggccaccac tcgaggtcga    300

ggtaccgttg tcaatcaatt ggcaagtcat aaaatgcatt aaaaaatatt ttcatactca    360

actacaaatc catgagtata actataatta taaagcaatg attagaatct gacaaggatt    420

ctggaaaatt acataaagga aagttcataa atgtctaaaa cacaagagga catacttgta    480

ttcagtaaca tttgcagctt ttctaggtct gaaaatatat ttgttgccta gtgaataagc    540

ataatggtac aactacaagt gttttactcc tcatattaac ttcggtcatt agaggccacg    600

atttgacaca tttttactca aaacaaaatg tttgcatatc tcttataatt tcaaattcaa    660

cacacaacaa ataagagaaa aaacaaataa tattaatttg agaatgaaca aaaggaccat    720

atcattcatt aactcttctc catccatttc catttcacag ttcgatagcg aaaaccgaat    780

aaaaaacaca gtaaattaca agcacaacaa atggtacaag aaaaacagtt ttcccaatgc    840

cataatactc aaactcagta ggattctggt gtgtgcgcaa tgaaactgat gcattgaact    900

tgacgaacgt tgtcgaaacc gatgatacga acgaaagcta ggcctcagcg agtaccgctg    960

gcgatctaat ccatgatatc gtgaacatca tctacattca aattcttatg agctttctta   1020
```

-continued

```
agggcatctg cagcattttt catagaatct aatacagcag tatttgtgct agctccttcg   1080
agggcttccc tctgcatttc aatagttgta agggttccat ctatttgtag ttgggtcttt   1140
tccaatcgtt tcttcttttt gagggcttgg agtgcaactc ttttattttt cgacgcattt   1200
ttctttgcgc tcctgcaggc ggccgcgtgg atgaggagtt aatcggtcgt gtgagagtag   1260
tgatcgagtg gatgtcgtcg agagtgatga gtgttgatgt tgttagtgat atgtggtaga   1320
aggtatcgtg ataaagcgtt aacgcgatcg cagtacttgc aaagaaaaat gcgtcgaaaa   1380
ataaaagagt tgcactccaa gccctcaaaa agaagaaacg attggaaaag acccaactac   1440
aaatagatgg aacccttaca actattgaaa tgcagaggga agccctcgaa ggagctagca   1500
caaatactgc tgtattagat tctatgaaaa atgctgcaga tgcccttaag aaagctcata   1560
agaatttgaa tgtagatgat gttcacgata tcatggatgg tatcgcacag cgactgctga   1620
gggacgtcga gctcccgctt ggtatctgca ttacaatgaa atgagcaaag actatgtgag   1680
taacactggt caacactagg gagaaggcat cgagcaagat acgtatgtaa agagaagcaa   1740
tatagtgtca gttggtagat actagatacc atcaggaggt aaggagagca acaaaaagga   1800
aactctttat ttttaaattt tgttacaaca aacaagcaga tcaatgcatc aaaatactgt   1860
cagtacttat ttcttcagac aacaatattt aaaacaagtg catctgatct tgacttatgg   1920
tcacaataaa ggagcagaga taaacatcaa aatttcgtca tttatattta ttccttcagg   1980
cgttaacaat ttaacagcac acaaacaaaa acagaatagg aatatctaat tttggcaaat   2040
aataagctct gcagacgaac aaattattat agtatcgcct ataaatatgaa tccctatact   2100
attgacccat gtagtatgaa gcctgtgcct aaattaacag caaacttctg aatccaagtg   2160
ccctataaca ccaacatgtg cttaaataaa taccgctaag caccaaatta cacatttctc   2220
gtattgctgt gtaggttcta tcttcgtttc gtactaccat gtccctatat tttgctgcta   2280
caaaggacgg caagtaatca gcacaggcag aacacgattt cagagtgtaa ttctagatcc   2340
agctaaacca ctctcagcaa tcaccacaca agagagcatt cagagaaacg tggcagtaac   2400
aaaggcagag ggcggagtga gcgcgtaccg aagacggttc agcgtgtcct ctccaaatga   2460
aatgaacttc cttatataga ggaagggtct tgcgaaggat agtgggattg tgcgtcatcc   2520
cttacgtcag tggagatatc acatcaatcc acttgctttg aagacgtggt tggaacgtct   2580
tctttttcca cgatgctcct cgtgggtggg ggtccatctt tgggaccact gtcggcagag   2640
gcatcttcaa cgatggcctt tcctttatcg caatgatggc atttgtagga gccaccttcc   2700
ttttccacta tcttcacaat aaagtgacag atagctgggc aatggaatcc gaggaggttt   2760
ccggatatta ccctttgttg aaaagtctca atcggaccat cacatcaatc cacttgcttt   2820
gaagacgtgg ttggaacgtc ttctttttcc acgatgctcc tcgtgggtgg gggtccatct   2880
ttgggaccac tgtcggcaga ggcatcttca acgatggcct ttcctttatc gcaatgatgg   2940
catttgtagg agccaccttc cttttccact atcttcacaa taaagtgaca gatagctggg   3000
caatggaatc cgaggaggtt tccggatatt accctttgtt gaaaagtctc aatcggacct   3060
gcagcctgca ggctagcggc gcgccacaaa tcacaggcca tgaaccctac tcatgcttcg   3120
atttgtccaa cacacactta ccaaaactca aatcatgtcc ttgacagtca ctcgggactc   3180
ataacatggg tacgtatcga ctatgtcaac tatatgtgtt ctcatcagat tatagattgg   3240
cctagtacgt agtgatattt ccactagcac tgtggttatg gctgtacctg atagtgatat   3300
cagcaccggg tcatggctct actaccaggt agtgagagtg acctttatac tgtcagactg   3360
taactaagga tttccaatca ctgttcggat cctaggctta gaattaagta aaactctatc   3420
```

-continued

```
actataggct gcagcacact cggtatatat tgatgggcca acagaaattg tgcgtactat   3480
gcgcgatgta aaatggacat aaaccctacc catatacaat gcaataactt ttgtccggtc   3540
tgggccaccg gttagcagag gtcctgattt cggtggtagt ggtagcttga tctggtcgtc   3600
gtatcgtaga gggatatata aaatcatgtc acttttgaag ggagcgctca cagaaataat   3660
aggtattcgc gggagccgcc cccgcagaac acaaaataag gcgagcacgc acacgcatca   3720
gtttcgataa aataataata gcgccagctg atcggaacaa ttccagctag cactaatgta   3780
tttctgcatt gatctgttta tacaacatgc tacctcgttg agtgattttg acatgatttg   3840
tcaacttgct ccgatcctat atctcgatcg atctccacat gacgatggtt gttgtcctgt   3900
atcccatgac aaccaggcaa cgctcaaagc acacatgcgt tgccgattac ccgtgcatgc   3960
cgccaagcac gaaagcacct ccctccacac cgtccatcag ctataaaaac catgccaagc   4020
accctgtgaa aagccccggg aaccatcttc cacacactca agccacacta ttggagaaca   4080
cacagggaca acacaccata agatccaagg gaggcctccg ccgccgccgg taaccacccc   4140
gcccctctcc tctttctttc tccgtttttt tttccgtctc ggtctcgatc tttggccttg   4200
gtagtttggg tgggcgagag gcggcttcgt gcgcgcccag atcggtgcgc gggaggggcg   4260
ggatctcgcg gctggggctc tcgccggcgt ggatccggcc cggatctcgc ggggaatggg   4320
gctctcggat gtagatctgc gatccgccgt tgttggggga gatgatgggg ggtttaaaat   4380
ttccgccgtg ctaaacaaga tcaggaagag gggaaaaggg cactatggtt tatattttta   4440
tatatttctg ctgcttcgtc aggcttagat gtgctagatc tttctttctt ctttttgtgg   4500
gtagaatttg aatccctcag cattgttcat cggtagtttt tcttttcatg atttgtgaca   4560
aatgcagcct cgtgcggagc ttttttgtag gtagaagtga tcaaccatgg ccaaccccaa   4620
caatcgctcc gagcacgaca cgatcaaggt cacccccaac tccgagctcc agaccaacca   4680
caaccagtac ccgctggccg acaaccccaa ctccaccctg gaagagctga actacaagga   4740
gttcctgcgc atgaccgagg actcctccac ggaggtcctg gacaactcca ccgtcaagga   4800
cgccgtcggg accggcatct ccgtcgttgg gcagatcctg ggcgtcgttg gcgtcccctt   4860
cgcaggtgct ctcacctcct tctaccagtc cttcctgaac accatctggc cctccgacgc   4920
cgacccctgg aaggccttca tggcccaagt cgaagtcctg atcgacaaga agatcgagga   4980
gtacgccaag tccaaggccc tggccgagct gcaaggcctg caaaacaact tcgaggacta   5040
cgtcaacgcg ctgaactcct ggaagaagac gcctctgtcc ctgcgctcca agcgctccca   5100
ggaccgcatc cgcgagctgt tctcccaggc cgagtcccac ttccgcaact ccatgccgtc   5160
cttcgccgtc tccaagttcg aggtcctgtt cctgcccacc tacgcccagg ctgccaacac   5220
ccacctcctg ttgctgaagg acgcccaggt cttcggcgag gaatggggct actcctcgga   5280
ggacgtcgcc gagttctacc gtcgccagct gaagctgacc caacagtaca ccgaccactg   5340
cgtcaactgg tacaacgtcg gcctgaacgg cctgaggggc tccacctacg acgcatgggt   5400
caagttcaac cgcttccgca gggagatgac cctgaccgtc ctggacctga tcgtcctgtt   5460
ccccttctac gacatccgcc tgtactccaa gggcgtcaag accgagctga cccgcgacat   5520
cttcacggac cccatcttcc tgctcacgac cctccagaag tacggtccca ccttcctgtc   5580
catcgagaac tccatccgca agccccacct gttcgactac ctccagggca tcgagttcca   5640
cacgcgcctg aggccaggct acttcggcaa ggactccttc aactactggt ccggcaacta   5700
cgtcgagacc aggccctcca tcggctcctc gaagacgatc acctcccctt tctacggcga   5760
```

-continued caagtccacc gagcccgtcc agaagctgtc cttcgacggc cagaaggtct accgcaccat 5820
cgccaacacc gacgtcgcgg cttggccgaa cggcaaggtc tacctgggcg tcacgaaggt 5880
cgacttctcc cagtacgatg accagaagaa cgagacctcc acccagacct acgactccaa 5940
gcgcaacaat ggccacgtct ccgcccagga ctccatcgac cagctgccgc ctgagaccac 6000
tgacgagccc ctggagaagg cctactccca ccagctgaac tacgcggagt gcttcctgat 6060
gcaagaccgc aggggcacca tccccttctt cacctggacc caccgctccg tcgacttctt 6120
caacaccatc gacgccgaga agatcaccca gctgcccgtg gtcaaggcct acgccctgtc 6180
ctcgggtgcc tccatcattg agggtccagg cttcaccggt ggcaacctgc tgttcctgaa 6240
ggagtcctcg aactccatcg ccaagttcaa ggtcaccctg aactccgctg ccttgctgca 6300
acgctaccgc gtccgcatcc gctacgcctc caccacgaac ctgcgcctgt tcgtccagaa 6360
ctccaacaat gacttcctgg tcatctacat caacaagacc atgaacaagg acgatgacct 6420
gacctaccag accttcgacc tcgccaccac gaactccaac atgggcttct cgggcgacaa 6480
gaatgaactg atcattggtg ctgagtcctt cgtctccaac gagaagatct acatcgacaa 6540
gatcgagttc atccccgtcc agctgtgata ggaactctga ttgaattctg catgcgtttg 6600
gacgtatgct cattcaggtt ggagccaatt tggttgatgt gtgtgcgagt tcttgcgagt 6660
ctgatgagac atctctgtat tgtgtttctt tccccagtgt tttctgtact tgtgtaatcg 6720
gctaatcgcc aacagattcg gcgatgaata aatgagaaat aaattgttct gattttgagt 6780
gcaaaaaaaa aggaattaga tctgtgtgtg tttttttggat cccattttcg acaagcttgc 6840
ctcgagacaa caacatgctt ctcatcaaca tggagggaag agggagggag aaagtgtcgc 6900
ctggtcacct ccattgtcac actagccact ggccagctct cccacaccac caatgccagg 6960
ggcgagcttt agcacagcca ccgcttcacc tccaccaccg cactacccta gcttcgccca 7020
acagccaccg tcaacgcctc ctctccgtca acataagaga gagagagaag aggagagtag 7080
ccatgtgggg aggaggaata gtacatgggg cctaccgttt ggcaagttat tttgggttgc 7140
caagttaggc caataagggg agggatttgg ccatccggtt ggaaaggtta ttggggtagt 7200
atctttttac tagaattgtc aaaaaaaaat agtttgagag ccatttggag aggatgttgc 7260
ctgttagagg tgctcttagg acatcaaatt ccataaaaac atcagaaaaa ttctctcgat 7320
gaagatttat aaccactaaa actgccctca attcgaaggg agttcaaaac aattaaaatc 7380
atgttcgaat tgagtttcaa tttcacttta accccttga aatctcaatg gtaaaacatc 7440
aacccgtcag gtagcatggt tctttttatt cctttcaaaa agagttaatt acaaacagaa 7500
tcaaaactaa cagttaggcc caaggcccat ccgagcaaac aatagatcat gggccaggcc 7560
tgccaccacc ctccccctcc tggctcccgc tcttgaattt caaaatccaa aaatatcggc 7620
acgactggcc gccgacggag cgggcggaaa atgacggaac aacccctcga attctacccc 7680
aactacgccc accaacccac acgccactga caatccggtc ccacccttgt gggcccacct 7740
acaagcgaga cgtcagtcgc tcgcagcaac cagtgggccc acctcccagt gagcggcggg 7800
tagatctgga ctcttaccca cccacactaa acaaaacggc atgaatattt tgcactaaaa 7860
ccctcagaaa aattccgata ttccaaacca gtacagttcc tgaccgttgg aggagccaaa 7920
gtggagcgga gtgtaaaatt gggaaactta atcgaggggg ttaaacgcaa aaacgccgag 7980
gcgcctcccg ctctatagaa aggggaggag tgggaggtgg aaaccctacc acaccgcaga 8040
gaaaggcgtc ttcgtactcg cctctctccg cgccctcctc cgccgccgct cgccgccgtt 8100
cgtctccgcc gccaccggct agccatccag gtaaaacaaa caaaaacgga tctgatgctt 8160

```
ccattcctcc gtttctcgta gtagcgcgct tcgatctgtg ggtggatctg ggtgatcctg   8220
gggtgtggtt cgttctgttt gatagatctg tcggtggatc tggccttctg tggttgtcga   8280
tgtccggatc tgcgttttga tcagtggtag ttcgtggatc tggcgaaatg ttttggatct   8340
ggcagtgaga cgctaagaat cgggaaatga tgcaatatta ggggggtttc ggatggggat   8400
ccactgaatt agtctgtctc cctgctgata atctgttcct ttttggtaga tctggttagt   8460
gtatgtttgt ttcggataga tctgatcaat gcttgtttgt tttttcaaat tttctaccta   8520
ggttgtatag gaatggcatg cggatctggt tggattgcca tgatccgtgc tgaaatgccc   8580
ctttggttga tggatcttga tattttactg ctgttcacct agatttgtac tcccgtttat   8640
acttaatttg ttgcttatta tgaatagatc tgtaacttag gcacatgtat ggacggagta   8700
tgtggatctg tagtatgtac attgctgcga gctaagaact atttcagagc aagcacagaa   8760
aaaaatattt agacagattg ggcaactatt tgatggtctt tggtatcatg ctttgtagtg   8820
ctcgtttctg cgtagtaatc ttttgatctg atctgaagat aggtgctatt atattcttaa   8880
aggtcattag aacgctatct gaaaggctgt attatgtgga ttggttcacc tgtgactccc   8940
tgttcgtctt gtcttgataa atcctgtgat aaaaaaaatt cttaaggcgt aatttgttga   9000
aatcttgttt tgtcctatgc agcctgatcc atggcgcaag ttagcagaat ctgcaatggt   9060
gtgcagaacc catctcttat ctccaatctc tcgaaatcca gtcaacgcaa atctccctta   9120
tcggtttctc tgaagacgca gcagcatcca cgagcttatc cgatttcgtc gtcgtgggga   9180
ttgaagaaga gtgggatgac gttaattggc tctgagcttc gtcctcttaa ggtcatgtct   9240
tctgtttcca cggcgtgcat gcttcacggt gcaagcagcc ggcccgcaac cgcccgcaaa   9300
tcctctggcc tttccggaac cgtccgcatt cccggcgaca agtcgatctc ccaccggtcc   9360
ttcatgttcg gcggtctcgc gagcggtgaa acgcgcatca ccggccttct ggaaggcgag   9420
gacgtcatca atacgggcaa ggccatgcag gcgatgggcg cccgcatccg taaggaaggc   9480
gacacctgga tcatcgatgg cgtcggcaat ggcggcctcc tggcgcctga ggcgccgctc   9540
gatttcggca atgccgccac gggctgccgc ctgacgatgg gcctcgtcgg ggtctacgat   9600
ttcgacagca ccttcatcgg cgacgcctcg ctcacaaagc gcccgatggg ccgcgtgttg   9660
aacccgctgc gcgaaatggg cgtgcaggtg aaatcggaag acggtgaccg tcttcccgtt   9720
accttgcgcg ggccgaagac gccgacgccg atcacctacc gcgtgccgat ggcctccgca   9780
caggtgaagt ccgccgtgct gctcgccggc ctcaacacgc ccggcatcac gacggtcatc   9840
gagccgatca tgacgcgcga tcatacggaa aagatgctgc agggctttgg cgccaacctt   9900
accgtcgaga cggatgcgga cggcgtgcgc accatccgcc tggaaggccg cggcaagctc   9960
accggccaag tcatcgacgt gccgggcgac ccgtcctcga cggccttccc gctggttgcg  10020
gccctgcttg ttccgggctc cgacgtcacc atcctcaacg tgctgatgaa ccccacccgc  10080
accggcctca tcctgacgct gcaggaaatg ggcgccgaca tcgaagtcat caacccgcgc  10140
cttgccggcg gcgaagacgt ggcggacctg cgcgttcgct cctccacgct gaagggcgtc  10200
acggtgccgg aagaccgcgc gccttcgatg atcgacgaat atccgattct cgctgtcgcc  10260
gccgccttcg cggaaggggc gaccgtgatg aacggtctgg aagaactccg cgtcaaggaa  10320
agcgaccgcc tctcggccgt cgccaatggc ctcaagctca atggcgtgga ttgcgatgag  10380
ggcgagacgt cgctcgtcgt gcgtggccgc cctgacggca aggggctcgg caacgcctcg  10440
ggcgccgccg tcgccaccca tctcgatcac cgcatcgcca tgagcttcct cgtcatgggc  10500
```

-continued

```
ctcgtgtcgg aaaaccctgt cacggtggac gatgccacga tgatcgccac gagcttcccg  10560

gagttcatgg acctgatggc cgggctgggc gcgaagatcg aactctccga tacgaaggct  10620

gcctgatgag ctccagggtt cttgcctggt gccttggcaa tgcttgatta ctgctgctat  10680

cctatgatct gtccgtgtgg gcttctatct atcagtttgt gtgtctggtt ttgaaaaaca  10740

tttgcttttc gattatgtag ggtttgcttg tagctttcgc tgctgtgacc tgtgttgttt  10800

atgtgaacct tctttgtggc atctttaata tccaagttcg tggtttgtcg taaaacgaag  10860

cctctacttc gtaaagttgt gtctatagca ttgaaatcgt ttttttgctc gagaataatt  10920

gtgaccttta gttggcgtga aactagtttt ggatatctga ttctctggtt cgcaatcttg  10980

agatcgtcgc tgcttaggtg agctaagtga tgttcctaag taaatgctcc tcaccagaat  11040

acgtagctgt gtgaaaagag aacgcgtgaa tacgtagctg tgtaaagatt gtgtcccaag  11100

taaacctcag tgatttttgt ttggattttt aatttagaaa cattcgactg ggagcggcta  11160

gagccacacc caagttccta actatgataa agttgctctg taacagaaaa caccatctag  11220

agcggccgcg tttaaactat cagtgttt                                     11248
```

```
<210> SEQ ID NO 5
<211> LENGTH: 313
<212> TYPE: DNA
<213> ORGANISM: Artificial Sequence
<220> FEATURE:
<223> OTHER INFORMATION: is a nucleotide sequence of event MON 87411
<220> FEATURE:
<221> NAME/KEY: misc_feature
<222> LOCATION: (1)..(50)
<223> OTHER INFORMATION: represents the genomic DNA flanking the left
      border of the TDNA
<220> FEATURE:
<221> NAME/KEY: misc_feature
<222> LOCATION: (51)..(313)
<223> OTHER INFORMATION: left border remnant

<400> SEQUENCE: 5

ttatttatta aaaggaaaat aaaaaggcaa aacactaatg aatagttaag tggcttcatg     60

tccgggaaat ctacatggat cagcaatgag tatgatggtc aatatggaga aaaagaaaga    120

gtaattacca attttttttc aattcaaaaa tgtagatgtc cgcagcgtta ttataaaatg    180

aaagtacatt ttgataaaac gacaaattac gatccgtcgt atttataggc gaaagcaata    240

aacaaattat tctaattcgg aaatctttat ttcgacgtgt ctacattcac gtccaaatgg    300

gggcttagat gag                                                       313
```

```
<210> SEQ ID NO 6
<211> LENGTH: 373
<212> TYPE: DNA
<213> ORGANISM: Artificial Sequence
<220> FEATURE:
<223> OTHER INFORMATION: is a nucleotide sequence of event MON 87411
<220> FEATURE:
<221> NAME/KEY: misc_feature
<222> LOCATION: (1)..(110)
<223> OTHER INFORMATION: represents the genomic DNA flanking the left
      border of the TDNA
<220> FEATURE:
<221> NAME/KEY: misc_feature
<222> LOCATION: (111)..(373)
<223> OTHER INFORMATION: left border remnant

<400> SEQUENCE: 6

tttcactgtc tacatgtatg tattttatga ctagacaata ggttcattta aagtgatgga     60

ttatttatta aaaggaaaat aaaaaggcaa aacactaatg aatagttaag tggcttcatg    120
```

```
tccgggaaat ctacatggat cagcaatgag tatgatggtc aatatggaga aaaagaaaga    180

gtaattacca atttttttc aattcaaaaa tgtagatgtc cgcagcgtta ttataaaatg    240

aaagtacatt ttgataaaac gacaaattac gatccgtcgt atttataggc gaaagcaata    300

aacaaattat tctaattcgg aaatctttat ttcgacgtgt ctacattcac gtccaaatgg    360

gggcttagat gag                                                       373


<210> SEQ ID NO 7
<211> LENGTH: 408
<212> TYPE: DNA
<213> ORGANISM: Artificial Sequence
<220> FEATURE:
<223> OTHER INFORMATION: is a nucleotide sequence of event MON 87411
<220> FEATURE:
<221> NAME/KEY: misc_feature
<222> LOCATION: (1)..(145)
<223> OTHER INFORMATION: represents the genomic DNA flanking the left
      border of the TDNA
<220> FEATURE:
<221> NAME/KEY: misc_feature
<222> LOCATION: (146)..(408)
<223> OTHER INFORMATION: left border remnant

<400> SEQUENCE: 7

cataatatta ttctctatct gtttaaatta taatatttca ctgtctacat gtatgtattt     60

tatgactaga caataggttc atttaaagtg atggattatt tattaaaagg aaaataaaaa    120

ggcaaaacac taatgaatag ttaagtggct tcatgtccgg gaaatctaca tggatcagca    180

atgagtatga tggtcaatat ggagaaaaag aaagagtaat taccaatttt ttttcaattc    240

aaaaatgtag atgtccgcag cgttattata aaatgaaagt acattttgat aaaacgacaa    300

attacgatcc gtcgtattta taggcgaaag caataaacaa attattctaa ttcggaaatc    360

tttatttcga cgtgtctaca ttcacgtcca aatgggggct tagatgag                 408


<210> SEQ ID NO 8
<211> LENGTH: 117
<212> TYPE: DNA
<213> ORGANISM: Artificial Sequence
<220> FEATURE:
<223> OTHER INFORMATION: is a nucleotide sequence of event MON 87411
<220> FEATURE:
<221> NAME/KEY: misc_feature
<222> LOCATION: (69)..(83)
<223> OTHER INFORMATION: right border remnant
<220> FEATURE:
<221> NAME/KEY: misc_feature
<222> LOCATION: (84)..(117)
<223> OTHER INFORMATION: represents the genomic DNA flanking the right
      border of the TDNA

<400> SEQUENCE: 8

acacccaagt tcctaactat gataaagttg ctctgtaaca gaaaacacca tctagagcgg     60

ccgcgtttaa actatcagtg tttagagaat cacaaacctc tagatgtatt aatctac       117


<210> SEQ ID NO 9
<211> LENGTH: 173
<212> TYPE: DNA
<213> ORGANISM: Artificial Sequence
<220> FEATURE:
<223> OTHER INFORMATION: is a nucleotide sequence of event MON 87411
<220> FEATURE:
<221> NAME/KEY: misc_feature
<222> LOCATION: (69)..(83)
<223> OTHER INFORMATION: right border remnant
<220> FEATURE:
```

-continued

<221> NAME/KEY: misc_feature
<222> LOCATION: (84)..(173)
<223> OTHER INFORMATION: represents the genomic DNA flanking the right
      border of the TDNA

<400> SEQUENCE: 9
acacccaagt tcctaactat gataaagttg ctctgtaaca gaaaacacca tctagagcgg 60
ccgcgtttaa actatcagtg tttagagaat cacaaacctc tagatgtatt aatctaccct 120
agaactagtt cacttttgtg tgcatacttt tctattgaac tggtgttcac ttt 173

<210> SEQ ID NO 10
<211> LENGTH: 338
<212> TYPE: DNA
<213> ORGANISM: Artificial Sequence
<220> FEATURE:
<223> OTHER INFORMATION: is a nucleotide sequence of event MON 87411
<220> FEATURE:
<221> NAME/KEY: misc_feature
<222> LOCATION: (69)..(83)
<223> OTHER INFORMATION: right border remnant
<220> FEATURE:
<221> NAME/KEY: misc_feature
<222> LOCATION: (84)..(338)
<223> OTHER INFORMATION: represents the genomic DNA flanking the right
      border of the TDNA

<400> SEQUENCE: 10
acacccaagt tcctaactat gataaagttg ctctgtaaca gaaaacacca tctagagcgg 60
ccgcgtttaa actatcagtg tttagagaat cacaaacctc tagatgtatt aatctaccct 120
agaactagtt cacttttgtg tgcatacttt tctattgaac tggtgttcac tttgttgcat 180
atgttttgtg tactgtttat ttgtcattgc ccaaatgtgt ttaatgagtg attgctttgc 240
gtagacaacg agcagttcaa ggtttccgag tgtgttgcaa aagacttccc tgagcagcaa 300
cctggtgaag gtaagtgtcc tctgacccat tatgtcat 338

<210> SEQ ID NO 11
<211> LENGTH: 663
<212> TYPE: DNA
<213> ORGANISM: Diabrotica virgifera virgifera
<220> FEATURE:
<221> NAME/KEY: misc_feature
<222> LOCATION: (1)..(660)
<223> OTHER INFORMATION: Dv_Snf7o ORF encoding a putative ESCRT-III
      complex subunit from Diabrotica virgifera

<400> SEQUENCE: 11
atgagctttt ttggaaaatt gttcgggggg aaaaaggaag agatagcccc tagtcctggg 60
gaggctattc aaaaactcag agagactgaa gaaatgttaa taaaaaaaca ggatttttta 120
gaaaagaaga tagaagaatt taccatggta gcaaagaaaa atgcgtcgaa aaataaaaga 180
gttgcactcc aagccctcaa aaagaagaaa cgattggaaa agacccaact acaaatagat 240
ggaaccctta caactattga aatgcagagg gaagccctcg aaggagctag cacaaatact 300
gctgtattag attctatgaa aaatgctgca gatgccctta agaaagctca taagaatttg 360
aatgtagatg atgttcacga tatcatggat gacatagccg aacaacacga catagccaac 420
gaaatcacaa acgctattag caatcctgtc ggattcaccg acgatctgga tgacgatgaa 480
ttagaaaaag aattagaaga gctcgaacaa gaaggattgg aagaagacct gctccaagtg 540
ccaggtccaa ctcaactgcc ggctgtgcct gctgatgcag ttgctactaa accaatcaaa 600
ccagcagcta aaaaagttga agatgatgac gatatgaaag aattggaagc ctgggcctcg 660
taa 663

<210> SEQ ID NO 12
<211> LENGTH: 2753
<212> TYPE: DNA
<213> ORGANISM: Artificial Sequence
<220> FEATURE:
<223> OTHER INFORMATION: is a nucleotide sequence representing the antisense strand of an inverted repeat RNA expression cassette
<220> FEATURE:
<221> NAME/KEY: 3'UTR
<222> LOCATION: (1)..(633)
<223> OTHER INFORMATION: Ps.RbcS2-E9 3' UTR antisense strand
<220> FEATURE:
<221> NAME/KEY: misc_feature
<222> LOCATION: (663)..(902)
<223> OTHER INFORMATION: inverted repeat Dv_Snf7o arm
<220> FEATURE:
<221> NAME/KEY: misc_feature
<222> LOCATION: (903)..(1052)
<223> OTHER INFORMATION: inverted repeat loop
<220> FEATURE:
<221> NAME/KEY: misc_feature
<222> LOCATION: (1053)..(1292)
<223> OTHER INFORMATION: inverted repeat Dv_Snf7o arm
<220> FEATURE:
<221> NAME/KEY: Intron
<222> LOCATION: (1329)..(2132)
<223> OTHER INFORMATION: Corn DnaK intron antisense strand
<220> FEATURE:
<221> NAME/KEY: misc_feature
<222> LOCATION: (2133)..(2141)
<223> OTHER INFORMATION: CaMV 35S leader antisense strand
<220> FEATURE:
<221> NAME/KEY: promoter
<222> LOCATION: (2142)..(2753)
<223> OTHER INFORMATION: represents the reverse complement sequence of an enhanced CaMV 35S promoter

<400> SEQUENCE: 12
gttgtcaatc aattggcaag tcataaaatg cattaaaaaa tattttcata ctcaactaca 60
aatccatgag tataactata attataaagc aatgattaga atctgacaag gattctggaa 120
aattacataa aggaaagttc ataaatgtct aaaacacaag aggacatact tgtattcagt 180
aacatttgca gcttttctag gtctgaaaat atatttgttg cctagtgaat aagcataatg 240
gtacaactac aagtgtttta ctcctcatat taacttcggt cattagaggc cacgatttga 300
cacattttta ctcaaaacaa aatgtttgca tatctcttat aatttcaaat tcaacacaca 360
acaaataaga gaaaaaacaa ataatattaa tttgagaatg aacaaaagga ccatatcatt 420
cattaactct tctccatcca tttccatttc acagttcgat agcgaaaacc gaataaaaaa 480
cacagtaaat tacaagcaca acaaatggta caagaaaaac agttttccca atgccataat 540
actcaaactc agtaggattc tggtgtgtgc gcaatgaaac tgatgcattg aacttgacga 600
acgttgtcga aaccgatgat acgaacgaaa gctaggcctc agcgagtacc gctggcgatc 660
taatccatga tatcgtgaac atcatctaca ttcaaattct tatgagcttt cttaagggca 720
tctgcagcat ttttcataga atctaataca gcagtatttg tgctagctcc ttcgagggct 780
tccctctgca tttcaatagt tgtaagggtt ccatctattt gtagttgggt cttttccaat 840
cgtttcttct ttttgagggc ttggagtgca actcttttat ttttcgacgc atttttcttt 900
gcgctcctgc aggcggccgc gtggatgagg agttaatcgg tcgtgtgaga gtagtgatcg 960
agtggatgtc gtcgagagtg atgagtgttg atgttgttag tgatatgtgg tagaaggtat 1020
cgtgataaag cgttaacgcg atcgcagtac ttgcaaagaa aaatgcgtcg aaaaataaaa 1080
gagttgcact ccaagccctc aaaaagaaga aacgattgga aaagacccaa ctacaaatag 1140
atggaaccct tacaactatt gaaatgcaga gggaagccct cgaaggagct agcacaaata 1200
ctgctgtatt agattctatg aaaaatgctg cagatgccct taagaaagct cataagaatt 1260
tgaatgtaga tgatgttcac gatatcatgg atggtatcgc acagcgactg ctgagggacg 1320
tcgagctccc gcttggtatc tgcattacaa tgaaatgagc aaagactatg tgagtaacac 1380
tggtcaacac tagggagaag gcatcgagca agatacgtat gtaaagagaa gcaatatagt 1440
gtcagttggt agatactaga taccatcagg aggtaaggag agcaacaaaa aggaaactct 1500
ttatttttaa attttgttac aacaaacaag cagatcaatg catcaaaata ctgtcagtac 1560
ttatttcttc agacaacaat atttaaaaca agtgcatctg atcttgactt atggtcacaa 1620
taaaggagca gagataaaca tcaaaatttc gtcatttata tttattcctt caggcgttaa 1680
caatttaaca gcacacaaac aaaaacagaa taggaatatc taattttggc aaataataag 1740
ctctgcagac gaacaaatta ttatagtatc gcctataata tgaatcccta tactattgac 1800
ccatgtagta tgaagcctgt gcctaaatta acagcaaact tctgaatcca agtgccctat 1860
aacaccaaca tgtgcttaaa taaataccgc taagcaccaa attacacatt tctcgtattg 1920
ctgtgtaggt tctatcttcg tttcgtacta ccatgtccct atattttgct gctacaaagg 1980
acggcaagta atcagcacag gcagaacacg atttcagagt gtaattctag atccagctaa 2040
accactctca gcaatcacca cacaagagag cattcagaga aacgtggcag taacaaaggc 2100
agagggcgga gtgagcgcgt accgaagacg gttcagcgtg tcctctccaa atgaaatgaa 2160
cttccttata tagaggaagg gtcttgcgaa ggatagtggg attgtgcgtc atcccttacg 2220
tcagtggaga tatcacatca atccacttgc tttgaagacg tggttggaac gtcttctttt 2280
tccacgatgc tcctcgtggg tgggggtcca tctttgggac cactgtcggc agaggcatct 2340
tcaacgatgg cctttccttt atcgcaatga tggcatttgt aggagccacc ttccttttcc 2400
actatcttca caataaagtg acagatagct gggcaatgga atccgaggag gtttccggat 2460
attacccttt gttgaaaagt ctcaatcgga ccatcacatc aatccacttg ctttgaagac 2520
gtggttggaa cgtcttcttt ttccacgatg ctcctcgtgg gtgggggtcc atctttggga 2580
ccactgtcgg cagaggcatc ttcaacgatg gcctttcctt tatcgcaatg atggcatttg 2640
taggagccac cttccttttc cactatcttc acaataaagt gacagatagc tgggcaatgg 2700
aatccgagga ggtttccgga tattaccctt tgttgaaaag tctcaatcgg acc 2753

<210> SEQ ID NO 13
<211> LENGTH: 240
<212> TYPE: RNA
<213> ORGANISM: Artificial Sequence
<220> FEATURE:
<223> OTHER INFORMATION: is a ribonucleotide sequence representing the Dv_Snf7o RNA inverted repeat

<400> SEQUENCE: 13
gcaaagaaaa augcgucgaa aaauaaaaga guugcacucc aagcccucaa aaagaagaaa 60
cgauuggaaa agacccaacu acaaauagau ggaacccuua caacuauuga aaugcagagg 120
gaagcccucg aaggagcuag cacaaauacu gcuguauuag auucuaugaa aaaugcugca 180
gaugcccuua agaaagcuca uaagaauuug aauguagaug auguucacga uaucauggau 240

<210> SEQ ID NO 14
<211> LENGTH: 3712
<212> TYPE: DNA
<213> ORGANISM: Artificial Sequence

```
<220> FEATURE:
<223> OTHER INFORMATION: is a nucleotide sequence representing the
      sense strand of a DNA expression cassette that includes a
      recombinant gene engineered to encode and express a Cry3Bb protein
<220> FEATURE:
<221> NAME/KEY: promoter
<222> LOCATION: (1)..(949)
<223> OTHER INFORMATION: Corn PIIG promoter
<220> FEATURE:
<221> NAME/KEY: misc_feature
<222> LOCATION: (956)..(1016)
<223> OTHER INFORMATION: Wheat Lhcb1 leader sense strand
<220> FEATURE:
<221> NAME/KEY: Intron
<222> LOCATION: (1033)..(1512)
<223> OTHER INFORMATION: Rice Act1 intron sense strand
<220> FEATURE:
<221> NAME/KEY: CDS
<222> LOCATION: (1522)..(3483)
<223> OTHER INFORMATION: cry3B2 ORF sense strand
<220> FEATURE:
<221> NAME/KEY: 3'UTR
<222> LOCATION: (3503)..(3712)
<223> OTHER INFORMATION: Wheat Hsp17 3' UTR sense strand

<400> SEQUENCE: 14

acaaatcaca ggccatgaac cctactcatg cttcgatttg tccaacacac acttaccaaa     60

actcaaatca tgtccttgac agtcactcgg gactcataac atgggtacgt atcgactatg    120

tcaactatat gtgttctcat cagattatag attggcctag tacgtagtga tatttccact    180

agcactgtgg ttatggctgt acctgatagt gatatcagca ccgggtcatg gctctactac    240

caggtagtga gagtgacctt tatactgtca gactgtaact aaggatttcc aatcactgtt    300

cggatcctag gcttagaatt aagtaaaact ctatcactat aggctgcagc acactcggta    360

tatattgatg ggccaacaga aattgtgcgt actatgcgcg atgtaaaatg gacataaacc    420

ctacccatat acaatgcaat aacttttgtc cggtctgggc caccggttag cagaggtcct    480

gatttcggtg gtagtggtag cttgatctgg tcgtcgtatc gtagagggat atataaaatc    540

atgtcacttt tgaagggagc gctcacagaa ataataggta ttcgcgggag ccgcccccgc    600

agaacacaaa ataaggcgag cacgcacacg catcagtttc gataaaataa taatagcgcc    660

agctgatcgg aacaattcca gctagcacta atgtatttct gcattgatct gtttatacaa    720

catgctacct cgttgagtga ttttgacatg atttgtcaac ttgctccgat cctatatctc    780

gatcgatctc cacatgacga tggttgttgt cctgtatccc atgacaacca ggcaacgctc    840

aaagcacaca tgcgttgccg attacccgtg catgccgcca agcacgaaag cacctccctc    900

cacaccgtcc atcagctata aaaaccatgc caagcaccct gtgaaaagcc ccgggaacca    960

tcttccacac actcaagcca cactattgga gaacacacag ggacaacaca ccataagatc   1020

caagggaggc ctccgccgcc gccggtaacc accccgcccc tctcctcttt ctttctccgt   1080

tttttttcc gtctcggtct cgatctttgg ccttggtagt ttgggtgggc gagaggcggc   1140

ttcgtgcgcg cccagatcgg tgcgcgggag gggcgggatc tcgcggctgg ggctctcgcc   1200

ggcgtggatc cggcccggat ctcgcgggga atggggctct cggatgtaga tctgcgatcc   1260

gccgttgttg ggggagatga tggggggttt aaaatttccg ccgtgctaaa caagatcagg   1320

aagaggggaa aagggcacta tggtttatat ttttatatat ttctgctgct tcgtcaggct   1380

tagatgtgct agatctttct ttcttctttt tgtgggtaga atttgaatcc ctcagcattg   1440

ttcatcggta gtttttcttt tcatgatttg tgacaaatgc agcctcgtgc ggagcttttt   1500

tgtaggtaga agtgatcaac c atg gcc aac ccc aac aat cgc tcc gag cac     1551
                        Met Ala Asn Pro Asn Asn Arg Ser Glu His
```

-continued

```
                        1               5                   10

gac acg atc aag gtc acc ccc aac tcc gag ctc cag acc aac cac aac     1599
Asp Thr Ile Lys Val Thr Pro Asn Ser Glu Leu Gln Thr Asn His Asn
                15                  20                  25

cag tac ccg ctg gcc gac aac ccc aac tcc acc ctg gaa gag ctg aac     1647
Gln Tyr Pro Leu Ala Asp Asn Pro Asn Ser Thr Leu Glu Glu Leu Asn
            30                  35                  40

tac aag gag ttc ctg cgc atg acc gag gac tcc tcc acg gag gtc ctg     1695
Tyr Lys Glu Phe Leu Arg Met Thr Glu Asp Ser Ser Thr Glu Val Leu
        45                  50                  55

gac aac tcc acc gtc aag gac gcc gtc ggg acc ggc atc tcc gtc gtt     1743
Asp Asn Ser Thr Val Lys Asp Ala Val Gly Thr Gly Ile Ser Val Val
    60                  65                  70

ggg cag atc ctg ggc gtc gtt ggc gtc ccc ttc gca ggt gct ctc acc     1791
Gly Gln Ile Leu Gly Val Val Gly Val Pro Phe Ala Gly Ala Leu Thr
75                  80                  85                  90

tcc ttc tac cag tcc ttc ctg aac acc atc tgg ccc tcc gac gcc gac     1839
Ser Phe Tyr Gln Ser Phe Leu Asn Thr Ile Trp Pro Ser Asp Ala Asp
                95                  100                 105

ccc tgg aag gcc ttc atg gcc caa gtc gaa gtc ctg atc gac aag aag     1887
Pro Trp Lys Ala Phe Met Ala Gln Val Glu Val Leu Ile Asp Lys Lys
            110                 115                 120

atc gag gag tac gcc aag tcc aag gcc ctg gcc gag ctg caa ggc ctg     1935
Ile Glu Glu Tyr Ala Lys Ser Lys Ala Leu Ala Glu Leu Gln Gly Leu
        125                 130                 135

caa aac aac ttc gag gac tac gtc aac gcg ctg aac tcc tgg aag aag     1983
Gln Asn Asn Phe Glu Asp Tyr Val Asn Ala Leu Asn Ser Trp Lys Lys
    140                 145                 150

acg cct ctg tcc ctg cgc tcc aag cgc tcc cag gac cgc atc cgc gag     2031
Thr Pro Leu Ser Leu Arg Ser Lys Arg Ser Gln Asp Arg Ile Arg Glu
155                 160                 165                 170

ctg ttc tcc cag gcc gag tcc cac ttc cgc aac tcc atg ccg tcc ttc     2079
Leu Phe Ser Gln Ala Glu Ser His Phe Arg Asn Ser Met Pro Ser Phe
                175                 180                 185

gcc gtc tcc aag ttc gag gtc ctg ttc ctg ccc acc tac gcc cag gct     2127
Ala Val Ser Lys Phe Glu Val Leu Phe Leu Pro Thr Tyr Ala Gln Ala
            190                 195                 200

gcc aac acc cac ctc ctg ttg ctg aag gac gcc cag gtc ttc ggc gag     2175
Ala Asn Thr His Leu Leu Leu Leu Lys Asp Ala Gln Val Phe Gly Glu
        205                 210                 215

gaa tgg ggc tac tcc tcg gag gac gtc gcc gag ttc tac cgt cgc cag     2223
Glu Trp Gly Tyr Ser Ser Glu Asp Val Ala Glu Phe Tyr Arg Arg Gln
    220                 225                 230

ctg aag ctg acc caa cag tac acc gac cac tgc gtc aac tgg tac aac     2271
Leu Lys Leu Thr Gln Gln Tyr Thr Asp His Cys Val Asn Trp Tyr Asn
235                 240                 245                 250

gtc ggc ctg aac ggc ctg agg ggc tcc acc tac gac gca tgg gtc aag     2319
Val Gly Leu Asn Gly Leu Arg Gly Ser Thr Tyr Asp Ala Trp Val Lys
                255                 260                 265

ttc aac cgc ttc cgc agg gag atg acc ctg acc gtc ctg gac ctg atc     2367
Phe Asn Arg Phe Arg Arg Glu Met Thr Leu Thr Val Leu Asp Leu Ile
            270                 275                 280

gtc ctg ttc ccc ttc tac gac atc cgc ctg tac tcc aag ggc gtc aag     2415
Val Leu Phe Pro Phe Tyr Asp Ile Arg Leu Tyr Ser Lys Gly Val Lys
        285                 290                 295

acc gag ctg acc cgc gac atc ttc acg gac ccc atc ttc ctg ctc acg     2463
Thr Glu Leu Thr Arg Asp Ile Phe Thr Asp Pro Ile Phe Leu Leu Thr
    300                 305                 310

acc ctc cag aag tac ggt ccc acc ttc ctg tcc atc gag aac tcc atc     2511
```

-continued

```
Thr Leu Gln Lys Tyr Gly Pro Thr Phe Leu Ser Ile Glu Asn Ser Ile
315                 320                 325                 330

cgc aag ccc cac ctg ttc gac tac ctc cag ggc atc gag ttc cac acg     2559
Arg Lys Pro His Leu Phe Asp Tyr Leu Gln Gly Ile Glu Phe His Thr
                335                 340                 345

cgc ctg agg cca ggc tac ttc ggc aag gac tcc ttc aac tac tgg tcc     2607
Arg Leu Arg Pro Gly Tyr Phe Gly Lys Asp Ser Phe Asn Tyr Trp Ser
            350                 355                 360

ggc aac tac gtc gag acc agg ccc tcc atc ggc tcc tcg aag acg atc     2655
Gly Asn Tyr Val Glu Thr Arg Pro Ser Ile Gly Ser Ser Lys Thr Ile
        365                 370                 375

acc tcc cct ttc tac ggc gac aag tcc acc gag ccc gtc cag aag ctg     2703
Thr Ser Pro Phe Tyr Gly Asp Lys Ser Thr Glu Pro Val Gln Lys Leu
    380                 385                 390

tcc ttc gac ggc cag aag gtc tac cgc acc atc gcc aac acc gac gtc     2751
Ser Phe Asp Gly Gln Lys Val Tyr Arg Thr Ile Ala Asn Thr Asp Val
395                 400                 405                 410

gcg gct tgg ccg aac ggc aag gtc tac ctg ggc gtc acg aag gtc gac     2799
Ala Ala Trp Pro Asn Gly Lys Val Tyr Leu Gly Val Thr Lys Val Asp
                415                 420                 425

ttc tcc cag tac gat gac cag aag aac gag acc tcc acc cag acc tac     2847
Phe Ser Gln Tyr Asp Asp Gln Lys Asn Glu Thr Ser Thr Gln Thr Tyr
            430                 435                 440

gac tcc aag cgc aac aat ggc cac gtc tcc gcc cag gac tcc atc gac     2895
Asp Ser Lys Arg Asn Asn Gly His Val Ser Ala Gln Asp Ser Ile Asp
        445                 450                 455

cag ctg ccg cct gag acc act gac gag ccc ctg gag aag gcc tac tcc     2943
Gln Leu Pro Pro Glu Thr Thr Asp Glu Pro Leu Glu Lys Ala Tyr Ser
    460                 465                 470

cac cag ctg aac tac gcg gag tgc ttc ctg atg caa gac cgc agg ggc     2991
His Gln Leu Asn Tyr Ala Glu Cys Phe Leu Met Gln Asp Arg Arg Gly
475                 480                 485                 490

acc atc ccc ttc ttc acc tgg acc cac cgc tcc gtc gac ttc ttc aac     3039
Thr Ile Pro Phe Phe Thr Trp Thr His Arg Ser Val Asp Phe Phe Asn
                495                 500                 505

acc atc gac gcc gag aag atc acc cag ctg ccc gtg gtc aag gcc tac     3087
Thr Ile Asp Ala Glu Lys Ile Thr Gln Leu Pro Val Val Lys Ala Tyr
            510                 515                 520

gcc ctg tcc tcg ggt gcc tcc atc att gag ggt cca ggc ttc acc ggt     3135
Ala Leu Ser Ser Gly Ala Ser Ile Ile Glu Gly Pro Gly Phe Thr Gly
        525                 530                 535

ggc aac ctg ctg ttc ctg aag gag tcc tcg aac tcc atc gcc aag ttc     3183
Gly Asn Leu Leu Phe Leu Lys Glu Ser Ser Asn Ser Ile Ala Lys Phe
    540                 545                 550

aag gtc acc ctg aac tcc gct gcc ttg ctg caa cgc tac cgc gtc cgc     3231
Lys Val Thr Leu Asn Ser Ala Ala Leu Leu Gln Arg Tyr Arg Val Arg
555                 560                 565                 570

atc cgc tac gcc tcc acc acg aac ctg cgc ctg ttc gtc cag aac tcc     3279
Ile Arg Tyr Ala Ser Thr Thr Asn Leu Arg Leu Phe Val Gln Asn Ser
                575                 580                 585

aac aat gac ttc ctg gtc atc tac atc aac aag acc atg aac aag gac     3327
Asn Asn Asp Phe Leu Val Ile Tyr Ile Asn Lys Thr Met Asn Lys Asp
            590                 595                 600

gat gac ctg acc tac cag acc ttc gac ctc gcc acc acg aac tcc aac     3375
Asp Asp Leu Thr Tyr Gln Thr Phe Asp Leu Ala Thr Thr Asn Ser Asn
        605                 610                 615

atg ggc ttc tcg ggc gac aag aat gaa ctg atc att ggt gct gag tcc     3423
Met Gly Phe Ser Gly Asp Lys Asn Glu Leu Ile Ile Gly Ala Glu Ser
    620                 625                 630
```

```
ttc gtc tcc aac gag aag atc tac atc gac aag atc gag ttc atc ccc     3471
Phe Val Ser Asn Glu Lys Ile Tyr Ile Asp Lys Ile Glu Phe Ile Pro
635                 640                 645                 650

gtc cag ctg tga taggaactct gattgaattc tgcatgcgtt tggacgtatg         3523
Val Gln Leu

ctcattcagg ttggagccaa tttggttgat gtgtgtgcga gttcttgcga gtctgatgag   3583

acatctctgt attgtgtttc tttccccagt gttttctgta cttgtgtaat cggctaatcg   3643

ccaacagatt cggcgatgaa taaatgagaa ataaattgtt ctgattttga gtgcaaaaaa   3703

aaaggaatt                                                            3712


<210> SEQ ID NO 15
<211> LENGTH: 653
<212> TYPE: PRT
<213> ORGANISM: Artificial Sequence
<220> FEATURE:
<223> OTHER INFORMATION: Synthetic Construct

<400> SEQUENCE: 15

Met Ala Asn Pro Asn Asn Arg Ser Glu His Asp Thr Ile Lys Val Thr
1               5                   10                  15

Pro Asn Ser Glu Leu Gln Thr Asn His Asn Gln Tyr Pro Leu Ala Asp
            20                  25                  30

Asn Pro Asn Ser Thr Leu Glu Glu Leu Asn Tyr Lys Glu Phe Leu Arg
        35                  40                  45

Met Thr Glu Asp Ser Ser Thr Glu Val Leu Asp Asn Ser Thr Val Lys
    50                  55                  60

Asp Ala Val Gly Thr Gly Ile Ser Val Val Gly Gln Ile Leu Gly Val
65                  70                  75                  80

Val Gly Val Pro Phe Ala Gly Ala Leu Thr Ser Phe Tyr Gln Ser Phe
                85                  90                  95

Leu Asn Thr Ile Trp Pro Ser Asp Ala Asp Pro Trp Lys Ala Phe Met
            100                 105                 110

Ala Gln Val Glu Val Leu Ile Asp Lys Lys Ile Glu Glu Tyr Ala Lys
        115                 120                 125

Ser Lys Ala Leu Ala Glu Leu Gln Gly Leu Gln Asn Asn Phe Glu Asp
    130                 135                 140

Tyr Val Asn Ala Leu Asn Ser Trp Lys Lys Thr Pro Leu Ser Leu Arg
145                 150                 155                 160

Ser Lys Arg Ser Gln Asp Arg Ile Arg Glu Leu Phe Ser Gln Ala Glu
                165                 170                 175

Ser His Phe Arg Asn Ser Met Pro Ser Phe Ala Val Ser Lys Phe Glu
            180                 185                 190

Val Leu Phe Leu Pro Thr Tyr Ala Gln Ala Ala Asn Thr His Leu Leu
        195                 200                 205

Leu Leu Lys Asp Ala Gln Val Phe Gly Glu Glu Trp Gly Tyr Ser Ser
    210                 215                 220

Glu Asp Val Ala Glu Phe Tyr Arg Arg Gln Leu Lys Leu Thr Gln Gln
225                 230                 235                 240

Tyr Thr Asp His Cys Val Asn Trp Tyr Asn Val Gly Leu Asn Gly Leu
                245                 250                 255

Arg Gly Ser Thr Tyr Asp Ala Trp Val Lys Phe Asn Arg Phe Arg Arg
            260                 265                 270

Glu Met Thr Leu Thr Val Leu Asp Leu Ile Val Leu Phe Pro Phe Tyr
        275                 280                 285
```

-continued

```
Asp Ile Arg Leu Tyr Ser Lys Gly Val Lys Thr Glu Leu Thr Arg Asp
    290                 295                 300

Ile Phe Thr Asp Pro Ile Phe Leu Leu Thr Thr Leu Gln Lys Tyr Gly
305                 310                 315                 320

Pro Thr Phe Leu Ser Ile Glu Asn Ser Ile Arg Lys Pro His Leu Phe
                325                 330                 335

Asp Tyr Leu Gln Gly Ile Glu Phe His Thr Arg Leu Arg Pro Gly Tyr
            340                 345                 350

Phe Gly Lys Asp Ser Phe Asn Tyr Trp Ser Gly Asn Tyr Val Glu Thr
        355                 360                 365

Arg Pro Ser Ile Gly Ser Ser Lys Thr Ile Thr Ser Pro Phe Tyr Gly
    370                 375                 380

Asp Lys Ser Thr Glu Pro Val Gln Lys Leu Ser Phe Asp Gly Gln Lys
385                 390                 395                 400

Val Tyr Arg Thr Ile Ala Asn Thr Asp Val Ala Ala Trp Pro Asn Gly
                405                 410                 415

Lys Val Tyr Leu Gly Val Thr Lys Val Asp Phe Ser Gln Tyr Asp Asp
            420                 425                 430

Gln Lys Asn Glu Thr Ser Thr Gln Thr Tyr Asp Ser Lys Arg Asn Asn
        435                 440                 445

Gly His Val Ser Ala Gln Asp Ser Ile Asp Gln Leu Pro Pro Glu Thr
    450                 455                 460

Thr Asp Glu Pro Leu Glu Lys Ala Tyr Ser His Gln Leu Asn Tyr Ala
465                 470                 475                 480

Glu Cys Phe Leu Met Gln Asp Arg Arg Gly Thr Ile Pro Phe Phe Thr
                485                 490                 495

Trp Thr His Arg Ser Val Asp Phe Phe Asn Thr Ile Asp Ala Glu Lys
            500                 505                 510

Ile Thr Gln Leu Pro Val Val Lys Ala Tyr Ala Leu Ser Ser Gly Ala
        515                 520                 525

Ser Ile Ile Glu Gly Pro Gly Phe Thr Gly Gly Asn Leu Leu Phe Leu
    530                 535                 540

Lys Glu Ser Ser Asn Ser Ile Ala Lys Phe Lys Val Thr Leu Asn Ser
545                 550                 555                 560

Ala Ala Leu Leu Gln Arg Tyr Arg Val Arg Ile Arg Tyr Ala Ser Thr
                565                 570                 575

Thr Asn Leu Arg Leu Phe Val Gln Asn Ser Asn Asn Asp Phe Leu Val
            580                 585                 590

Ile Tyr Ile Asn Lys Thr Met Asn Lys Asp Asp Asp Leu Thr Tyr Gln
        595                 600                 605

Thr Phe Asp Leu Ala Thr Thr Asn Ser Asn Met Gly Phe Ser Gly Asp
    610                 615                 620

Lys Asn Glu Leu Ile Ile Gly Ala Glu Ser Phe Val Ser Asn Glu Lys
625                 630                 635                 640

Ile Tyr Ile Asp Lys Ile Glu Phe Ile Pro Val Gln Leu
                645                 650
```

<210> SEQ ID NO 16
<211> LENGTH: 4370
<212> TYPE: DNA
<213> ORGANISM: Artificial Sequence
<220> FEATURE:
<223> OTHER INFORMATION: is a nucleotide sequence representing the sense strand of a DNA expression cassette that includes a recombinant gene engineered to encode and express a 5-enolpyruvylshikimate-3-phosphate synthase (EPSPS) protein

<400> SEQUENCE: 16
gacaacaaca tgcttctcat caacatggag ggaagaggga gggagaaagt gtcgcctggt 60
cacctccatt gtcacactag ccactggcca gctctcccac accaccaatg ccaggggcga 120
gctttagcac agccaccgct tcacctccac caccgcacta ccctagcttc gcccaacagc 180
caccgtcaac gcctcctctc cgtcaacata agagagagag agaagaggag agtagccatg 240
tggggaggag gaatagtaca tggggcctac cgtttggcaa gttattttgg gttgccaagt 300
taggccaata aggggaggga tttggccatc cggttggaaa ggttattggg gtagtatctt 360
tttactagaa ttgtcaaaaa aaaatagttt gagagccatt tggagaggat gttgcctgtt 420
agaggtgctc ttaggacatc aaattccata aaaacatcag aaaaattctc tcgatgaaga 480
tttataacca ctaaaactgc cctcaattcg aagggagttc aaaacaatta aaatcatgtt 540
cgaattgagt ttcaatttca ctttaacccc tttgaaatct caatggtaaa acatcaaccc 600
gtcaggtagc atggttcttt ttattccttt caaaaagagt taattacaaa cagaatcaaa 660
actaacagtt aggcccaagg cccatccgag caaacaatag atcatgggcc aggcctgcca 720
ccaccctccc cctcctggct cccgctcttg aatttcaaaa tccaaaaata tcggcacgac 780
tggccgccga cggagcgggc ggaaaatgac ggaacaaccc ctcgaattct accccaacta 840
cgcccaccaa cccacacgcc actgacaatc cggtcccacc cttgtgggcc cacctacaag 900
cgagacgtca gtcgctcgca gcaaccagtg ggcccacctc ccagtgagcg gcgggtagat 960
ctggactctt acccacccac actaaacaaa acggcatgaa tattttgcac taaaaccctc 1020
agaaaaattc cgatattcca aaccagtaca gttcctgacc gttggaggag ccaaagtgga 1080
gcggagtgta aaattgggaa acttaatcga gggggttaaa cgcaaaaacg ccgaggcgcc 1140
tcccgctcta tagaaagggg aggagtggga ggtggaaacc ctaccacacc gcagagaaag 1200
gcgtcttcgt actcgcctct ctccgcgccc tcctccgccg ccgctcgccg ccgttcgtct 1260
ccgccgccac cggctagcca tccaggtaaa acaaacaaaa acggatctga tgcttccatt 1320
cctccgtttc tcgtagtagc gcgcttcgat ctgtgggtgg atctgggtga tcctggggtg 1380
tggttcgttc tgtttgatag atctgtcggt ggatctggcc ttctgtggtt gtcgatgtcc 1440
ggatctgcgt tttgatcagt ggtagttcgt ggatctggcg aaatgttttg gatctggcag 1500
tgagacgcta agaatcggga aatgatgcaa tattaggggg gtttcggatg gggatccact 1560
gaattagtct gtctccctgc tgataatctg ttcctttttg gtagatctgg ttagtgtatg 1620
tttgtttcgg atagatctga tcaatgcttg tttgtttttt caaattttct acctaggttg 1680
tataggaatg gcatgcggat ctggttggat tgccatgatc cgtgctgaaa tgcccctttg 1740
gttgatggat cttgatattt tactgctgtt cacctagatt tgtactcccg tttatactta 1800
atttgttgct tattatgaat agatctgtaa cttaggcaca tgtatggacg gagtatgtgg 1860
atctgtagta tgtacattgc tgcgagctaa gaactatttc agagcaagca cagaaaaaaa 1920
tatttagaca gattgggcaa ctatttgatg gtctttggta tcatgctttg tagtgctcgt 1980
ttctgcgtag taatcttttg atctgatctg aagataggtg ctattatatt cttaaaggtc 2040
attagaacgc tatctgaaag gctgtattat gtggattggt tcacctgtga ctccctgttc 2100
gtcttgtctt gataaatcct gtgataaaaa aaattcttaa ggcgtaattt gttgaaatct 2160
tgttttgtcc tatgcagcct gatccatggc gcaagttagc agaatctgca atggtgtgca 2220
gaacccatct cttatctcca atctctcgaa atccagtcaa cgcaaatctc ccttatcggt 2280

-continued

```
ttctctgaag acgcagcagc atccacgagc ttatccgatt tcgtcgtcgt ggggattgaa   2340

gaagagtggg atgacgttaa ttggctctga gcttcgtcct cttaaggtca tgtcttctgt   2400

ttccacggcg tgcatgcttc acggtgcaag cagccggccc gcaaccgccc gcaaatcctc   2460

tggcctttcc ggaaccgtcc gcattcccgg cgacaagtcg atctcccacc ggtccttcat   2520

gttcggcggt ctcgcgagcg gtgaaacgcg catcaccggc cttctggaag gcgaggacgt   2580

catcaatacg ggcaaggcca tgcaggcgat gggcgcccgc atccgtaagg aaggcgacac   2640

ctggatcatc gatggcgtcg gcaatggcgg cctcctggcg cctgaggcgc cgctcgattt   2700

cggcaatgcc gccacgggct gccgcctgac gatgggcctc gtcggggtct acgatttcga   2760

cagcaccttc atcggcgacg cctcgctcac aaagcgcccg atgggccgcg tgttgaaccc   2820

gctgcgcgaa atgggcgtgc aggtgaaatc ggaagacggt gaccgtcttc ccgttacctt   2880

gcgcgggccg aagacgccga cgccgatcac ctaccgcgtg ccgatggcct ccgcacaggt   2940

gaagtccgcc gtgctgctcg ccggcctcaa cacgcccggc atcacgacgg tcatcgagcc   3000

gatcatgacg cgcgatcata cggaaaagat gctgcagggc tttggcgcca accttaccgt   3060

cgagacggat gcggacggcg tgcgcaccat ccgcctggaa ggccgcggca agctcaccgg   3120

ccaagtcatc gacgtgccgg gcgacccgtc ctcgacggcc ttcccgctgg ttgcggccct   3180

gcttgttccg ggctccgacg tcaccatcct caacgtgctg atgaacccca cccgcaccgg   3240

cctcatcctg acgctgcagg aaatgggcgc cgacatcgaa gtcatcaacc cgcgccttgc   3300

cggcggcgaa gacgtggcgg acctgcgcgt tcgctcctcc acgctgaagg gcgtcacggt   3360

gccggaagac cgcgcgcctt cgatgatcga cgaatatccg attctcgctg tcgccgccgc   3420

cttcgcggaa ggggcgaccg tgatgaacgg tctggaagaa ctccgcgtca aggaaagcga   3480

ccgcctctcg gccgtcgcca atggcctcaa gctcaatggc gtggattgcg atgagggcga   3540

gacgtcgctc gtcgtgcgtg gccgccctga cggcaagggg ctcggcaacg cctcgggcgc   3600

cgccgtcgcc acccatctcg atcaccgcat cgccatgagc ttcctcgtca tgggcctcgt   3660

gtcggaaaac cctgtcacgg tggacgatgc cacgatgatc gccacgagct tcccggagtt   3720

catggacctg atggccgggc tgggcgcgaa gatcgaactc tccgatacga aggctgcctg   3780

atgagctcca gggttcttgc ctggtgcctt ggcaatgctt gattactgct gctatcctat   3840

gatctgtccg tgtgggcttc tatctatcag tttgtgtgtc tggttttgaa aaacatttgc   3900

ttttcgatta tgtagggttt gcttgtagct ttcgctgctg tgacctgtgt tgtttatgtg   3960

aaccttcttt gtggcatctt taatatccaa gttcgtggtt tgtcgtaaaa cgaagcctct   4020

acttcgtaaa gttgtgtcta tagcattgaa atcgtttttt tgctcgagaa taattgtgac   4080

ctttagttgg cgtgaaacta gttttggata tctgattctc tggttcgcaa tcttgagatc   4140

gtcgctgctt aggtgagcta agtgatgttc ctaagtaaat gctcctcacc agaatacgta   4200

gctgtgtgaa aagagaacgc gtgaatacgt agctgtgtaa agattgtgtc ccaagtaaac   4260

ctcagtgatt tttgtttgga tttttaattt agaaacattc gactgggagc ggctagagcc   4320

acacccaagt tcctaactat gataaagttg ctctgtaaca gaaaacacca              4370
```

<210> SEQ ID NO 17
<211> LENGTH: 531
<212> TYPE: PRT
<213> ORGANISM: Artificial Sequence
<220> FEATURE:
<223> OTHER INFORMATION: is an amino acid sequence translation of nucleotide positions 2186 through 3781 of SEQ ID NO: 16
<220> FEATURE:

<221> NAME/KEY: misc_feature
<222> LOCATION: (1)..(76)
<223> OTHER INFORMATION: chloroplast transit peptide (CTP) from
Arabidopsis thaliana (thale cress)
<220> FEATURE:
<221> NAME/KEY: misc_feature
<222> LOCATION: (77)..(531)
<223> OTHER INFORMATION: 5-enolpyruvylshikimate-3-phosphate synthase
gene (EPSPS) from Agrobacterium sp strain CP4

<400> SEQUENCE: 17

```
Met Ala Gln Val Ser Arg Ile Cys Asn Gly Val Gln Asn Pro Ser Leu
1               5                   10                  15

Ile Ser Asn Leu Ser Lys Ser Ser Gln Arg Lys Ser Pro Leu Ser Val
            20                  25                  30

Ser Leu Lys Thr Gln Gln His Pro Arg Ala Tyr Pro Ile Ser Ser Ser
        35                  40                  45

Trp Gly Leu Lys Lys Ser Gly Met Thr Leu Ile Gly Ser Glu Leu Arg
    50                  55                  60

Pro Leu Lys Val Met Ser Ser Val Ser Thr Ala Cys Met Leu His Gly
65                  70                  75                  80

Ala Ser Ser Arg Pro Ala Thr Ala Arg Lys Ser Ser Gly Leu Ser Gly
                85                  90                  95

Thr Val Arg Ile Pro Gly Asp Lys Ser Ile Ser His Arg Ser Phe Met
            100                 105                 110

Phe Gly Gly Leu Ala Ser Gly Glu Thr Arg Ile Thr Gly Leu Leu Glu
        115                 120                 125

Gly Glu Asp Val Ile Asn Thr Gly Lys Ala Met Gln Ala Met Gly Ala
    130                 135                 140

Arg Ile Arg Lys Glu Gly Asp Thr Trp Ile Ile Asp Gly Val Gly Asn
145                 150                 155                 160

Gly Gly Leu Leu Ala Pro Glu Ala Pro Leu Asp Phe Gly Asn Ala Ala
                165                 170                 175

Thr Gly Cys Arg Leu Thr Met Gly Leu Val Gly Val Tyr Asp Phe Asp
            180                 185                 190

Ser Thr Phe Ile Gly Asp Ala Ser Leu Thr Lys Arg Pro Met Gly Arg
        195                 200                 205

Val Leu Asn Pro Leu Arg Glu Met Gly Val Gln Val Lys Ser Glu Asp
    210                 215                 220

Gly Asp Arg Leu Pro Val Thr Leu Arg Gly Pro Lys Thr Pro Thr Pro
225                 230                 235                 240

Ile Thr Tyr Arg Val Pro Met Ala Ser Ala Gln Val Lys Ser Ala Val
                245                 250                 255

Leu Leu Ala Gly Leu Asn Thr Pro Gly Ile Thr Thr Val Ile Glu Pro
            260                 265                 270

Ile Met Thr Arg Asp His Thr Glu Lys Met Leu Gln Gly Phe Gly Ala
        275                 280                 285

Asn Leu Thr Val Glu Thr Asp Ala Asp Gly Val Arg Thr Ile Arg Leu
    290                 295                 300

Glu Gly Arg Gly Lys Leu Thr Gly Gln Val Ile Asp Val Pro Gly Asp
305                 310                 315                 320

Pro Ser Ser Thr Ala Phe Pro Leu Val Ala Ala Leu Leu Val Pro Gly
                325                 330                 335

Ser Asp Val Thr Ile Leu Asn Val Leu Met Asn Pro Thr Arg Thr Gly
            340                 345                 350

Leu Ile Leu Thr Leu Gln Glu Met Gly Ala Asp Ile Glu Val Ile Asn
```

```
        355                 360                 365

Pro Arg Leu Ala Gly Gly Glu Asp Val Ala Asp Leu Arg Val Arg Ser
    370                 375                 380

Ser Thr Leu Lys Gly Val Thr Val Pro Glu Asp Arg Ala Pro Ser Met
385                 390                 395                 400

Ile Asp Glu Tyr Pro Ile Leu Ala Val Ala Ala Ala Phe Ala Glu Gly
                405                 410                 415

Ala Thr Val Met Asn Gly Leu Glu Glu Leu Arg Val Lys Glu Ser Asp
            420                 425                 430

Arg Leu Ser Ala Val Ala Asn Gly Leu Lys Leu Asn Gly Val Asp Cys
        435                 440                 445

Asp Glu Gly Glu Thr Ser Leu Val Val Arg Gly Arg Pro Asp Gly Lys
    450                 455                 460

Gly Leu Gly Asn Ala Ser Gly Ala Ala Val Ala Thr His Leu Asp His
465                 470                 475                 480

Arg Ile Ala Met Ser Phe Leu Val Met Gly Leu Val Ser Glu Asn Pro
                485                 490                 495

Val Thr Val Asp Asp Ala Thr Met Ile Ala Thr Ser Phe Pro Glu Phe
            500                 505                 510

Met Asp Leu Met Ala Gly Leu Gly Ala Lys Ile Glu Leu Ser Asp Thr
        515                 520                 525

Lys Ala Ala
    530


<210> SEQ ID NO 18
<211> LENGTH: 29
<212> TYPE: DNA
<213> ORGANISM: artificial sequence
<220> FEATURE:
<223> OTHER INFORMATION: is a nucleotide sequence of a synthetic
      oligonucleotide, and is referred to as SQ27011

<400> SEQUENCE: 18

aaggaaaata aaaaggcaaa acactaatg                                        29


<210> SEQ ID NO 19
<211> LENGTH: 14
<212> TYPE: DNA
<213> ORGANISM: artificial sequence
<220> FEATURE:
<223> OTHER INFORMATION: is a nucleotide sequence of a synthetic
      oligonucleotide, and is referred to as PB3552

<400> SEQUENCE: 19

ccggacatga agcc                                                        14


<210> SEQ ID NO 20
<211> LENGTH: 26
<212> TYPE: DNA
<213> ORGANISM: artificial sequence
<220> FEATURE:
<223> OTHER INFORMATION: is a nucleotide sequence of a synthetic
      oligonucleotide, and is referred to as SQ9085

<400> SEQUENCE: 20

actcattgct gatccatgta gatttc                                           26


<210> SEQ ID NO 21
<211> LENGTH: 80
<212> TYPE: DNA
<213> ORGANISM: artificial sequence
```

<220> FEATURE:
<223> OTHER INFORMATION: is a nucleotide sequence of Event MON 87411
corresponding to positions 462 through 541 of SEQ ID NO: 1

<400> SEQUENCE: 21
aaggaaaata aaaaggcaaa acactaatga atagttaagt ggcttcatgt ccgggaaatc 60
tacatggatc agcaatgagt 80

<210> SEQ ID NO 22
<211> LENGTH: 19
<212> TYPE: DNA
<213> ORGANISM: artificial sequence
<220> FEATURE:
<223> OTHER INFORMATION: is a nucleotide sequence of a synthetic
oligonucleotide referred to as SQ27066

<400> SEQUENCE: 22
acaccatcta gagcggccg 19

<210> SEQ ID NO 23
<211> LENGTH: 25
<212> TYPE: DNA
<213> ORGANISM: artificial sequence
<220> FEATURE:
<223> OTHER INFORMATION: is a nucleotide sequence of a synthetic
oligonucleotide referred to as PB11300

<400> SEQUENCE: 23
tttaaactat cagtgtttag agaat 25

<210> SEQ ID NO 24
<211> LENGTH: 29
<212> TYPE: DNA
<213> ORGANISM: artificial sequence
<220> FEATURE:
<223> OTHER INFORMATION: is a nucleotide sequence of a synthetic
oligonucleotide referred to as SQ26977

<400> SEQUENCE: 24
gggtagatta atacatctag aggtttgtg 29

<210> SEQ ID NO 25
<211> LENGTH: 75
<212> TYPE: DNA
<213> ORGANISM: artificial sequence
<220> FEATURE:
<223> OTHER INFORMATION: is a nucleotide sequence of Event MON 87411
corresponding to positions 11710 through 11784 of SEQ ID NO: 1

<400> SEQUENCE: 25
acaccatcta gagcggccgc gtttaaacta tcagtgttta gagaatcaca aacctctaga 60
tgtattaatc taccc 75

<210> SEQ ID NO 26
<211> LENGTH: 11743
<212> TYPE: DNA
<213> ORGANISM: Artificial Sequence
<220> FEATURE:
<223> OTHER INFORMATION: DNA construct 417
<220> FEATURE:
<221> NAME/KEY: promoter
<222> LOCATION: (2627)..(3238)
<223> OTHER INFORMATION: represents the reverse complement sequence of
an enhanced CaMV 35S promoter
<220> FEATURE:
<221> NAME/KEY: promoter
<222> LOCATION: (2627)..(4213)

-continued

```
<223> OTHER INFORMATION: represents a divergent promoter region that
      promotes bidirectional transcription
<220> FEATURE:
<221> NAME/KEY: promoter
<222> LOCATION: (3265)..(4213)
<223> OTHER INFORMATION: Corn PIIG promoter

<400> SEQUENCE: 26

aaaagtccca tgtggatcac tccgttgccc cgtcgctcac cgtgttgggg ggaaggtgca     60

catggctcag ttctcaatgg aaattatctg cctaaccggc tcagttctgc gtagaaacca    120

acatgcaagc tccaccgggt gcaaagcggc agcggcggca ggatatattc aattgtaaat    180

ggcttcatgt ccgggaaatc tacatggatc agcaatgagt atgatggtca atatggagaa    240

aaagaaagag taattaccaa tttttttca attcaaaaat gtagatgtcc gcagcgttat    300

tataaaatga aagtacattt tgataaaacg acaaattacg atccgtcgta tttataggcg    360

aaagcaataa acaaattatt ctaattcgga aatctttatt tcgacgtgtc tacattcacg    420

tccaaatggg ggcttagatg agaaacttca cgatcgatgc ggccaccact cgaggtcgag    480

gtaccgttgt caatcaattg gcaagtcata aaatgcatta aaaaatattt tcatactcaa    540

ctacaaatcc atgagtataa ctataattat aaagcaatga ttagaatctg acaaggattc    600

tggaaaatta cataaaggaa agttcataaa tgtctaaaac acaagaggac atacttgtat    660

tcagtaacat ttgcagcttt tctaggtctg aaaatatatt tgttgcctag tgaataagca    720

taatggtaca actacaagtg ttttactcct catattaact tcggtcatta gaggccacga    780

tttgacacat ttttactcaa aacaaaatgt ttgcatatct cttataattt caaattcaac    840

acacaacaaa taagagaaaa aacaaataat attaatttga gaatgaacaa aaggaccata    900

tcattcatta actcttctcc atccatttcc atttcacagt tcgatagcga aaaccgaata    960

aaaaacacag taaattacaa gcacaacaaa tggtacaaga aaaacagttt tcccaatgcc   1020

ataatactca aactcagtag gattctggtg tgtgcgcaat gaaactgatg cattgaactt   1080

gacgaacgtt gtcgaaaccg atgatacgaa cgaaagctag gcctcagcga gtaccgctgg   1140

cgatctaatc catgatatcg tgaacatcat ctacattcaa attcttatga gctttcttaa   1200

gggcatctgc agcatttttc atagaatcta atacagcagt atttgtgcta gctccttcga   1260

gggcttccct ctgcatttca atagttgtaa gggttccatc tatttgtagt tgggtctttt   1320

ccaatcgttt cttctttttg agggcttgga gtgcaactct tttatttttc gacgcatttt   1380

tctttgcgct cctgcaggcg gccgcgtgga tgaggagtta atcggtcgtg tgagagtagt   1440

gatcgagtgg atgtcgtcga gagtgatgag tgttgatgtt gttagtgata tgtggtagaa   1500

ggtatcgtga taaagcgtta acgcgatcgc agtacttgca aagaaaaatg cgtcgaaaaa   1560

taaaagagtt gcactccaag ccctcaaaaa gaagaaacga ttggaaaaga cccaactaca   1620

aatagatgga acccttacaa ctattgaaat gcagagggaa gccctcgaag gagctagcac   1680

aaatactgct gtattagatt ctatgaaaaa tgctgcagat gcccttaaga aagctcataa   1740

gaatttgaat gtagatgatg ttcacgatat catggatggt atcgcacagc gactgctgag   1800

ggacgtcgag ctcccgcttg gtatctgcat tacaatgaaa tgagcaaaga ctatgtgagt   1860

aacactggtc aacactaggg agaaggcatc gagcaagata cgtatgtaaa gagaagcaat   1920

atagtgtcag ttggtagata ctagatacca tcaggaggta aggagagcaa caaaaaggaa   1980

actctttatt tttaaatttt gttacaacaa acaagcagat caatgcatca aaatactgtc   2040

agtacttatt tcttcagaca acaatattta aaacaagtgc atctgatctt gacttatggt   2100
```

```
cacaataaag gagcagagat aaacatcaaa atttcgtcat ttatatttat tccttcaggc   2160
gttaacaatt taacagcaca caaacaaaaa cagaatagga atatctaatt ttggcaaata   2220
ataagctctg cagacgaaca aattattata gtatcgccta taatatgaat ccctatacta   2280
ttgacccatg tagtatgaag cctgtgccta aattaacagc aaacttctga atccaagtgc   2340
cctataacac caacatgtgc ttaaataaat accgctaagc accaaattac acatttctcg   2400
tattgctgtg taggttctat cttcgtttcg tactaccatg tccctatatt ttgctgctac   2460
aaaggacggc aagtaatcag cacaggcaga acacgatttc agagtgtaat tctagatcca   2520
gctaaaccac tctcagcaat caccacacaa gagagcattc agagaaacgt ggcagtaaca   2580
aaggcagagg gcggagtgag cgcgtaccga agacggttca gcgtgtcctc tccaaatgaa   2640
atgaacttcc ttatatagag gaagggtctt gcgaaggata gtgggattgt gcgtcatccc   2700
ttacgtcagt ggagatatca catcaatcca cttgctttga agacgtggtt ggaacgtctt   2760
ctttttccac gatgctcctc gtgggtgggg gtccatcttt gggaccactg tcggcagagg   2820
catcttcaac gatggccttt cctttatcgc aatgatggca tttgtaggag ccaccttcct   2880
tttccactat cttcacaata aagtgacaga tagctgggca atggaatccg aggaggtttc   2940
cggatattac cctttgttga aaagtctcaa tcggaccatc acatcaatcc acttgctttg   3000
aagacgtggt tggaacgtct tctttttcca cgatgctcct cgtgggtggg ggtccatctt   3060
tgggaccact gtcggcagag gcatcttcaa cgatggcctt tcctttatcg caatgatggc   3120
atttgtagga gccaccttcc ttttccacta tcttcacaat aaagtgacag atagctgggc   3180
aatggaatcc gaggaggttt ccggatatta ccctttgttg aaaagtctca atcggacctg   3240
cagcctgcag gctagcggcg cgccacaaat cacaggccat gaaccctact catgcttcga   3300
tttgtccaac acacacttac caaaactcaa atcatgtcct tgacagtcac tcgggactca   3360
taacatgggt acgtatcgac tatgtcaact atatgtgttc tcatcagatt atagattggc   3420
ctagtacgta gtgatatttc cactagcact gtggttatgg ctgtacctga tagtgatatc   3480
agcaccgggt catggctcta ctaccaggta gtgagagtga cctttatact gtcagactgt   3540
aactaaggat ttccaatcac tgttcggatc ctaggcttag aattaagtaa aactctatca   3600
ctataggctg cagcacactc ggtatatatt gatgggccaa cagaaattgt gcgtactatg   3660
cgcgatgtaa aatggacata aaccctaccc atatacaatg caataacttt tgtccggtct   3720
gggccaccgg ttagcagagg tcctgatttc ggtggtagtg gtagcttgat ctggtcgtcg   3780
tatcgtagag ggatatataa aatcatgtca cttttgaagg gagcgctcac agaaataata   3840
ggtattcgcg ggagccgccc ccgcagaaca caaaataagg cgagcacgca cacgcatcag   3900
tttcgataaa ataataatag cgccagctga tcggaacaat tccagctagc actaatgtat   3960
ttctgcattg atctgtttat acaacatgct acctcgttga gtgattttga catgatttgt   4020
caacttgctc cgatcctata tctcgatcga tctccacatg acgatggttg ttgtcctgta   4080
tcccatgaca accaggcaac gctcaaagca cacatgcgtt gccgattacc cgtgcatgcc   4140
gccaagcacg aaagcacctc cctccacacc gtccatcagc tataaaaacc atgccaagca   4200
ccctgtgaaa agccccggga accatcttcc acacactcaa gccacactat tggagaacac   4260
acagggacaa cacaccataa gatccaaggg aggcctccgc cgccgccggt aaccaccccg   4320
cccctctcct ctttctttct ccgttttttt ttccgtctcg gtctcgatct ttggccttgg   4380
tagtttgggt gggcgagagg cggcttcgtg cgcgcccaga tcggtgcgcg ggaggggcgg   4440
gatctcgcgg ctggggctct cgccggcgtg gatccggccc ggatctcgcg gggaatgggg   4500
```

```
ctctcggatg tagatctgcg atccgccgtt gttgggggag atgatggggg gtttaaaatt   4560
tccgccgtgc taaacaagat caggaagagg ggaaaagggc actatggttt atatttttat   4620
atatttctgc tgcttcgtca ggcttagatg tgctagatct ttctttcttc tttttgtggg   4680
tagaatttga atccctcagc attgttcatc ggtagttttt cttttcatga tttgtgacaa   4740
atgcagcctc gtgcggagct tttttgtagg tagaagtgat caaccatggc caaccccaac   4800
aatcgctccg agcacgacac gatcaaggtc acccccaact ccgagctcca gaccaaccac   4860
aaccagtacc cgctggccga caaccccaac tccaccctgg aagagctgaa ctacaaggag   4920
ttcctgcgca tgaccgagga ctcctccacg gaggtcctgg acaactccac cgtcaaggac   4980
gccgtcggga ccggcatctc cgtcgttggg cagatcctgg gcgtcgttgg cgtccccttc   5040
gcaggtgctc tcacctcctt ctaccagtcc ttcctgaaca ccatctggcc ctccgacgcc   5100
gacccctgga aggccttcat ggcccaagtc gaagtcctga tcgacaagaa gatcgaggag   5160
tacgccaagt ccaaggccct ggccgagctg caaggcctgc aaaacaactt cgaggactac   5220
gtcaacgcgc tgaactcctg gaagaagacg cctctgtccc tgcgctccaa gcgctcccag   5280
gaccgcatcc gcgagctgtt ctcccaggcc gagtcccact tccgcaactc catgccgtcc   5340
ttcgccgtct ccaagttcga ggtcctgttc ctgcccacct acgcccaggc tgccaacacc   5400
cacctcctgt tgctgaagga cgcccaggtc ttcggcgagg aatggggcta ctcctcggag   5460
gacgtcgccg agttctaccg tcgccagctg aagctgaccc aacagtacac cgaccactgc   5520
gtcaactggt acaacgtcgg cctgaacggc ctgaggggct ccacctacga cgcatgggtc   5580
aagttcaacc gcttccgcag ggagatgacc ctgaccgtcc tggacctgat cgtcctgttc   5640
cccttctacg acatccgcct gtactccaag ggcgtcaaga ccgagctgac ccgcgacatc   5700
ttcacggacc ccatcttcct gctcacgacc ctccagaagt acggtcccac cttcctgtcc   5760
atcgagaact ccatccgcaa gccccacctg ttcgactacc tccagggcat cgagttccac   5820
acgcgcctga ggccaggcta cttcggcaag gactccttca actactggtc cggcaactac   5880
gtcgagacca ggccctccat cggctcctcg aagacgatca cctccccttt ctacggcgac   5940
aagtccaccg agcccgtcca gaagctgtcc ttcgacggcc agaaggtcta ccgcaccatc   6000
gccaacaccg acgtcgcggc ttggccgaac ggcaaggtct acctgggcgt cacgaaggtc   6060
gacttctccc agtacgatga ccagaagaac gagacctcca cccagaccta cgactccaag   6120
cgcaacaatg gccacgtctc cgcccaggac tccatcgacc agctgccgcc tgagaccact   6180
gacgagcccc tggagaaggc ctactcccac cagctgaact acgcggagtg cttcctgatg   6240
caagaccgca ggggcaccat ccccttcttc acctggaccc accgctccgt cgacttcttc   6300
aacaccatcg acgccgagaa gatcacccag ctgcccgtgg tcaaggccta cgccctgtcc   6360
tcgggtgcct ccatcattga gggtccaggc ttcaccggtg gcaacctgct gttcctgaag   6420
gagtcctcga actccatcgc caagttcaag gtcaccctga actccgctgc cttgctgcaa   6480
cgctaccgcg tccgcatccg ctacgcctcc accacgaacc tgcgcctgtt cgtccagaac   6540
tccaacaatg acttcctggt catctacatc aacaagacca tgaacaagga cgatgacctg   6600
acctaccaga ccttcgacct cgccaccacg aactccaaca tgggcttctc gggcgacaag   6660
aatgaactga tcattggtgc tgagtccttc gtctccaacg agaagatcta catcgacaag   6720
atcgagttca tccccgtcca gctgtgatag gaactctgat tgaattctgc atgcgtttgg   6780
acgtatgctc attcaggttg gagccaattt ggttgatgtg tgtgcgagtt cttgcgagtc   6840
```

-continued

```
tgatgagaca tctctgtatt gtgtttcttt ccccagtgtt ttctgtactt gtgtaatcgg   6900
ctaatcgcca acagattcgg cgatgaataa atgagaaata aattgttctg attttgagtg   6960
caaaaaaaaa ggaattagat ctgtgtgtgt tttttggatc ccattttcga caagcttgcc   7020
tcgagacaac aacatgcttc tcatcaacat ggagggaaga gggagggaga aagtgtcgcc   7080
tggtcacctc cattgtcaca ctagccactg gccagctctc ccacaccacc aatgccaggg   7140
gcgagcttta gcacagccac cgcttcacct ccaccaccgc actaccctag cttcgcccaa   7200
cagccaccgt caacgcctcc tctccgtcaa cataagagag agagagaaga ggagagtagc   7260
catgtgggga ggaggaatag tacatggggc ctaccgtttg gcaagttatt ttgggttgcc   7320
aagttaggcc aataagggga gggatttggc catccggttg gaaaggttat tggggtagta   7380
tctttttact agaattgtca aaaaaaaata gtttgagagc catttggaga ggatgttgcc   7440
tgttagaggt gctcttagga catcaaattc cataaaaaca tcagaaaaat tctctcgatg   7500
aagatttata accactaaaa ctgccctcaa ttcgaaggga gttcaaaaca attaaaatca   7560
tgttcgaatt gagtttcaat ttcactttaa ccccttttgaa atctcaatgg taaaacatca   7620
acccgtcagg tagcatggtt ctttttattc ctttcaaaaa gagttaatta caaacagaat   7680
caaaactaac agttaggccc aaggcccatc cgagcaaaca atagatcatg ggccaggcct   7740
gccaccaccc tccccctcct ggctcccgct cttgaatttc aaaatccaaa aatatcggca   7800
cgactggccg ccgacggagc gggcggaaaa tgacggaaca acccctcgaa ttctacccca   7860
actacgccca ccaacccaca cgccactgac aatccggtcc cacccttgtg ggcccaccta   7920
caagcgagac gtcagtcgct cgcagcaacc agtgggccca cctcccagtg agcggcgggt   7980
agatctggac tcttacccac ccacactaaa caaaacggca tgaatatttt gcactaaaac   8040
cctcagaaaa attccgatat tccaaaccag tacagttcct gaccgttgga ggagccaaag   8100
tggagcggag tgtaaaattg ggaaacttaa tcgagggggt taaacgcaaa aacgccgagg   8160
cgcctcccgc tctatagaaa ggggaggagt gggaggtgga aaccctacca caccgcagag   8220
aaaggcgtct tcgtactcgc ctctctccgc gccctcctcc gccgccgctc gccgccgttc   8280
gtctccgccg ccaccggcta gccatccagg taaaacaaac aaaaacggat ctgatgcttc   8340
cattcctccg tttctcgtag tagcgcgctt cgatctgtgg gtggatctgg gtgatcctgg   8400
ggtgtggttc gttctgtttg atagatctgt cggtggatct ggccttctgt ggttgtcgat   8460
gtccggatct gcgttttgat cagtggtagt tcgtggatct ggcgaaatgt tttggatctg   8520
gcagtgagac gctaagaatc gggaaatgat gcaatattag gggggtttcg gatggggatc   8580
cactgaatta gtctgtctcc ctgctgataa tctgttcctt tttggtagat ctggttagtg   8640
tatgtttgtt tcggatagat ctgatcaatg cttgtttgtt ttttcaaatt ttctacctag   8700
gttgtatagg aatggcatgc ggatctggtt ggattgccat gatccgtgct gaaatgcccc   8760
tttggttgat ggatcttgat attttactgc tgttcaccta gatttgtact cccgtttata   8820
cttaatttgt tgcttattat gaatagatct gtaacttagg cacatgtatg gacggagtat   8880
gtggatctgt agtatgtaca ttgctgcgag ctaagaacta tttcagagca agcacagaaa   8940
aaaatattta gacagattgg gcaactattt gatggtcttt ggtatcatgc tttgtagtgc   9000
tcgtttctgc gtagtaatct tttgatctga tctgaagata ggtgctatta tattcttaaa   9060
ggtcattaga acgctatctg aaaggctgta ttatgtggat tggttcacct gtgactccct   9120
gttcgtcttg tcttgataaa tcctgtgata aaaaaaattc ttaaggcgta atttgttgaa   9180
atcttgtttt gtcctatgca gcctgatcca tggcgcaagt tagcagaatc tgcaatggtg   9240
```

```
tgcagaaccc atctcttatc tccaatctct cgaaatccag tcaacgcaaa tctcccttat   9300
cggtttctct gaagacgcag cagcatccac gagcttatcc gatttcgtcg tcgtggggat   9360
tgaagaagag tgggatgacg ttaattggct ctgagcttcg tcctcttaag gtcatgtctt   9420
ctgtttccac ggcgtgcatg cttcacggtg caagcagccg gcccgcaacc gcccgcaaat   9480
cctctggcct ttccggaacc gtccgcattc ccggcgacaa gtcgatctcc caccggtcct   9540
tcatgttcgg cggtctcgcg agcggtgaaa cgcgcatcac cggccttctg gaaggcgagg   9600
acgtcatcaa tacgggcaag gccatgcagg cgatgggcgc ccgcatccgt aaggaaggcg   9660
acacctggat catcgatggc gtcggcaatg gcggcctcct ggcgcctgag gcgccgctcg   9720
atttcggcaa tgccgccacg ggctgccgcc tgacgatggg cctcgtcggg gtctacgatt   9780
tcgacagcac cttcatcggc gacgcctcgc tcacaaagcg cccgatgggc cgcgtgttga   9840
acccgctgcg cgaaatgggc gtgcaggtga aatcggaaga cggtgaccgt cttcccgtta   9900
ccttgcgcgg gccgaagacg ccgacgccga tcacctaccg cgtgccgatg gcctccgcac   9960
aggtgaagtc cgccgtgctg ctcgccggcc tcaacacgcc cggcatcacg acggtcatcg  10020
agccgatcat gacgcgcgat catacggaaa agatgctgca gggctttggc gccaacctta  10080
ccgtcgagac ggatgcggac ggcgtgcgca ccatccgcct ggaaggccgc ggcaagctca  10140
ccggccaagt catcgacgtg ccgggcgacc cgtcctcgac ggccttcccg ctggttgcgg  10200
ccctgcttgt tccgggctcc gacgtcacca tcctcaacgt gctgatgaac ccccacccgca  10260
ccggcctcat cctgacgctg caggaaatgg gcgccgacat cgaagtcatc aacccgcgcc  10320
ttgccggcgg cgaagacgtg gcggacctgc gcgttcgctc ctccacgctg aagggcgtca  10380
cggtgccgga agaccgcgcg ccttcgatga tcgacgaata tccgattctc gctgtcgccg  10440
ccgccttcgc ggaaggggcg accgtgatga acggtctgga agaactccgc gtcaaggaaa  10500
gcgaccgcct ctcggccgtc gccaatggcc tcaagctcaa tggcgtggat tgcgatgagg  10560
gcgagacgtc gctcgtcgtg cgtggccgcc ctgacggcaa ggggctcggc aacgcctcgg  10620
gcgccgccgt cgccacccat ctcgatcacc gcatcgccat gagcttcctc gtcatgggcc  10680
tcgtgtcgga aaaccctgtc acggtggacg atgccacgat gatcgccacg agcttcccgg  10740
agttcatgga cctgatggcc gggctgggcg cgaagatcga actctccgat acgaaggctg  10800
cctgatgagc tccagggttc ttgcctggtg ccttggcaat gcttgattac tgctgctatc  10860
ctatgatctg tccgtgtggg cttctatcta tcagtttgtg tgtctggttt tgaaaaacat  10920
ttgcttttcg attatgtagg gtttgcttgt agctttcgct gctgtgacct gtgttgttta  10980
tgtgaacctt ctttgtggca tctttaatat ccaagttcgt ggtttgtcgt aaaacgaagc  11040
ctctacttcg taaagttgtg tctatagcat tgaaatcgtt tttttgctcg agaataattg  11100
tgacctttag ttggcgtgaa actagttttg gatatctgat tctctggttc gcaatcttga  11160
gatcgtcgct gcttaggtga gctaagtgat gttcctaagt aaatgctcct caccagaata  11220
cgtagctgtg tgaaaagaga acgcgtgaat acgtagctgt gtaaagattg tgtcccaagt  11280
aaacctcagt gatttttgtt tggatttta atttagaaac attcgactgg gagcggctag  11340
agccacaccc aagttcctaa ctatgataaa gttgctctgt aacagaaaac accatctaga  11400
gcggccgcgt ttaaactatc agtgtttgac aggatatatt ggcgggtaaa cctaagagaa  11460
aagagcgttt attagaataa tcggatattt aaaagggcgt gaaaaggttt atccgttcgt  11520
ccatttgtat gtgcatgcca accacagggt tcccctcggg agtgcttggc attccgtgcg  11580
```

-continued

```
ataatgactt ctgttcaacc acccaaacgt cggaaagcct gacgacggag cagcattcca  11640

aaaagatccc ttggctcgtc tgggtcggct agaaggtcga gtgggctgct gtggcttgat  11700

ccctcaacgc ggtcgcggac gtagcgcagc gccgaaaaat cct                    11743
```

<210> SEQ ID NO 27
<211> LENGTH: 12322
<212> TYPE: DNA
<213> ORGANISM: Artificial Sequence
<220> FEATURE:
<223> OTHER INFORMATION: DNA construct 416

<400> SEQUENCE: 27

```
aaaagtccca tgtggatcac tccgttgccc cgtcgctcac cgtgttgggg ggaaggtgca    60

catggctcag ttctcaatgg aaattatctg cctaaccggc tcagttctgc gtagaaacca   120

acatgcaagc tccaccgggt gcaaagcggc agcggcggca ggatatattc aattgtaaat   180

ggcttcatgt ccgggaaatc tacatggatc agcaatgagt atgatggtca atatggagaa   240

aaagaaagag taattaccaa ttttttttca attcaaaaat gtagatgtcc gcagcgttat   300

tataaaatga aagtacattt tgataaaacg acaaattacg atccgtcgta tttataggcg   360

aaagcaataa acaaattatt ctaattcgga aatctttatt tcgacgtgtc tacattcacg   420

tccaaatggg ggcttagatg agaaacttca cgatcgatgc ggccaccact cgaggtcgag   480

gtaccgttgt caatcaattg gcaagtcata aaatgcatta aaaaatattt tcatactcaa   540

ctacaaatcc atgagtataa ctataattat aaagcaatga ttagaatctg acaaggattc   600

tggaaaatta cataaaggaa agttcataaa tgtctaaaac acaagaggac atacttgtat   660

tcagtaacat ttgcagcttt tctaggtctg aaaatatatt tgttgcctag tgaataagca   720

taatggtaca actacaagtg ttttactcct catattaact tcggtcatta gaggccacga   780

tttgacacat ttttactcaa aacaaaatgt ttgcatatct cttataattt caaattcaac   840

acacaacaaa taagagaaaa aacaaataat attaatttga gaatgaacaa aaggaccata   900

tcattcatta actcttctcc atccatttcc atttcacagt tcgatagcga aaaccgaata   960

aaaaacacag taaattacaa gcacaacaaa tggtacaaga aaaacagttt tcccaatgcc  1020

ataatactca aactcagtag gattctggtg tgtgcgcaat gaaactgatg cattgaactt  1080

gacgaacgtt gtcgaaaccg atgatacgaa cgaaagctag gcctcagcga gtaccgctgg  1140

cgatctaatc catgatatcg tgaacatcat ctacattcaa attcttatga gctttcttaa  1200

gggcatctgc agcatttttc atagaatcta atacagcagt atttgtgcta gctccttcga  1260

gggcttccct ctgcatttca atagttgtaa gggttccatc tatttgtagt tgggtctttt  1320

ccaatcgttt cttcttttg agggcttgga gtgcaactct tttattttc gacgcatttt  1380

tctttgcgct cctgcaggcg gccgcgtgga tgaggagtta atcggtcgtg tgagagtagt  1440

gatcgagtgg atgtcgtcga gagtgatgag tgttgatgtt gttagtgata tgtggtagaa  1500

ggtatcgtga taaagcgtta acgcgatcgc agtacttgca aagaaaaatg cgtcgaaaaa  1560

taaaagagtt gcactccaag ccctcaaaaa gaagaaacga ttggaaaaga cccaactaca  1620

aatagatgga acccttacaa ctattgaaat gcagagggaa gccctcgaag gagctagcac  1680

aaatactgct gtattagatt ctatgaaaaa tgctgcagat gcccttaaga aagctcataa  1740

gaatttgaat gtagatgatg ttcacgatat catggatggt atcgcacagc gactgctgag  1800

ggacgtcgag ctcccgcttg gtatctgcat tacaatgaaa tgagcaaaga ctatgtgagt  1860

aacactggtc aacactaggg agaaggcatc gagcaagata cgtatgtaaa gagaagcaat  1920
```

```
atagtgtcag ttggtagata ctagatacca tcaggaggta aggagagcaa caaaaaggaa   1980
actctttatt tttaaatttt gttacaacaa acaagcagat caatgcatca aaatactgtc   2040
agtacttatt tcttcagaca acaatattta aaacaagtgc atctgatctt gacttatggt   2100
cacaataaag gagcagagat aaacatcaaa atttcgtcat ttatatttat tccttcaggc   2160
gttaacaatt taacagcaca caaacaaaaa cagaatagga atatctaatt ttggcaaata   2220
ataagctctg cagacgaaca aattattata gtatcgccta taatatgaat ccctatacta   2280
ttgacccatg tagtatgaag cctgtgccta aattaacagc aaacttctga atccaagtgc   2340
cctataacac caacatgtgc ttaaataaat accgctaagc accaaattac acatttctcg   2400
tattgctgtg taggttctat cttcgtttcg tactaccatg tccctatatt ttgctgctac   2460
aaaggacggc aagtaatcag cacaggcaga acacgatttc agagtgtaat tctagatcca   2520
gctaaaccac tctcagcaat caccacacaa gagagcattc agagaaacgt ggcagtaaca   2580
aaggcagagg gcggagtgag cgcgtaccga agacggttca gcgtgtcctc tccaaatgaa   2640
atgaacttcc ttatatagag gaagggtctt gcgaaggata gtgggattgt gcgtcatccc   2700
ttacgtcagt ggagatatca catcaatcca cttgctttga agacgtggtt ggaacgtctt   2760
ctttttccac gatgctcctc gtgggtgggg gtccatcttt gggaccactg tcggcagagg   2820
catcttcaac gatggccttt cctttatcgc aatgatggca tttgtaggag ccaccttcct   2880
tttccactat cttcacaata aagtgacaga tagctgggca atggaatccg aggaggtttc   2940
cggatattac cctttgttga aaagtctcaa tcggaccatc acatcaatcc acttgctttg   3000
aagacgtggt tggaacgtct tctttttcca cgatgctcct cgtgggtggg ggtccatctt   3060
tgggaccact gtcggcagag gcatcttcaa cgatggcctt tcctttatcg caatgatggc   3120
atttgtagga gccaccttcc ttttccacta tcttcacaat aaagtgacag atagctgggc   3180
aatggaatcc gaggaggttt ccggatatta ccctttgttg aaaagtctca atcggacctg   3240
cagcctgcag gctagcggcg cgccggaagc taactagtca cggcgaatac atgacgacat   3300
cggcctacaa cgcacaactt cttggcataa aagcttcaat ttcaatgccc ctatctggaa   3360
gccctaggcg ccgcgcaaat gtaaaacatt cgcttcgctt ggcttgttat ccaaaataga   3420
gtatggacct ccgacagatt ggcaacccgt gggtaatcga aaatggctcc atctgcccct   3480
ttgtcgaagg aatcaggaaa cggccctcac ctcctggcgg agtgtagata tgtgaaagaa   3540
tctaggcgac acttgcagac tggacaacat gtgaacaaat aagaccaacg ttatggcaac   3600
aagcctcgac gctactcaag tggtgggagg ccaccgcatg ttccaacgaa gcgccaaaga   3660
aagccttgca gactctaatg ctattagtcg cctaggatat ttggaatgaa aggaaccgca   3720
gagtttttca gcaccaagag cttccggtgg ctagtctgat agccaaaatt aaggaggatg   3780
ccaaaacatg ggtcttggcg ggcgcgaaac accttgatag gtggcttacc ttttaacatg   3840
ttcgggccaa aggccttgag acggtaaagt tttctatttg cgcttgcgca tgtacaattt   3900
tattcctcta ttcaatgaaa ttggtggctc actggttcat taaaaaaaaa agaatctagc   3960
ctgttcggga agaagaggat tttattcgtg agagagagag agagagagag agagagaggg   4020
agagagaagg aggaggagga ttttcaggct tcgcattgcc caacctctgc ttctgttggc   4080
ccaagaagaa tcccaggcgc ccatgggctg gcagtttacc acggacctac ctagcctacc   4140
ttagctatct aagcgggccg acctagtagc tacgtgccta gtgtagatta aagttggcgg   4200
gccagcagga agccacgctg caatggcatc ttcccctgtc cttcgcgtac gtgaaaacaa   4260
```

-continued acccaggtaa gcttagaatc ttcttgcccg ttggactggg acacccacca atcccaccat 4320
gccccgatat tcctccggtc tcggttcatg tgatgtcctc tcttgtgtga tcacggagca 4380
agcattctta aacggcaaaa gaaaatcacc aacttgctca cgcagtcacg ctgcaccgcg 4440
cgaagcgacg cccgataggc caagatcgcg agataaaata acaaccaatg atcataagga 4500
aacaagcccg cgatgtgtcg tgtgcagcaa tcttggtcat ttgcgggatc gagtgcttca 4560
cggctaacca aatattcggc cgatgattta acacattatc agcgtagatg tacgtacgat 4620
ttgttaatta atctacgagc cttgctaggg caggtgttct gccagccaat ccagatcgcc 4680
ctcgtatgca cgctcacatg atggcagggc agggttcaca tgagctctaa cggtcgatta 4740
attaatcccg gggctcgact ataaatacct ccctaatccc atgatcaaaa cccccgggaa 4800
ccatcttcca cacactcaag ccacactatt ggagaacaca cagggacaac acaccataag 4860
atccaaggga ggcctccgcc gccgccggta accaccccgc ccctctcctc tttctttctc 4920
cgtttttttt tccgtctcgg tctcgatctt tggccttggt agtttgggtg ggcgagaggc 4980
ggcttcgtgc gcgcccagat cggtgcgcgg gaggggcggg atctcgcggc tggggctctc 5040
gccggcgtgg atccggcccg gatctcgcgg ggaatggggc tctcggatgt agatctgcga 5100
tccgccgttg ttgggggaga tgatgggggg tttaaaattt ccgccgtgct aaacaagatc 5160
aggaagaggg gaaaagggca ctatggttta tatttttata tatttctgct gcttcgtcag 5220
gcttagatgt gctagatctt tctttcttct ttttgtgggt agaatttgaa tccctcagca 5280
ttgttcatcg gtagtttttc ttttcatgat ttgtgacaaa tgcagcctcg tgcggagctt 5340
ttttgtaggt agaagtgatc aaccatggcc aaccccaaca atcgctccga gcacgacacg 5400
atcaaggtca cccccaactc cgagctccag accaaccaca accagtaccc gctggccgac 5460
aaccccaact ccaccctgga agagctgaac tacaaggagt tcctgcgcat gaccgaggac 5520
tcctccacgg aggtcctgga caactccacc gtcaaggacg ccgtcgggac cggcatctcc 5580
gtcgttgggc agatcctggg cgtcgttggc gtccccttcg caggtgctct cacctccttc 5640
taccagtcct tcctgaacac catctggccc tccgacgccg acccctggaa ggccttcatg 5700
gcccaagtcg aagtcctgat cgacaagaag atcgaggagt acgccaagtc caaggccctg 5760
gccgagctgc aaggcctgca aaacaacttc gaggactacg tcaacgcgct gaactcctgg 5820
aagaagacgc ctctgtccct gcgctccaag cgctcccagg accgcatccg cgagctgttc 5880
tcccaggccg agtcccactt ccgcaactcc atgccgtcct tcgccgtctc caagttcgag 5940
gtcctgttcc tgcccaccta cgcccaggct gccaacaccc acctcctgtt gctgaaggac 6000
gcccaggtct tcggcgagga atggggctac tcctcggagg acgtcgccga gttctaccgt 6060
cgccagctga agctgaccca acagtacacc gaccactgcg tcaactggta caacgtcggc 6120
ctgaacggcc tgaggggctc cacctacgac gcatgggtca agttcaaccg cttccgcagg 6180
gagatgaccc tgaccgtcct ggacctgatc gtcctgttcc ccttctacga catccgcctg 6240
tactccaagg gcgtcaagac cgagctgacc cgcgacatct tcacggaccc catcttcctg 6300
ctcacgaccc tccagaagta cggtcccacc ttcctgtcca tcgagaactc catccgcaag 6360
ccccacctgt tcgactacct ccagggcatc gagttccaca cgcgcctgag gccaggctac 6420
ttcggcaagg actccttcaa ctactggtcc ggcaactacg tcgagaccag gccctccatc 6480
ggctcctcga agacgatcac ctccccttc tacggcgaca agtccaccga gcccgtccag 6540
aagctgtcct tcgacggcca gaaggtctac cgcaccatcg ccaacaccga cgtcgcggct 6600
tggccgaacg gcaaggtcta cctgggcgtc acgaaggtcg acttctccca gtacgatgac 6660

-continued cagaagaacg agacctccac ccagacctac gactccaagc gcaacaatgg ccacgtctcc 6720
gcccaggact ccatcgacca gctgccgcct gagaccactg acgagcccct ggagaaggcc 6780
tactcccacc agctgaacta cgcggagtgc ttcctgatgc aagaccgcag ggcaccatc 6840
cccttcttca cctggaccca ccgctccgtc gacttcttca acaccatcga cgccgagaag 6900
atcacccagc tgcccgtggt caaggcctac gccctgtcct cgggtgcctc catcattgag 6960
ggtccaggct tcaccggtgg caacctgctg ttcctgaagg agtcctcgaa ctccatcgcc 7020
aagttcaagg tcaccctgaa ctccgctgcc ttgctgcaac gctaccgcgt ccgcatccgc 7080
tacgcctcca ccacgaacct gcgcctgttc gtccagaact ccaacaatga cttcctggtc 7140
atctacatca acaagaccat gaacaaggac gatgacctga cctaccagac cttcgacctc 7200
gccaccacga actccaacat gggcttctcg ggcgacaaga atgaactgat cattggtgct 7260
gagtccttcg tctccaacga gaagatctac atcgacaaga tcgagttcat ccccgtccag 7320
ctgtgatagg aactctgatt gaattctgca tgcgtttgga cgtatgctca ttcaggttgg 7380
agccaatttg gttgatgtgt gtgcgagttc ttgcgagtct gatgagacat ctctgtattg 7440
tgtttctttc cccagtgttt tctgtacttg tgtaatcggc taatcgccaa cagattcggc 7500
gatgaataaa tgagaaataa attgttctga ttttgagtgc aaaaaaaaag gaattagatc 7560
tgtgtgtgtt ttttggatcc cattttcgac aagcttgcct cgagacaaca acatgcttct 7620
catcaacatg gagggaagag ggagggagaa agtgtcgcct ggtcacctcc attgtcacac 7680
tagccactgg ccagctctcc cacaccacca atgccagggg cgagctttag cacagccacc 7740
gcttcacctc caccaccgca ctaccctagc ttcgcccaac agccaccgtc aacgcctcct 7800
ctccgtcaac ataagagaga gagagaagag gagagtagcc atgtggggag gaggaatagt 7860
acatggggcc taccgtttgg caagttattt tgggttgcca agttaggcca ataaggggag 7920
ggatttggcc atccggttgg aaaggttatt ggggtagtat ctttttacta gaattgtcaa 7980
aaaaaaatag tttgagagcc atttggagag gatgttgcct gttagaggtg ctcttaggac 8040
atcaaattcc ataaaaacat cagaaaaatt ctctcgatga agatttataa ccactaaaac 8100
tgccctcaat tcgaagggag ttcaaaacaa ttaaaatcat gttcgaattg agtttcaatt 8160
tcactttaac ccctttgaaa tctcaatggt aaaacatcaa cccgtcaggt agcatggttc 8220
tttttattcc tttcaaaaag agttaattac aaacagaatc aaaactaaca gttaggccca 8280
aggcccatcc gagcaaacaa tagatcatgg gccaggcctg ccaccaccct cccccctcctg 8340
gctcccgctc ttgaatttca aaatccaaaa atatcggcac gactggccgc cgacggagcg 8400
ggcggaaaat gacggaacaa cccctcgaat tctaccccaa ctacgcccac caacccacac 8460
gccactgaca atccggtccc acccttgtgg gcccacctac aagcgagacg tcagtcgctc 8520
gcagcaacca gtgggcccac ctcccagtga gcggcgggta gatctggact cttacccacc 8580
cacactaaac aaaacggcat gaatattttg cactaaaacc ctcagaaaaa ttccgatatt 8640
ccaaaccagt acagttcctg accgttggag gagccaaagt ggagcggagt gtaaaattgg 8700
gaaacttaat cgaggggggtt aaacgcaaaa acgccgaggc gcctcccgct ctatagaaag 8760
gggaggagtg ggaggtggaa accctaccac accgcagaga aaggcgtctt cgtactcgcc 8820
tctctccgcg ccctcctccg ccgccgctcg ccgccgttcg tctccgccgc caccggctag 8880
ccatccaggt aaaacaaaca aaaacggatc tgatgcttcc attcctccgt ttctcgtagt 8940
agcgcgcttc gatctgtggg tggatctggg tgatcctggg gtgtggttcg ttctgtttga 9000

```
tagatctgtc ggtggatctg gccttctgtg gttgtcgatg tccggatctg cgttttgatc   9060
agtggtagtt cgtggatctg gcgaaatgtt ttggatctgg cagtgagacg ctaagaatcg   9120
ggaaatgatg caatattagg ggggtttcgg atggggatcc actgaattag tctgtctccc   9180
tgctgataat ctgttccttt ttggtagatc tggttagtgt atgtttgttt cggatagatc   9240
tgatcaatgc ttgtttgttt tttcaaattt tctacctagg ttgtatagga atggcatgcg   9300
gatctggttg gattgccatg atccgtgctg aaatgcccct ttggttgatg gatcttgata   9360
ttttactgct gttcacctag atttgtactc ccgtttatac ttaatttgtt gcttattatg   9420
aatagatctg taacttaggc acatgtatgg acggagtatg tggatctgta gtatgtacat   9480
tgctgcgagc taagaactat ttcagagcaa gcacagaaaa aaatatttag acagattggg   9540
caactatttg atggtctttg gtatcatgct ttgtagtgct cgtttctgcg tagtaatctt   9600
ttgatctgat ctgaagatag gtgctattat attcttaaag gtcattagaa cgctatctga   9660
aaggctgtat tatgtggatt ggttcacctg tgactccctg ttcgtcttgt cttgataaat   9720
cctgtgataa aaaaaattct taaggcgtaa tttgttgaaa tcttgttttg tcctatgcag   9780
cctgatccat ggcgcaagtt agcagaatct gcaatggtgt gcagaaccca tctcttatct   9840
ccaatctctc gaaatccagt caacgcaaat ctcccttatc ggtttctctg aagacgcagc   9900
agcatccacg agcttatccg atttcgtcgt cgtggggatt gaagaagagt gggatgacgt   9960
taattggctc tgagcttcgt cctcttaagg tcatgtcttc tgtttccacg gcgtgcatgc  10020
ttcacggtgc aagcagccgg cccgcaaccg cccgcaaatc ctctggcctt tccggaaccg  10080
tccgcattcc cggcgacaag tcgatctccc accggtcctt catgttcggc ggtctcgcga  10140
gcggtgaaac gcgcatcacc ggccttctgg aaggcgagga cgtcatcaat acgggcaagg  10200
ccatgcaggc gatgggcgcc cgcatccgta aggaaggcga cacctggatc atcgatggcg  10260
tcggcaatgg cggcctcctg gcgcctgagg cgccgctcga tttcggcaat gccgccacgg  10320
gctgccgcct gacgatgggc ctcgtcgggg tctacgattt cgacagcacc ttcatcggcg  10380
acgcctcgct cacaaagcgc ccgatgggcc gcgtgttgaa cccgctgcgc gaaatgggcg  10440
tgcaggtgaa atcggaagac ggtgaccgtc ttcccgttac cttgcgcggg ccgaagacgc  10500
cgacgccgat cacctaccgc gtgccgatgg cctccgcaca ggtgaagtcc gccgtgctgc  10560
tcgccggcct caacacgccc ggcatcacga cggtcatcga gccgatcatg acgcgcgatc  10620
atacggaaaa gatgctgcag ggctttggcg ccaaccttac cgtcgagacg gatgcggacg  10680
gcgtgcgcac catccgcctg gaaggccgcg gcaagctcac cggccaagtc atcgacgtgc  10740
cgggcgaccc gtcctcgacg gccttcccgc tggttgcggc cctgcttgtt ccgggctccg  10800
acgtcaccat cctcaacgtg ctgatgaacc ccacccgcac cggcctcatc ctgacgctgc  10860
aggaaatggg cgccgacatc gaagtcatca acccgcgcct tgccggcggc gaagacgtgg  10920
cggacctgcg cgttcgctcc tccacgctga agggcgtcac ggtgccggaa gaccgcgcgc  10980
cttcgatgat cgacgaatat ccgattctcg ctgtcgccgc cgccttcgcg gaaggggcga  11040
ccgtgatgaa cggtctggaa gaactccgcg tcaaggaaag cgaccgcctc tcggccgtcg  11100
ccaatggcct caagctcaat ggcgtggatt gcgatgaggg cgagacgtcg ctcgtcgtgc  11160
gtggccgccc tgacggcaag gggctcggca acgcctcggg cgccgccgtc gccacccatc  11220
tcgatcaccg catcgccatg agcttcctcg tcatgggcct cgtgtcggaa aaccctgtca  11280
cggtggacga tgccacgatg atcgccacga gcttcccgga gttcatggac ctgatggccg  11340
ggctgggcgc gaagatcgaa ctctccgata cgaaggctgc ctgatgagct ccagggttct  11400
```

```
tgcctggtgc cttggcaatg cttgattact gctgctatcc tatgatctgt ccgtgtgggc  11460
ttctatctat cagtttgtgt gtctggtttt gaaaaacatt tgcttttcga ttatgtaggg  11520
tttgcttgta gctttcgctg ctgtgacctg tgttgtttat gtgaaccttc tttgtggcat  11580
ctttaatatc caagttcgtg gtttgtcgta aaacgaagcc tctacttcgt aaagttgtgt  11640
ctatagcatt gaaatcgttt ttttgctcga gaataattgt gacctttagt tggcgtgaaa  11700
ctagttttgg atatctgatt ctctggttcg caatcttgag atcgtcgctg cttaggtgag  11760
ctaagtgatg ttcctaagta aatgctcctc accagaatac gtagctgtgt gaaaagagaa  11820
cgcgtgaata cgtagctgtg taaagattgt gtcccaagta aacctcagtg atttttgttt  11880
ggatttttaa tttagaaaca ttcgactggg agcggctaga gccacaccca agttcctaac  11940
tatgataaag ttgctctgta acagaaaaca ccatctagag cggccgcgtt taaactatca  12000
gtgtttgaca ggatatattg gcgggtaaac ctaagagaaa agagcgttta ttagaataat  12060
cggatattta aaagggcgtg aaaaggttta tccgttcgtc catttgtatg tgcatgccaa  12120
ccacagggtt cccctcggga gtgcttggca ttccgtgcga taatgacttc tgttcaacca  12180
cccaaacgtc ggaaagcctg acgacggagc agcattccaa aaagatccct tggctcgtct  12240
gggtcggcta gaaggtcgag tgggctgctg tggcttgatc cctcaacgcg gtcgcggacg  12300
tagcgcagcg ccgaaaaatc ct                                           12322
```

```
<210> SEQ ID NO 28
<211> LENGTH: 11787
<212> TYPE: DNA
<213> ORGANISM: Artificial Sequence
<220> FEATURE:
<223> OTHER INFORMATION: DNA construct 418

<400> SEQUENCE: 28
```

```
aaaagtccca tgtggatcac tccgttgccc cgtcgctcac cgtgttgggg ggaaggtgca     60
catggctcag ttctcaatgg aaattatctg cctaaccggc tcagttctgc gtagaaacca    120
acatgcaagc tccaccgggt gcaaagcggc agcggcggca ggatatattc aattgtaaat    180
ggcttcatgt ccgggaaatc tacatggatc agcaatgagt atgatggtca atatggagaa    240
aaagaaagag taattaccaa ttttttttca attcaaaaat gtagatgtcc gcagcgttat    300
tataaaatga aagtacattt tgataaaacg acaaattacg atccgtcgta tttataggcg    360
aaagcaataa acaaattatt ctaattcgga aatctttatt tcgacgtgtc tacattcacg    420
tccaaatggg ggcttagatg agaaacttca cgatcgatgc ggccaccact cgaggtcgag    480
gtaccgttgt caatcaattg gcaagtcata aaatgcatta aaaaatattt tcatactcaa    540
ctacaaatcc atgagtataa ctataattat aaagcaatga ttagaatctg acaaggattc    600
tggaaaatta cataaaggaa agttcataaa tgtctaaaac acaagaggac atacttgtat    660
tcagtaacat ttgcagcttt tctaggtctg aaaatatatt tgttgcctag tgaataagca    720
taatggtaca actacaagtg ttttactcct catattaact tcggtcatta gaggccacga    780
tttgacacat ttttactcaa aacaaaatgt ttgcatatct cttataattt caaattcaac    840
acacaacaaa taagagaaaa aacaaataat attaatttga gaatgaacaa aaggaccata    900
tcattcatta actcttctcc atccatttcc atttcacagt tcgatagcga aaaccgaata    960
aaaaacacag taaattacaa gcacaacaaa tggtacaaga aaaacagttt tcccaatgcc   1020
ataatactca aactcagtag gattctggtg tgtgcgcaat gaaactgatg cattgaactt   1080
```

-continued gacgaacgtt gtcgaaaccg atgatacgaa cgaaagctag gcctcagcga gtaccgctgg 1140
cgatctaatc catgatatcg tgaacatcat ctacattcaa attcttatga gctttcttaa 1200
gggcatctgc agcatttttc atagaatcta atacagcagt atttgtgcta gctccttcga 1260
gggcttccct ctgcatttca atagttgtaa gggttccatc tatttgtagt tgggtctttt 1320
ccaatcgttt cttcttttg agggcttgga gtgcaactct tttattttc gacgcatttt 1380 tctttgcgct cctgcaggcg gccgcgtgga tgaggagtta atcggtcgtg tgagagtagt 1440
gatcgagtgg atgtcgtcga gagtgatgag tgttgatgtt gttagtgata tgtggtagaa 1500
ggtatcgtga taaagcgtta acgcgatcgc agtacttgca aagaaaaatg cgtcgaaaaa 1560
taaaagagtt gcactccaag ccctcaaaaa gaagaaacga ttggaaaaga cccaactaca 1620
aatagatgga acccttacaa ctattgaaat gcagagggaa gccctcgaag gagctagcac 1680
aaatactgct gtattagatt ctatgaaaaa tgctgcagat gcccttaaga aagctcataa 1740
gaatttgaat gtagatgatg ttcacgatat catggatggt atcgcacagc gactgctgag 1800
ggacgtcgag ctcccgcttg gtatctgcat tacaatgaaa tgagcaaaga ctatgtgagt 1860
aacactggtc aacactaggg agaaggcatc gagcaagata cgtatgtaaa gagaagcaat 1920
atagtgtcag ttggtagata ctagatacca tcaggaggta aggagagcaa caaaaaggaa 1980
actctttatt tttaaatttt gttacaacaa acaagcagat caatgcatca aaatactgtc 2040
agtacttatt tcttcagaca acaatattta aaacaagtgc atctgatctt gacttatggt 2100
cacaataaag gagcagagat aaacatcaaa atttcgtcat ttatatttat tccttcaggc 2160
gttaacaatt taacagcaca caaacaaaaa cagaatagga atatctaatt ttggcaaata 2220
ataagctctg cagacgaaca aattattata gtatcgccta taatatgaat ccctatacta 2280
ttgacccatg tagtatgaag cctgtgccta aattaacagc aaacttctga atccaagtgc 2340
cctataacac caacatgtgc ttaaataaat accgctaagc accaaattac acatttctcg 2400
tattgctgtg taggttctat cttcgtttcg tactaccatg tccctatatt ttgctgctac 2460
aaaggacggc aagtaatcag cacaggcaga acacgatttc agagtgtaat tctagatcca 2520
gctaaaccac tctcagcaat caccacacaa gagagcattc agagaaacgt ggcagtaaca 2580
aaggcagagg gcggagtgag cgcgtaccga agacggttca gcgtgtcctc tccaaatgaa 2640
atgaacttcc ttatatagag gaagggtctt gcgaaggata gtgggattgt gcgtcatccc 2700
ttacgtcagt ggagatatca catcaatcca cttgctttga agacgtggtt ggaacgtctt 2760
ctttttccac gatgctcctc gtgggtgggg gtccatcttt gggaccactg tcggcagagg 2820
catcttcaac gatggccttt cctttatcgc aatgatggca tttgtaggag ccaccttcct 2880
tttccactat cttcacaata aagtgacaga tagctgggca atggaatccg aggaggtttc 2940
cggatattac cctttgttga aaagtctcaa tcggaccatc acatcaatcc acttgctttg 3000
aagacgtggt tggaacgtct tctttttcca cgatgctcct cgtgggtggg ggtccatctt 3060
tgggaccact gtcggcagag gcatcttcaa cgatggcctt tcctttatcg caatgatggc 3120
atttgtagga gccaccttcc ttttccacta tcttcacaat aaagtgacag atagctgggc 3180
aatggaatcc gaggaggttt ccggatatta ccctttgttg aaaagtctca atcggacctg 3240
cagcctgcag gctagcggcg cgccgggatc caaaaaacac acacagatct aattcctttt 3300
tttttgcact caaaatcaga acaatttatt tctcatttat tcatcgccga atctgttggc 3360
gattagccga ttacacaagt acagaaaaca ctggggaaag aaacacaata cagagatgtc 3420
tcatcagact cgcaagaact cgcacacaca tcaaccaaat tggctccaac ctgaatgagc 3480

-continued atacgtccaa acgcatgcag aattcaatca gagttcctat cacagctgga cggggatgaa 3540
ctcgatcttg tcgatgtaga tcttctcgtt ggagacgaag gactcagcac caatgatcag 3600
ttcattcttg tcgcccgaga agcccatgtt ggagttcgtg gtggcgaggt cgaaggtctg 3660
gtaggtcagg tcatcgtcct tgttcatggt cttgttgatg tagatgacca ggaagtcatt 3720
gttggagttc tggacgaaca ggcgcaggtt cgtggtggag gcgtagcgga tgcggacgcg 3780
gtagcgttgc agcaaggcag cggagttcag ggtgaccttg aacttggcga tggagttcga 3840
ggactccttc aggaacagca ggttgccacc ggtgaagcct ggaccctcaa tgatggaggc 3900
acccgaggac agggcgtagg ccttgaccac gggcagctgg gtgatcttct cggcgtcgat 3960
ggtgttgaag aagtcgacgg agcggtgggt ccaggtgaag aaggggatgg tgcccctgcg 4020
gtcttgcatc aggaagcact ccgcgtagtt cagctggtgg gagtaggcct tctccagggg 4080
ctcgtcagtg gtctcaggcg gcagctggtc gatggagtcc tgggcggaga cgtggccatt 4140
gttgcgcttg gagtcgtagg tctgggtgga ggtctcgttc ttctggtcat cgtactggga 4200
gaagtcgacc ttcgtgacgc ccaggtagac cttgccgttc ggccaagccg cgacgtcggt 4260
gttggcgatg gtgcggtaga ccttctggcc gtcgaaggac agcttctgga cgggctcggt 4320
ggacttgtcg ccgtagaaag gggaggtgat cgtcttcgag gagccgatgg agggcctggt 4380
ctcgacgtag ttgccggacc agtagttgaa ggagtccttg ccgaagtagc ctggcctcag 4440
gcgcgtgtgg aactcgatgc cctggaggta gtcgaacagg tggggcttgc ggatggagtt 4500
ctcgatggac aggaaggtgg gaccgtactt ctggagggtc gtgagcagga agatggggtc 4560
cgtgaagatg tcgcgggtca gctcggtctt gacgcccttg gagtacaggc ggatgtcgta 4620
gaaggggaac aggacgatca ggtccaggac ggtcagggtc atctccctgc ggaagcggtt 4680
gaacttgacc catgcgtcgt aggtggagcc cctcaggccg ttcaggccga cgttgtacca 4740
gttgacgcag tggtcggtgt actgttgggt cagcttcagc tggcgacggt agaactcggc 4800
gacgtcctcc gaggagtagc cccattcctc gccgaagacc tgggcgtcct tcagcaacag 4860
gaggtgggtg ttggcagcct gggcgtaggt gggcaggaac aggacctcga acttggagac 4920
ggcgaaggac ggcatggagt tgcggaagtg ggactcggcc tgggagaaca gctcgcggat 4980
gcggtcctgg gagcgcttgg agcgcaggga cagaggcgtc ttcttccagg agttcagcgc 5040
gttgacgtag tcctcgaagt tgttttgcag gccttgcagc tcggccaggg ccttggactt 5100
ggcgtactcc tcgatcttct tgtcgatcag gacttcgact tgggccatga aggccttcca 5160
ggggtcggcg tcggagggcc agatggtgtt caggaaggac tggtagaagg aggtgagagc 5220
acctgcgaag gggacgccaa cgacgcccag gatctgccca acgacggaga tgccggtccc 5280
gacggcgtcc ttgacggtgg agttgtccag gacctccgtg gaggagtcct cggtcatgcg 5340
caggaactcc ttgtagttca gctcttccag ggtggagttg gggttgtcgg ccagcgggta 5400
ctggttgtgg ttggtctgga gctcggagtt gggggtgacc ttgatcgtgt cgtgctcgga 5460
gcgattgttg gggttggcca tggttgatca cttctaccta caaaaaagct ccgcacgagg 5520
ctgcatttgt cacaaatcat gaaaagaaaa actaccgatg aacaatgctg agggattcaa 5580
attctaccca caaaaagaag aaagaaagat ctagcacatc taagcctgac gaagcagcag 5640
aaatatataa aaatataaac catagtgccc ttttcccctc ttcctgatct tgtttagcac 5700
ggcggaaatt ttaaaccccc catcatctcc cccaacaacg gcggatcgca gatctacatc 5760
cgagagcccc attccccgcg agatccgggc cggatccacg ccggcgagag ccccagccgc 5820

-continued gagatcccgc ccctcccgcg caccgatctg ggcgcgcacg aagccgcctc tcgcccaccc 5880
aaactaccaa ggccaaagat cgagaccgag acggaaaaaa aaacggagaa agaaagagga 5940
gaggggcggg gtggttaccg gcggcggcgg aggcctccct tggatcttat ggtgtgttgt 6000
ccctgtgtgt tctccaatag tgtggcttga gtgtgtggaa gatggttccc ggggtatctg 6060
atgatccttc aaatgggaat gaatgccttc ttatatagag ggaattcttt tgtggtcgtc 6120
actgcgttcg tcatacgcat tagtgagtgg gctgtcagga cagctctttt ccacgttatt 6180
ttgttcccca cttgtactag aggaatctgc tttatctttg caataaaggc aaagatgctt 6240
ttggtaggtg cgcctaacaa ttctgcacca ttcctttttt gtctggtccc cacaagccag 6300
ctgctcgatg ttgacaagat tactttcaaa gatgcccact aactttaagt cttcggtgga 6360
tgtctttttc tgaaacttac tgaccatgat gcatgtgctg gaacagtagt ttactttgat 6420
tgaagattct tcattgatct cctgtagctt ttggctaatg gtttggagac tctgtaccct 6480
gaccttgttg aggctttgga ctgagaattc ttccttacaa acctttgagg atgggagttc 6540
cttcttggtt ttggcgatac caatttgaat aaagtgatat ggctcgtacc ttgttgattg 6600
aacccaatct ggaatgctgc taaatcctga gctcaagcta attcttttgt ggtcgtcact 6660
gcgttcgtca tacgcattag tgagtgggct gtcaggacag ctcttttcca cgttattttg 6720
ttccccactt gtactagagg aatctgcttt atctttgcaa taaaggcaaa gatgcttttg 6780
gtaggtgcgc ctaacaattc tgcaccattc ctttttttgtc tggtccccac aagccagctg 6840
ctcgatgttg acaagattac tttcaaagat gcccactaac tttaagtctt cggtggatgt 6900
ctttttctga aacttactga ccatgatgca tgtgctggaa cagtagttta ctttgattga 6960
agattcttca ttgatctcct gtagcttttg gctaatggtt tggagactct gtaccctgac 7020
cttgttgagg ctttggactg agaattattt tcgacaagct tgcctcgaga caacaacatg 7080
cttctcatca acatggaggg aagagggagg gagaaagtgt cgcctggtca cctccattgt 7140
cacactagcc actggccagc tctcccacac caccaatgcc aggggcgagc tttagcacag 7200
ccaccgcttc acctccacca ccgcactacc ctagcttcgc ccaacagcca ccgtcaacgc 7260
ctcctctccg tcaacataag agagagagag aagaggagag tagccatgtg gggaggagga 7320
atagtacatg gggcctaccg tttggcaagt tattttgggt tgccaagtta ggccaataag 7380
gggagggatt tggccatccg gttggaaagg ttattggggt agtatctttt tactagaatt 7440
gtcaaaaaaa aatagtttga gagccatttg gagaggatgt tgcctgttag aggtgctctt 7500
aggacatcaa attccataaa aacatcagaa aaattctctc gatgaagatt tataaccact 7560
aaaactgccc tcaattcgaa gggagttcaa aacaattaaa atcatgttcg aattgagttt 7620
caatttcact ttaacccctt tgaaatctca atggtaaaac atcaacccgt caggtagcat 7680
ggttcttttt attcctttca aaaagagtta attacaaaca gaatcaaaac taacagttag 7740
gcccaaggcc catccgagca aacaatagat catgggccag gcctgccacc accctccccc 7800
tcctggctcc cgctcttgaa tttcaaaatc caaaaatatc ggcacgactg gccgccgacg 7860
gagcgggcgg aaaatgacgg aacaacccct cgaattctac cccaactacg cccaccaacc 7920
cacacgccac tgacaatccg gtcccaccct tgtgggccca cctacaagcg agacgtcagt 7980
cgctcgcagc aaccagtggg cccacctccc agtgagcggc gggtagatct ggactcttac 8040
ccacccacac taaacaaaac ggcatgaata ttttgcacta aaaccctcag aaaaattccg 8100
atattccaaa ccagtacagt tcctgaccgt tggaggagcc aaagtggagc ggagtgtaaa 8160
attgggaaac ttaatcgagg gggttaaacg caaaaacgcc gaggcgcctc ccgctctata 8220
gaaaggggag gagtgggagg tggaaaccct accacaccgc agagaaaggc gtcttcgtac 8280
tcgcctctct ccgcgccctc ctccgccgcc gctcgccgcc gttcgtctcc gccgccaccg 8340
gctagccatc caggtaaaac aaacaaaaac ggatctgatg cttccattcc tccgtttctc 8400
gtagtagcgc gcttcgatct gtgggtggat ctgggtgatc ctggggtgtg gttcgttctg 8460
tttgatagat ctgtcggtgg atctggcctt ctgtggttgt cgatgtccgg atctgcgttt 8520
tgatcagtgg tagttcgtgg atctggcgaa atgttttgga tctggcagtg agacgctaag 8580
aatcgggaaa tgatgcaata ttaggggggt ttcggatggg gatccactga attagtctgt 8640
ctccctgctg ataatctgtt cctttttggt agatctggtt agtgtatgtt tgtttcggat 8700
agatctgatc aatgcttgtt tgtttttca aattttctac ctaggttgta taggaatggc 8760
atgcggatct ggttggattg ccatgatccg tgctgaaatg cccctttggt tgatggatct 8820
tgatatttta ctgctgttca cctagatttg tactcccgtt tatacttaat ttgttgctta 8880
ttatgaatag atctgtaact taggcacatg tatggacgga gtatgtggat ctgtagtatg 8940
tacattgctg cgagctaaga actatttcag agcaagcaca gaaaaaaata tttagacaga 9000
ttgggcaact atttgatggt ctttggtatc atgctttgta gtgctcgttt ctgcgtagta 9060
atcttttgat ctgatctgaa gataggtgct attatattct taaaggtcat tagaacgcta 9120
tctgaaaggc tgtattatgt ggattggttc acctgtgact ccctgttcgt cttgtcttga 9180
taaatcctgt gataaaaaaa attcttaagg cgtaatttgt tgaaatcttg ttttgtccta 9240
tgcagcctga tccatggcgc aagttagcag aatctgcaat ggtgtgcaga acccatctct 9300
tatctccaat ctctcgaaat ccagtcaacg caaatctccc ttatcggttt ctctgaagac 9360
gcagcagcat ccacgagctt atccgatttc gtcgtcgtgg ggattgaaga agagtgggat 9420
gacgttaatt ggctctgagc ttcgtcctct taaggtcatg tcttctgttt ccacggcgtg 9480
catgcttcac ggtgcaagca gccggcccgc aaccgcccgc aaatcctctg gcctttccgg 9540
aaccgtccgc attcccggcg acaagtcgat ctcccaccgg tccttcatgt tcggcggtct 9600
cgcgagcggt gaaacgcgca tcaccggcct tctggaaggc gaggacgtca tcaatacggg 9660
caaggccatg caggcgatgg gcgcccgcat ccgtaaggaa ggcgacacct ggatcatcga 9720
tggcgtcggc aatggcggcc tcctggcgcc tgaggcgccg ctcgatttcg gcaatgccgc 9780
cacgggctgc cgcctgacga tgggcctcgt cggggtctac gatttcgaca gcaccttcat 9840
cggcgacgcc tcgctcacaa agcgcccgat gggccgcgtg ttgaacccgc tgcgcgaaat 9900
gggcgtgcag gtgaaatcgg aagacggtga ccgtcttccc gttaccttgc gcgggccgaa 9960
gacgccgacg ccgatcacct accgcgtgcc gatggcctcc gcacaggtga agtccgccgt 10020
gctgctcgcc ggcctcaaca cgcccggcat cacgacggtc atcgagccga tcatgacgcg 10080
cgatcatacg gaaaagatgc tgcagggctt tggcgccaac cttaccgtcg agacggatgc 10140
ggacggcgtg cgcaccatcc gcctggaagg ccgcggcaag ctcaccggcc aagtcatcga 10200
cgtgccgggc gacccgtcct cgacggcctt cccgctggtt gcggccctgc ttgttccggg 10260
ctccgacgtc accatcctca acgtgctgat gaaccccacc cgcaccggcc tcatcctgac 10320
gctgcaggaa atgggcgccg acatcgaagt catcaacccg cgccttgccg gcggcgaaga 10380
cgtggcggac ctgcgcgttc gctcctccac gctgaagggc gtcacggtgc cggaagaccg 10440
cgcgccttcg atgatcgacg aatatccgat tctcgctgtc gccgccgcct tcgcggaagg 10500
ggcgaccgtg atgaacggtc tggaagaact ccgcgtcaag gaaagcgacc gcctctcggc 10560

-continued

```
cgtcgccaat ggcctcaagc tcaatggcgt ggattgcgat gagggcgaga cgtcgctcgt  10620

cgtgcgtggc cgccctgacg gcaaggggct cggcaacgcc tcgggcgccg ccgtcgccac  10680

ccatctcgat caccgcatcg ccatgagctt cctcgtcatg ggcctcgtgt cggaaaaccc  10740

tgtcacggtg gacgatgcca cgatgatcgc cacgagcttc ccggagttca tggacctgat  10800

ggccgggctg ggcgcgaaga tcgaactctc cgatacgaag gctgcctgat gagctccagg  10860

gttcttgcct ggtgccttgg caatgcttga ttactgctgc tatcctatga tctgtccgtg  10920

tgggcttcta tctatcagtt tgtgtgtctg gttttgaaaa acatttgctt ttcgattatg  10980

tagggtttgc ttgtagcttt cgctgctgtg acctgtgttg tttatgtgaa ccttctttgt  11040

ggcatcttta atatccaagt tcgtggtttg tcgtaaaacg aagcctctac ttcgtaaagt  11100

tgtgtctata gcattgaaat cgtttttttg ctcgagaata attgtgacct ttagttggcg  11160

tgaaactagt tttggatatc tgattctctg gttcgcaatc ttgagatcgt cgctgcttag  11220

gtgagctaag tgatgttcct aagtaaatgc tcctcaccag aatacgtagc tgtgtgaaaa  11280

gagaacgcgt gaatacgtag ctgtgtaaag attgtgtccc aagtaaacct cagtgatttt  11340

tgtttggatt tttaatttag aaacattcga ctgggagcgg ctagagccac acccaagttc  11400

ctaactatga taaagttgct ctgtaacaga aaacaccatc tagagcggcc gcgtttaaac  11460

tatcagtgtt tgacaggata tattggcggg taaacctaag agaaaagagc gtttattaga  11520

ataatcggat atttaaaagg gcgtgaaaag gtttatccgt tcgtccattt gtatgtgcat  11580

gccaaccaca gggttcccct cgggagtgct tggcattccg tgcgataatg acttctgttc  11640

aaccacccaa acgtcggaaa gcctgacgac ggagcagcat tccaaaaaga tcccttggct  11700

cgtctgggtc ggctagaagg tcgagtgggc tgctgtggct tgatccctca acgcggtcgc  11760

ggacgtagcg cagcgccgaa aaatcct                                      11787
```

<210> SEQ ID NO 29
<211> LENGTH: 12322
<212> TYPE: DNA
<213> ORGANISM: Artificial Sequence
<220> FEATURE:
<223> OTHER INFORMATION: DNA construct 419

<400> SEQUENCE: 29

```
aaaagtccca tgtggatcac tccgttgccc cgtcgctcac cgtgttgggg ggaaggtgca     60

catggctcag ttctcaatgg aaattatctg cctaaccggc tcagttctgc gtagaaacca    120

acatgcaagc tccaccgggt gcaaagcggc agcggcggca ggatatattc aattgtaaat    180

ggcttcatgt ccgggaaatc tacatggatc agcaatgagt atgatggtca atatggagaa    240

aaagaaagag taattaccaa tttttttca attcaaaaat gtagatgtcc gcagcgttat    300

tataaaatga aagtacattt tgataaaacg acaaattacg atccgtcgta tttataggcg    360

aaagcaataa acaaattatt ctaattcgga aatctttatt tcgacgtgtc tacattcacg    420

tccaaatggg ggcttagatg agaaacttca cgatcgatgc ggccaccact cgaggtcgag    480

gtaccgttgt caatcaattg gcaagtcata aaatgcatta aaaaatattt tcatactcaa    540

ctacaaatcc atgagtataa ctataattat aaagcaatga ttagaatctg acaaggattc    600

tggaaaatta cataaaggaa agttcataaa tgtctaaaac acaagaggac atacttgtat    660

tcagtaacat ttgcagcttt tctaggtctg aaaatatatt tgttgcctag tgaataagca    720

taatggtaca actacaagtg ttttactcct catattaact tcggtcatta gaggccacga    780

tttgacacat ttttactcaa aacaaaatgt ttgcatatct cttataattt caaattcaac    840
```

-continued

```
acacaacaaa taagagaaaa aacaaataat attaatttga gaatgaacaa aaggaccata    900
tcattcatta actcttctcc atccatttcc atttcacagt tcgatagcga aaaccgaata    960
aaaaacacag taaattacaa gcacaacaaa tggtacaaga aaaacagttt tcccaatgcc   1020
ataatactca aactcagtag gattctggtg tgtgcgcaat gaaactgatg cattgaactt   1080
gacgaacgtt gtcgaaaccg atgatacgaa cgaaagctag gcctcagcga gtaccgctgg   1140
cgatctaatc catgatatcg tgaacatcat ctacattcaa attcttatga gctttcttaa   1200
gggcatctgc agcatttttc atagaatcta atacagcagt atttgtgcta gctccttcga   1260
gggcttccct ctgcatttca atagttgtaa gggttccatc tatttgtagt tgggtctttt   1320
ccaatcgttt cttcttttg agggcttgga gtgcaactct tttattttc gacgcatttt     1380
tctttgcgct cctgcaggcg gccgcgtgga tgaggagtta atcggtcgtg tgagagtagt   1440
gatcgagtgg atgtcgtcga gagtgatgag tgttgatgtt gttagtgata tgtggtagaa   1500
ggtatcgtga taaagcgtta acgcgatcgc agtacttgca aagaaaaatg cgtcgaaaaa   1560
taaaagagtt gcactccaag ccctcaaaaa gaagaaacga ttggaaaaga cccaactaca   1620
aatagatgga acccttacaa ctattgaaat gcagagggaa gccctcgaag gagctagcac   1680
aaatactgct gtattagatt ctatgaaaaa tgctgcagat gcccttaaga aagctcataa   1740
gaatttgaat gtagatgatg ttcacgatat catggatggt atcgcacagc gactgctgag   1800
ggacgtcgag ctcccgcttg gtatctgcat tacaatgaaa tgagcaaaga ctatgtgagt   1860
aacactggtc aacactaggg agaaggcatc gagcaagata cgtatgtaaa gagaagcaat   1920
atagtgtcag ttggtagata ctagatacca tcaggaggta aggagagcaa caaaaaggaa   1980
actctttatt tttaaatttt gttacaacaa acaagcagat caatgcatca aaatactgtc   2040
agtacttatt tcttcagaca acaatattta aaacaagtgc atctgatctt gacttatggt   2100
cacaataaag gagcagagat aaacatcaaa atttcgtcat ttatatttat tccttcaggc   2160
gttaacaatt taacagcaca caaacaaaaa cagaatagga atatctaatt ttggcaaata   2220
ataagctctg cagacgaaca aattattata gtatcgccta taatatgaat ccctatacta   2280
ttgacccatg tagtatgaag cctgtgccta aattaacagc aaacttctga atccaagtgc   2340
cctataacac caacatgtgc ttaaataaat accgctaagc accaaattac acatttctcg   2400
tattgctgtg taggttctat cttcgtttcg tactaccatg tccctatatt ttgctgctac   2460
aaaggacggc aagtaatcag cacaggcaga acacgatttc agagtgtaat tctagatcca   2520
gctaaaccac tctcagcaat caccacacaa gagagcattc agagaaacgt ggcagtaaca   2580
aaggcagagg gcggagtgag cgcgtaccga agacggttca gcgtgtcctc tccaaatgaa   2640
atgaacttcc ttatatagag gaagggtctt gcgaaggata gtgggattgt gcgtcatccc   2700
ttacgtcagt ggagatatca catcaatcca cttgctttga agacgtggtt ggaacgtctt   2760
ctttttccac gatgctcctc gtgggtgggg gtccatcttt gggaccactg tcggcagagg   2820
catcttcaac gatggccttt cctttatcgc aatgatggca tttgtaggag ccaccttcct   2880
tttccactat cttcacaata aagtgacaga tagctgggca atggaatccg aggaggtttc   2940
cggatattac cctttgttga aaagtctcaa tcggaccatc acatcaatcc acttgctttg   3000
aagacgtggt tggaacgtct tctttttcca cgatgctcct cgtgggtggg ggtccatctt   3060
tgggaccact gtcggcagag gcatcttcaa cgatggcctt tcctttatcg caatgatggc   3120
atttgtagga gccaccttcc ttttccacta tcttcacaat aaagtgacag atagctgggc   3180
```

-continued

```
aatggaatcc gaggaggttt ccggatatta ccctttgttg aaaagtctca atcggacctg   3240
cagcctgcag gctagcggcg cgccgggatc caaaaaacac acacagatct aattcctttt   3300
tttttgcact caaaatcaga acaatttatt tctcatttat tcatcgccga atctgttggc   3360
gattagccga ttacacaagt acagaaaaca ctggggaaag aaacacaata cagagatgtc   3420
tcatcagact cgcaagaact cgcacacaca tcaaccaaat tggctccaac ctgaatgagc   3480
atacgtccaa acgcatgcag aattcaatca gagttcctat cacagctgga cggggatgaa   3540
ctcgatcttg tcgatgtaga tcttctcgtt ggagacgaag gactcagcac caatgatcag   3600
ttcattcttg tcgcccgaga agcccatgtt ggagttcgtg gtggcgaggt cgaaggtctg   3660
gtaggtcagg tcatcgtcct tgttcatggt cttgttgatg tagatgacca ggaagtcatt   3720
gttggagttc tggacgaaca ggcgcaggtt cgtggtggag gcgtagcgga tgcggacgcg   3780
gtagcgttgc agcaaggcag cggagttcag ggtgaccttg aacttggcga tggagttcga   3840
ggactccttc aggaacagca ggttgccacc ggtgaagcct ggaccctcaa tgatggaggc   3900
acccgaggac agggcgtagg ccttgaccac gggcagctgg gtgatcttct cggcgtcgat   3960
ggtgttgaag aagtcgacgg agcggtgggt ccaggtgaag aaggggatgg tgcccctgcg   4020
gtcttgcatc aggaagcact ccgcgtagtt cagctggtgg gagtaggcct tctccagggg   4080
ctcgtcagtg gtctcaggcg gcagctggtc gatggagtcc tgggcggaga cgtggccatt   4140
gttgcgcttg gagtcgtagg tctgggtgga ggtctcgttc ttctggtcat cgtactggga   4200
gaagtcgacc ttcgtgacgc ccaggtagac cttgccgttc ggccaagccg cgacgtcggt   4260
gttggcgatg gtgcggtaga ccttctggcc gtcgaaggac agcttctgga cgggctcggt   4320
ggacttgtcg ccgtagaaag gggaggtgat cgtcttcgag gagccgatgg agggcctggt   4380
ctcgacgtag ttgccggacc agtagttgaa ggagtccttg ccgaagtagc ctggcctcag   4440
gcgcgtgtgg aactcgatgc cctggaggta gtcgaacagg tggggcttgc ggatggagtt   4500
ctcgatggac aggaaggtgg gaccgtactt ctggagggtc gtgagcagga agatggggtc   4560
cgtgaagatg tcgcgggtca gctcggtctt gacgcccttg gagtacaggc ggatgtcgta   4620
gaaggggaac aggacgatca ggtccaggac ggtcagggtc atctccctgc ggaagcggtt   4680
gaacttgacc catgcgtcgt aggtggagcc cctcaggccg ttcaggccga cgttgtacca   4740
gttgacgcag tggtcggtgt actgttgggt cagcttcagc tggcgacggt agaactcggc   4800
gacgtcctcc gaggagtagc cccattcctc gccgaagacc tgggcgtcct tcagcaacag   4860
gaggtgggtg ttggcagcct gggcgtaggt gggcaggaac aggacctcga acttggagac   4920
ggcgaaggac ggcatggagt tgcggaagtg ggactcggcc tgggagaaca gctcgcggat   4980
gcggtcctgg gagcgcttgg agcgcaggga cagaggcgtc ttcttccagg agttcagcgc   5040
gttgacgtag tcctcgaagt tgttttgcag gccttgcagc tcggccaggg ccttggactt   5100
ggcgtactcc tcgatcttct tgtcgatcag gacttcgact tgggccatga aggccttcca   5160
ggggtcggcg tcggagggcc agatggtgtt caggaaggac tggtagaagg aggtgagagc   5220
acctgcgaag gggacgccaa cgacgcccag gatctgccca acgacggaga tgccggtccc   5280
gacggcgtcc ttgacggtgg agttgtccag gacctccgtg gaggagtcct cggtcatgcg   5340
caggaactcc ttgtagttca gctcttccag ggtggagttg gggttgtcgg ccagcgggta   5400
ctggttgtgg ttggtctgga gctcggagtt gggggtgacc ttgatcgtgt cgtgctcgga   5460
gcgattgttg gggttggcca tggttgatca cttctaccta caaaaaagct ccgcacgagg   5520
ctgcatttgt cacaaatcat gaaaagaaaa actaccgatg aacaatgctg agggattcaa   5580
```

-continued

```
attctaccca caaaaagaag aaagaaagat ctagcacatc taagcctgac gaagcagcag   5640
aaatatataa aaatataaac catagtgccc ttttcccctc ttcctgatct tgtttagcac   5700
ggcggaaatt ttaaaccccc catcatctcc cccaacaacg gcggatcgca gatctacatc   5760
cgagagcccc attccccgcg agatccgggc cggatccacg ccggcgagag ccccagccgc   5820
gagatcccgc ccctcccgcg caccgatctg ggcgcgcacg aagccgcctc tcgcccaccc   5880
aaactaccaa ggccaaagat cgagaccgag acggaaaaaa aaacggagaa agaaagagga   5940
gaggggcggg gtggttaccg gcggcggcgg aggcctccct tggatcttat ggtgtgttgt   6000
ccctgtgtgt tctccaatag tgtggcttga gtgtgtggaa gatggttccc gggggttttg   6060
atcatgggat tagggaggta tttatagtcg agccccggga ttaattaatc gaccgttaga   6120
gctcatgtga accctgccct gccatcatgt gagcgtgcat acgagggcga tctggattgg   6180
ctggcagaac acctgcccta gcaaggctcg tagattaatt aacaaatcgt acgtacatct   6240
acgctgataa tgtgttaaat catcggccga atatttggtt agccgtgaag cactcgatcc   6300
cgcaaatgac caagattgct gcacacgaca catcgcgggc ttgtttcctt atgatcattg   6360
gttgttattt tatctcgcga tcttggccta tcgggcgtcg cttcgcgcgg tgcagcgtga   6420
ctgcgtgagc aagttggtga ttttcttttg ccgtttaaga atgcttgctc cgtgatcaca   6480
caagagagga catcacatga accgagaccg gaggaatatc ggggcatggt gggattggtg   6540
ggtgtcccag tccaacgggc aagaagattc taagcttacc tgggtttgtt ttcacgtacg   6600
cgaaggacag gggaagatgc cattgcagcg tggcttcctg ctggcccgcc aactttaatc   6660
tacactaggc acgtagctac taggtcggcc cgcttagata gctaaggtag gctaggtagg   6720
tccgtggtaa actgccagcc catgggcgcc tgggattctt cttgggccaa cagaagcaga   6780
ggttgggcaa tgcgaagcct gaaaatcctc ctcctccttc tctctccctc tctctctctc   6840
tctctctctc tctctcacga ataaaatcct cttcttcccg aacaggctag attctttttt   6900
ttttaatgaa ccagtgagcc accaatttca ttgaatagag gaataaaatt gtacatgcgc   6960
aagcgcaaat agaaaacttt accgtctcaa ggcctttggc ccgaacatgt taaaaggtaa   7020
gccacctatc aaggtgtttc gcgcccgcca agacccatgt tttggcatcc tccttaattt   7080
tggctatcag actagccacc ggaagctctt ggtgctgaaa aactctgcgg ttcctttcat   7140
tccaaatatc ctaggcgact aatagcatta gagtctgcaa ggctttcttt ggcgcttcgt   7200
tggaacatgc ggtggcctcc caccacttga gtagcgtcga ggcttgttgc cataacgttg   7260
gtcttatttg ttcacatgtt gtccagtctg caagtgtcgc ctagattctt tcacatatct   7320
acactccgcc aggaggtgag ggccgtttcc tgattccttc gacaaagggg cagatggagc   7380
cattttcgat tacccacggg ttgccaatct gtcggaggtc catactctat tttggataac   7440
aagccaagcg aagcgaatgt tttacatttg cgcggcgcct agggcttcca gataggggca   7500
ttgaaattga agcttttatg ccaagaagtt gtgcgttgta ggccgatgtc gtcatgtatt   7560
cgccgtgact agttagcttc cattttcgac aagcttgcct cgagacaaca acatgcttct   7620
catcaacatg gagggaagag ggagggagaa agtgtcgcct ggtcacctcc attgtcacac   7680
tagccactgg ccagctctcc cacaccacca atgccagggg cgagctttag cacagccacc   7740
gcttcacctc caccaccgca ctaccctagc ttcgcccaac agccaccgtc aacgcctcct   7800
ctccgtcaac ataagagaga gagagaagag gagagtagcc atgtggggag gaggaatagt   7860
acatggggcc taccgtttgg caagttattt tgggttgcca agttaggcca ataaggggag   7920
```

-continued

```
ggatttggcc atccggttgg aaaggttatt ggggtagtat ctttttacta gaattgtcaa   7980
aaaaaaatag tttgagagcc atttggagag gatgttgcct gttagaggtg ctcttaggac   8040
atcaaattcc ataaaaacat cagaaaaatt ctctcgatga agatttataa ccactaaaac   8100
tgccctcaat tcgaagggag ttcaaaacaa ttaaaatcat gttcgaattg agtttcaatt   8160
tcactttaac cccttttgaaa tctcaatggt aaaacatcaa cccgtcaggt agcatggttc  8220
tttttattcc tttcaaaaag agttaattac aaacagaatc aaaactaaca gttaggccca   8280
aggcccatcc gagcaaacaa tagatcatgg gccaggcctg ccaccaccct ccccctcctg   8340
gctcccgctc ttgaatttca aaatccaaaa atatcggcac gactggccgc cgacggagcg   8400
ggcggaaaat gacggaacaa cccctcgaat tctaccccaa ctacgcccac caacccacac   8460
gccactgaca atccggtccc acccttgtgg gcccacctac aagcgagacg tcagtcgctc   8520
gcagcaacca gtgggcccac ctcccagtga gcggcgggta gatctggact cttacccacc   8580
cacactaaac aaaacggcat gaatattttg cactaaaacc ctcagaaaaa ttccgatatt   8640
ccaaaccagt acagttcctg accgttggag gagccaaagt ggagcggagt gtaaaattgg   8700
gaaacttaat cgaggggggtt aaacgcaaaa acgccgaggc gcctcccgct ctatagaaag  8760
gggaggagtg ggaggtggaa accctaccac accgcagaga aaggcgtctt cgtactcgcc   8820
tctctccgcg ccctcctccg ccgccgctcg ccgccgttcg tctccgccgc caccggctag   8880
ccatccaggt aaaacaaaca aaaacggatc tgatgcttcc attcctccgt ttctcgtagt   8940
agcgcgcttc gatctgtggg tggatctggg tgatcctggg gtgtggttcg ttctgtttga   9000
tagatctgtc ggtggatctg gccttctgtg gttgtcgatg tccggatctg cgttttgatc   9060
agtggtagtt cgtggatctg gcgaaatgtt ttggatctgg cagtgagacg ctaagaatcg   9120
ggaaatgatg caatattagg ggggtttcgg atggggatcc actgaattag tctgtctccc   9180
tgctgataat ctgttccttt ttggtagatc tggttagtgt atgtttgttt cggatagatc   9240
tgatcaatgc ttgtttgttt tttcaaattt tctacctagg ttgtatagga atggcatgcg   9300
gatctggttg gattgccatg atccgtgctg aaatgcccct ttggttgatg gatcttgata   9360
ttttactgct gttcacctag atttgtactc ccgtttatac ttaatttgtt gcttattatg   9420
aatagatctg taacttaggc acatgtatgg acggagtatg tggatctgta gtatgtacat   9480
tgctgcgagc taagaactat ttcagagcaa gcacagaaaa aaatatttag acagattggg   9540
caactatttg atggtctttg gtatcatgct ttgtagtgct cgtttctgcg tagtaatctt   9600
ttgatctgat ctgaagatag gtgctattat attcttaaag gtcattagaa cgctatctga   9660
aaggctgtat tatgtggatt ggttcacctg tgactccctg ttcgtcttgt cttgataaat   9720
cctgtgataa aaaaaattct taaggcgtaa tttgttgaaa tcttgttttg tcctatgcag   9780
cctgatccat ggcgcaagtt agcagaatct gcaatggtgt gcagaaccca tctcttatct   9840
ccaatctctc gaaatccagt caacgcaaat ctcccttatc ggtttctctg aagacgcagc   9900
agcatccacg agcttatccg atttcgtcgt cgtggggatt gaagaagagt gggatgacgt   9960
taattggctc tgagcttcgt cctcttaagg tcatgtcttc tgtttccacg gcgtgcatgc  10020
ttcacggtgc aagcagccgg cccgcaaccg cccgcaaatc ctctggcctt tccggaaccg  10080
tccgcattcc cggcgacaag tcgatctccc accggtcctt catgttcggc ggtctcgcga  10140
gcggtgaaac gcgcatcacc ggccttctgg aaggcgagga cgtcatcaat acgggcaagg  10200
ccatgcaggc gatgggcgcc cgcatccgta aggaaggcga cacctggatc atcgatggcg  10260
tcggcaatgg cggcctcctg gcgcctgagg cgccgctcga tttcggcaat gccgccacgg  10320
```

gctgccgcct gacgatgggc ctcgtcgggg tctacgattt cgacagcacc ttcatcggcg 10380
acgcctcgct cacaaagcgc ccgatgggcc gcgtgttgaa cccgctgcgc gaaatgggcg 10440
tgcaggtgaa atcggaagac ggtgaccgtc ttcccgttac cttgcgcggg ccgaagacgc 10500
cgacgccgat cacctaccgc gtgccgatgg cctccgcaca ggtgaagtcc gccgtgctgc 10560
tcgccggcct caacacgccc ggcatcacga cggtcatcga gccgatcatg acgcgcgatc 10620
atacggaaaa gatgctgcag ggctttggcg ccaaccttac cgtcgagacg gatgcggacg 10680
gcgtgcgcac catccgcctg gaaggccgcg gcaagctcac cggccaagtc atcgacgtgc 10740
cgggcgaccc gtcctcgacg gccttcccgc tggttgcggc cctgcttgtt ccgggctccg 10800
acgtcaccat cctcaacgtg ctgatgaacc ccacccgcac cggcctcatc ctgacgctgc 10860
aggaaatggg cgccgacatc gaagtcatca acccgcgcct tgccggcggc gaagacgtgg 10920
cggacctgcg cgttcgctcc tccacgctga agggcgtcac ggtgccggaa gaccgcgcgc 10980
cttcgatgat cgacgaatat ccgattctcg ctgtcgccgc cgccttcgcg gaaggggcga 11040
ccgtgatgaa cggtctggaa gaactccgcg tcaaggaaag cgaccgcctc tcggccgtcg 11100
ccaatggcct caagctcaat ggcgtggatt gcgatgaggg cgagacgtcg ctcgtcgtgc 11160
gtggccgccc tgacggcaag gggctcggca acgcctcggg cgccgccgtc gccacccatc 11220
tcgatcaccg catcgccatg agcttcctcg tcatgggcct cgtgtcggaa aaccctgtca 11280
cggtggacga tgccacgatg atcgccacga gcttcccgga gttcatggac ctgatggccg 11340
ggctgggcgc gaagatcgaa ctctccgata cgaaggctgc ctgatgagct ccagggttct 11400
tgcctggtgc cttggcaatg cttgattact gctgctatcc tatgatctgt ccgtgtgggc 11460
ttctatctat cagtttgtgt gtctggtttt gaaaaacatt tgcttttcga ttatgtaggg 11520
tttgcttgta gctttcgctg ctgtgacctg tgttgtttat gtgaaccttc tttgtggcat 11580
ctttaatatc caagttcgtg gtttgtcgta aaacgaagcc tctacttcgt aaagttgtgt 11640
ctatagcatt gaaatcgttt ttttgctcga gaataattgt gacctttagt tggcgtgaaa 11700
ctagttttgg atatctgatt ctctggttcg caatcttgag atcgtcgctg cttaggtgag 11760
ctaagtgatg ttcctaagta aatgctcctc accagaatac gtagctgtgt gaaaagagaa 11820
cgcgtgaata cgtagctgtg taaagattgt gtcccaagta aacctcagtg atttttgttt 11880
ggatttttaa tttagaaaca ttcgactggg agcggctaga gccacaccca agttcctaac 11940
tatgataaag ttgctctgta acagaaaaca ccatctagag cggccgcgtt taaactatca 12000
gtgtttgaca ggatatattg gcgggtaaac ctaagagaaa agagcgttta ttagaataat 12060
cggatattta aaagggcgtg aaaaggttta tccgttcgtc catttgtatg tgcatgccaa 12120
ccacagggtt cccctcggga gtgcttggca ttccgtgcga taatgacttc tgttcaacca 12180
cccaaacgtc ggaaagcctg acgacggagc agcattccaa aaagatccct tggctcgtct 12240
gggtcggcta gaaggtcgag tgggctgctg tggcttgatc cctcaacgcg gtcgcggacg 12300
tagcgcagcg ccgaaaaatc ct 12322

<210> SEQ ID NO 30
<211> LENGTH: 12797
<212> TYPE: DNA
<213> ORGANISM: Artificial Sequence
<220> FEATURE:
<223> OTHER INFORMATION: DNA construct 402

<400> SEQUENCE: 30

-continued

```
aaaagtccca tgtggatcac tccgttgccc cgtcgctcac cgtgttgggg ggaaggtgca     60
catggctcag ttctcaatgg aaattatctg cctaaccggc tcagttctgc gtagaaacca    120
acatgcaagc tccaccgggt gcaaagcggc agcggcggca ggatatattc aattgtaaat    180
ggcttcatgt ccgggaaatc tacatggatc agcaatgagt atgatggtca atatggagaa    240
aaagaaagag taattaccaa tttttttca attcaaaaat gtagatgtcc gcagcgttat    300
tataaaatga aagtacattt tgataaaacg acaaattacg atccgtcgta tttataggcg    360
aaagcaataa acaaattatt ctaattcgga aatctttatt tcgacgtgtc tacattcacg    420
tccaaatggg ggcttagatg agaaacttca cgatcgatgc ggccaccact cgaggtcgag    480
gtaccgttgt caatcaattg gcaagtcata aaatgcatta aaaaatattt tcatactcaa    540
ctacaaatcc atgagtataa ctataattat aaagcaatga ttagaatctg acaaggattc    600
tggaaaatta cataaaggaa agttcataaa tgtctaaaac acaagaggac atacttgtat    660
tcagtaacat ttgcagcttt tctaggtctg aaaatatatt tgttgcctag tgaataagca    720
taatggtaca actacaagtg ttttactcct catattaact tcggtcatta gaggccacga    780
tttgacacat ttttactcaa aacaaaatgt ttgcatatct cttataattt caaattcaac    840
acacaacaaa taagagaaaa aacaaataat attaatttga gaatgaacaa aaggaccata    900
tcattcatta actcttctcc atccatttcc atttcacagt tcgatagcga aaaccgaata    960
aaaaacacag taaattacaa gcacaacaaa tggtacaaga aaaacagttt tcccaatgcc   1020
ataatactca aactcagtag gattctggtg tgtgcgcaat gaaactgatg cattgaactt   1080
gacgaacgtt gtcgaaaccg atgatacgaa cgaaagctag gcctcagcga gtaccgctgg   1140
cgatctaatc catgatatcg tgaacatcat ctacattcaa attcttatga gctttcttaa   1200
gggcatctgc agcatttttc atagaatcta atacagcagt atttgtgcta gctccttcga   1260
gggcttccct ctgcatttca atagttgtaa gggttccatc tatttgtagt tgggtctttt   1320
ccaatcgttt cttcttttg agggcttgga gtgcaactct tttatttttc gacgcatttt   1380
tctttgcgct cctgcaggcg gccgcgtgga tgaggagtta atcggtcgtg tgagagtagt   1440
gatcgagtgg atgtcgtcga gagtgatgag tgttgatgtt gttagtgata tgtggtagaa   1500
ggtatcgtga taaagcgtta acgcgatcgc agtacttgca aagaaaaatg cgtcgaaaaa   1560
taaaagagtt gcactccaag ccctcaaaaa gaagaaacga ttggaaaaga cccaactaca   1620
aatagatgga acccttacaa ctattgaaat gcagagggaa gccctcgaag gagctagcac   1680
aaatactgct gtattagatt ctatgaaaaa tgctgcagat gcccttaaga aagctcataa   1740
gaatttgaat gtagatgatg ttcacgatat catggatggt atcgcacagc gactgctgag   1800
ggacgtcggt ccatggagat cctctagagg ccgcttggta tctgcattac aatgaaatga   1860
gcaaagacta tgtgagtaac actggtcaac actagggaga aggcatcgag caagatacgt   1920
atgtaaagag aagcaatata gtgtcagttg gtagatacta gataccatca ggaggtaagg   1980
agagcaacaa aaaggaaact ctttattttt aaattttgtt acaacaaaca agcagatcaa   2040
tgcatcaaaa tactgtcagt acttatttct tcagacaaca atatttaaaa caagtgcatc   2100
tgatcttgac ttatggtcac aataaaggag cagagataaa catcaaaatt tcgtcattta   2160
tatttattcc ttcaggcgtt aacaatttaa cagcacacaa acaaaaacag aataggaata   2220
tctaattttg gcaaataata agctctgcag acgaacaaat tattatagta tcgcctataa   2280
tatgaatccc tatactattg acccatgtag tatgaagcct gtgcctaaat taacagcaaa   2340
cttctgaatc caagtgccct ataacaccaa catgtgctta aataaatacc gctaagcacc   2400
```

-continued aaattacaca tttctcgtat tgctgtgtag gttctatctt cgtttcgtac taccatgtcc 2460
ctatattttg ctgctacaaa ggacggcaag taatcagcac aggcagaaca cgatttcaga 2520
gtgtaattct agatccagct aaaccactct cagcaatcac cacacaagag agcattcaga 2580
gaaacgtggc agtaacaaag gcagagggcg gagtgagcgc gtaccgaaga cggtgggccg 2640
cttatggtgt gttgtccctg tgtgttctcc aatagtgtgg cttgagtgtg tggaagatgg 2700
ttgtatctga tgatccttca aatgggaatg aatgccttct tatatagagg gaattctttt 2760
gtggtcgtca ctgcgttcgt catacgcatt agtgagtggg ctgtcaggac agctcttttc 2820
cacgttattt tgttccccac ttgtactaga ggaatctgct ttatctttgc aataaaggca 2880
aagatgcttt tggtaggtgc gcctaacaat tctgcaccat tcctttttg tctggtcccc 2940
acaagccagc tgctcgatgt tgacaagatt actttcaaag atgcccacta actttaagtc 3000
ttcggtggat gtctttttct gaaacttact gaccatgatg catgtgctgg aacagtagtt 3060
tactttgatt gaagattctt cattgatctc ctgtagcttt tggctaatgg tttggagact 3120
ctgtaccctg accttgttga ggctttggac tgagaattct tccttacaaa cctttgagga 3180
tgggagttcc ttcttggttt tggcgatacc aatttgaata aagtgatatg gctcgtacct 3240
tgttgattga acccaatctg gaatgctgct aaatcctgag ctcaagctaa ttcttttgtg 3300
gtcgtcactg cgttcgtcat acgcattagt gagtgggctg tcaggacagc tcttttccac 3360
gttattttgt tccccacttg tactagagga atctgcttta tctttgcaat aaaggcaaag 3420
atgcttttgg taggtgcgcc taacaattct gcaccattcc tttttgtct ggtccccaca 3480
agccagctgc tcgatgttga caagattact ttcaaagatg cccactaact ttaagtcttc 3540
ggtggatgtc tttttctgaa acttactgac catgatgcat gtgctggaac agtagtttac 3600
tttgattgaa gattcttcat tgatctcctg tagcttttgg ctaatggttt ggagactctg 3660
taccctgacc ttgttgaggc tttggactga gaattagctt ccactcgaag cttgttaacc 3720
tgcaggctag cggcgcgccg gaagctaact agtcacggcg aatacatgac gacatcggcc 3780
tacaacgcac aacttcttgg cataaaagct tcaatttcaa tgcccctatc tggaagccct 3840
aggcgccgcg caaatgtaaa acattcgctt cgcttggctt gttatccaaa atagagtatg 3900
gacctccgac agattggcaa cccgtgggta atcgaaaatg gctccatctg cccctttgtc 3960
gaaggaatca ggaaacggcc ctcacctcct ggcggagtgt agatatgtga aagaatctag 4020
gcgacacttg cagactggac aacatgtgaa caaataagac caacgttatg gcaacaagcc 4080
tcgacgctac tcaagtggtg ggaggccacc gcatgttcca acgaagcgcc aaagaaagcc 4140
ttgcagactc taatgctatt agtcgcctag gatatttgga atgaaaggaa ccgcagagtt 4200
tttcagcacc aagagcttcc ggtggctagt ctgatagcca aaattaagga ggatgccaaa 4260
acatgggtct tggcgggcgc gaaacacctt gataggtggc ttaccttta acatgttcgg 4320
gccaaaggcc ttgagacggt aaagttttct atttgcgctt gcgcatgtac aattttattc 4380
ctctattcaa tgaaattggt ggctcactgg ttcattaaaa aaaaaagaat ctagcctgtt 4440
cgggaagaag aggattttat tcgtgagaga gagagagaga gagagagaga gagggagaga 4500
gaaggaggag gaggattttc aggcttcgca ttgcccaacc tctgcttctg ttggcccaag 4560
aagaatccca ggcgcccatg ggctggcagt ttaccacgga cctacctagc ctaccttagc 4620
tatctaagcg ggccgaccta gtagctacgt gcctagtgta gattaaagtt ggcgggccag 4680
caggaagcca cgctgcaatg gcatcttccc ctgtccttcg cgtacgtgaa aacaaaccca 4740

-continued

```
ggtaagctta gaatcttctt gcccgttgga ctgggacacc caccaatccc accatgcccc   4800
gatattcctc cggtctcggt tcatgtgatg tcctctcttg tgtgatcacg gagcaagcat   4860
tcttaaacgg caaaagaaaa tcaccaactt gctcacgcag tcacgctgca ccgcgcgaag   4920
cgacgcccga taggccaaga tcgcgagata aaataacaac caatgatcat aaggaaacaa   4980
gcccgcgatg tgtcgtgtgc agcaatcttg gtcatttgcg ggatcgagtg cttcacggct   5040
aaccaaatat tcggccgatg atttaacaca ttatcagcgt agatgtacgt acgatttgtt   5100
aattaatcta cgagccttgc tagggcaggt gttctgccag ccaatccaga tcgccctcgt   5160
atgcacgctc acatgatggc agggcagggt tcacatgagc tctaacggtc gattaattaa   5220
tcccggggct cgactataaa tacctcccta atcccatgat caaaaccccc gggaaccatc   5280
ttccacacac tcaagccaca ctattggaga acacacaggg acaacacacc ataagatcca   5340
agggaggcct ccgccgccgc cggtaaccac cccgcccctc tcctctttct ttctccgttt   5400
tttttccgt ctcggtctcg atctttggcc ttggtagttt gggtgggcga gaggcggctt   5460
cgtgcgcgcc cagatcggtg cgcgggaggg gcgggatctc gcggctgggg ctctcgccgg   5520
cgtggatccg gcccggatct cgcggggaat ggggctctcg gatgtagatc tgcgatccgc   5580
cgttgttggg ggagatgatg gggggtttaa aatttccgcc gtgctaaaca agatcaggaa   5640
gaggggaaaa gggcactatg gtttatattt ttatatattt ctgctgcttc gtcaggctta   5700
gatgtgctag atctttcttt cttcttttg tgggtagaat ttgaatccct cagcattgtt   5760
catcggtagt ttttcttttc atgatttgtg acaaatgcag cctcgtgcgg agcttttttg   5820
taggtagaag tgatcaacca tggccaaccc caacaatcgc tccgagcacg acacgatcaa   5880
ggtcaccccc aactccgagc tccagaccaa ccacaaccag tacccgctgg ccgacaaccc   5940
caactccacc ctggaagagc tgaactacaa ggagttcctg cgcatgaccg aggactcctc   6000
cacggaggtc ctggacaact ccaccgtcaa ggacgccgtc gggaccggca tctccgtcgt   6060
tgggcagatc ctgggcgtcg ttggcgtccc cttcgcaggt gctctcacct ccttctacca   6120
gtccttcctg aacaccatct ggccctccga cgccgacccc tggaaggcct tcatggccca   6180
agtcgaagtc ctgatcgaca agaagatcga ggagtacgcc aagtccaagg ccctggccga   6240
gctgcaaggc ctgcaaaaca acttcgagga ctacgtcaac gcgctgaact cctggaagaa   6300
gacgcctctg tccctgcgct ccaagcgctc ccaggaccgc atccgcgagc tgttctccca   6360
ggccgagtcc cacttccgca actccatgcc gtccttcgcc gtctccaagt tcgaggtcct   6420
gttcctgccc acctacgccc aggctgccaa cacccacctc ctgttgctga aggacgccca   6480
ggtcttcggc gaggaatggg gctactcctc ggaggacgtc gccgagttct accgtcgcca   6540
gctgaagctg acccaacagt acaccgacca ctgcgtcaac tggtacaacg tcggcctgaa   6600
cggcctgagg ggctccacct acgacgcatg ggtcaagttc aaccgcttcc gcagggagat   6660
gaccctgacc gtcctggacc tgatcgtcct gttccccttc tacgacatcc gcctgtactc   6720
caagggcgtc aagaccgagc tgacccgcga catcttcacg gaccccatct tcctgctcac   6780
gaccctccag aagtacggtc ccaccttcct gtccatcgag aactccatcc gcaagcccca   6840
cctgttcgac tacctccagg gcatcgagtt ccacacgcgc ctgaggccag gctacttcgg   6900
caaggactcc ttcaactact ggtccggcaa ctacgtcgag accaggccct ccatcggctc   6960
ctcgaagacg atcacctccc ctttctacgg cgacaagtcc accgagcccg tccagaagct   7020
gtccttcgac ggccagaagg tctaccgcac catcgccaac accgacgtcg cggcttggcc   7080
gaacggcaag gtctacctgg gcgtcacgaa ggtcgacttc tcccagtacg atgaccagaa   7140
```

gaacgagacc tccacccaga cctacgactc caagcgcaac aatggccacg tctccgccca 7200
ggactccatc gaccagctgc cgcctgagac cactgacgag cccctggaga aggcctactc 7260
ccaccagctg aactacgcgg agtgcttcct gatgcaagac cgcaggggca ccatcccctt 7320
cttcacctgg acccaccgct ccgtcgactt cttcaacacc atcgacgccg agaagatcac 7380
ccagctgccc gtggtcaagg cctacgccct gtcctcgggt gcctccatca ttgagggtcc 7440
aggcttcacc ggtggcaacc tgctgttcct gaaggagtcc tcgaactcca tcgccaagtt 7500
caaggtcacc ctgaactccg ctgccttgct gcaacgctac cgcgtccgca tccgctacgc 7560
ctccaccacg aacctgcgcc tgttcgtcca gaactccaac aatgacttcc tggtcatcta 7620
catcaacaag accatgaaca aggacgatga cctgacctac cagaccttcg acctcgccac 7680
cacgaactcc aacatgggct tctcgggcga caagaatgaa ctgatcattg gtgctgagtc 7740
cttcgtctcc aacgagaaga tctacatcga caagatcgag ttcatccccg tccagctgtg 7800
ataggaactc tgattgaatt ctgcatgcgt ttggacgtat gctcattcag gttggagcca 7860
atttggttga tgtgtgtgcg agttcttgcg agtctgatga gacatctctg tattgtgttt 7920
ctttccccag tgttttctgt acttgtgtaa tcggctaatc gccaacagat tcggcgatga 7980
ataaatgaga aataaattgt tctgattttg agtgcaaaaa aaaaggaatt agatctgtgt 8040
gtgttttttg gatcccattt tcgacaagct tgcctcgaga caacaacatg cttctcatca 8100
acatggaggg aagagggagg gagaaagtgt cgcctggtca cctccattgt cacactagcc 8160
actggccagc tctcccacac caccaatgcc aggggcgagc tttagcacag ccaccgcttc 8220
acctccacca ccgcactacc ctagcttcgc ccaacagcca ccgtcaacgc ctcctctccg 8280
tcaacataag agagagagag aagaggagag tagccatgtg gggaggagga atagtacatg 8340
gggcctaccg tttggcaagt tattttgggt tgccaagtta ggccaataag gggagggatt 8400
tggccatccg gttggaaagg ttattggggt agtatctttt tactagaatt gtcaaaaaaa 8460
aatagtttga gagccatttg gagaggatgt tgcctgttag aggtgctctt aggacatcaa 8520
attccataaa aacatcagaa aaattctctc gatgaagatt tataaccact aaaactgccc 8580
tcaattcgaa gggagttcaa aacaattaaa atcatgttcg aattgagttt caatttcact 8640
ttaacccctt tgaaatctca atggtaaaac atcaacccgt caggtagcat ggttcttttt 8700
attcctttca aaaagagtta attacaaaca gaatcaaaac taacagttag gcccaaggcc 8760
catccgagca aacaatagat catgggccag gcctgccacc accctccccc tcctggctcc 8820
cgctcttgaa tttcaaaatc caaaaatatc ggcacgactg gccgccgacg gagcgggcgg 8880
aaaatgacgg aacaacccct cgaattctac cccaactacg cccaccaacc cacacgccac 8940
tgacaatccg gtcccaccct tgtgggccca cctacaagcg agacgtcagt cgctcgcagc 9000
aaccagtggg cccacctccc agtgagcggc gggtagatct ggactcttac ccacccacac 9060
taaacaaaac ggcatgaata ttttgcacta aaaccctcag aaaaattccg atattccaaa 9120
ccagtacagt tcctgaccgt tggaggagcc aaagtggagc ggagtgtaaa attgggaaac 9180
ttaatcgagg gggttaaacg caaaaacgcc gaggcgcctc ccgctctata gaaaggggag 9240
gagtgggagg tggaaaccct accacaccgc agagaaaggc gtcttcgtac tcgcctctct 9300
ccgcgccctc ctccgccgcc gctcgccgcc gttcgtctcc gccgccaccg gctagccatc 9360
caggtaaaac aaacaaaaac ggatctgatg cttccattcc tccgtttctc gtagtagcgc 9420
gcttcgatct gtgggtggat ctgggtgatc ctggggtgtg gttcgttctg tttgatagat 9480

-continued

```
ctgtcggtgg atctggcctt ctgtggttgt cgatgtccgg atctgcgttt tgatcagtgg   9540
tagttcgtgg atctggcgaa atgttttgga tctggcagtg agacgctaag aatcgggaaa   9600
tgatgcaata ttaggggggt ttcggatggg gatccactga attagtctgt ctccctgctg   9660
ataatctgtt cctttttggt agatctggtt agtgtatgtt tgtttcggat agatctgatc   9720
aatgcttgtt tgttttttca aattttctac ctaggttgta taggaatggc atgcggatct   9780
ggttggattg ccatgatccg tgctgaaatg cccctttggt tgatggatct tgatatttta   9840
ctgctgttca cctagatttg tactcccgtt tatacttaat ttgttgctta ttatgaatag   9900
atctgtaact taggcacatg tatggacgga gtatgtggat ctgtagtatg tacattgctg   9960
cgagctaaga actatttcag agcaagcaca gaaaaaaata tttagacaga ttgggcaact  10020
atttgatggt ctttggtatc atgctttgta gtgctcgttt ctgcgtagta atcttttgat  10080
ctgatctgaa gataggtgct attatattct taaaggtcat tagaacgcta tctgaaaggc  10140
tgtattatgt ggattggttc acctgtgact ccctgttcgt cttgtcttga taaatcctgt  10200
gataaaaaaa attcttaagg cgtaatttgt tgaaatcttg ttttgtccta tgcagcctga  10260
tccatggcgc aagttagcag aatctgcaat ggtgtgcaga acccatctct tatctccaat  10320
ctctcgaaat ccagtcaacg caaatctccc ttatcggttt ctctgaagac gcagcagcat  10380
ccacgagctt atccgatttc gtcgtcgtgg ggattgaaga agagtgggat gacgttaatt  10440
ggctctgagc ttcgtcctct taaggtcatg tcttctgttt ccacggcgtg catgcttcac  10500
ggtgcaagca gccggcccgc aaccgcccgc aaatcctctg gcctttccgg aaccgtccgc  10560
attcccggcg acaagtcgat ctcccaccgg tccttcatgt tcggcggtct cgcgagcggt  10620
gaaacgcgca tcaccggcct tctggaaggc gaggacgtca tcaatacggg caaggccatg  10680
caggcgatgg gcgcccgcat ccgtaaggaa ggcgacacct ggatcatcga tggcgtcggc  10740
aatggcggcc tcctggcgcc tgaggcgccg ctcgatttcg gcaatgccgc cacgggctgc  10800
cgcctgacga tgggcctcgt cggggtctac gatttcgaca gcaccttcat cggcgacgcc  10860
tcgctcacaa agcgcccgat gggccgcgtg ttgaacccgc tgcgcgaaat gggcgtgcag  10920
gtgaaatcgg aagacggtga ccgtcttccc gttaccttgc gcgggccgaa gacgccgacg  10980
ccgatcacct accgcgtgcc gatggcctcc gcacaggtga agtccgccgt gctgctcgcc  11040
ggcctcaaca cgcccggcat cacgacggtc atcgagccga tcatgacgcg cgatcatacg  11100
gaaaagatgc tgcagggctt tggcgccaac cttaccgtcg agacggatgc ggacggcgtg  11160
cgcaccatcc gcctggaagg ccgcggcaag ctcaccggcc aagtcatcga cgtgccgggc  11220
gacccgtcct cgacggcctt cccgctggtt gcggccctgc ttgttccggg ctccgacgtc  11280
accatcctca acgtgctgat gaaccccacc cgcaccggcc tcatcctgac gctgcaggaa  11340
atgggcgccg acatcgaagt catcaacccg cgccttgccg gcggcgaaga cgtggcggac  11400
ctgcgcgttc gctcctccac gctgaagggc gtcacggtgc cggaagaccg cgcgccttcg  11460
atgatcgacg aatatccgat tctcgctgtc gccgccgcct tcgcggaagg ggcgaccgtg  11520
atgaacggtc tggaagaact ccgcgtcaag gaaagcgacc gcctctcggc cgtcgccaat  11580
ggcctcaagc tcaatggcgt ggattgcgat gagggcgaga cgtcgctcgt cgtgcgtggc  11640
cgccctgacg gcaaggggct cggcaacgcc tcgggcgccg ccgtcgccac ccatctcgat  11700
caccgcatcg ccatgagctt cctcgtcatg ggcctcgtgt cggaaaaccc tgtcacggtg  11760
gacgatgcca cgatgatcgc cacgagcttc ccggagttca tggacctgat ggccgggctg  11820
ggcgcgaaga tcgaactctc cgatacgaag gctgcctgat gagctccagg gttcttgcct  11880
```

-continued ggtgccttgg caatgcttga ttactgctgc tatcctatga tctgtccgtg tgggcttcta 11940
tctatcagtt tgtgtgtctg gttttgaaaa acatttgctt ttcgattatg tagggtttgc 12000
ttgtagcttt cgctgctgtg acctgtgttg tttatgtgaa ccttctttgt ggcatcttta 12060
atatccaagt tcgtggtttg tcgtaaaacg aagcctctac ttcgtaaagt tgtgtctata 12120
gcattgaaat cgtttttttg ctcgagaata attgtgacct ttagttggcg tgaaactagt 12180
tttggatatc tgattctctg gttcgcaatc ttgagatcgt cgctgcttag gtgagctaag 12240
tgatgttcct aagtaaatgc tcctcaccag aatacgtagc tgtgtgaaaa gagaacgcgt 12300
gaatacgtag ctgtgtaaag attgtgtccc aagtaaacct cagtgatttt tgtttggatt 12360
tttaatttag aaacattcga ctgggagcgg ctagagccac acccaagttc ctaactatga 12420
taaagttgct ctgtaacaga aaacaccatc tagagcggcc gcgtttaaac tatcagtgtt 12480
tgacaggata tattggcggg taaacctaag agaaaagagc gtttattaga ataatcggat 12540
atttaaaagg gcgtgaaaag gtttatccgt tcgtccattt gtatgtgcat gccaaccaca 12600
gggttcccct cgggagtgct tggcattccg tgcgataatg acttctgttc aaccacccaa 12660
acgtcggaaa gcctgacgac ggagcagcat tccaaaaaga tcccttggct cgtctgggtc 12720
ggctagaagg tcgagtgggc tgctgtggct tgatccctca acgcggtcgc ggacgtagcg 12780
cagcgccgaa aaatcct 12797

<210> SEQ ID NO 31
<211> LENGTH: 12218
<212> TYPE: DNA
<213> ORGANISM: Artificial Sequence
<220> FEATURE:
<223> OTHER INFORMATION: DNA construct 403

<400> SEQUENCE: 31
aaaagtccca tgtggatcac tccgttgccc cgtcgctcac cgtgttgggg ggaaggtgca 60
catggctcag ttctcaatgg aaattatctg cctaaccggc tcagttctgc gtagaaacca 120
acatgcaagc tccaccgggt gcaaagcggc agcggcggca ggatatattc aattgtaaat 180
ggcttcatgt ccgggaaatc tacatggatc agcaatgagt atgatggtca atatggagaa 240
aaagaaagag taattaccaa ttttttttca attcaaaaat gtagatgtcc gcagcgttat 300
tataaaatga aagtacattt tgataaaacg acaaattacg atccgtcgta tttataggcg 360
aaagcaataa acaaattatt ctaattcgga aatctttatt tcgacgtgtc tacattcacg 420
tccaaatggg ggcttagatg agaaacttca cgatcgatgc ggccaccact cgaggtcgag 480
gtaccgttgt caatcaattg gcaagtcata aaatgcatta aaaaatattt tcatactcaa 540
ctacaaatcc atgagtataa ctataattat aaagcaatga ttagaatctg acaaggattc 600
tggaaaatta cataaaggaa agttcataaa tgtctaaaac acaagaggac atacttgtat 660
tcagtaacat ttgcagcttt tctaggtctg aaaatatatt tgttgcctag tgaataagca 720
taatggtaca actacaagtg ttttactcct catattaact tcggtcatta gaggccacga 780
tttgacacat ttttactcaa aacaaaatgt ttgcatatct cttataattt caaattcaac 840
acacaacaaa taagagaaaa aacaaataat attaatttga gaatgaacaa aaggaccata 900
tcattcatta actcttctcc atccatttcc atttcacagt tcgatagcga aaaccgaata 960
aaaaacacag taaattacaa gcacaacaaa tggtacaaga aaaacagttt tcccaatgcc 1020
ataatactca aactcagtag gattctggtg tgtgcgcaat gaaactgatg cattgaactt 1080

-continued

```
gacgaacgtt gtcgaaaccg atgatacgaa cgaaagctag gcctcagcga gtaccgctgg   1140
cgatctaatc catgatatcg tgaacatcat ctacattcaa attcttatga gctttcttaa   1200
gggcatctgc agcatttttc atagaatcta atacagcagt atttgtgcta gctccttcga   1260
gggcttccct ctgcatttca atagttgtaa gggttccatc tatttgtagt tgggtctttt   1320
ccaatcgttt cttcttttg agggcttgga gtgcaactct tttattttc gacgcatttt   1380
tctttgcgct cctgcaggcg gccgcgtgga tgaggagtta atcggtcgtg tgagagtagt   1440
gatcgagtgg atgtcgtcga gagtgatgag tgttgatgtt gttagtgata tgtggtagaa   1500
ggtatcgtga taaagcgtta acgcgatcgc agtacttgca aagaaaaatg cgtcgaaaaa   1560
taaaagagtt gcactccaag ccctcaaaaa gaagaaacga ttggaaaaga cccaactaca   1620
aatagatgga acccttacaa ctattgaaat gcagagggaa gccctcgaag gagctagcac   1680
aaatactgct gtattagatt ctatgaaaaa tgctgcagat gcccttaaga aagctcataa   1740
gaatttgaat gtagatgatg ttcacgatat catggatggt atcgcacagc gactgctgag   1800
ggacgtcggt ccatggagat cctctagagg ccgcttggta tctgcattac aatgaaatga   1860
gcaaagacta tgtgagtaac actggtcaac actagggaga aggcatcgag caagatacgt   1920
atgtaaagag aagcaatata gtgtcagttg gtagatacta gataccatca ggaggtaagg   1980
agagcaacaa aaaggaaact ctttattttt aaattttgtt acaacaaaca agcagatcaa   2040
tgcatcaaaa tactgtcagt acttatttct tcagacaaca atatttaaaa caagtgcatc   2100
tgatcttgac ttatggtcac aataaaggag cagagataaa catcaaaatt tcgtcattta   2160
tatttattcc ttcaggcgtt aacaatttaa cagcacacaa acaaaaacag aataggaata   2220
tctaattttg gcaaataata agctctgcag acgaacaaat tattatagta tcgcctataa   2280
tatgaatccc tatactattg acccatgtag tatgaagcct gtgcctaaat taacagcaaa   2340
cttctgaatc caagtgccct ataacaccaa catgtgctta aataaatacc gctaagcacc   2400
aaattacaca tttctcgtat tgctgtgtag gttctatctt cgtttcgtac taccatgtcc   2460
ctatattttg ctgctacaaa ggacggcaag taatcagcac aggcagaaca cgatttcaga   2520
gtgtaattct agatccagct aaaccactct cagcaatcac cacacaagag agcattcaga   2580
gaaacgtggc agtaacaaag gcagagggcg gagtgagcgc gtaccgaaga cggtgggccg   2640
cttatggtgt gttgtccctg tgtgttctcc aatagtgtgg cttgagtgtg tggaagatgg   2700
ttgtatctga tgatccttca aatgggaatg aatgccttct tatatagagg gaattctttt   2760
gtggtcgtca ctgcgttcgt catacgcatt agtgagtggg ctgtcaggac agctcttttc   2820
cacgttattt tgttccccac ttgtactaga ggaatctgct ttatctttgc aataaaggca   2880
aagatgcttt tggtaggtgc gcctaacaat tctgcaccat tccttttttg tctggtcccc   2940
acaagccagc tgctcgatgt tgacaagatt actttcaaag atgcccacta actttaagtc   3000
ttcggtggat gtctttttct gaaacttact gaccatgatg catgtgctgg aacagtagtt   3060
tactttgatt gaagattctt cattgatctc ctgtagcttt tggctaatgg tttggagact   3120
ctgtaccctg accttgttga ggctttggac tgagaattct tccttacaaa cctttgagga   3180
tgggagttcc ttcttggttt tggcgatacc aatttgaata aagtgatatg gctcgtacct   3240
tgttgattga acccaatctg gaatgctgct aaatcctgag ctcaagctaa ttcttttgtg   3300
gtcgtcactg cgttcgtcat acgcattagt gagtgggctg tcaggacagc tcttttccac   3360
gttattttgt tccccacttg tactagagga atctgcttta tctttgcaat aaaggcaaag   3420
atgcttttgg taggtgcgcc taacaattct gcaccattcc tttttgtct ggtccccaca   3480
```

-continued

```
agccagctgc tcgatgttga caagattact ttcaaagatg cccactaact ttaagtcttc   3540
ggtggatgtc tttttctgaa acttactgac catgatgcat gtgctggaac agtagtttac   3600
tttgattgaa gattcttcat tgatctcctg tagcttttgg ctaatggttt ggagactctg   3660
taccctgacc ttgttgaggc tttggactga gaattagctt ccactcgaag cttgttaacc   3720
tgcaggctag cggcgcgcca caaatcacag gccatgaacc ctactcatgc ttcgatttgt   3780
ccaacacaca cttaccaaaa ctcaaatcat gtccttgaca gtcactcggg actcataaca   3840
tgggtacgta tcgactatgt caactatatg tgttctcatc agattataga ttggcctagt   3900
acgtagtgat atttccacta gcactgtggt tatggctgta cctgatagtg atatcagcac   3960
cgggtcatgg ctctactacc aggtagtgag agtgaccttt atactgtcag actgtaacta   4020
aggatttcca atcactgttc ggatcctagg cttagaatta agtaaaactc tatcactata   4080
ggctgcagca cactcggtat atattgatgg gccaacagaa attgtgcgta ctatgcgcga   4140
tgtaaaatgg acataaaccc tacccatata caatgcaata acttttgtcc ggtctgggcc   4200
accggttagc agaggtcctg atttcggtgg tagtggtagc ttgatctggt cgtcgtatcg   4260
tagagggata tataaaatca tgtcactttt gaagggagcg ctcacagaaa taataggtat   4320
tcgcgggagc cgcccccgca gaacacaaaa taaggcgagc acgcacacgc atcagtttcg   4380
ataaaataat aatagcgcca gctgatcgga acaattccag ctagcactaa tgtatttctg   4440
cattgatctg tttatacaac atgctacctc gttgagtgat tttgacatga tttgtcaact   4500
tgctccgatc ctatatctcg atcgatctcc acatgacgat ggttgttgtc ctgtatccca   4560
tgacaaccag gcaacgctca aagcacacat gcgttgccga ttacccgtgc atgccgccaa   4620
gcacgaaagc acctccctcc acaccgtcca tcagctataa aaaccatgcc aagcaccctg   4680
tgaaaagccc cgggaaccat cttccacaca ctcaagccac actattggag aacacacagg   4740
gacaacacac cataagatcc aagggaggcc tccgccgccg ccggtaacca ccccgcccct   4800
ctcctctttc tttctccgtt tttttttccg tctcggtctc gatctttggc cttggtagtt   4860
tgggtgggcg agaggcggct tcgtgcgcgc ccagatcggt gcgcgggagg ggcgggatct   4920
cgcggctggg gctctcgccg gcgtggatcc ggcccggatc tcgcggggaa tggggctctc   4980
ggatgtagat ctgcgatccg ccgttgttgg gggagatgat ggggggttta aaatttccgc   5040
cgtgctaaac aagatcagga agaggggaaa agggcactat ggtttatatt tttatatatt   5100
tctgctgctt cgtcaggctt agatgtgcta gatctttctt tcttcttttt gtgggtagaa   5160
tttgaatccc tcagcattgt tcatcggtag tttttctttt catgatttgt gacaaatgca   5220
gcctcgtgcg gagctttttt gtaggtagaa gtgatcaacc atggccaacc ccaacaatcg   5280
ctccgagcac gacacgatca aggtcacccc caactccgag ctccagacca accacaacca   5340
gtacccgctg gccgacaacc ccaactccac cctggaagag ctgaactaca aggagttcct   5400
gcgcatgacc gaggactcct ccacggaggt cctggacaac tccaccgtca aggacgccgt   5460
cgggaccggc atctccgtcg ttgggcagat cctgggcgtc gttggcgtcc ccttcgcagg   5520
tgctctcacc tccttctacc agtccttcct gaacaccatc tggccctccg acgccgaccc   5580
ctggaaggcc ttcatggccc aagtcgaagt cctgatcgac aagaagatcg aggagtacgc   5640
caagtccaag gccctggccg agctgcaagg cctgcaaaac aacttcgagg actacgtcaa   5700
cgcgctgaac tcctggaaga agacgcctct gtccctgcgc tccaagcgct cccaggaccg   5760
catccgcgag ctgttctccc aggccgagtc ccacttccgc aactccatgc cgtccttcgc   5820
```

```
cgtctccaag ttcgaggtcc tgttcctgcc cacctacgcc caggctgcca acacccacct   5880
cctgttgctg aaggacgccc aggtcttcgg cgaggaatgg ggctactcct cggaggacgt   5940
cgccgagttc taccgtcgcc agctgaagct gacccaacag tacaccgacc actgcgtcaa   6000
ctggtacaac gtcggcctga acggcctgag gggctccacc tacgacgcat gggtcaagtt   6060
caaccgcttc cgcagggaga tgaccctgac cgtcctggac ctgatcgtcc tgttcccctt   6120
ctacgacatc cgcctgtact ccaagggcgt caagaccgag ctgacccgcg acatcttcac   6180
ggaccccatc ttcctgctca cgaccctcca gaagtacggt cccaccttcc tgtccatcga   6240
gaactccatc cgcaagcccc acctgttcga ctacctccag ggcatcgagt tccacacgcg   6300
cctgaggcca ggctacttcg gcaaggactc cttcaactac tggtccggca actacgtcga   6360
gaccaggccc tccatcggct cctcgaagac gatcacctcc cctttctacg gcgacaagtc   6420
caccgagccc gtccagaagc tgtccttcga cggccagaag gtctaccgca ccatcgccaa   6480
caccgacgtc gcggcttggc cgaacggcaa ggtctacctg ggcgtcacga aggtcgactt   6540
ctcccagtac gatgaccaga agaacgagac ctccacccag acctacgact ccaagcgcaa   6600
caatggccac gtctccgccc aggactccat cgaccagctg ccgcctgaga ccactgacga   6660
gcccctggag aaggcctact cccaccagct gaactacgcg gagtgcttcc tgatgcaaga   6720
ccgcaggggc accatcccct tcttcacctg gacccaccgc tccgtcgact tcttcaacac   6780
catcgacgcc gagaagatca cccagctgcc cgtggtcaag gcctacgccc tgtcctcggg   6840
tgcctccatc attgagggtc caggcttcac cggtggcaac ctgctgttcc tgaaggagtc   6900
ctcgaactcc atcgccaagt tcaaggtcac cctgaactcc gctgccttgc tgcaacgcta   6960
ccgcgtccgc atccgctacg cctccaccac gaacctgcgc ctgttcgtcc agaactccaa   7020
caatgacttc ctggtcatct acatcaacaa gaccatgaac aaggacgatg acctgaccta   7080
ccagaccttc gacctcgcca ccacgaactc caacatgggc ttctcgggcg acaagaatga   7140
actgatcatt ggtgctgagt ccttcgtctc caacgagaag atctacatcg acaagatcga   7200
gttcatcccc gtccagctgt gataggaact ctgattgaat tctgcatgcg tttggacgta   7260
tgctcattca ggttggagcc aatttggttg atgtgtgtgc gagttcttgc gagtctgatg   7320
agacatctct gtattgtgtt tctttcccca gtgttttctg tacttgtgta atcggctaat   7380
cgccaacaga ttcggcgatg aataaatgag aaataaattg ttctgatttt gagtgcaaaa   7440
aaaaaggaat tagatctgtg tgtgtttttt ggatcccatt ttcgacaagc ttgcctcgag   7500
acaacaacat gcttctcatc aacatggagg gaagagggag ggagaaagtg tcgcctggtc   7560
acctccattg tcacactagc cactggccag ctctcccaca ccaccaatgc caggggcgag   7620
ctttagcaca gccaccgctt cacctccacc accgcactac cctagcttcg cccaacagcc   7680
accgtcaacg cctcctctcc gtcaacataa gagagagaga gaagaggaga gtagccatgt   7740
ggggaggagg aatagtacat ggggcctacc gtttggcaag ttattttggg ttgccaagtt   7800
aggccaataa ggggagggat ttggccatcc ggttggaaag gttattgggg tagtatcttt   7860
ttactagaat tgtcaaaaaa aaatagtttg agagccattt ggagaggatg ttgcctgtta   7920
gaggtgctct taggacatca aattccataa aaacatcaga aaaattctct cgatgaagat   7980
ttataaccac taaaactgcc ctcaattcga agggagttca aaacaattaa aatcatgttc   8040
gaattgagtt tcaatttcac tttaacccct ttgaaatctc aatggtaaaa catcaacccg   8100
tcaggtagca tggttctttt tattcctttc aaaaagagtt aattacaaac agaatcaaaa   8160
ctaacagtta ggcccaaggc ccatccgagc aaacaataga tcatgggcca ggcctgccac   8220
```

-continued

```
caccctcccc ctcctggctc ccgctcttga atttcaaaat ccaaaaatat cggcacgact   8280
ggccgccgac ggagcgggcg gaaaatgacg gaacaacccc tcgaattcta ccccaactac   8340
gcccaccaac ccacacgcca ctgacaatcc ggtcccaccc ttgtgggccc acctacaagc   8400
gagacgtcag tcgctcgcag caaccagtgg gcccacctcc cagtgagcgg cgggtagatc   8460
tggactctta cccacccaca ctaaacaaaa cggcatgaat attttgcact aaaaccctca   8520
gaaaaattcc gatattccaa accagtacag ttcctgaccg ttggaggagc caaagtggag   8580
cggagtgtaa aattgggaaa cttaatcgag gggttaaac gcaaaaaacgc cgaggcgcct   8640
cccgctctat agaaagggga ggagtgggag gtggaaaccc taccacaccg cagagaaagg   8700
cgtcttcgta ctcgcctctc tccgcgccct cctccgccgc cgctcgccgc cgttcgtctc   8760
cgccgccacc ggctagccat ccaggtaaaa caaacaaaaa cggatctgat gcttccattc   8820
ctccgtttct cgtagtagcg cgcttcgatc tgtgggtgga tctgggtgat cctggggtgt   8880
ggttcgttct gtttgataga tctgtcggtg gatctggcct tctgtggttg tcgatgtccg   8940
gatctgcgtt ttgatcagtg gtagttcgtg gatctggcga aatgttttgg atctggcagt   9000
gagacgctaa gaatcgggaa atgatgcaat attagggggg tttcggatgg ggatccactg   9060
aattagtctg tctccctgct gataatctgt tcctttttgg tagatctggt tagtgtatgt   9120
ttgtttcgga tagatctgat caatgcttgt ttgtttttc aaattttcta cctaggttgt   9180
ataggaatgg catgcggatc tggttggatt gccatgatcc gtgctgaaat gcccctttgg   9240
ttgatggatc ttgatatttt actgctgttc acctagattt gtactcccgt ttatacttaa   9300
tttgttgctt attatgaata gatctgtaac ttaggcacat gtatggacgg agtatgtgga   9360
tctgtagtat gtacattgct gcgagctaag aactatttca gagcaagcac agaaaaaaat   9420
atttagacag attgggcaac tatttgatgg tctttggtat catgctttgt agtgctcgtt   9480
tctgcgtagt aatcttttga tctgatctga agataggtgc tattatattc ttaaaggtca   9540
ttagaacgct atctgaaagg ctgtattatg tggattggtt cacctgtgac tccctgttcg   9600
tcttgtcttg ataaatcctg tgataaaaaa aattcttaag gcgtaatttg ttgaaatctt   9660
gttttgtcct atgcagcctg atccatggcg caagttagca gaatctgcaa tggtgtgcag   9720
aacccatctc ttatctccaa tctctcgaaa tccagtcaac gcaaatctcc cttatcggtt   9780
tctctgaaga cgcagcagca tccacgagct tatccgattt cgtcgtcgtg gggattgaag   9840
aagagtggga tgacgttaat tggctctgag cttcgtcctc ttaaggtcat gtcttctgtt   9900
tccacggcgt gcatgcttca cggtgcaagc agccggcccg caaccgcccg caaatcctct   9960
ggcctttccg gaaccgtccg cattcccggc gacaagtcga tctcccaccg gtccttcatg  10020
ttcggcggtc tcgcgagcgg tgaaacgcgc atcaccggcc ttctggaagg cgaggacgtc  10080
atcaatacgg gcaaggccat gcaggcgatg ggcgcccgca tccgtaagga aggcgacacc  10140
tggatcatcg atggcgtcgg caatggcggc ctcctggcgc ctgaggcgcc gctcgatttc  10200
ggcaatgccg ccacgggctg ccgcctgacg atgggcctcg tcggggtcta cgatttcgac  10260
agcaccttca tcggcgacgc ctcgctcaca aagcgcccga tgggccgcgt gttgaacccg  10320
ctgcgcgaaa tgggcgtgca ggtgaaatcg gaagacggtg accgtcttcc cgttaccttg  10380
cgcgggccga agacgccgac gccgatcacc taccgcgtgc cgatggcctc cgcacaggtg  10440
aagtccgccg tgctgctcgc cggcctcaac acgcccggca tcacgacggt catcgagccg  10500
atcatgacgc gcgatcatac ggaaaagatg ctgcagggct ttggcgccaa ccttaccgtc  10560
```

-continued

```
gagacggatg cggacggcgt gcgcaccatc cgcctggaag gccgcggcaa gctcaccggc  10620

caagtcatcg acgtgccggg cgacccgtcc tcgacggcct tcccgctggt tgcggccctg  10680

cttgttccgg gctccgacgt caccatcctc aacgtgctga tgaaccccac ccgcaccggc  10740

ctcatcctga cgctgcagga aatgggcgcc gacatcgaag tcatcaaccc gcgccttgcc  10800

ggcggcgaag acgtggcgga cctgcgcgtt cgctcctcca cgctgaaggg cgtcacggtg  10860

ccggaagacc gcgcgccttc gatgatcgac gaatatccga ttctcgctgt cgccgccgcc  10920

ttcgcggaag gggcgaccgt gatgaacggt ctggaagaac tccgcgtcaa ggaaagcgac  10980

cgcctctcgg ccgtcgccaa tggcctcaag ctcaatggcg tggattgcga tgagggcgag  11040

acgtcgctcg tcgtgcgtgg ccgccctgac ggcaaggggc tcggcaacgc ctcgggcgcc  11100

gccgtcgcca cccatctcga tcaccgcatc gccatgagct tcctcgtcat gggcctcgtg  11160

tcggaaaacc ctgtcacggt ggacgatgcc acgatgatcg ccacgagctt cccggagttc  11220

atggacctga tggccgggct gggcgcgaag atcgaactct ccgatacgaa ggctgcctga  11280

tgagctccag ggttcttgcc tggtgccttg gcaatgcttg attactgctg ctatcctatg  11340

atctgtccgt gtgggcttct atctatcagt ttgtgtgtct ggttttgaaa aacatttgct  11400

tttcgattat gtagggtttg cttgtagctt tcgctgctgt gacctgtgtt gtttatgtga  11460

accttctttg tggcatcttt aatatccaag ttcgtggttt gtcgtaaaac gaagcctcta  11520

cttcgtaaag ttgtgtctat agcattgaaa tcgttttttt gctcgagaat aattgtgacc  11580

tttagttggc gtgaaactag ttttggatat ctgattctct ggttcgcaat cttgagatcg  11640

tcgctgctta ggtgagctaa gtgatgttcc taagtaaatg ctcctcacca gaatacgtag  11700

ctgtgtgaaa agagaacgcg tgaatacgta gctgtgtaaa gattgtgtcc caagtaaacc  11760

tcagtgattt ttgtttggat ttttaattta gaaacattcg actgggagcg gctagagcca  11820

cacccaagtt cctaactatg ataaagttgc tctgtaacag aaaacaccat ctagagcggc  11880

cgcgtttaaa ctatcagtgt ttgacaggat atattggcgg gtaaacctaa gagaaaagag  11940

cgtttattag aataatcgga tatttaaaag ggcgtgaaaa ggtttatccg ttcgtccatt  12000

tgtatgtgca tgccaaccac agggttcccc tcgggagtgc ttggcattcc gtgcgataat  12060

gacttctgtt caaccaccca aacgtcggaa agcctgacga cggagcagca ttccaaaaag  12120

atcccttggc tcgtctgggt cggctagaag gtcgagtggg ctgctgtggc ttgatccctc  12180

aacgcggtcg cggacgtagc gcagcgccga aaaatcct                          12218
```

```
<210> SEQ ID NO 32
<211> LENGTH: 12797
<212> TYPE: DNA
<213> ORGANISM: Artificial Sequence
<220> FEATURE:
<223> OTHER INFORMATION: DNA construct 404

<400> SEQUENCE: 32

aaaagtccca tgtggatcac tccgttgccc cgtcgctcac cgtgttgggg ggaaggtgca     60

catggctcag ttctcaatgg aaattatctg cctaaccggc tcagttctgc gtagaaacca    120

acatgcaagc tccaccgggt gcaaagcggc agcggcggca ggatatattc aattgtaaat    180

ggcttcatgt ccgggaaatc tacatggatc agcaatgagt atgatggtca atatggagaa    240

aaagaaagag taattaccaa ttttttttca attcaaaaat gtagatgtcc gcagcgttat    300

tataaaatga aagtacattt tgataaaacg acaaattacg atccgtcgta tttataggcg    360

aaagcaataa acaaattatt ctaattcgga aatctttatt tcgacgtgtc tacattcacg    420
```

-continued

```
tccaaatggg ggcttagatg agaaacttca cgatcgatgc ggccaccact cgaggtcgag    480
gtaccgttgt caatcaattg gcaagtcata aaatgcatta aaaaatattt tcatactcaa    540
ctacaaatcc atgagtataa ctataattat aaagcaatga ttagaatctg acaaggattc    600
tggaaaatta cataaaggaa agttcataaa tgtctaaaac acaagaggac atacttgtat    660
tcagtaacat ttgcagcttt tctaggtctg aaaatatatt tgttgcctag tgaataagca    720
taatggtaca actacaagtg ttttactcct catattaact tcggtcatta gaggccacga    780
tttgacacat ttttactcaa aacaaaatgt ttgcatatct cttataattt caaattcaac    840
acacaacaaa taagagaaaa aacaaataat attaatttga gaatgaacaa aaggaccata    900
tcattcatta actcttctcc atccatttcc atttcacagt tcgatagcga aaaccgaata    960
aaaaacacag taaattacaa gcacaacaaa tggtacaaga aaaacagttt tcccaatgcc   1020
ataatactca aactcagtag gattctggtg tgtgcgcaat gaaactgatg cattgaactt   1080
gacgaacgtt gtcgaaaccg atgatacgaa cgaaagctag gcctcagcga gtaccgctgg   1140
cgatctaatc catgatatcg tgaacatcat ctacattcaa attcttatga gctttcttaa   1200
gggcatctgc agcatttttc atagaatcta atacagcagt atttgtgcta gctccttcga   1260
gggcttccct ctgcatttca atagttgtaa gggttccatc tatttgtagt tgggtctttt   1320
ccaatcgttt cttctttttg agggcttgga gtgcaactct tttatttttc gacgcatttt   1380
tctttgcgct cctgcaggcg gccgcgtgga tgaggagtta atcggtcgtg tgagagtagt   1440
gatcgagtgg atgtcgtcga gagtgatgag tgttgatgtt gttagtgata tgtggtagaa   1500
ggtatcgtga taaagcgtta acgcgatcgc agtacttgca aagaaaaatg cgtcgaaaaa   1560
taaaagagtt gcactccaag ccctcaaaaa gaagaaacga ttggaaaaga cccaactaca   1620
aatagatgga acccttacaa ctattgaaat gcagagggaa gccctcgaag gagctagcac   1680
aaatactgct gtattagatt ctatgaaaaa tgctgcagat gcccttaaga aagctcataa   1740
gaatttgaat gtagatgatg ttcacgatat catggatggt atcgcacagc gactgctgag   1800
ggacgtcggt ccatggagat cctctagagg ccgcttggta tctgcattac aatgaaatga   1860
gcaaagacta tgtgagtaac actggtcaac actagggaga aggcatcgag caagatacgt   1920
atgtaaagag aagcaatata gtgtcagttg gtagatacta gataccatca ggaggtaagg   1980
agagcaacaa aaaggaaact ctttattttt aaattttgtt acaacaaaca agcagatcaa   2040
tgcatcaaaa tactgtcagt acttatttct tcagacaaca atatttaaaa caagtgcatc   2100
tgatcttgac ttatggtcac aataaaggag cagagataaa catcaaaatt tcgtcattta   2160
tatttattcc ttcaggcgtt aacaatttaa cagcacacaa acaaaaacag aataggaata   2220
tctaattttg gcaaataata agctctgcag acgaacaaat tattatagta tcgcctataa   2280
tatgaatccc tatactattg acccatgtag tatgaagcct gtgcctaaat taacagcaaa   2340
cttctgaatc caagtgccct ataacaccaa catgtgctta aataaatacc gctaagcacc   2400
aaattacaca tttctcgtat tgctgtgtag gttctatctt cgtttcgtac taccatgtcc   2460
ctatattttg ctgctacaaa ggacggcaag taatcagcac aggcagaaca cgatttcaga   2520
gtgtaattct agatccagct aaaccactct cagcaatcac cacacaagag agcattcaga   2580
gaaacgtggc agtaacaaag gcagagggcg gagtgagcgc gtaccgaaga cggtgggccg   2640
cttatggtgt gttgtccctg tgtgttctcc aatagtgtgg cttgagtgtg tggaagatgg   2700
ttgtatctga tgatccttca aatgggaatg aatgccttct tatatagagg gaattctttt   2760
```

-continued

```
gtggtcgtca ctgcgttcgt catacgcatt agtgagtggg ctgtcaggac agctcttttc   2820
cacgttattt tgttccccac ttgtactaga ggaatctgct ttatctttgc aataaaggca   2880
aagatgcttt tggtaggtgc gcctaacaat tctgcaccat tcctttttttg tctggtcccc   2940
acaagccagc tgctcgatgt tgacaagatt actttcaaag atgcccacta actttaagtc   3000
ttcggtggat gtctttttct gaaacttact gaccatgatg catgtgctgg aacagtagtt   3060
tactttgatt gaagattctt cattgatctc ctgtagcttt tggctaatgg tttggagact   3120
ctgtaccctg accttgttga ggctttggac tgagaattct tccttacaaa cctttgagga   3180
tgggagttcc ttcttggttt tggcgatacc aatttgaata aagtgatatg gctcgtacct   3240
tgttgattga acccaatctg gaatgctgct aaatcctgag ctcaagctaa ttcttttgtg   3300
gtcgtcactg cgttcgtcat acgcattagt gagtgggctg tcaggacagc tcttttccac   3360
gttattttgt tccccacttg tactagagga atctgcttta tctttgcaat aaaggcaaag   3420
atgcttttgg taggtgcgcc taacaattct gcaccattcc tttttgtct ggtccccaca   3480
agccagctgc tcgatgttga caagattact ttcaaagatg cccactaact ttaagtcttc   3540
ggtggatgtc tttttctgaa acttactgac catgatgcat gtgctggaac agtagtttac   3600
tttgattgaa gattcttcat tgatctcctg tagcttttgg ctaatggttt ggagactctg   3660
taccctgacc ttgttgaggc tttggactga gaattagctt ccactcgaag cttgttaacc   3720
tgcaggctag cggcgcgccg ggatccaaaa aacacacaca gatctaattc cttttttttt   3780
gcactcaaaa tcagaacaat ttatttctca tttattcatc gccgaatctg ttggcgatta   3840
gccgattaca caagtacaga aaacactggg gaaagaaaca caatacagag atgtctcatc   3900
agactcgcaa gaactcgcac acacatcaac caaattggct ccaacctgaa tgagcatacg   3960
tccaaacgca tgcagaattc aatcagagtt cctatcacag ctggacgggg atgaactcga   4020
tcttgtcgat gtagatcttc tcgttggaga cgaaggactc agcaccaatg atcagttcat   4080
tcttgtcgcc cgagaagccc atgttggagt tcgtggtggc gaggtcgaag gtctggtagg   4140
tcaggtcatc gtccttgttc atggtcttgt tgatgtagat gaccaggaag tcattgttgg   4200
agttctggac gaacaggcgc aggttcgtgg tggaggcgta gcggatgcgg acgcggtagc   4260
gttgcagcaa ggcagcggag ttcagggtga ccttgaactt ggcgatggag ttcgaggact   4320
ccttcaggaa cagcaggttg ccaccggtga agcctggacc ctcaatgatg gaggcacccg   4380
aggacagggc gtaggccttg accacgggca gctgggtgat cttctcggcg tcgatggtgt   4440
tgaagaagtc gacggagcgg tgggtccagg tgaagaaggg gatggtgccc ctgcggtctt   4500
gcatcaggaa gcactccgcg tagttcagct ggtgggagta ggccttctcc aggggctcgt   4560
cagtggtctc aggcggcagc tggtcgatgg agtcctgggc ggagacgtgg ccattgttgc   4620
gcttggagtc gtaggtctgg gtggaggtct cgttcttctg gtcatcgtac tgggagaagt   4680
cgaccttcgt gacgcccagg tagaccttgc cgttcggcca agccgcgacg tcggtgttgg   4740
cgatggtgcg gtagaccttc tggccgtcga aggacagctt ctggacgggc tcggtggact   4800
tgtcgccgta gaaaggggag gtgatcgtct tcgaggagcc gatggagggc ctggtctcga   4860
cgtagttgcc ggaccagtag ttgaaggagt ccttgccgaa gtagcctggc ctcaggcgcg   4920
tgtggaactc gatgccctgg aggtagtcga acaggtgggg cttgcggatg gagttctcga   4980
tggacaggaa ggtgggaccg tacttctgga gggtcgtgag caggaagatg gggtccgtga   5040
agatgtcgcg ggtcagctcg gtcttgacgc ccttggagta caggcggatg tcgtagaagg   5100
ggaacaggac gatcaggtcc aggacggtca gggtcatctc cctgcggaag cggttgaact   5160
```

tgacccatgc gtcgtaggtg gagcccctca ggccgttcag gccgacgttg taccagttga 5220
cgcagtggtc ggtgtactgt tgggtcagct tcagctggcg acggtagaac tcggcgacgt 5280
cctccgagga gtagccccat tcctcgccga agacctgggc gtccttcagc aacaggaggt 5340
gggtgttggc agcctgggcg taggtgggca ggaacaggac ctcgaacttg gagacggcga 5400
aggacggcat ggagttgcgg aagtgggact cggcctggga gaacagctcg cggatgcggt 5460
cctgggagcg cttggagcgc agggacagag gcgtcttctt ccaggagttc agcgcgttga 5520
cgtagtcctc gaagttgttt tgcaggcctt gcagctcggc cagggccttg gacttggcgt 5580
actcctcgat cttcttgtcg atcaggactt cgacttgggc catgaaggcc ttccaggggt 5640
cggcgtcgga gggccagatg gtgttcagga aggactggta gaaggaggtg agagcacctg 5700
cgaaggggac gccaacgacg cccaggatct gcccaacgac ggagatgccg gtcccgacgg 5760
cgtccttgac ggtggagttg tccaggacct ccgtggagga gtcctcggtc atgcgcagga 5820
actccttgta gttcagctct tccagggtgg agttggggtt gtcggccagc gggtactggt 5880
tgtggttggt ctggagctcg gagttggggg tgaccttgat cgtgtcgtgc tcggagcgat 5940
tgttggggtt ggccatggtt gatcacttct acctacaaaa aagctccgca cgaggctgca 6000
tttgtcacaa atcatgaaaa gaaaaactac cgatgaacaa tgctgaggga ttcaaattct 6060
acccacaaaa agaagaaaga aagatctagc acatctaagc ctgacgaagc agcagaaata 6120
tataaaaata taaaccatag tgccctttc ccctcttcct gatcttgttt agcacggcgg 6180
aaattttaaa ccccccatca tctcccccaa caacggcgga tcgcagatct acatccgaga 6240
gccccattcc ccgcgagatc cggccggat ccacgccggc gagagcccca gccgcgagat 6300
cccgcccctc ccgcgcaccg atctgggcgc gcacgaagcc gcctctcgcc cacccaaact 6360
accaaggcca aagatcgaga ccgagacgga aaaaaaaacg gagaaagaaa gaggagaggg 6420
gcggggtggt taccggcggc ggcggaggcc tcccttggat cttatggtgt gttgtccctg 6480
tgtgttctcc aatagtgtgg cttgagtgtg tggaagatgg ttcccggggg ttttgatcat 6540
gggattaggg aggtatttat agtcgagccc cgggattaat taatcgaccg ttagagctca 6600
tgtgaaccct gccctgccat catgtgagcg tgcatacgag ggcgatctgg attggctggc 6660
agaacacctg ccctagcaag gctcgtagat taattaacaa atcgtacgta catctacgct 6720
gataatgtgt taaatcatcg gccgaatatt tggttagccg tgaagcactc gatcccgcaa 6780
atgaccaaga ttgctgcaca cgacacatcg cgggcttgtt tccttatgat cattggttgt 6840
tattttatct cgcgatcttg gcctatcggg cgtcgcttcg cgcggtgcag cgtgactgcg 6900
tgagcaagtt ggtgattttc ttttgccgtt taagaatgct tgctccgtga tcacacaaga 6960
gaggacatca catgaaccga gaccggagga atatcggggc atggtgggat tggtgggtgt 7020
cccagtccaa cgggcaagaa gattctaagc ttacctgggt ttgttttcac gtacgcgaag 7080
gacaggggaa gatgccattg cagcgtggct tcctgctggc ccgccaactt taatctacac 7140
taggcacgta gctactaggt cggcccgctt agatagctaa ggtaggctag gtaggtccgt 7200
ggtaaactgc cagcccatgg gcgcctggga ttcttcttgg gccaacagaa gcagaggttg 7260
ggcaatgcga agcctgaaaa tcctcctcct ccttctctct ccctctctct ctctctctct 7320
ctctctctct cacgaataaa atcctcttct tcccgaacag gctagattct ttttttttta 7380
atgaaccagt gagccaccaa tttcattgaa tagaggaata aaattgtaca tgcgcaagcg 7440
caaatagaaa actttaccgt ctcaaggcct ttggcccgaa catgttaaaa ggtaagccac 7500

-continued

```
ctatcaaggt gtttcgcgcc cgccaagacc catgttttgg catcctcctt aattttggct   7560
atcagactag ccaccggaag ctcttggtgc tgaaaaactc tgcggttcct ttcattccaa   7620
atatcctagg cgactaatag cattagagtc tgcaaggctt tctttggcgc ttcgttggaa   7680
catgcggtgg cctcccacca cttgagtagc gtcgaggctt gttgccataa cgttggtctt   7740
atttgttcac atgttgtcca gtctgcaagt gtcgcctaga ttctttcaca tatctacact   7800
ccgccaggag gtgagggccg tttcctgatt ccttcgacaa aggggcagat ggagccattt   7860
tcgattaccc acgggttgcc aatctgtcgg aggtccatac tctattttgg ataacaagcc   7920
aagcgaagcg aatgttttac atttgcgcgg cgcctagggc ttccagatag ggcattgaa    7980
attgaagctt ttatgccaag aagttgtgcg ttgtaggccg atgtcgtcat gtattcgccg   8040
tgactagtta gcttccattt tcgacaagct tgcctcgaga caacaacatg cttctcatca   8100
acatggaggg aagagggagg gagaaagtgt cgcctggtca cctccattgt cacactagcc   8160
actggccagc tctcccacac caccaatgcc aggggcgagc tttagcacag ccaccgcttc   8220
acctccacca ccgcactacc ctagcttcgc ccaacagcca ccgtcaacgc ctcctctccg   8280
tcaacataag agagagagag aagaggagag tagccatgtg gggaggagga atagtacatg   8340
gggcctaccg tttggcaagt tattttgggt tgccaagtta ggccaataag gggagggatt   8400
tggccatccg gttggaaagg ttattggggt agtatctttt tactagaatt gtcaaaaaaa   8460
aatagtttga gagccatttg gagaggatgt tgcctgttag aggtgctctt aggacatcaa   8520
attccataaa aacatcagaa aaattctctc gatgaagatt tataaccact aaaactgccc   8580
tcaattcgaa gggagttcaa aacaattaaa atcatgttcg aattgagttt caatttcact   8640
ttaacccctt tgaaatctca atggtaaaac atcaacccgt caggtagcat ggttcttttt   8700
attcctttca aaaagagtta attacaaaca gaatcaaaac taacagttag gcccaaggcc   8760
catccgagca aacaatagat catgggccag gcctgccacc accctccccc tcctggctcc   8820
cgctcttgaa tttcaaaatc caaaaatatc ggcacgactg gccgccgacg gagcgggcgg   8880
aaaatgacgg aacaacccct cgaattctac cccaactacg cccaccaacc cacacgccac   8940
tgacaatccg gtcccaccct tgtgggccca cctacaagcg agacgtcagt cgctcgcagc   9000
aaccagtggg cccacctccc agtgagcggc gggtagatct ggactcttac ccacccacac   9060
taaacaaaac ggcatgaata ttttgcacta aaaccctcag aaaaattccg atattccaaa   9120
ccagtacagt tcctgaccgt tggaggagcc aaagtggagc ggagtgtaaa attgggaaac   9180
ttaatcgagg gggttaaacg caaaaacgcc gaggcgcctc ccgctctata gaaaggggag   9240
gagtgggagg tggaaaccct accacaccgc agagaaaggc gtcttcgtac tcgcctctct   9300
ccgcgccctc ctccgccgcc gctcgccgcc gttcgtctcc gccgccaccg gctagccatc   9360
caggtaaaac aaacaaaaac ggatctgatg cttccattcc tccgtttctc gtagtagcgc   9420
gcttcgatct gtgggtggat ctgggtgatc ctggggtgtg gttcgttctg tttgatagat   9480
ctgtcggtgg atctggcctt ctgtggttgt cgatgtccgg atctgcgttt tgatcagtgg   9540
tagttcgtgg atctggcgaa atgttttgga tctggcagtg agacgctaag aatcgggaaa   9600
tgatgcaata ttaggggggt ttcggatggg gatccactga attagtctgt ctccctgctg   9660
ataatctgtt cctttttggt agatctggtt agtgtatgtt tgtttcggat agatctgatc   9720
aatgcttgtt tgttttttca aattttctac ctaggttgta taggaatggc atgcggatct   9780
ggttggattg ccatgatccg tgctgaaatg ccccttttggt tgatggatct tgatatttta  9840
ctgctgttca cctagatttg tactcccgtt tatacttaat ttgttgctta ttatgaatag   9900
```

-continued atctgtaact taggcacatg tatggacgga gtatgtggat ctgtagtatg tacattgctg 9960
cgagctaaga actatttcag agcaagcaca gaaaaaaata tttagacaga ttgggcaact 10020
atttgatggt ctttggtatc atgctttgta gtgctcgttt ctgcgtagta atcttttgat 10080
ctgatctgaa gataggtgct attatattct taaaggtcat tagaacgcta tctgaaaggc 10140
tgtattatgt ggattggttc acctgtgact ccctgttcgt cttgtcttga taaatcctgt 10200
gataaaaaaa attcttaagg cgtaatttgt tgaaatcttg ttttgtccta tgcagcctga 10260
tccatggcgc aagttagcag aatctgcaat ggtgtgcaga acccatctct tatctccaat 10320
ctctcgaaat ccagtcaacg caaatctccc ttatcggttt ctctgaagac gcagcagcat 10380
ccacgagctt atccgatttc gtcgtcgtgg ggattgaaga agagtgggat gacgttaatt 10440
ggctctgagc ttcgtcctct taaggtcatg tcttctgttt ccacggcgtg catgcttcac 10500
ggtgcaagca gccggcccgc aaccgcccgc aaatcctctg gcctttccgg aaccgtccgc 10560
attcccggcg acaagtcgat ctcccaccgg tccttcatgt tcggcggtct cgcgagcggt 10620
gaaacgcgca tcaccggcct tctggaaggc gaggacgtca tcaatacggg caaggccatg 10680
caggcgatgg gcgcccgcat ccgtaaggaa ggcgacacct ggatcatcga tggcgtcggc 10740
aatggcggcc tcctggcgcc tgaggcgccg ctcgatttcg gcaatgccgc cacgggctgc 10800
cgcctgacga tgggcctcgt cggggtctac gatttcgaca gcaccttcat cggcgacgcc 10860
tcgctcacaa agcgcccgat gggccgcgtg ttgaacccgc tgcgcgaaat gggcgtgcag 10920
gtgaaatcgg aagacggtga ccgtcttccc gttaccttgc gcgggccgaa gacgccgacg 10980
ccgatcacct accgcgtgcc gatggcctcc gcacaggtga agtccgccgt gctgctcgcc 11040
ggcctcaaca cgcccggcat cacgacggtc atcgagccga tcatgacgcg cgatcatacg 11100
gaaaagatgc tgcagggctt tggcgccaac cttaccgtcg agacggatgc ggacggcgtg 11160
cgcaccatcc gcctggaagg ccgcggcaag ctcaccggcc aagtcatcga cgtgccgggc 11220
gacccgtcct cgacggcctt cccgctggtt gcggccctgc ttgttccggg ctccgacgtc 11280
accatcctca acgtgctgat gaaccccacc cgcaccggcc tcatcctgac gctgcaggaa 11340
atgggcgccg acatcgaagt catcaacccg cgccttgccg gcggcgaaga cgtggcggac 11400
ctgcgcgttc gctcctccac gctgaagggc gtcacggtgc cggaagaccg cgcgccttcg 11460
atgatcgacg aatatccgat tctcgctgtc gccgccgcct tcgcggaagg ggcgaccgtg 11520
atgaacggtc tggaagaact ccgcgtcaag gaaagcgacc gcctctcggc cgtcgccaat 11580
ggcctcaagc tcaatggcgt ggattgcgat gagggcgaga cgtcgctcgt cgtgcgtggc 11640
cgccctgacg gcaaggggct cggcaacgcc tcgggcgccg ccgtcgccac ccatctcgat 11700
caccgcatcg ccatgagctt cctcgtcatg ggcctcgtgt cggaaaaccc tgtcacggtg 11760
gacgatgcca cgatgatcgc cacgagcttc ccggagttca tggacctgat ggccgggctg 11820
ggcgcgaaga tcgaactctc cgatacgaag gctgcctgat gagctccagg gttcttgcct 11880
ggtgccttgg caatgcttga ttactgctgc tatcctatga tctgtccgtg tgggcttcta 11940
tctatcagtt tgtgtgtctg gttttgaaaa acatttgctt ttcgattatg tagggtttgc 12000
ttgtagcttt cgctgctgtg acctgtgttg tttatgtgaa ccttctttgt ggcatcttta 12060
atatccaagt tcgtggtttg tcgtaaaacg aagcctctac ttcgtaaagt tgtgtctata 12120
gcattgaaat cgtttttttg ctcgagaata attgtgacct ttagttggcg tgaaactagt 12180
tttggatatc tgattctctg gttcgcaatc ttgagatcgt cgctgcttag gtgagctaag 12240

-continued

```
tgatgttcct aagtaaatgc tcctcaccag aatacgtagc tgtgtgaaaa gagaacgcgt  12300

gaatacgtag ctgtgtaaag attgtgtccc aagtaaacct cagtgatttt tgtttggatt  12360

tttaatttag aaacattcga ctgggagcgg ctagagccac acccaagttc ctaactatga  12420

taaagttgct ctgtaacaga aaacaccatc tagagcggcc gcgtttaaac tatcagtgtt  12480

tgacaggata tattggcggg taaacctaag agaaaagagc gtttattaga ataatcggat  12540

atttaaaagg gcgtgaaaag gtttatccgt tcgtccattt gtatgtgcat gccaaccaca  12600

gggttcccct cgggagtgct tggcattccg tgcgataatg acttctgttc aaccacccaa  12660

acgtcggaaa gcctgacgac ggagcagcat tccaaaaaga tcccttggct cgtctgggtc  12720

ggctagaagg tcgagtgggc tgctgtggct tgatccctca acgcggtcgc ggacgtagcg  12780

cagcgccgaa aaatcct                                                12797


<210> SEQ ID NO 33
<211> LENGTH: 11906
<212> TYPE: DNA
<213> ORGANISM: Artificial Sequence
<220> FEATURE:
<223> OTHER INFORMATION: DNA construct 423

<400> SEQUENCE: 33

aaaagtccca tgtggatcac tccgttgccc cgtcgctcac cgtgttgggg ggaaggtgca     60

catggctcag ttctcaatgg aaattatctg cctaaccggc tcagttctgc gtagaaacca    120

acatgcaagc tccaccgggt gcaaagcggc agcggcggca ggatatattc aattgtaaat    180

ggcttcatgt ccgggaaatc tacatggatc agcaatgagt atgatggtca atatggagaa    240

aaagaaagag taattaccaa tttttttca attcaaaaat gtagatgtcc gcagcgttat    300

tataaaatga aagtacattt tgataaaacg acaaattacg atccgtcgta tttataggcg    360

aaagcaataa acaaattatt ctaattcgga aatctttatt tcgacgtgtc tacattcacg    420

tccaaatggg ggcttagatg agaaacttca cgatcgatgc ggccaccact cgaggtcgag    480

gtaccacaca cagatctaat tcctttttt ttgcactcaa aatcagaaca atttatttct    540

catttattca tcgccgaatc tgttggcgat tagccgatta cacaagtaca gaaaacactg    600

gggaaagaaa cacaatacag agatgtctca tcagactcgc aagaactcgc acacacatca    660

accaaattgg ctccaacctg aatgagcata cgtccaaacg catgcagaat tcaatcagag    720

ttcctatcac agctggacgg ggatgaactc gatcttgtcg atgtagatct tctcgttgga    780

gacgaaggac tcagcaccaa tgatcagttc attcttgtcg cccgagaagc ccatgttgga    840

gttcgtggtg gcgaggtcga aggtctggta ggtcaggtca tcgtccttgt tcatggtctt    900

gttgatgtag atgaccagga agtcattgtt ggagttctgg acgaacaggc gcaggttcgt    960

ggtggaggcg tagcggatgc ggacgcggta gcgttgcagc aaggcagcgg agttcagggt   1020

gaccttgaac ttggcgatgg agttcgagga ctccttcagg aacagcaggt tgccaccggt   1080

gaagcctgga ccctcaatga tggaggcacc cgaggacagg gcgtaggcct tgaccacggg   1140

cagctgggtg atcttctcgg cgtcgatggt gttgaagaag tcgacggagc ggtgggtcca   1200

ggtgaagaag gggatggtgc ccctgcggtc ttgcatcagg aagcactccg cgtagttcag   1260

ctggtgggag taggccttct ccaggggctc gtcagtggtc tcaggcggca gctggtcgat   1320

ggagtcctgg gcggagacgt ggccattgtt gcgcttggag tcgtaggtct gggtggaggt   1380

ctcgttcttc tggtcatcgt actgggagaa gtcgaccttc gtgacgccca ggtagacctt   1440

gccgttcggc caagccgcga cgtcggtgtt ggcgatggtg cggtagacct tctggccgtc   1500
```

-continued

```
gaaggacagc ttctggacgg gctcggtgga cttgtcgccg tagaaagggg aggtgatcgt   1560
cttcgaggag ccgatggagg gcctggtctc gacgtagttg ccggaccagt agttgaagga   1620
gtccttgccg aagtagcctg gcctcaggcg cgtgtggaac tcgatgccct ggaggtagtc   1680
gaacaggtgg ggcttgcgga tggagttctc gatggacagg aaggtgggac cgtacttctg   1740
gagggtcgtg agcaggaaga tggggtccgt gaagatgtcg cgggtcagct cggtcttgac   1800
gcccttggag tacaggcgga tgtcgtagaa ggggaacagg acgatcaggt ccaggacggt   1860
cagggtcatc tccctgcgga agcggttgaa cttgacccat gcgtcgtagg tggagcccct   1920
caggccgttc aggccgacgt tgtaccagtt gacgcagtgg tcggtgtact gttgggtcag   1980
cttcagctgg cgacggtaga actcggcgac gtcctccgag gagtagcccc attcctcgcc   2040
gaagacctgg gcgtccttca gcaacaggag gtgggtgttg gcagcctggg cgtaggtggg   2100
caggaacagg acctcgaact tggagacggc gaaggacggc atggagttgc ggaagtggga   2160
ctcggcctgg gagaacagct cgcggatgcg gtcctgggag cgcttggagc gcagggacag   2220
aggcgtcttc ttccaggagt tcagcgcgtt gacgtagtcc tcgaagttgt tttgcaggcc   2280
ttgcagctcg gccagggcct tggacttggc gtactcctcg atcttcttgt cgatcaggac   2340
ttcgacttgg gccatgaagg ccttccaggg gtcggcgtcg gagggccaga tggtgttcag   2400
gaaggactgg tagaaggagg tgagagcacc tgcgaagggg acgccaacga cgcccaggat   2460
ctgcccaacg acggagatgc cggtcccgac ggcgtccttg acggtggagt tgtccaggac   2520
ctccgtggag gagtcctcgg tcatgcgcag gaactccttg tagttcagct cttccagggt   2580
ggagttgggg ttgtcggcca gcgggtactg gttgtggttg gtctggagct cggagttggg   2640
ggtgaccttg atcgtgtcgt gctcggagcg attgttgggg ttggccatgg ttgatcactt   2700
ctacctacaa aaaagctccg cacgaggctg catttgtcac aaatcatgaa aagaaaaact   2760
accgatgaac aatgctgagg gattcaaatt ctacccacaa aaagaagaaa gaaagatcta   2820
gcacatctaa gcctgacgaa gcagcagaaa tatataaaaa tataaaccat agtgcccttt   2880
tcccctcttc ctgatcttgt ttagcacggc ggaaatttta aacccccccat catctccccc   2940
aacaacggcg gatcgcagat ctacatccga gagccccatt ccccgcgaga tccgggccgg   3000
atccacgccg gcgagagccc cagccgcgag atcccgcccc tcccgcgcac cgatctgggc   3060
gcgcacgaag ccgcctctcg cccacccaaa ctaccaaggc caaagatcga gaccgagacg   3120
gaaaaaaaaa cggagaaaga aagaggagag gggcggggtg gttaccggcg gcggcggagg   3180
cctcccttgg atcttatggt gtgttgtccc tgtgtgttct ccaatagtgt ggcttgagtg   3240
tgtggaagat ggttctagag gatctgctag agtcagcttg tcagcgtgtc ctctccaaat   3300
gaaatgaact tccttatata gaggaagggt cttgcgaagg atagtgggat tgtgcgtcat   3360
cccttacgtc agtggagata tcacatcaat ccacttgctt tgaagacgtg gttggaacgt   3420
cttctttttc cacgatgctc ctcgtgggtg ggggtccatc tttgggacca ctgtcggcag   3480
aggcatcttc aacgatggcc tttcctttat cgcaatgatg gcatttgtag gagccacctt   3540
ccttttccac tatcttcaca ataaagtgac agatagctgg gcaatggaat ccgaggaggt   3600
ttccggatat tacccttttgt tgaaaagtct caatcggacc atcacatcaa tccacttgct   3660
ttgaagacgt ggttggaacg tcttcttttt ccacgatgct cctcgtgggt gggggtccat   3720
ctttgggacc actgtcggca gaggcatctt caacgatggc ctttccttta tcgcaatgat   3780
ggcatttgta ggagccacct tccttttcca ctatcttcac aataaagtga cagatagctg   3840
```

-continued

```
ggcaatggaa tccgaggagg tttccggata ttaccctttg ttgaaaagtc tcaatcggac   3900
ctggtaccgt tgtcaatcaa ttggcaagtc ataaaatgca ttaaaaaata ttttcatact   3960
caactacaaa tccatgagta taactataat tataaagcaa tgattagaat ctgacaagga   4020
ttctggaaaa ttacataaag gaaagttcat aaatgtctaa aacacaagag gacatacttg   4080
tattcagtaa catttgcagc ttttctaggt ctgaaaatat atttgttgcc tagtgaataa   4140
gcataatggt acaactacaa gtgttttact cctcatatta acttcggtca ttagaggcca   4200
cgatttgaca catttttact caaaacaaaa tgtttgcata tctcttataa tttcaaattc   4260
aacacacaac aaataagaga aaaaacaaat aatattaatt tgagaatgaa caaaaggacc   4320
atatcattca ttaactcttc tccatccatt tccatttcac agttcgatag cgaaaaccga   4380
ataaaaaaca cagtaaatta caagcacaac aaatggtaca agaaaaacag ttttcccaat   4440
gccataatac tcaaactcag taggattctg gtgtgtgcgc aatgaaactg atgcattgaa   4500
cttgacgaac gttgtcgaaa ccgatgatac gaacgaaagc taggcctcag cgagtaccgc   4560
tggcgatcta atccatgata tcgtgaacat catctacatt caaattctta tgagctttct   4620
taagggcatc tgcagcattt ttcatagaat ctaatacagc agtatttgtg ctagctcctt   4680
cgagggcttc cctctgcatt tcaatagttg taagggttcc atctatttgt agttgggtct   4740
tttccaatcg tttcttcttt ttgagggctt ggagtgcaac tcttttattt ttcgacgcat   4800
ttttctttgc gctcctgcag gcggccgcgt ggatgaggag ttaatcggtc gtgtgagagt   4860
agtgatcgag tggatgtcgt cgagagtgat gagtgttgat gttgttagtg atatgtggta   4920
gaaggtatcg tgataaagcg ttaacgcgat cgcagtactt gcaaagaaaa atgcgtcgaa   4980
aaataaaaga gttgcactcc aagccctcaa aaagaagaaa cgattggaaa agacccaact   5040
acaaatagat ggaaccctta caactattga aatgcagagg gaagccctcg aaggagctag   5100
cacaaatact gctgtattag attctatgaa aaatgctgca gatgccctta agaaagctca   5160
taagaatttg aatgtagatg atgttcacga tatcatggat ggtatcgcac agcgactgct   5220
gagggacgtc ggtccatgga gatcctctag aggccgcttg gtatctgcat tacaatgaaa   5280
tgagcaaaga ctatgtgagt aacactggtc aacactaggg agaaggcatc gagcaagata   5340
cgtatgtaaa gagaagcaat atagtgtcag ttggtagata ctagatacca tcaggaggta   5400
aggagagcaa caaaaaggaa actctttatt tttaaatttt gttacaacaa acaagcagat   5460
caatgcatca aaatactgtc agtacttatt tcttcagaca acaatattta aaacaagtgc   5520
atctgatctt gacttatggt cacaataaag gagcagagat aaacatcaaa atttcgtcat   5580
ttatatttat tccttcaggc gttaacaatt taacagcaca caaacaaaaa cagaatagga   5640
atatctaatt ttggcaaata ataagctctg cagacgaaca aattattata gtatcgccta   5700
taatatgaat ccctatacta ttgacccatg tagtatgaag cctgtgccta aattaacagc   5760
aaacttctga atccaagtgc cctataacac caacatgtgc ttaaataaat accgctaagc   5820
accaaattac acatttctcg tattgctgtg taggttctat cttcgtttcg tactaccatg   5880
tccctatatt ttgctgctac aaaggacggc aagtaatcag cacaggcaga acacgatttc   5940
agagtgtaat tctagatcca gctaaaccac tctcagcaat caccacacaa gagagcattc   6000
agagaaacgt ggcagtaaca aaggcagagg gcggagtgag cgcgtaccga agacggtggg   6060
ccgcttatgg tgtgttgtcc ctgtgtgttc tccaatagtg tggcttgagt gtgtggaaga   6120
tggttgtatc tgatgatcct tcaaatggga atgaatgcct tcttatatag agggaattct   6180
tttgtggtcg tcactgcgtt cgtcatacgc attagtgagt gggctgtcag gacagctctt   6240
```

-continued

```
ttccacgtta ttttgttccc cacttgtact agaggaatct gctttatctt tgcaataaag   6300
gcaaagatgc ttttggtagg tgcgcctaac aattctgcac cattcctttt ttgtctggtc   6360
cccacaagcc agctgctcga tgttgacaag attactttca aagatgccca ctaactttaa   6420
gtcttcggtg gatgtctttt tctgaaactt actgaccatg atgcatgtgc tggaacagta   6480
gtttactttg attgaagatt cttcattgat ctcctgtagc ttttggctaa tggtttggag   6540
actctgtacc ctgaccttgt tgaggctttg gactgagaat tcttccttac aaacctttga   6600
ggatgggagt tccttcttgg ttttggcgat accaatttga ataaagtgat atggctcgta   6660
ccttgttgat tgaacccaat ctggaatgct gctaaatcct gagctcaagc taattctttt   6720
gtggtcgtca ctgcgttcgt catacgcatt agtgagtggg ctgtcaggac agctcttttc   6780
cacgttattt tgttccccac ttgtactaga ggaatctgct ttatctttgc aataaaggca   6840
aagatgcttt tggtaggtgc gcctaacaat tctgcaccat tccttttttg tctggtcccc   6900
acaagccagc tgctcgatgt tgacaagatt actttcaaag atgcccacta actttaagtc   6960
ttcggtggat gtctttttct gaaacttact gaccatgatg catgtgctgg aacagtagtt   7020
tactttgatt gaagattctt cattgatctc ctgtagcttt tggctaatgg tttggagact   7080
ctgtaccctg accttgttga ggctttggac tgagaattag cttccactcg aagcttgtta   7140
acctgcaggc tagcggcgcg ccagtctagt cgacaagctt gcctcgagac aacaacatgc   7200
ttctcatcaa catggaggga agagggaggg agaaagtgtc gcctggtcac ctccattgtc   7260
acactagcca ctggccagct ctcccacacc accaatgcca ggggcgagct ttagcacagc   7320
caccgcttca cctccaccac cgcactaccc tagcttcgcc caacagccac cgtcaacgcc   7380
tcctctccgt caacataaga gagagagaga agaggagagt agccatgtgg ggaggaggaa   7440
tagtacatgg ggcctaccgt ttggcaagtt attttgggtt gccaagttag gccaataagg   7500
ggagggattt ggccatccgg ttggaaaggt tattggggta gtatcttttt actagaattg   7560
tcaaaaaaaa atagtttgag agccatttgg agaggatgtt gcctgttaga ggtgctctta   7620
ggacatcaaa ttccataaaa acatcagaaa aattctctcg atgaagattt ataaccacta   7680
aaactgccct caattcgaag ggagttcaaa acaattaaaa tcatgttcga attgagtttc   7740
aatttcactt taacccccttt gaaatctcaa tggtaaaaca tcaacccgtc aggtagcatg   7800
gttcttttta ttcctttcaa aaagagttaa ttacaaacag aatcaaaact aacagttagg   7860
cccaaggccc atccgagcaa acaatagatc atgggccagg cctgccacca ccctccccct   7920
cctggctccc gctcttgaat ttcaaaatcc aaaaatatcg gcacgactgg ccgccgacgg   7980
agcgggcgga aaatgacgga acaacccctc gaattctacc ccaactacgc ccaccaaccc   8040
acacgccact gacaatccgg tcccaccctt gtgggcccac ctacaagcga gacgtcagtc   8100
gctcgcagca accagtgggc ccacctccca gtgagcggcg ggtagatctg gactcttacc   8160
cacccacact aaacaaaacg gcatgaatat tttgcactaa aaccctcaga aaaattccga   8220
tattccaaac cagtacagtt cctgaccgtt ggaggagcca aagtggagcg gagtgtaaaa   8280
ttgggaaact taatcgaggg ggttaaacgc aaaaacgccg aggcgcctcc cgctctatag   8340
aaaggggagg agtgggaggt ggaaacccta ccacaccgca gagaaaggcg tcttcgtact   8400
cgcctctctc cgcgccctcc tccgccgccg ctcgccgccg ttcgtctccg ccgccaccgg   8460
ctagccatcc aggtaaaaca aacaaaaacg gatctgatgc ttccattcct ccgtttctcg   8520
tagtagcgcg cttcgatctg tgggtggatc tgggtgatcc tggggtgtgg ttcgttctgt   8580
```

ttgatagatc tgtcggtgga tctggccttc tgtggttgtc gatgtccgga tctgcgtttt 8640
gatcagtggt agttcgtgga tctggcgaaa tgttttggat ctggcagtga gacgctaaga 8700
atcgggaaat gatgcaatat tagggggggtt tcggatgggg atccactgaa ttagtctgtc 8760
tccctgctga taatctgttc ctttttggta gatctggtta gtgtatgttt gtttcggata 8820
gatctgatca atgcttgttt gtttttttcaa atttctacc taggttgtat aggaatggca 8880
tgcggatctg gttggattgc catgatccgt gctgaaatgc ccctttggtt gatggatctt 8940
gatattttac tgctgttcac ctagatttgt actcccgttt atacttaatt tgttgcttat 9000
tatgaataga tctgtaactt aggcacatgt atggacggag tatgtggatc tgtagtatgt 9060
acattgctgc gagctaagaa ctatttcaga gcaagcacag aaaaaaatat ttagacagat 9120
tgggcaacta tttgatggtc tttggtatca tgctttgtag tgctcgtttc tgcgtagtaa 9180
tcttttgatc tgatctgaag ataggtgcta ttatattctt aaaggtcatt agaacgctat 9240
ctgaaaggct gtattatgtg gattggttca cctgtgactc cctgttcgtc ttgtcttgat 9300
aaatcctgtg ataaaaaaaa ttcttaaggc gtaatttgtt gaaatcttgt tttgtcctat 9360
gcagcctgat ccatggcgca agttagcaga atctgcaatg gtgtgcagaa cccatctctt 9420
atctccaatc tctcgaaatc cagtcaacgc aaatctccct tatcggtttc tctgaagacg 9480
cagcagcatc cacgagctta tccgatttcg tcgtcgtggg gattgaagaa gagtgggatg 9540
acgttaattg gctctgagct tcgtcctctt aaggtcatgt cttctgtttc cacggcgtgc 9600
atgcttcacg gtgcaagcag ccggcccgca accgcccgca aatcctctgg cctttccgga 9660
accgtccgca ttcccggcga caagtcgatc tcccaccggt ccttcatgtt cggcggtctc 9720
gcgagcggtg aaacgcgcat caccggcctt ctggaaggcg aggacgtcat caatacgggc 9780
aaggccatgc aggcgatggg cgcccgcatc cgtaaggaag gcgacacctg gatcatcgat 9840
ggcgtcggca atggcggcct cctggcgcct gaggcgccgc tcgatttcgg caatgccgcc 9900
acgggctgcc gcctgacgat gggcctcgtc ggggtctacg atttcgacag caccttcatc 9960
ggcgacgcct cgctcacaaa gcgcccgatg ggccgcgtgt tgaacccgct gcgcgaaatg 10020
ggcgtgcagg tgaaatcgga agacggtgac cgtcttcccg ttaccttgcg cgggccgaag 10080
acgccgacgc cgatcaccta ccgcgtgccg atggcctccg cacaggtgaa gtccgccgtg 10140
ctgctcgccg gcctcaacac gcccggcatc acgacggtca tcgagccgat catgacgcgc 10200
gatcatacgg aaaagatgct gcagggcttt ggcgccaacc ttaccgtcga gacggatgcg 10260
gacggcgtgc gcaccatccg cctggaaggc cgcggcaagc tcaccggcca agtcatcgac 10320
gtgccgggcg acccgtcctc gacggccttc ccgctggttg cggccctgct tgttccgggc 10380
tccgacgtca ccatcctcaa cgtgctgatg aaccccaccc gcaccggcct catcctgacg 10440
ctgcaggaaa tgggcgccga catcgaagtc atcaacccgc gccttgccgg cggcgaagac 10500
gtggcggacc tgcgcgttcg ctcctccacg ctgaagggcg tcacggtgcc ggaagaccgc 10560
gcgccttcga tgatcgacga atatccgatt ctcgctgtcg ccgccgcctt cgcggaaggg 10620
gcgaccgtga tgaacggtct ggaagaactc cgcgtcaagg aaagcgaccg cctctcggcc 10680
gtcgccaatg gcctcaagct caatggcgtg gattgcgatg agggcgagac gtcgctcgtc 10740
gtgcgtggcc gccctgacgg caaggggctc ggcaacgcct cgggcgccgc cgtcgccacc 10800
catctcgatc accgcatcgc catgagcttc ctcgtcatgg gcctcgtgtc ggaaaaccct 10860
gtcacggtgg acgatgccac gatgatcgcc acgagcttcc cggagttcat ggacctgatg 10920
gccgggctgg gcgcgaagat cgaactctcc gatacgaagg ctgcctgatg agctccaggg 10980

```
ttcttgcctg gtgccttggc aatgcttgat tactgctgct atcctatgat ctgtccgtgt  11040
gggcttctat ctatcagttt gtgtgtctgg ttttgaaaaa catttgcttt tcgattatgt  11100
agggtttgct tgtagctttc gctgctgtga cctgtgttgt ttatgtgaac cttctttgtg  11160
gcatctttaa tatccaagtt cgtggtttgt cgtaaaacga agcctctact tcgtaaagtt  11220
gtgtctatag cattgaaatc gttttttttgc tcgagaataa ttgtgacctt tagttggcgt  11280
gaaactagtt ttggatatct gattctctgg ttcgcaatct tgagatcgtc gctgcttagg  11340
tgagctaagt gatgttccta agtaaatgct cctcaccaga atacgtagct gtgtgaaaag  11400
agaacgcgtg aatacgtagc tgtgtaaaga ttgtgtccca agtaaacctc agtgattttt  11460
gtttggattt ttaatttaga aacattcgac tgggagcggc tagagccaca cccaagttcc  11520
taactatgat aaagttgctc tgtaacagaa aacaccatct agagcggccg cgtttaaact  11580
atcagtgttt gacaggatat attggcgggt aaacctaaga gaaaagagcg tttattagaa  11640
taatcggata tttaaaaggg cgtgaaaagg tttatccgtt cgtccatttg tatgtgcatg  11700
ccaaccacag ggttcccctc gggagtgctt ggcattccgt gcgataatga cttctgttca  11760
accacccaaa cgtcggaaag cctgacgacg gagcagcatt ccaaaaagat cccttggctc  11820
gtctgggtcg gctagaaggt cgagtgggct gctgtggctt gatccctcaa cgcggtcgcg  11880
gacgtagcgc agcgccgaaa aatcct                                        11906
```

<210> SEQ ID NO 34
<211> LENGTH: 7158
<212> TYPE: DNA
<213> ORGANISM: Artificial Sequence
<220> FEATURE:
<223> OTHER INFORMATION: DNA construct 405

<400> SEQUENCE: 34

```
aaaagtccca tgtggatcac tccgttgccc cgtcgctcac cgtgttgggg ggaaggtgca     60
catggctcag ttctcaatgg aaattatctg cctaaccggc tcagttctgc gtagaaacca    120
acatgcaagc tccaccgggt gcaaagcggc agcggcggca ggatatattc aattgtaaat    180
ggcttcatgt ccgggaaatc tacatggatc agcaatgagt atgatggtca atatggagaa    240
aaagaaagag taattaccaa tttttttttca attcaaaaat gtagatgtcc gcagcgttat    300
tataaaatga aagtacattt tgataaaacg acaaattacg atccgtcgta tttataggcg    360
aaagcaataa acaaattatt ctaattcgga aatctttatt tcgacgtgtc tacattcacg    420
tccaaatggg ggcttagatg agaaacttca cgatcgatgc ggcccacgtg gattaccctg    480
ttatccctag aattcgatat cagttcgctc gtggccgtca cggccagcgc ctgcgttggc    540
ctagtaggcc aagcaggacg tattcgtttg ttgtgcggcc gctacctcag caaatcaacc    600
tcactctatt taaatgaggt ggtaggattt gctgaggagg ctgctccgtt gtcctgcagg    660
agacgagaaa cacctttaat taacctcagc gcgtgttctg ctggcgatcg caacaggcac    720
agcgctgagg gtaccgttgt caatcaattg gcaagtcata aaatgcatta aaaaatattt    780
tcatactcaa ctacaaatcc atgagtataa ctataattat aaagcaatga ttagaatctg    840
acaaggattc tggaaaatta cataaaggaa agttcataaa tgtctaaaac acaagaggac    900
atacttgtat tcagtaacat ttgcagcttt tctaggtctg aaaatatatt tgttgcctag    960
tgaataagca taatggtaca actacaagtg ttttactcct catattaact tcggtcatta   1020
gaggccacga tttgacacat ttttactcaa aacaaaatgt ttgcatatct cttataattt   1080
```

-continued

```
caaattcaac acacaacaaa taagagaaaa aacaaataat attaatttga gaatgaacaa   1140
aaggaccata tcattcatta actcttctcc atccatttcc atttcacagt tcgatagcga   1200
aaaccgaata aaaaacacag taaattacaa gcacaacaaa tggtacaaga aaaacagttt   1260
tcccaatgcc ataatactca aactcagtag gattctggtg tgtgcgcaat gaaactgatg   1320
cattgaactt gacgaacgtt gtcgaaaccg atgatacgaa cgaaagctag gcctcagcga   1380
gtaccgctgg cgatctaatc catgatatcg tgaacatcat ctacattcaa attcttatga   1440
gctttcttaa gggcatctgc agcatttttc atagaatcta atacagcagt atttgtgcta   1500
gctccttcga gggcttccct ctgcatttca atagttgtaa gggttccatc tatttgtagt   1560
tgggtctttt ccaatcgttt cttctttttg agggcttgga gtgcaactct tttatttttc   1620
gacgcatttt tctttgcgct cctgcaggcg gccgcgtgga tgaggagtta atcggtcgtg   1680
tgagagtagt gatcgagtgg atgtcgtcga gagtgatgag tgttgatgtt gttagtgata   1740
tgtggtagaa ggtatcgtga taaagcgtta acgcgatcgc agtacttgca aagaaaaatg   1800
cgtcgaaaaa taaaagagtt gcactccaag ccctcaaaaa gaagaaacga ttggaaaaga   1860
cccaactaca aatagatgga acccttacaa ctattgaaat gcagagggaa gccctcgaag   1920
gagctagcac aaatactgct gtattagatt ctatgaaaaa tgctgcagat gcccttaaga   1980
aagctcataa gaatttgaat gtagatgatg ttcacgatat catggatggt atcgcacagc   2040
gactgctgag ggacgtcgag ctcccgcttg gtatctgcat tacaatgaaa tgagcaaaga   2100
ctatgtgagt aacactggtc aacactaggg agaaggcatc gagcaagata cgtatgtaaa   2160
gagaagcaat atagtgtcag ttggtagata ctagatacca tcaggaggta aggagagcaa   2220
caaaaaggaa actctttatt tttaaatttt gttacaacaa acaagcagat caatgcatca   2280
aaatactgtc agtacttatt tcttcagaca acaatattta aaacaagtgc atctgatctt   2340
gacttatggt cacaataaag gagcagagat aaacatcaaa atttcgtcat ttatatttat   2400
tccttcaggc gttaacaatt taacagcaca caaacaaaaa cagaatagga atatctaatt   2460
ttggcaaata ataagctctg cagacgaaca aattattata gtatcgccta taatatgaat   2520
ccctatacta ttgacccatg tagtatgaag cctgtgccta aattaacagc aaacttctga   2580
atccaagtgc cctataacac caacatgtgc ttaaataaat accgctaagc accaaattac   2640
acatttctcg tattgctgtg taggttctat cttcgtttcg tactaccatg tccctatatt   2700
ttgctgctac aaaggacggc aagtaatcag cacaggcaga acacgatttc agagtgtaat   2760
tctagatcca gctaaaccac tctcagcaat caccacacaa gagagcattc agagaaacgt   2820
ggcagtaaca aaggcagagg gcggagtgag cgcgtaccga agacggtcct tcaaatggga   2880
atgaatgcct tcttatatag agggaattct tttgtggtcg tcactgcgtt cgtcatacgc   2940
attagtgagt gggctgtcag gacagctctt ttccacgtta ttttgttccc cacttgtact   3000
agaggaatct gctttatctt tgcaataaag gcaaagatgc ttttggtagg tgcgcctaac   3060
aattctgcac cattcctttt ttgtctggtc cccacaagcc agctgctcga tgttgacaag   3120
attactttca aagatgccca ctaactttaa gtcttcggtg gatgtctttt tctgaaactt   3180
actgaccatg atgcatgtgc tggaacagta gtttactttg attgaagatt cttcattgat   3240
ctcctgtagc ttttggctaa tggtttggag actctgtacc ctgaccttgt tgaggctttg   3300
gactgagaat tcttccttac aaacctttga ggatgggagt tccttcttgg ttttggcgat   3360
accaatttga ataaagtgat atggctcgta ccttgttgat tgaacccaat ctggaatgcg   3420
gcgcgccaag cttctgcagg tccgattgag acttttcaac aaagggtaat atccggaaac   3480
```

-continued

```
ctcctcggat tccattgccc agctatctgt cactttattg tgaagatagt ggaaaaggaa   3540
ggtggctcct acaaatgcca tcattgcgat aaaggaaagg ccatcgttga agatgcctct   3600
gccgacagtg gtcccaaaga tggaccccca cccacgagga gcatcgtgga aaaagaagac   3660
gttccaacca cgtcttcaaa gcaagtggat tgatgtgatg gtccgattga gacttttcaa   3720
caaagggtaa tatccggaaa cctcctcgga ttccattgcc cagctatctg tcactttatt   3780
gtgaagatag tggaaaagga aggtggctcc tacaaatgcc atcattgcga taaaggaaag   3840
gccatcgttg aagatgcctc tgccgacagt ggtcccaaag atggaccccc acccacgagg   3900
agcatcgtgg aaaaagaaga cgttccaacc acgtcttcaa agcaagtgga ttgatgtgat   3960
atctccactg acgtaaggga tgacgcacaa tcccactatc cttcgcaaga cccttcctct   4020
atataaggaa gttcatttca tttggagagg acacgctgac aagctgactc tagcagatcc   4080
tctagaacca tcttccacac actcaagcca cactattgga gaacacacag ggacaacaca   4140
ccataagatc caagggaggc ctccgccgcc gccggtaacc accccgcccc tctcctcttt   4200
ctttctccgt tttttttcc gtctcggtct cgatctttgg ccttggtagt ttgggtgggc   4260
gagaggcggc ttcgtgcgcg cccagatcgg tgcgcgggag ggcgggatc tcgcggctgg   4320
ggctctcgcc ggcgtggatc cggcccggat ctcgcgggga atggggctct cggatgtaga   4380
tctgcgatcc gccgttgttg ggggagatga tggggggttt aaaatttccg ccgtgctaaa   4440
caagatcagg aagaggggaa aagggcacta tggtttatat ttttatatat ttctgctgct   4500
tcgtcaggct tagatgtgct agatctttct ttcttctttt tgtgggtaga atttgaatcc   4560
ctcagcattg ttcatcggta gtttttcttt tcatgatttg tgacaaatgc agcctcgtgc   4620
ggagcttttt tgtaggtaga agtgatcaac catggccaac ccccaacaatc gctccgagca   4680
cgacacgatc aaggtcaccc ccaactccga gctccagacc aaccacaacc agtacccgct   4740
ggccgacaac cccaactcca ccctggaaga gctgaactac aaggagttcc tgcgcatgac   4800
cgaggactcc tccacggagg tcctggacaa ctccaccgtc aaggacgccg tcgggaccgg   4860
catctccgtc gttgggcaga tcctgggcgt cgttggcgtc cccttcgcag gtgctctcac   4920
ctccttctac cagtccttcc tgaacaccat ctggccctcc gacgccgacc cctggaaggc   4980
cttcatggcc caagtcgaag tcctgatcga caagaagatc gaggagtacg ccaagtccaa   5040
ggccctggcc gagctgcaag gcctgcaaaa caacttcgag gactacgtca acgcgctgaa   5100
ctcctggaag aagacgcctc tgtccctgcg ctccaagcgc tcccaggacc gcatccgcga   5160
gctgttctcc caggccgagt cccacttccg caactccatg ccgtccttcg ccgtctccaa   5220
gttcgaggtc ctgttcctgc ccacctacgc ccaggctgcc aacacccacc tcctgttgct   5280
gaaggacgcc caggtcttcg gcgaggaatg gggctactcc tcggaggacg tcgccgagtt   5340
ctaccgtcgc cagctgaagc tgacccaaca gtacaccgac cactgcgtca actggtacaa   5400
cgtcggcctg aacggcctga ggggctccac ctacgacgca tgggtcaagt tcaaccgctt   5460
ccgcagggag atgaccctga ccgtcctgga cctgatcgtc ctgttcccct tctacgacat   5520
ccgcctgtac tccaagggcg tcaagaccga gctgacccgc gacatcttca cggaccccat   5580
cttcctgctc acgaccctcc agaagtacgg tcccaccttc ctgtccatcg agaactccat   5640
ccgcaagccc cacctgttcg actacctcca gggcatcgag ttccacacgc gcctgaggcc   5700
aggctacttc ggcaaggact ccttcaacta ctggtccggc aactacgtcg agaccaggcc   5760
ctccatcggc tcctcgaaga cgatcacctc ccctttctac ggcgacaagt ccaccgagcc   5820
```

cgtccagaag ctgtccttcg acggccagaa ggtctaccgc accatcgcca acaccgacgt 5880
cgcggcttgg ccgaacggca aggtctacct gggcgtcacg aaggtcgact tctcccagta 5940
cgatgaccag aagaacgaga cctccaccca gacctacgac tccaagcgca acaatggcca 6000
cgtctccgcc caggactcca tcgaccagct gccgcctgag accactgacg agcccctgga 6060
gaaggcctac tcccaccagc tgaactacgc ggagtgcttc ctgatgcaag accgcagggg 6120
caccatcccc ttcttcacct ggacccaccg ctccgtcgac ttcttcaaca ccatcgacgc 6180
cgagaagatc acccagctgc ccgtggtcaa ggcctacgcc ctgtcctcgg gtgcctccat 6240
cattgagggt ccaggcttca ccggtggcaa cctgctgttc ctgaaggagt cctcgaactc 6300
catcgccaag ttcaaggtca ccctgaactc cgctgccttg ctgcaacgct accgcgtccg 6360
catccgctac gcctccacca cgaacctgcg cctgttcgtc cagaactcca acaatgactt 6420
cctggtcatc tacatcaaca agaccatgaa caaggacgat gacctgacct accagacctt 6480
cgacctcgcc accacgaact ccaacatggg cttctcgggc gacaagaatg aactgatcat 6540
tggtgctgag tccttcgtct ccaacgagaa gatctacatc gacaagatcg agttcatccc 6600
cgtccagctg tgataggaac tctgattgaa ttctgcatgc gtttggacgt atgctcattc 6660
aggttggagc caatttggtt gatgtgtgtg cgagttcttg cgagtctgat gagacatctc 6720
tgtattgtgt ttctttcccc agtgttttct gtacttgtgt aatcggctaa tcgccaacag 6780
attcggcgat gaataaatga gaaataaatt gttctgattt tgagtgcaaa aaaaaaggaa 6840
ttagatctgt gtgtgttttt tggatccgtc gacagacctc aattgcgagc tttctaattt 6900
caaactattc gggcctaact tttggtgtga tgatgctgac tggcaggata tataccgttg 6960
taatttgagc tcgtgtgaat aagtcgctgt gtatgtttgt ttgattgttt ctgttggagt 7020
gcagcccatt tcaccggaca agtcggctag attgatttag ccctgatgaa ctgccgaggg 7080
gaagccatct tgagcgcgga atgggaatgg atttcgttgt acaacgagac gacagaacac 7140
ccacgggacc gagcttcg 7158

<210> SEQ ID NO 35
<211> LENGTH: 8208
<212> TYPE: DNA
<213> ORGANISM: Artificial Sequence
<220> FEATURE:
<223> OTHER INFORMATION: DNA construct 406

<400> SEQUENCE: 35
aaaagtccca tgtggatcac tccgttgccc cgtcgctcac cgtgttgggg ggaaggtgca 60
catggctcag ttctcaatgg aaattatctg cctaaccggc tcagttctgc gtagaaacca 120
acatgcaagc tccaccgggt gcaaagcggc agcggcggca ggatatattc aattgtaaat 180
ggcttcatgt ccgggaaatc tacatggatc agcaatgagt atgatggtca atatggagaa 240
aaagaaagag taattaccaa tttttttca attcaaaaat gtagatgtcc gcagcgttat 300
tataaaatga aagtacattt tgataaaacg acaaattacg atccgtcgta tttataggcg 360
aaagcaataa acaaattatt ctaattcgga aatctttatt tcgacgtgtc tacattcacg 420
tccaaatggg ggcttagatg agaaacttca cgatcgatgc ggcccacgtg gattaccctg 480
ttatccctag aattcgatat cagttcgctc gtggccgtca cggccagcgc ctgcgttggc 540
ctagtaggcc aagcaggacg tattcgtttg ttgtgcggcc gcgttaacaa gcttctgcag 600
gtccgattga gacttttcaa caaagggtaa tatccggaaa cctcctcgga ttccattgcc 660
cagctatctg tcactttatt gtgaagatag tggaaaagga aggtggctcc tacaaatgcc 720

```
atcattgcga taaaggaaag gccatcgttg aagatgcctc tgccgacagt ggtcccaaag    780
atggaccccc acccacgagg agcatcgtgg aaaaagaaga cgttccaacc acgtcttcaa    840
agcaagtgga ttgatgtgat ggtccgattg agacttttca acaaagggta atatccggaa    900
acctcctcgg attccattgc ccagctatct gtcactttat tgtgaagata gtggaaaagg    960
aaggtggctc ctacaaatgc catcattgcg ataaaggaaa ggccatcgtt gaagatgcct   1020
ctgccgacag tggtcccaaa gatggacccc cacccacgag gagcatcgtg gaaaaagaag   1080
acgttccaac cacgtcttca aagcaagtgg attgatgtga tatctccact gacgtaaggg   1140
atgacgcaca atcccactat ccttcgcaag acccttcctc tatataagga agttcatttc   1200
atttggagag gacacgctga caagctgact ctagcagatc ctctagaacc atcttccaca   1260
cactcaagcc acactattgg agaacacaca gggacaacac accataagat ccaagggagg   1320
cctccgccgc cgccggtaac caccccgccc ctctcctctt tctttctccg tttttttttc   1380
cgtctcggtc tcgatctttg gccttggtag tttgggtggg cgagaggcgg cttcgtgcgc   1440
gcccagatcg gtgcgcggga ggggcgggat ctcgcggctg gggctctcgc cggcgtggat   1500
ccggcccgga tctcgcgggg aatggggctc tcggatgtag atctgcgatc cgccgttgtt   1560
gggggagatg atggggggtt taaaatttcc gccgtgctaa acaagatcag gaagagggga   1620
aaagggcact atggtttata tttttatata tttctgctgc ttcgtcaggc ttagatgtgc   1680
tagatctttc tttcttcttt ttgtgggtag aatttgaatc cctcagcatt gttcatcggt   1740
agtttttctt ttcatgattt gtgacaaatg cagcctcgtg cggagctttt ttgtaggtag   1800
aagtgatcaa ccatggccaa ccccaacaat cgctccgagc acgacacgat caaggtcacc   1860
cccaactccg agctccagac caaccacaac cagtacccgc tggccgacaa ccccaactcc   1920
accctggaag agctgaacta caaggagttc ctgcgcatga ccgaggactc ctccacggag   1980
gtcctggaca actccaccgt caaggacgcc gtcgggaccg gcatctccgt cgttgggcag   2040
atcctgggcg tcgttggcgt ccccttcgca ggtgctctca cctccttcta ccagtccttc   2100
ctgaacacca tctggccctc cgacgccgac ccctggaagg ccttcatggc ccaagtcgaa   2160
gtcctgatcg acaagaagat cgaggagtac gccaagtcca aggccctggc cgagctgcaa   2220
ggcctgcaaa acaacttcga ggactacgtc aacgcgctga actcctggaa gaagacgcct   2280
ctgtccctgc gctccaagcg ctcccaggac cgcatccgcg agctgttctc ccaggccgag   2340
tcccacttcc gcaactccat gccgtccttc gccgtctcca agttcgaggt cctgttcctg   2400
cccacctacg cccaggctgc caacacccac ctcctgttgc tgaaggacgc ccaggtcttc   2460
ggcgaggaat ggggctactc ctcggaggac gtcgccgagt tctaccgtcg ccagctgaag   2520
ctgacccaac agtacaccga ccactgcgtc aactggtaca acgtcggcct gaacggcctg   2580
aggggctcca cctacgacgc atgggtcaag ttcaaccgct tccgcaggga gatgaccctg   2640
accgtcctgg acctgatcgt cctgttcccc ttctacgaca tccgcctgta ctccaagggc   2700
gtcaagaccg agctgacccg cgacatcttc acggacccca tcttcctgct cacgaccctc   2760
cagaagtacg gtcccacctt cctgtccatc gagaactcca tccgcaagcc ccacctgttc   2820
gactacctcc agggcatcga gttccacacg cgcctgaggc caggctactt cggcaaggac   2880
tccttcaact actggtccgg caactacgtc gagaccaggc cctccatcgg ctcctcgaag   2940
acgatcacct cccctttcta cggcgacaag tccaccgagc ccgtccagaa gctgtccttc   3000
gacggccaga aggtctaccg caccatcgcc aacaccgacg tcgcggcttg gccgaacggc   3060
```

-continued aaggtctacc tgggcgtcac gaaggtcgac ttctcccagt acgatgacca gaagaacgag 3120
acctccaccc agacctacga ctccaagcgc aacaatggcc acgtctccgc ccaggactcc 3180
atcgaccagc tgccgcctga gaccactgac gagcccctgg agaaggccta ctcccaccag 3240
ctgaactacg cggagtgctt cctgatgcaa gaccgcaggg gcaccatccc cttcttcacc 3300
tggacccacc gctccgtcga cttcttcaac accatcgacg ccgagaagat cacccagctg 3360
cccgtggtca aggcctacgc cctgtcctcg ggtgcctcca tcattgaggg tccaggcttc 3420
accggtggca acctgctgtt cctgaaggag tcctcgaact ccatcgccaa gttcaaggtc 3480
accctgaact ccgctgcctt gctgcaacgc taccgcgtcc gcatccgcta cgcctccacc 3540
acgaacctgc gcctgttcgt ccagaactcc aacaatgact tcctggtcat ctacatcaac 3600
aagaccatga acaaggacga tgacctgacc taccagacct tcgacctcgc caccacgaac 3660
tccaacatgg gcttctcggg cgacaagaat gaactgatca ttggtgctga gtccttcgtc 3720
tccaacgaga agatctacat cgacaagatc gagttcatcc ccgtccagct gtgataggaa 3780
ctctgattga attctgcatg cgtttggacg tatgctcatt caggttggag ccaatttggt 3840
tgatgtgtgt gcgagttctt gcgagtctga tgagacatct ctgtattgtg tttctttccc 3900
cagtgttttc tgtacttgtg taatcggcta atcgccaaca gattcggcga tgaataaatg 3960
agaaataaat tgttctgatt ttgagtgcaa aaaaaaagga attagatctg tgtgtgtttt 4020
ttggatcccc ggggcggccg ctacctcagc aaatcaacct cactctattt aaatgaggtg 4080
gtaggatttg ctgaggaggc tgctccgttg tcctgcagga gacgagaaac acctttaatt 4140
aacaaatcac aggccatgaa ccctactcat gcttcgattt gtccaacaca cacttaccaa 4200
aactcaaatc atgtccttga cagtcactcg ggactcataa catgggtacg tatcgactat 4260
gtcaactata tgtgttctca tcagattata gattggccta gtacgtagtg atatttccac 4320
tagcactgtg gttatggctg tacctgatag tgatatcagc accgggtcat ggctctacta 4380
ccaggtagtg agagtgacct ttatactgtc agactgtaac taaggatttc caatcactgt 4440
tcggatccta ggcttagaat taagtaaaac tctatcacta taggctgcag cacactcggt 4500
atatattgat gggccaacag aaattgtgcg tactatgcgc gatgtaaaat ggacataaac 4560
cctacccata tacaatgcaa taacttttgt ccggtctggg ccaccggtta gcagaggtcc 4620
tgatttcggt ggtagtggta gcttgatctg gtcgtcgtat cgtagaggga tatataaaat 4680
catgtcactt ttgaagggag cgctcacaga aataataggt attcgcggga gccgcccccg 4740
cagaacacaa aataaggcga gcacgcacac gcatcagttt cgataaaata ataatagcgc 4800
cagctgatcg gaacaattcc agctagcact aatgtatttc tgcattgatc tgtttataca 4860
acatgctacc tcgttgagtg attttgacat gatttgtcaa cttgctccga tcctatatct 4920
cgatcgatct ccacatgacg atggttgttg tcctgtatcc catgacaacc aggcaacgct 4980
caaagcacac atgcgttgcc gattacccgt gcatgccgcc aagcacgaaa gcacctccct 5040
ccacaccgtc catcagcggt ccgattgaga cttttcaaca aagggtaata tccggaaacc 5100
tcctcggatt ccattgccca gctatctgtc actttattgt gaagatagtg gaaaaggaag 5160
gtggctccta caaatgccat cattgcgata aaggaaaggc catcgttgaa gatgcctctg 5220
ccgacagtgg tcccaaagat ggacccccac ccacgaggag catcgtggaa aaagaagacg 5280
ttccaaccac gtcttcaaag caagtggatt gatgtgatgg tccgattgag acttttcaac 5340
aaagggtaat atccggaaac ctcctcggat tccattgccc agctatctgt cactttattg 5400
tgaagatagt ggaaaaggaa ggtggctcct acaaatgcca tcattgcgat aaaggaaagg 5460

-continued

```
ccatcgttga agatgcctct gccgacagtg gtcccaaaga tggacccca cccacgagga   5520
gcatcgtgga aaaagaagac gttccaacca cgtcttcaaa gcaagtggat tgatgtgata   5580
tctccactga cgtaagggat gacgcacaat cccactatcc ttcgcaagac ccttcctcta   5640
tataaggaag ttcatttcat ttggagagga cacgctgaac cgtcttcggt acgcgctcac   5700
tccgccctct gcctttgtta ctgccacgtt tctctgaatg ctctcttgtg tggtgattgc   5760
tgagagtggt ttagctggat ctagaattac actctgaaat cgtgttctgc ctgtgctgat   5820
tacttgccgt cctttgtagc agcaaaatat agggacatgg tagtacgaaa cgaagataga   5880
acctacacag caatacgaga aatgtgtaat ttggtgctta gcggtattta tttaagcaca   5940
tgttggtgtt atagggcact tggattcaga agtttgctgt taatttaggc acaggcttca   6000
tactacatgg gtcaatagta tagggattca tattataggc gatactataa taatttgttc   6060
gtctgcagag cttattattt gccaaaatta gatattccta ttctgttttt gtttgtgtgc   6120
tgttaaattg ttaacgcctg aaggaataaa tataaatgac gaaattttga tgtttatctc   6180
tgctccttta ttgtgaccat aagtcaagat cagatgcact tgttttaaat attgttgtct   6240
gaagaaataa gtactgacag tattttgatg cattgatctg cttgtttgtt gtaacaaaat   6300
ttaaaaataa agagtttcct tttgttgct ctccttacct cctgatggta tctagtatct   6360
accaactgac actatattgc ttctctttac atacgtatct tgctcgatgc cttctcccta   6420
gtgttgacca gtgttactca catagtcttt gctcatttca ttgtaatgca gataccaagc   6480
gggagctcga cgtccctcag cagtcgctgt gcgataccat ccatgatatc gtgaacatca   6540
tctacattca aattcttatg agctttctta agggcatctg cagcattttt catagaatct   6600
aatacagcag tatttgtgct agctccttcg agggcttccc tctgcatttc aatagttgta   6660
agggttccat ctatttgtag ttgggtcttt tccaatcgtt tcttcttttt gagggcttgg   6720
agtgcaactc ttttattttt cgacgcattt ttctttgcaa gtactgcgat cgcgttaacg   6780
ctttatcacg ataccttcta ccacatatca ctaacaacat caacactcat cactctcgac   6840
gacatccact cgatcactac tctcacacga ccgattaact cctcatccac gcggccgcct   6900
gcaggagcgc aaagaaaaat gcgtcgaaaa ataaaagagt tgcactccaa gccctcaaaa   6960
agaagaaacg attggaaaag acccaactac aaatagatgg aacccttaca actattgaaa   7020
tgcagaggga agccctcgaa ggagctagca caaatactgc tgtattagat tctatgaaaa   7080
atgctgcaga tgcccttaag aaagctcata agaatttgaa tgtagatgat gttcacgata   7140
tcatggatta gatcgccagc ggtactcgct gaggcctagc tttcgttcgt atcatcggtt   7200
tcgacaacgt tcgtcaagtt caatgcatca gtttcattgc gcacacacca gaatcctact   7260
gagtttgagt attatggcat tgggaaaact gtttttcttg taccatttgt tgtgcttgta   7320
atttactgtg ttttttattc ggttttcgct atcgaactgt gaaatggaaa tggatggaga   7380
agagttaatg aatgatatgg tccttttgtt cattctcaaa ttaatattat ttgttttttc   7440
tcttatttgt tgtgtgttga atttgaaatt ataagagata tgcaaacatt ttgttttgag   7500
taaaaatgtg tcaaatcgtg gcctctaatg accgaagtta atatgaggag taaaacactt   7560
gtagttgtac cattatgctt attcactagg caacaaatat attttcagac ctagaaaagc   7620
tgcaaatgtt actgaataca agtatgtcct cttgtgtttt agacatttat gaactttcct   7680
ttatgtaatt ttccagaatc cttgtcagat tctaatcatt gctttataat tatagttata   7740
ctcatggatt tgtagttgag tatgaaaata ttttttaatg cattttatga cttgccaatt   7800
```

-continued

```
gattgacaac ggtaccgtcg gtccgagttt gcgtcttggc gcgccaagaa gaacgattcg   7860

ctaccttagg accgttatag ttagaattcg atatctagtt agggataaca gggtaatgtc   7920

gacagacctc aattgcgagc tttctaattt caaactattc gggcctaact tttggtgtga   7980

tgatgctgac tggcaggata tataccgttg taatttgagc tcgtgtgaat aagtcgctgt   8040

gtatgtttgt ttgattgttt ctgttggagt gcagcccatt tcaccggaca agtcggctag   8100

attgatttag ccctgatgaa ctgccgaggg gaagccatct tgagcgcgga atgggaatgg   8160

atttcgttgt acaacgagac gacagaacac ccacgggacc gagcttcg                8208


<210> SEQ ID NO 36
<211> LENGTH: 2632
<212> TYPE: DNA
<213> ORGANISM: Artificial Sequence
<220> FEATURE:
<223> OTHER INFORMATION: DNA construct 890

<400> SEQUENCE: 36

aaaagtccca tgtggatcac tccgttgccc cgtcgctcac cgtgttgggg ggaaggtgca     60

catggctcag ttctcaatgg aaattatctg cctaaccggc tcagttctgc gtagaaacca    120

acatgcaagc tccaccgggt gcaaagcggc agcggcggca ggatatattc aattgtaaat    180

ggcttcatgt ccgggaaatc tacatggatc agcaatgagt atgatggtca atatggagaa    240

aaagaaagag taattaccaa tttttttca attcaaaaat gtagatgtcc gcagcgttat    300

tataaaatga aagtacattt tgataaaacg acaaattacg atccgtcgta tttataggcg    360

aaagcaataa acaaattatt ctaattcgga aatctttatt tcgacgtgtc tacattcacg    420

tccaaatggg ggcttagatg agaaacttca cgatcgatgc ggccgcttaa ttaaggcgcg    480

ccgctagcct gcaggctgca ggtccgattg agacttttca acaaagggta atatccggaa    540

acctcctcgg attccattgc ccagctatct gtcactttat tgtgaagata gtggaaaagg    600

aaggtggctc ctacaaatgc catcattgcg ataaaggaaa ggccatcgtt gaagatgcct    660

ctgccgacag tggtcccaaa gatggacccc cacccacgag gagcatcgtg gaaaaagaag    720

acgttccaac cacgtcttca aagcaagtgg attgatgtga tggtccgatt gagacttttc    780

aacaaagggt aatatccgga aacctcctcg gattccattg cccagctatc tgtcacttta    840

ttgtgaagat agtggaaaag gaaggtggct cctacaaatg ccatcattgc gataaaggaa    900

aggccatcgt tgaagatgcc tctgccgaca gtggtcccaa agatggaccc ccacccacga    960

ggagcatcgt ggaaaaagaa gacgttccaa ccacgtcttc aaagcaagtg gattgatgtg   1020

atatctccac tgacgtaagg gatgacgcac aatcccacta tccttcgcaa gacccttcct   1080

ctatataagg aagttcattt catttggaga ggacacgctg agggcccacc gtcttcggta   1140

cgcgctcact ccgccctctg cctttgttac tgccacgttt ctctgaatgc tctcttgtgt   1200

ggtgattgct gagagtggtt tagctggatc tagaattaca ctctgaaatc gtgttctgcc   1260

tgtgctgatt acttgccgtc ctttgtagca gcaaaatata gggacatggt agtacgaaac   1320

gaagatagaa cctacacagc aatacgagaa atgtgtaatt tggtgcttag cggtatttat   1380

ttaagcacat gttggtgtta tagggcactt ggattcagaa gtttgctgtt aatttaggca   1440

caggcttcat actacatggg tcaatagtat agggattcat attataggcg atactataat   1500

aatttgttcg tctgcagagc ttattatttg ccaaaattag atattcctat tctgtttttg   1560

tttgtgtgct gttaaattgt taacgcctga aggaataaat ataaatgacg aaattttgat   1620

gtttatctct gctcctttat tgtgaccata agtcaagatc agatgcactt gttttaaata   1680
```

```
ttgttgtctg aagaaataag tactgacagt attttgatgc attgatctgc ttgtttgttg   1740

taacaaaatt taaaaataaa gagtttcctt tttgttgctc tccttacctc ctgatggtat   1800

ctagtatcta ccaactgaca ctatattgct tctctttaca tacgtatctt gctcgatgcc   1860

ttctccctag tgttgaccag tgttactcac atagtctttg ctcatttcat tgtaatgcag   1920

ataccaagcg ggagctcgac gtccctcagc agtcgctgtg cgataccatc catgatatcg   1980

tgaacatcat ctacattcaa attcttatga gctttcttaa gggcatctgc agcatttttc   2040

atagaatcta atacagcagt atttgtgcta gctccttcga gggcttccct ctgcatttca   2100

atagttgtaa gggttccatc tatttgtagt tgggtctttt ccaatcgttt cttctttttg   2160

agggcttgga gtgcaactct tttatttttc gacgcatttt tctttgcaag tactgcgatc   2220

gcgttaacgc tttatcacga taccttctac cacatatcac taacaacatc aacactcatc   2280

actctcgacg acatccactc gatcactact ctcacacgac cgattaactc ctcatccacg   2340

cggccgcctg caggagcgca aagaaaaatg cgtcgaaaaa taaaagagtt gcactccaag   2400

ccctcaaaaa gaagaaacga ttggaaaaga cccaactaca aatagatgga acccttacaa   2460

ctattgaaat gcagagggaa gccctcgaag gagctagcac aaatactgct gtattagatt   2520

ctatgaaaaa tgctgcagat gcccttaaga aagctcataa gaatttgaat gtagatgatg   2580

ttcacgatat catggattag atcgccagcg gtactcgctg aggcctagct tt           2632
```

```
<210> SEQ ID NO 37
<211> LENGTH: 193
<212> TYPE: DNA
<213> ORGANISM: Zea mays
<220> FEATURE:
<221> NAME/KEY: misc_feature
<223> OTHER INFORMATION: represents a segment of the integration site
      in the LH244 corn genome at which TDNA from DNA construct #417
      was inserted to create Event MON 87411

<400> SEQUENCE: 37

aaggaaaata aaaaggcaaa acactaatga atagttaagt ggttaacttt gtgaaattaa     60

tctcatgtaa tatatgatcc cacccctgaa ataactttag taattcatta agatagctat    120

agttaagtta tgtaatacat tgagatgggt agtacttaga gaatcacaaa cctctagatg    180

tattaatcta ccc                                                       193


<210> SEQ ID NO 38
<211> LENGTH: 28
<212> TYPE: DNA
<213> ORGANISM: artificial sequence
<220> FEATURE:
<223> OTHER INFORMATION: is a nucleotide sequence representing a
      synthetic oligonucleotide, and is referred to as SQ20221

<400> SEQUENCE: 38

gttgctatgt actaacagaa ctgcatgt                                        28


<210> SEQ ID NO 39
<211> LENGTH: 24
<212> TYPE: DNA
<213> ORGANISM: artificial sequence
<220> FEATURE:
<223> OTHER INFORMATION: is a nucleotide sequence representing a
      synthetic oligonucleotide, and is referred to as PB10065

<400> SEQUENCE: 39

gccctatgac ttaccgagag ttca                                            24
```

<210> SEQ ID NO 40
<211> LENGTH: 29
<212> TYPE: DNA
<213> ORGANISM: artificial sequence
<220> FEATURE:
<223> OTHER INFORMATION: is a nucleotide sequence representing a synthetic oligonucleotide, and is referred to as SQ20222

<400> SEQUENCE: 40
ttgttgtgtg gctccattct gacttgtga 29

<210> SEQ ID NO 41
<211> LENGTH: 60
<212> TYPE: DNA
<213> ORGANISM: Artificial Sequence
<220> FEATURE:
<223> OTHER INFORMATION: is a nucleotide sequence of event MON 87411

<400> SEQUENCE: 41
gatgcggcca ccactcgagg tcgaggtacc gttgtcaatc aattggcaag tcataaaatg 60

<210> SEQ ID NO 42
<211> LENGTH: 89
<212> TYPE: DNA
<213> ORGANISM: Artificial Sequence
<220> FEATURE:
<223> OTHER INFORMATION: a unique junction sequence within the transgenic insert of event MON 87411

<400> SEQUENCE: 42
ttgtcgaaac cgatgatacg aacgaaagct aggcctcagc gagtaccgct ggcgatctaa 60
tccatgatat cgtgaacatc atctacatt 89

<210> SEQ ID NO 43
<211> LENGTH: 96
<212> TYPE: DNA
<213> ORGANISM: Artificial Sequence
<220> FEATURE:
<223> OTHER INFORMATION: a unique junction sequence within the transgenic insert of event MON 87411

<400> SEQUENCE: 43
aatgtagatg atgttcacga tatcatggat ggtatcgcac agcgactgct gagggacgtc 60
gagctcccgc ttggtatctg cattacaatg aaatga 96

<210> SEQ ID NO 44
<211> LENGTH: 347
<212> TYPE: DNA
<213> ORGANISM: Artificial Sequence
<220> FEATURE:
<223> OTHER INFORMATION: a unique junction sequence within the transgenic insert of event MON 87411

<400> SEQUENCE: 44
taccctttgt tgaaaagtct caatcggacc atcacatcaa tccacttgct ttgaagacgt 60
ggttggaacg tcttcttttt ccacgatgct cctcgtgggt gggggtccat ctttgggacc 120
actgtcggca gaggcatctt caacgatggc ctttccttta tcgcaatgat ggcatttgta 180
ggagccacct tccttttcca ctatcttcac aataaagtga cagatagctg ggcaatggaa 240
tccgaggagg tttccggata ttaccctttg ttgaaaagtc tcaatcggac ctgcagcctg 300
caggctagcg gcgcgccaca aatcacaggc catgaaccct actcatg 347

<210> SEQ ID NO 45
<211> LENGTH: 76
<212> TYPE: DNA
<213> ORGANISM: Artificial Sequence
<220> FEATURE:
<223> OTHER INFORMATION: a unique junction sequence within the transgenic insert of event MON 87411

<400> SEQUENCE: 45
gctataaaaa ccatgccaag caccctgtga aaagccccgg gaaccatctt ccacacactc 60
aagccacact attgga 76

<210> SEQ ID NO 46
<211> LENGTH: 86
<212> TYPE: DNA
<213> ORGANISM: Artificial Sequence
<220> FEATURE:
<223> OTHER INFORMATION: a junction sequence within the transgenic insert of event MON 87411

<400> SEQUENCE: 46
actattggag aacacacagg gacaacacac cataagatcc aagggaggcc tccgccgccg 60
ccggtaacca ccccgcccct ctcctc 86

<210> SEQ ID NO 47
<211> LENGTH: 79
<212> TYPE: DNA
<213> ORGANISM: Artificial Sequence
<220> FEATURE:
<223> OTHER INFORMATION: a junction sequence within the transgenic insert of event MON 87411

<400> SEQUENCE: 47
tgcagcctcg tgcggagctt ttttgtaggt agaagtgatc aaccatggcc aaccccaaca 60
atcgctccga gcacgacac 79

<210> SEQ ID NO 48
<211> LENGTH: 89
<212> TYPE: DNA
<213> ORGANISM: Artificial Sequence
<220> FEATURE:
<223> OTHER INFORMATION: a junction sequence within the transgenic insert of event MON 87411

<400> SEQUENCE: 48
tcgacaagat cgagttcatc cccgtccagc tgtgatagga actctgattg aattctgcat 60
gcgtttggac gtatgctcat tcaggttgg 89

<210> SEQ ID NO 49
<211> LENGTH: 108
<212> TYPE: DNA
<213> ORGANISM: Artificial Sequence
<220> FEATURE:
<223> OTHER INFORMATION: a unique junction sequence within the transgenic insert of event MON 87411

<400> SEQUENCE: 49
tctgattttg agtgcaaaaa aaaaggaatt agatctgtgt gtgttttttg gatcccattt 60
tcgacaagct tgcctcgaga caacaacatg cttctcatca acatggag 108

<210> SEQ ID NO 50
<211> LENGTH: 104
<212> TYPE: DNA

-continued

```
<213> ORGANISM: Artificial Sequence
<220> FEATURE:
<223> OTHER INFORMATION: a unique junction sequence within the
      transgenic insert of event MON 87411

<400> SEQUENCE: 50

aattcttaag gcgtaatttg ttgaaatctt gttttgtcct atgcagcctg atccatggcg     60

caagttagca gaatctgcaa tggtgtgcag aacccatctc ttat                     104


<210> SEQ ID NO 51
<211> LENGTH: 107
<212> TYPE: DNA
<213> ORGANISM: Artificial Sequence
<220> FEATURE:
<223> OTHER INFORMATION: a unique junction sequence within the
      transgenic insert of event MON 87411

<400> SEQUENCE: 51

tggccgggct gggcgcgaag atcgaactct ccgatacgaa ggctgcctga tgagctccag     60

ggttcttgcc tggtgccttg gcaatgcttg attactgctg ctatcct                  107


<210> SEQ ID NO 52
<211> LENGTH: 103
<212> TYPE: DNA
<213> ORGANISM: Artificial Sequence
<220> FEATURE:
<223> OTHER INFORMATION: is a nucleotide sequence of event MON 87411

<400> SEQUENCE: 52

tatgataaag ttgctctgta acagaaaaca ccatctagag cggccgcgtt taaactatca     60

gtgtttagag aatcacaaac ctctagatgt attaatctac cct                      103
```